US012522607B2

(12) United States Patent
Xie et al.

(10) Patent No.: US 12,522,607 B2
(45) Date of Patent: Jan. 13, 2026

(54) SUBSTITUTED PYRAZOLO[3,4-D]PYRIMIDINES AS WEE-1 INHIBITORS

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 622 days.

(21) Appl. No.: 17/917,706

(22) PCT Filed: Jun. 16, 2021

(86) PCT No.: PCT/CN2021/100347

§ 371 (c)(1),
(2) Date: Oct. 7, 2022

(87) PCT Pub. No.: WO2021/254389

PCT Pub. Date: Dec. 23, 2021

(65) Prior Publication Data

US 2023/0159540 A1 May 25, 2023

(30) Foreign Application Priority Data

Jun. 17, 2020 (CN) ........................ 202010557580.X

(51) Int. Cl.
*A61K 31/519* (2006.01)
*C07D 487/04* (2006.01)
*C07D 519/00* (2006.01)

(52) U.S. Cl.
CPC ......... *C07D 487/04* (2013.01); *C07D 519/00* (2013.01); *C07B 2200/13* (2013.01)

(58) Field of Classification Search
CPC ............................ A61K 31/519; C07D 487/04
USPC ........................................ 514/262.1; 544/262
See application file for complete search history.

(56) References Cited

FOREIGN PATENT DOCUMENTS

| | | | | |
|---|---|---|---|---|
| CN | 101432284 | A | 5/2009 | |
| CN | 108623615 | A | 10/2018 | |
| CN | 109422754 | A | 3/2019 | |
| CN | 111094253 | A | 5/2020 | |
| EP | 4169919 | A1 * | 4/2023 | ........... C07D 487/04 |
| WO | 2009054332 | A1 | 4/2009 | |
| WO | 2015183776 | A1 | 12/2015 | |
| WO | 2018011569 | A1 | 1/2018 | |
| WO | 2018133829 | A1 | 7/2018 | |
| WO | 2019165204 | A1 | 8/2019 | |
| WO | 2019169065 | A2 | 9/2019 | |
| WO | 2019173082 | A8 | 10/2019 | |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Ye Tan et al., A Wee1 kinase inhibitor: adavosertib, Drugs & Clinic, vol. 33, No. 4, pp. 989-996 (Apr. 19, 2018).

* cited by examiner

*Primary Examiner* — Douglas M Willis
(74) *Attorney, Agent, or Firm* — SZDC Law PC

(57) ABSTRACT

The present invention relates to a novel compound of general formula (1) and/or a pharmaceutically acceptable salt thereof, a composition containing the compound of general formula (1) and/or the pharmaceutically acceptable salt thereof, a method for preparing the same, and use of the same as a Wee-1 inhibitor in preparing anti-tumor drugs.

(1)

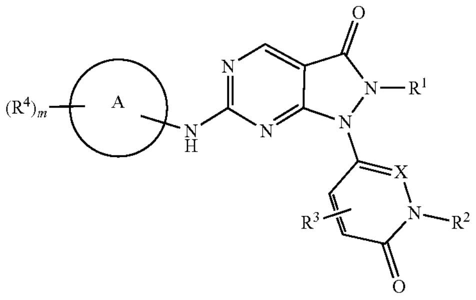

9 Claims, No Drawings

SUBSTITUTED PYRAZOLO[3,4-D]PYRIMIDINES AS WEE-1 INHIBITORS

CROSS-REFERENCE TO RELATED APPLICATIONS

The present application is the National Stage Application of PCT/CN2021/100347, filed on Jun. 16, 2021, which claims priority to Chinese Patent Application CN 202010557580.X filed on Jun. 17, 2020, which is incorporated herein by reference in its entirety.

BACKGROUND OF THE INVENTION

Filed of the Invention

The present invention relates to the field of pharmaceutical chemistry, and particularly to a novel compound with inhibitory effect on Wee-1 kinase, a method for preparing the same and use of such compounds in preparing anti-tumor drugs.

Description of Related Art

Wee-1 protein kinase is an important negative regulatory protein in cell cycle checkpoints. The cell cycle checkpoints include a G1 checkpoint for the transition from G1 phase (cell resting phase) to S phase (DNA synthesis phase), a G2 checkpoint for the transition from G2 phase (cell division preparation phase) to M phase (cell division phase), and a spindle checkpoint for the transition from metaphase (cell division metaphase) to anaphase (cell division anaphase) of the M phase. The Wee-1 protein kinase plays an important role in the G2 phase checkpoint. Cell entry into M phase depends on CDK1 kinase activity, and Wee-1 inhibits the activity of CDK1 by phosphorylating Tyr 15 of CDK1 protein, preventing cells from entering M phase (cell division phase). In contrast, polo kinase phosphorylates Wee-1 activates the degradation of Wee-1 protein, promoting cells to enter M phase. Thus, Wee-1 kinase activity determines the activity of the G2 checkpoint, thereby regulating the transition from G2 to M phase of cells. The cell cycle checkpoints are activated primarily following DNA damage and play an important role in the repair of DNA in cells. The normal activation of the cell cycle checkpoints blocks the cell cycle and promotes DNA repair. If the functions of the checkpoints are inhibited, the DNA damage is unable to be repaired, and the cells undergo apoptosis. Compared with normal cells, a plurality of tumor cells repair DNA damage and avoid apoptosis mainly depending on the activation of the G2 phase checkpoint due to the impaired function of the important protein p53 protein of the G1 phase checkpoint. Therefore, tumor cells can be selectively killed by inhibiting the G2 phase checkpoint. The important role of Wee-1 kinase activity in the G2 phase checkpoint suggests that Wee-1 kinase determines the repair or death of tumor cells after DNA damage, and inhibition of Wee-1 activity can promote unrepaired tumor cells after DNA damage to enter M phase and induce apoptosis.

Studies have shown that in addition to its role in the G2 checkpoint, Wee-1 is involved in DNA synthesis, DNA homologous repair, post-translational modification of chromosomal histones, and other functions closely related to the development and progression of tumors. The expression of Wee-1 is greatly increased in a large number of tumors including liver cancer, breast cancer, cervical cancer, melanoma, lung cancer and the like. The high expression of Wee-1 is in positive correlation with the tumor development and poor prognosis, suggesting that Wee-1 kinase may be involved in the occurrence and progression of tumors. Studies on in vitro cell models and in vivo animal models have shown that inhibiting Wee-1 activity while inducing DNA damage can significantly inhibit the growth of a variety of tumors.

Therefore, the development of specific and highly active small-molecule inhibitors against Wee-1 kinase would be of important clinical value for tumor treatment, especially targeting tumors with impaired G1 checkpoints such as P53 deletion.

At present, the Wee-1 inhibitor AZD-1775 of AstraZeneca has entered the clinical phase II stage, and more than 30 clinical trials are under development and have shown good therapeutic effects. Patents related to AZD-1775 include US20070254892, WO2007126122, EP2213673, WO2008133866, WO2011034743 and the like. Abbott and Abbvie also have conducted research on Wee-1 inhibitors. The related patents include mainly US2012220572, WO2013126656, WO2013012681, WO2013059485, WO2013013031 and the like. Patents related to Wee-1 inhibitors of Almac include WO2014167347, WO2015019037, WO2015092431, WO2018011570, WO2018062932, WO2019138227 and the like. Patents related to Wee-1 of Girafpharma include WO2019074979 and WO2019074981. Patents related to Wee-1 research of Zeno include WO2018028008 and WO2019173082.

Currently, there are still some problems with Wee-1 inhibitors under study, for example, the metabolic properties of AZD-1775 are not good enough, and there is a large space for optimization.

BRIEF SUMMARY OF THE INVENTION

The present invention provides a compound with a structure as shown in general formula (1) or isomers, crystalline forms, pharmaceutically acceptable salts, hydrates or solvates thereof:

(1)

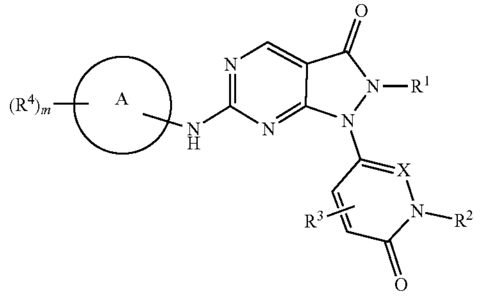

wherein m is an integer of 1, 2 or 3;

X is N or CH;

A is a divalent or more than divalent aryl, a divalent or more than divalent heteroaryl, a divalent or more than divalent cycloalkyl-aryl, a divalent or more than divalent heterocycloalkyl-aryl, or a divalent or more than divalent heterocycloalkyl-heteroaryl;

$R^1$ is C1-C6 alkyl, halogen-substituted C1-C3 alkyl, C3-C6 cycloalkyl, —$CH_2$(C3-C6) cycloalkyl or C3-C5 alkenyl;

$R^2$ is C1-C6 alkyl, C3-C6 cycloalkyl or (4- to 6-membered) heterocycloalkyl, wherein the alkyl, cycloalkyl and heterocycloalkyl can be optionally substituted with 1 to 3 of the following groups: H, halogen, OH, Me or OMe;

$R^3$ is H, halogen, CN, C1-C3 alkyl, halogen-substituted C1-C3 alkyl or C1-C3 alkoxy; each $R^4$ is independently H, halogen, C1-C3 alkyl, halogen-substituted C1-C3 alkyl, hydroxyl-substituted C1-C3 alkyl, C1-C3 alkoxy, $NMe_2$-substituted C1-C3 alkyl, $NMe_2$-substituted C1-C3 alkoxy,

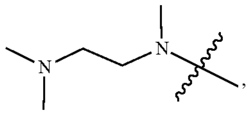 [SMILES: *N(C)CCN(C)C], $NMe_2$, C3-C6 cycloalkyl, (4- to 12-membered) heterocycloalkyl or —$CH_2$ (4- to 12-membered) heterocycloalkyl, wherein the (4- to 12-membered) heterocycloalkyl can be optionally substituted with 1 to 3 $R^5$, and each $R^5$ is independently H, halogen, CN, OH, C1-C3 alkyl, halogen-substituted C1-C3 alkyl, hydroxyl-substituted C1-C3 alkyl cyano-substituted C1-C3 alkyl, C3-C6 cycloalkyl, halogen-substituted C3-C6 cycloalkyl,

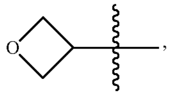 [SMILES: *C1COC1], $NR^6R^7$ or —(C1-C3 alkyl)-$NR^6R^7$, wherein $R^6$ and $R^7$ are independently H or C1-C3 alkyl, or $R^6$ and $R^7$ form a 4- to 7-membered heterocycloalkyl with an N atom to which they are both connected; wherein two $R^4$ can, together with C atoms, form a C2-C3 alkylene; wherein $R^4$ or $R^5$ cannot be halogen when connected to a heteroatom.

In some embodiments of the present invention, the $R^1$ is Me, Et,

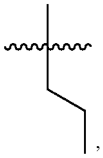, 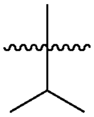, 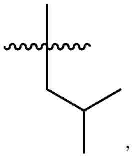, 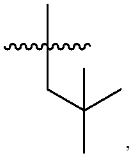,

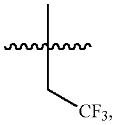 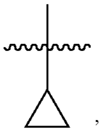, 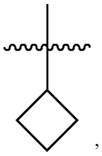, 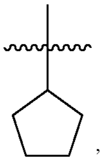,

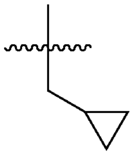, 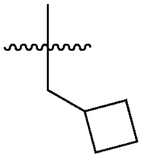, 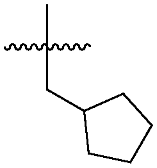,

-continued

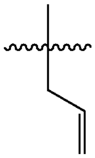 or 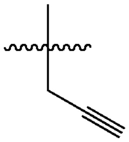.

In some embodiments of the present invention, the $R^2$ is Me, Et,

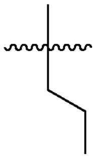, 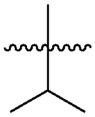, 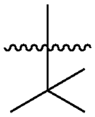, 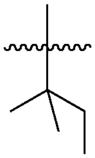,

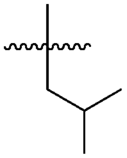, 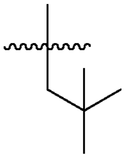, 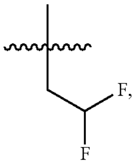 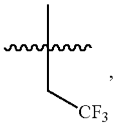,

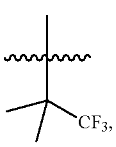 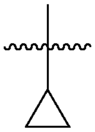, 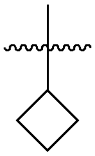, 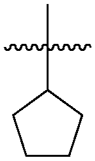,

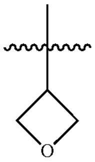, 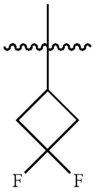, 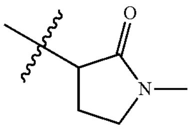,

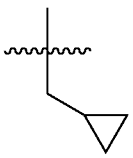, 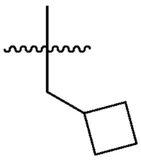, 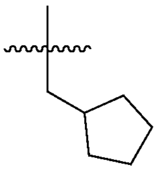,

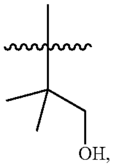 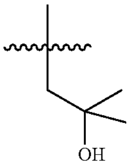, 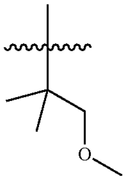 or

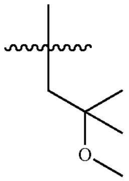.

In some embodiments of the present invention, the $R^3$ is H, F Me Et,

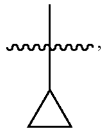,
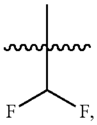, $CF_3$, OMe or OEt.

In some embodiments of the present invention, the

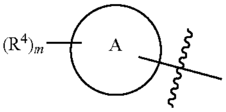

is the following group:

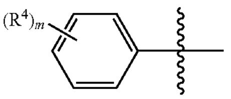,
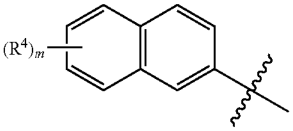,
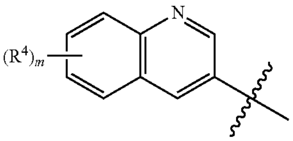,
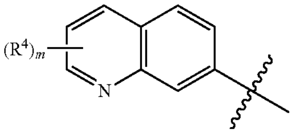,
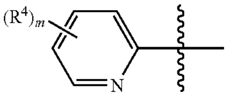,
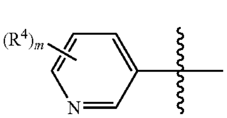,
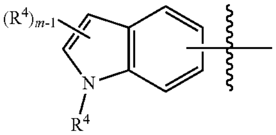,
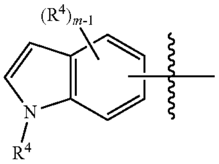,
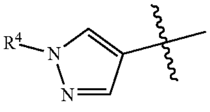,
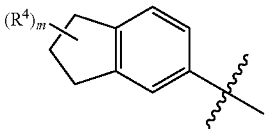,
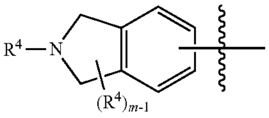 or -continued

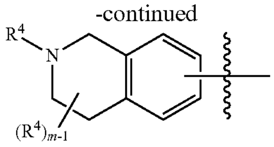, wherein m is an integer of 1, 2 or 3, each $R^4$ is independently H, halogen, C1-C3 alkyl, halogen-substituted C1-C3 alkyl, hydroxyl-substituted C1-C3 alkyl, C1-C3 alkoxy, $NMe_2$-substituted C1-C3 alkyl, $NMe_2$-substituted C1-C3 alkoxy,

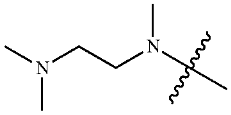, $NMe_2$, C3-C6 cycloalkyl, (4- to 12-membered) heterocycloalkyl or —$CH_2$ (4- to 12-membered) heterocycloalkyl, wherein the (4- to 12-membered) heterocycloalkyl can be optionally substituted with 1 to 3 $R^5$, and $R^5$ is independently H, halogen, CN, OH, C1-C3 alkyl, halogen-substituted C1-C3 alkyl, hydroxyl-substituted C1-C3 alkyl, cyano-substituted C1-C3 alkyl, C3-C6 cycloalkyl, halogen-substituted C3-C6 cycloalkyl,

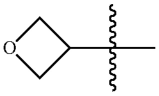, $NR^6R^7$ or —(C1-C3 alkyl)-$NR^6R^7$, wherein $R^6$ and $R^7$ are independently H or C1-C3 alkyl, or $R^6$ and $R^7$ form a 4- to 7-membered heterocycloalkyl with an N atom to which they are both attached; wherein two $R^4$ can, together with C atoms, form a C2-C3 alkylene; wherein $R^4$ or $R^5$ cannot be halogen when connected to a heteroatom.

In some embodiments of the present invention, $R^4$ is independently H, F, Cl, Me, Et,

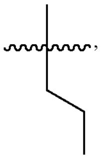,
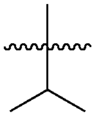, $CF_3$, $CH_2CF_3$, $CH_2OH$, $CH_2CH_2OH$, OMe, OEt,

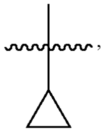,
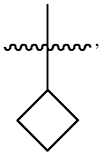,
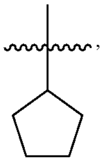,

NMe$_2$,
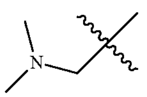, 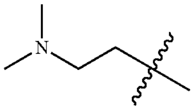,
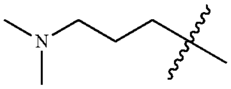, 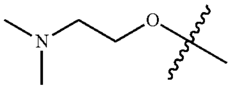,
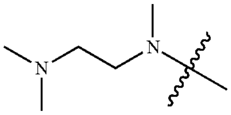, 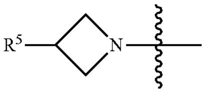,
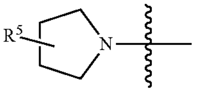, 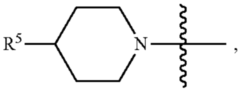,
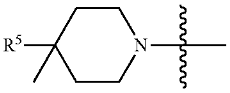, 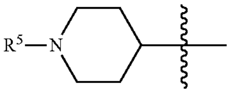,
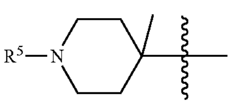, 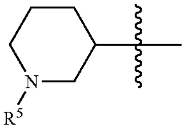,
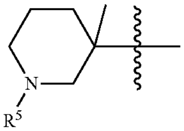, 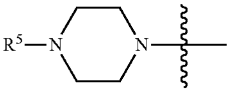,
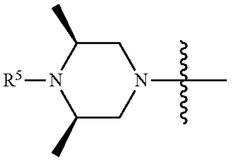, 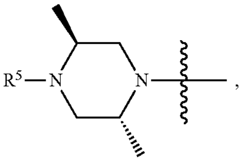,
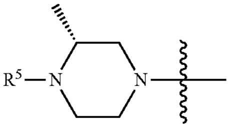, 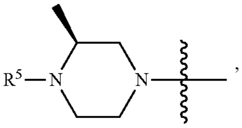,
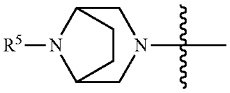, 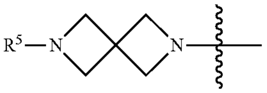,
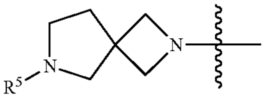,
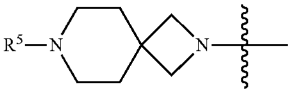,
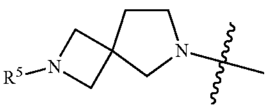, 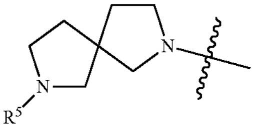,
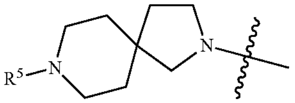,
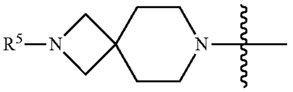,
-continued
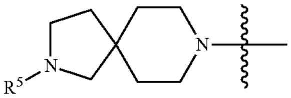,
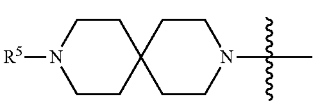, 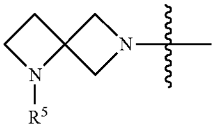,
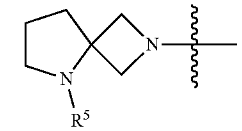, 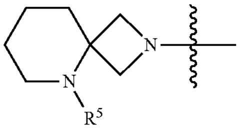,
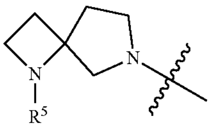, 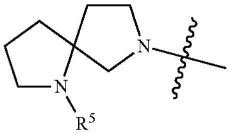,
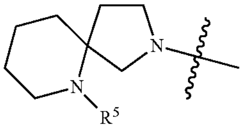, 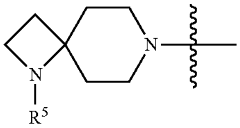 or
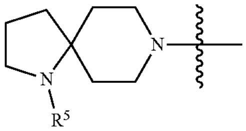,
or wherein two $R^4$, together with C atoms, form spirocycloprpyl
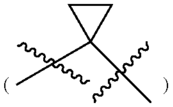 [SMILES: *C1(*)CC1]
or spirocyclobutyl
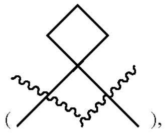,
wherein $R^5$ is H, halogen, CN, OH, C1-C3 alkyl, halogen-substituted C1-C3 alkyl, hydroxyl-substituted C1-C3 alkyl, cyano-substituted C1-C3 alkyl, C3-C6 cycloalkyl, halogen-substituted C3-C6 cycloalkyl, NaH$_2$, NHMe, NMe$_2$
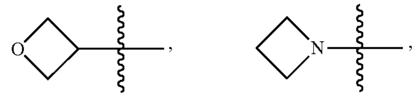
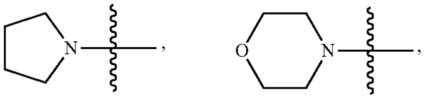

-continued
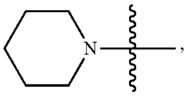,
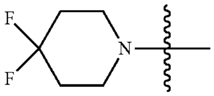,
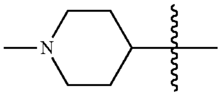
or
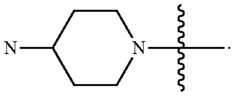.
In some embodiments of the present invention, the
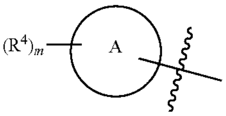
is the following group:
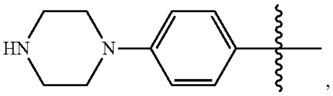,
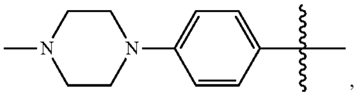,
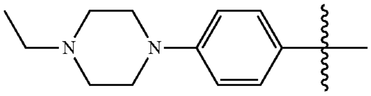,
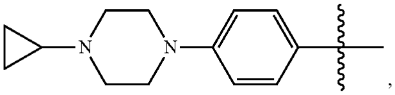,
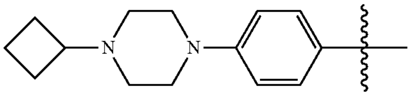,
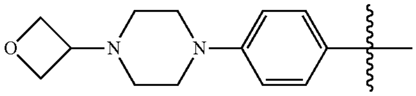,
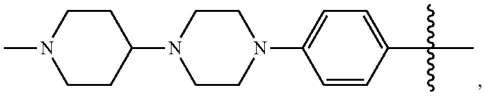,
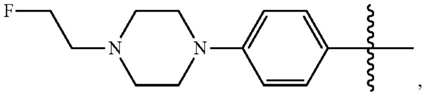,
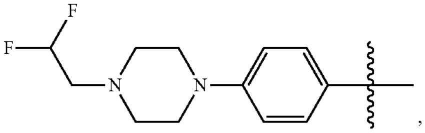,
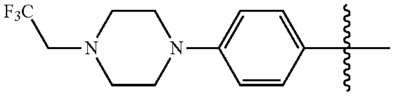,
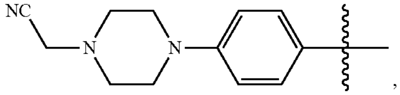,
-continued
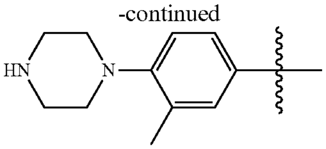,
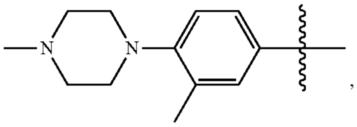,
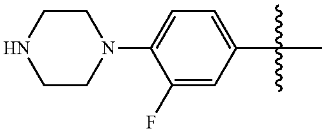,
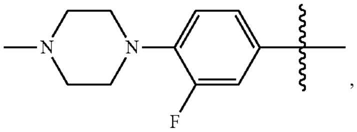,
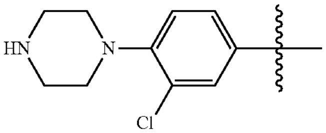,
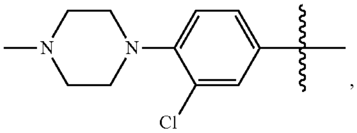,
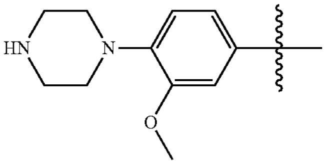,
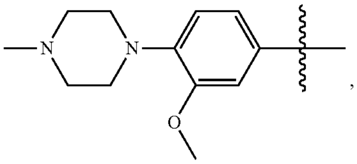,
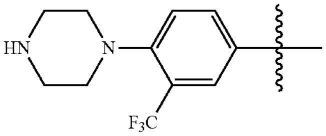,
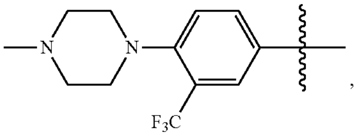,
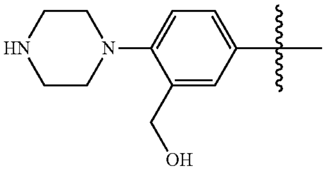,
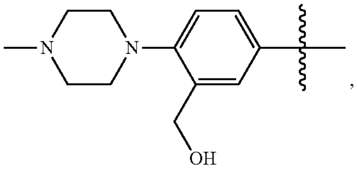, -continued
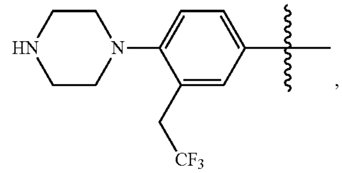,
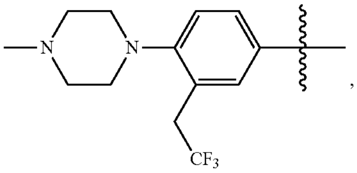,
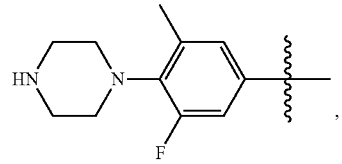,
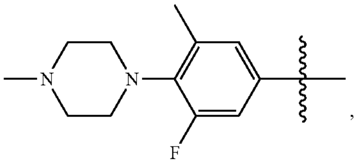,
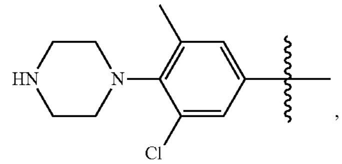,
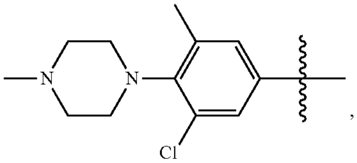,
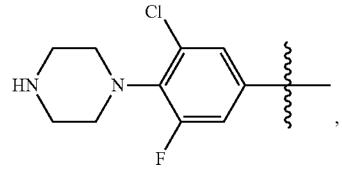,
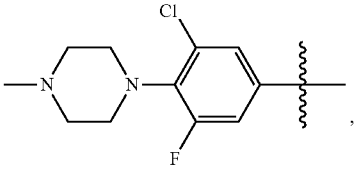,
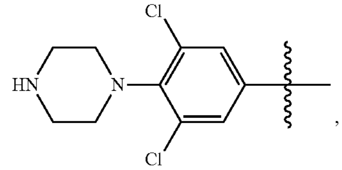,
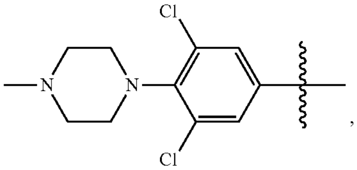,
-continued
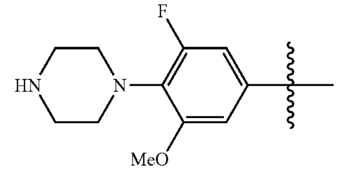,
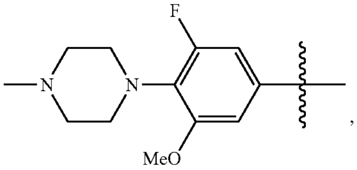,
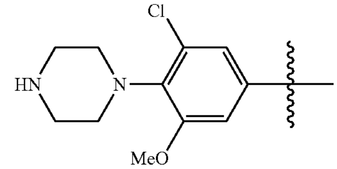,
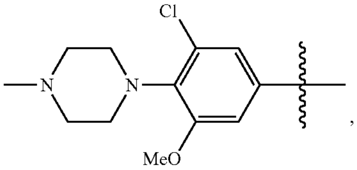,
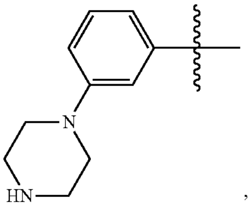,
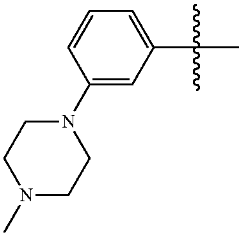,
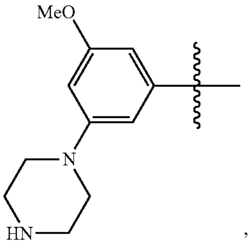,
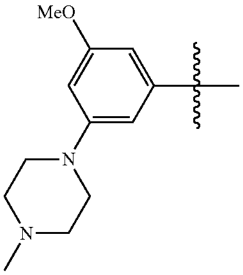,
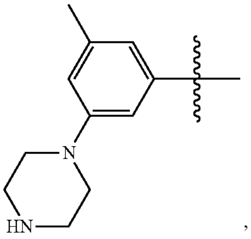,
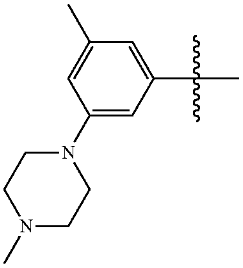,
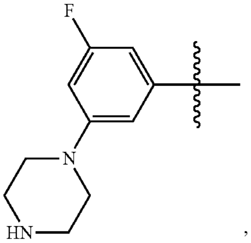,
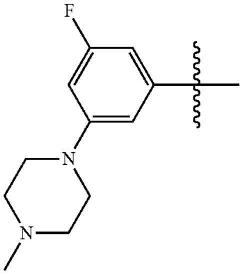, -continued
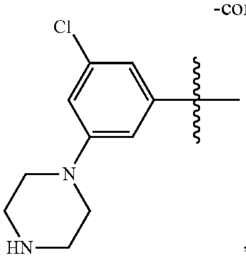
,
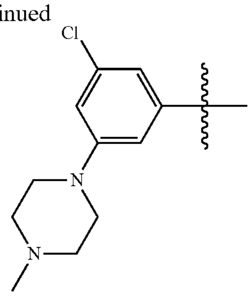
,
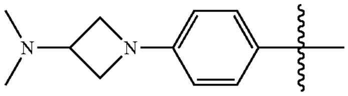
,
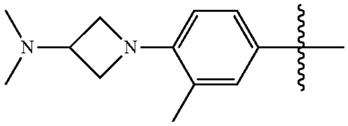
,
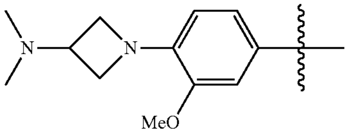
,
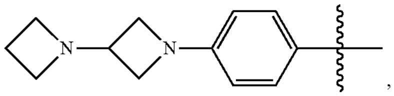
,
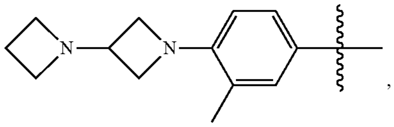
,
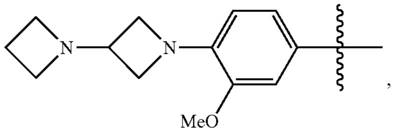
,
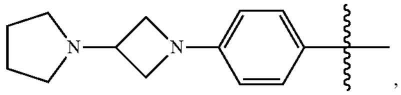
,
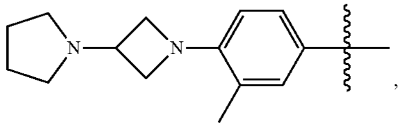
,
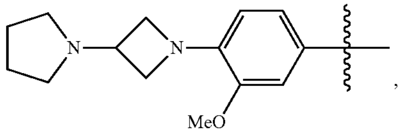
,
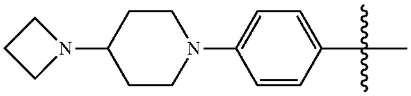
,
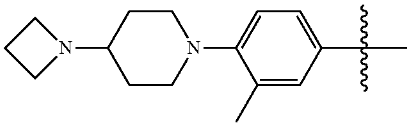
,
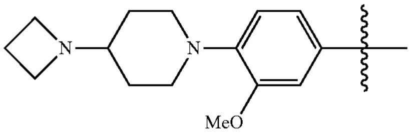
,
-continued
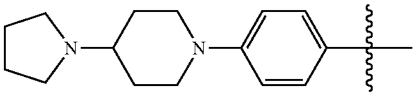
,
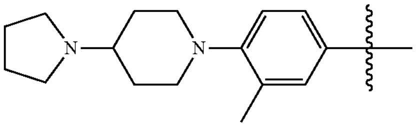
,
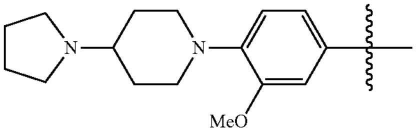
,
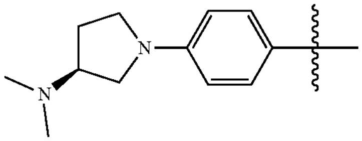
,
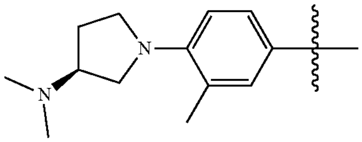
,
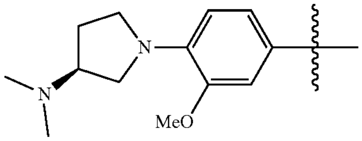
,
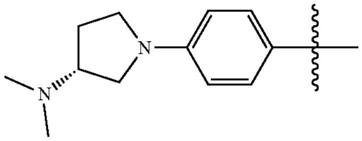
,
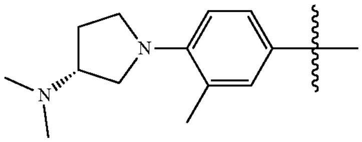
,
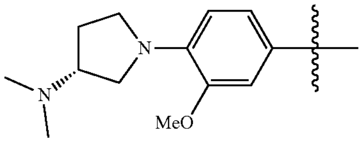
,
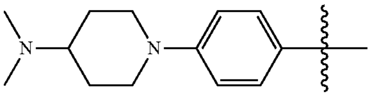
,
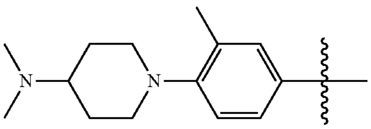
,
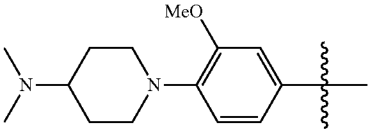
,
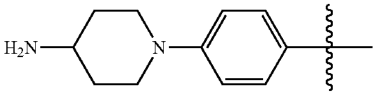
, -continued
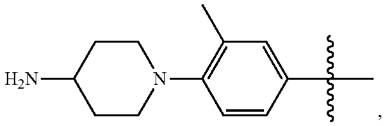,
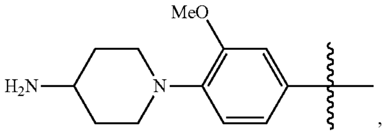,
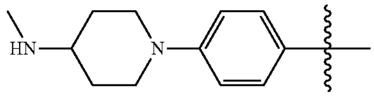,
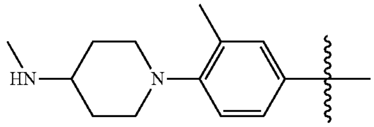,
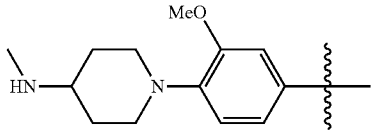,
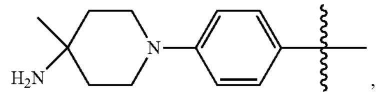,
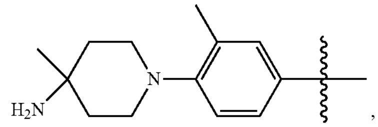,
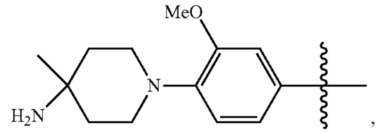,
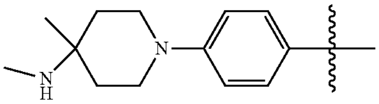,
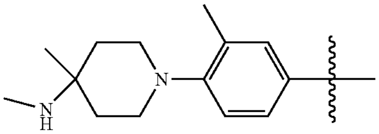,
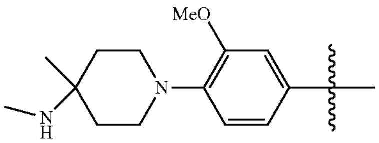,
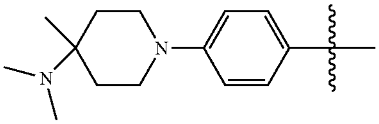,
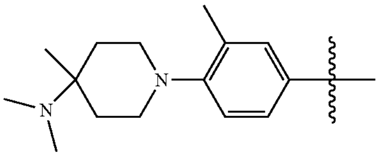,
-continued
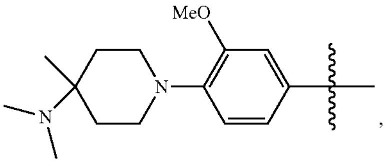,
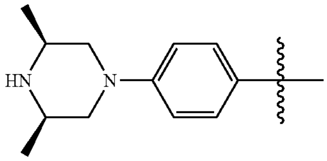,
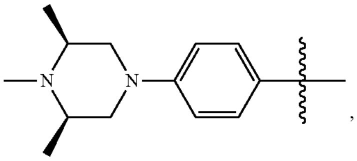,
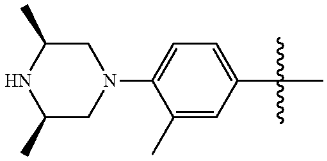,
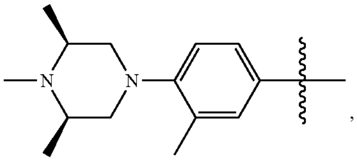,
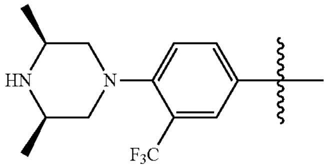,
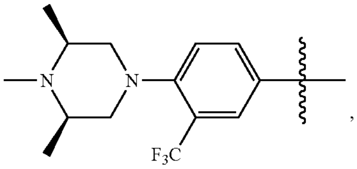,
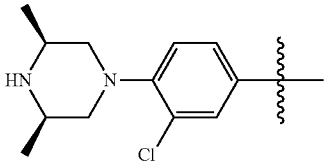,
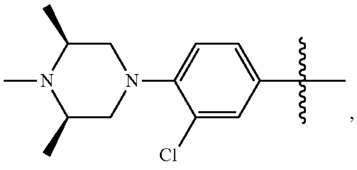,
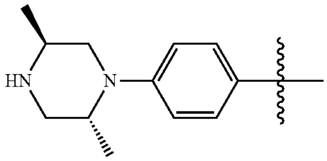, -continued
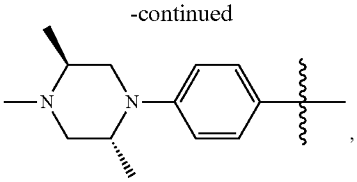
,
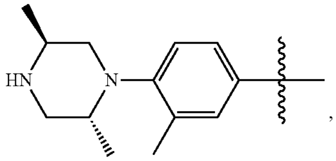
,
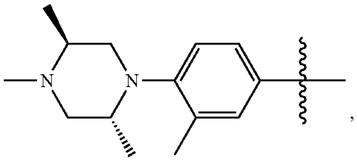
,
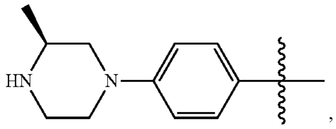
,
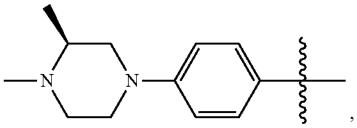
,
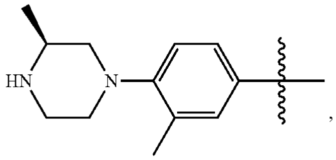
,
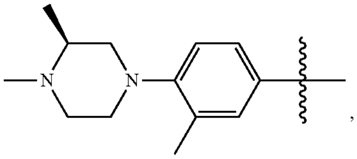
,
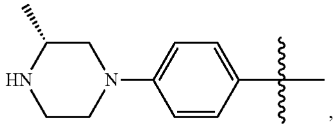
,
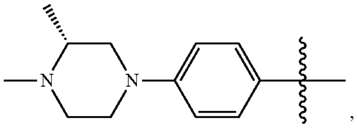
,
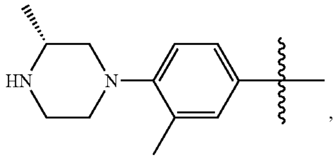
,
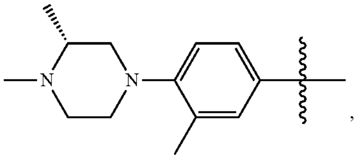
,
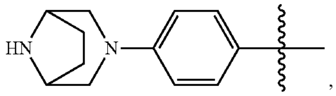
,
-continued
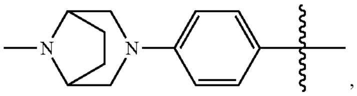
,
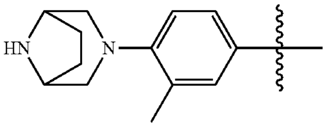
,
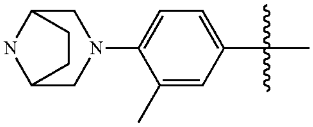
,
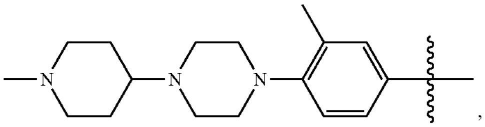
,
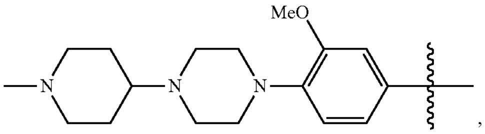
,
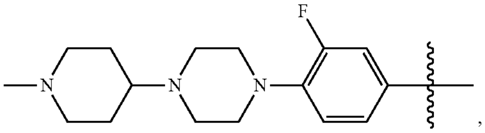
,
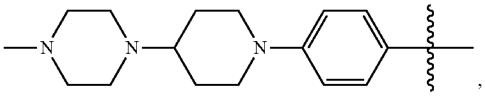
,
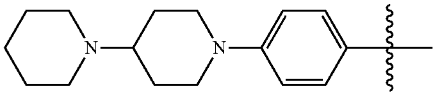
,
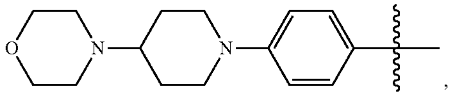
,
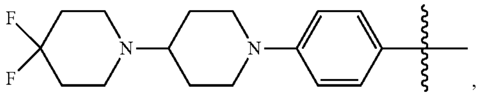
,
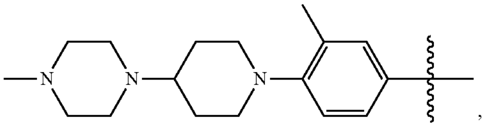
,
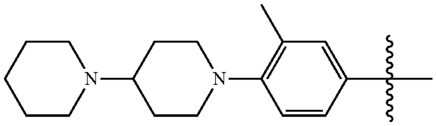
,
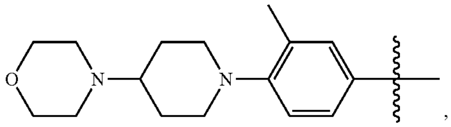
,
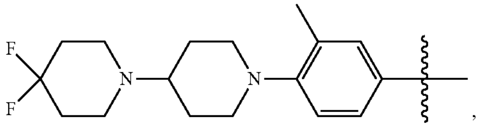
, -continued
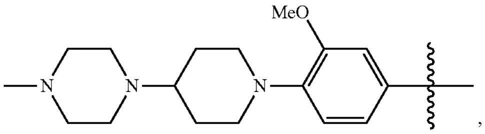
,
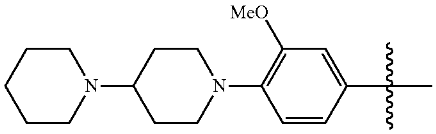
,
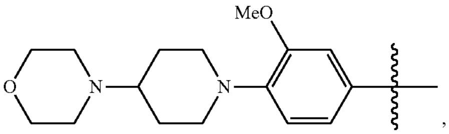
,
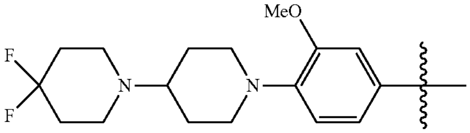
,
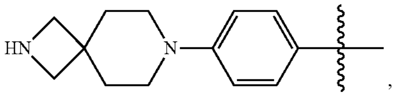
,
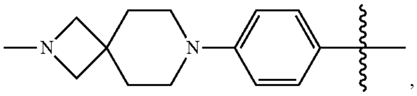
,
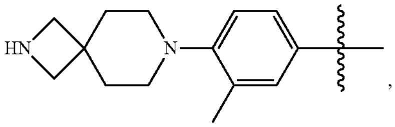
,
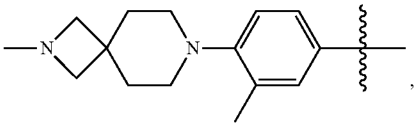
,
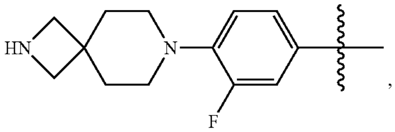
,
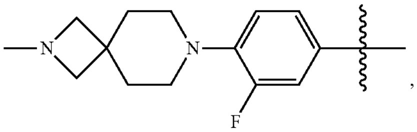
,
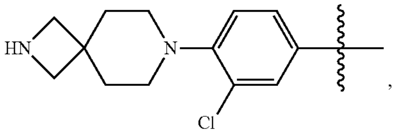
,
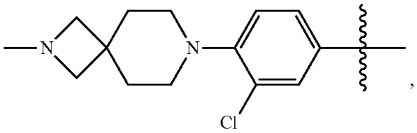
,
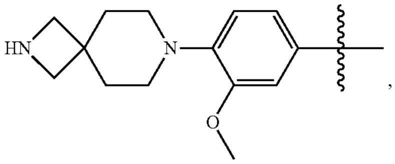
,
-continued
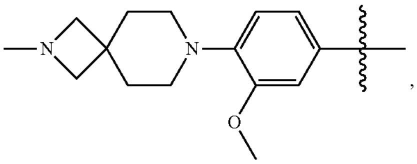
,
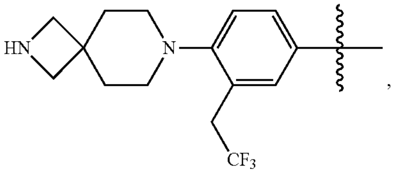
,
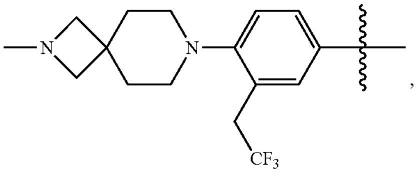
,
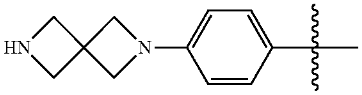
,
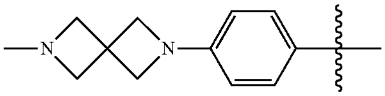
,
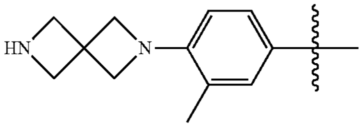
,
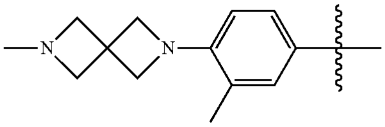
,
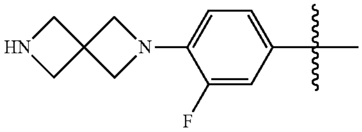
,
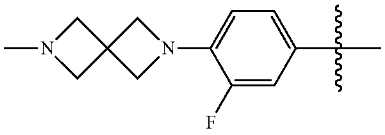
,
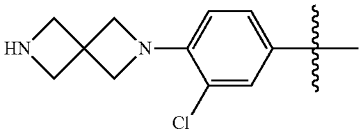
,
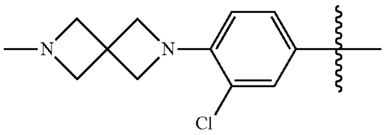
,
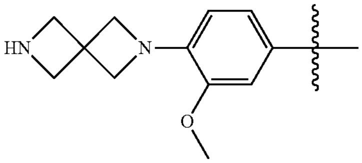
, -continued
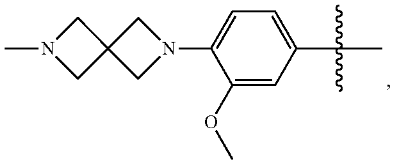,
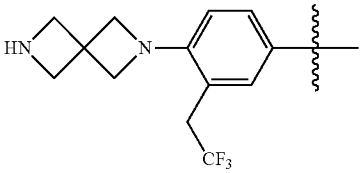,
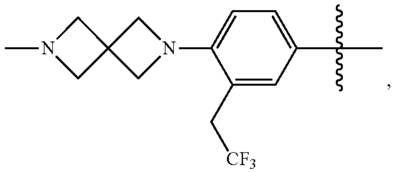,
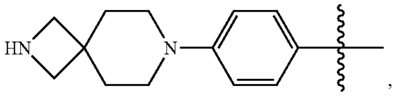,
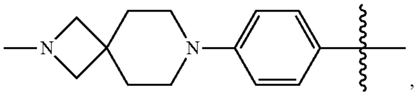,
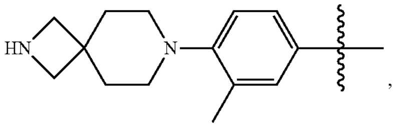,
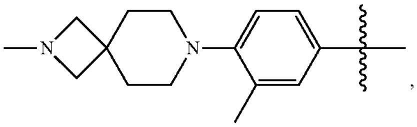,
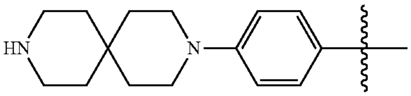,
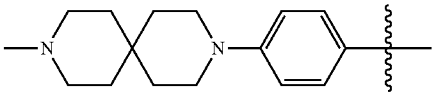,
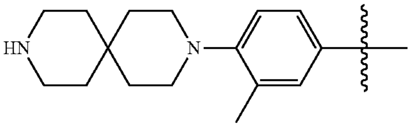,
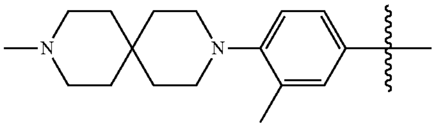,
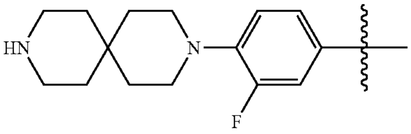,
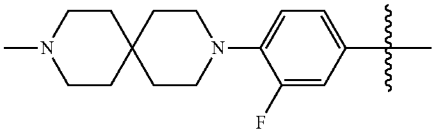,
-continued
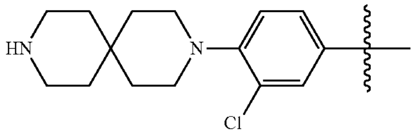,
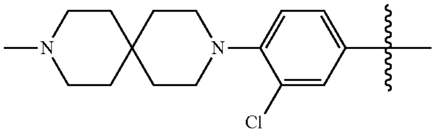,
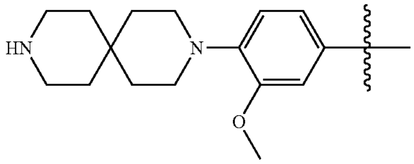,
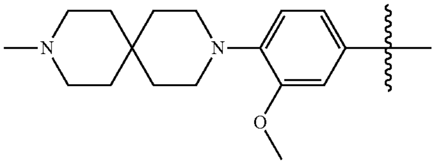,
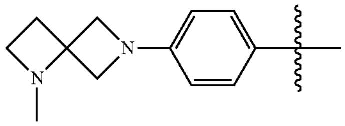,
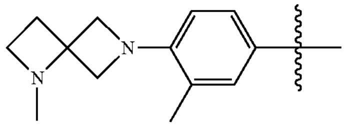,
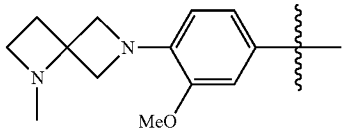,
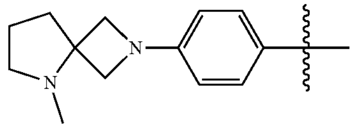,
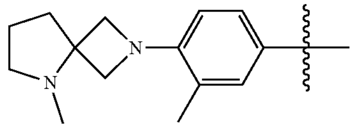,
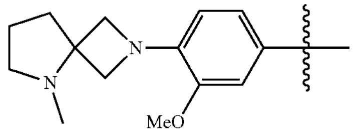,
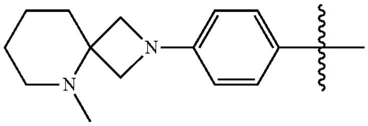,
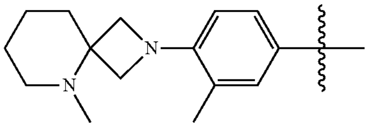, -continued
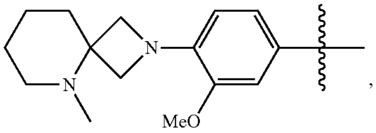,
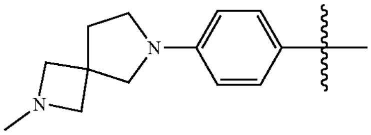,
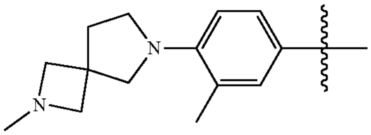,
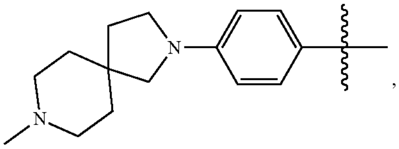,
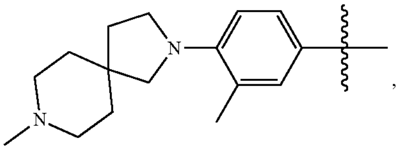,
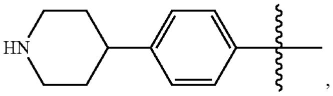,
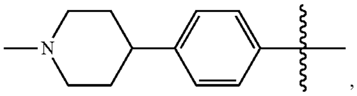,
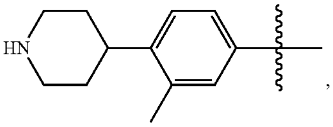,
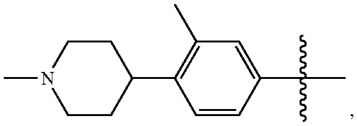,
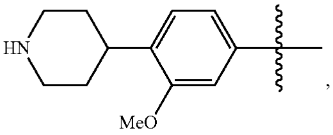,
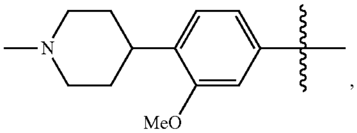,
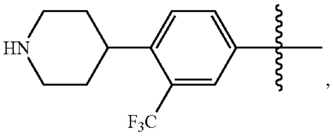,
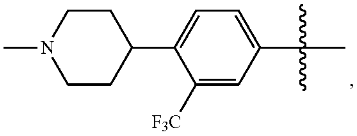,
-continued
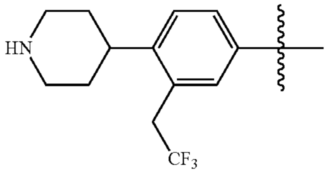,
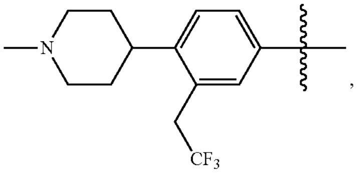,
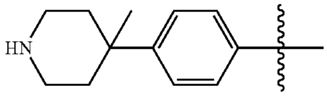,
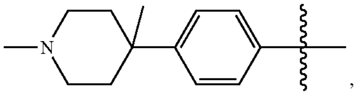,
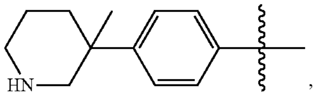,
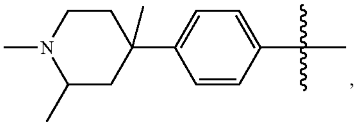,
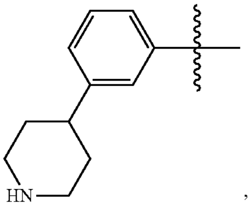, 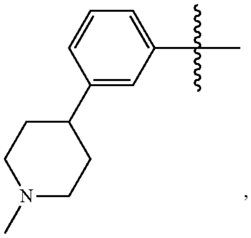,
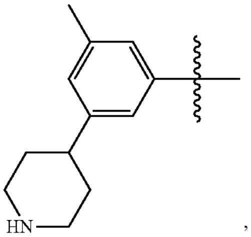, 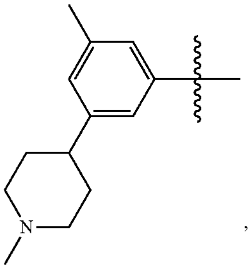,
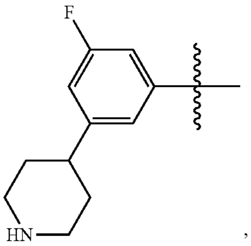, 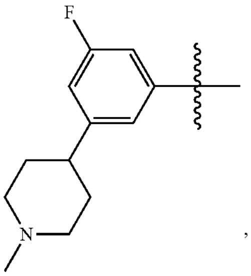, -continued
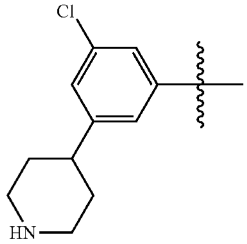,
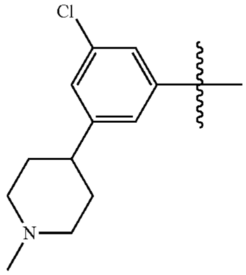,
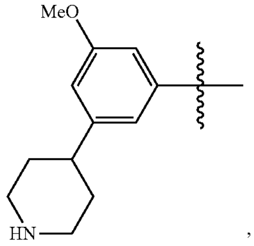,
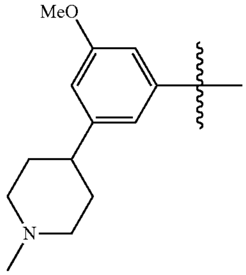,
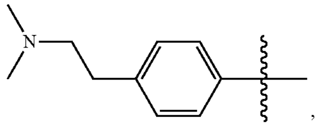,
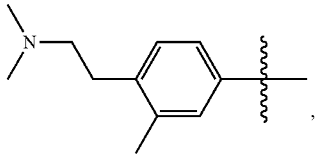,
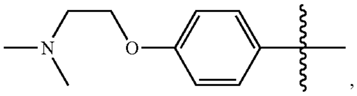,
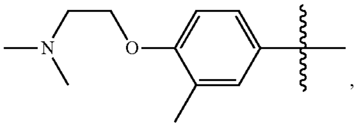,
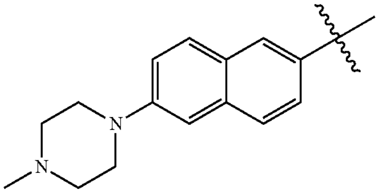,
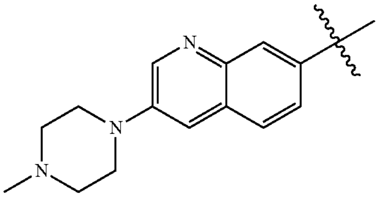,
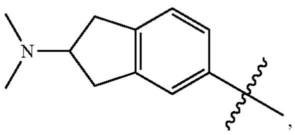,
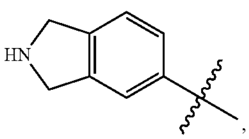,
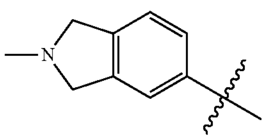,
-continued
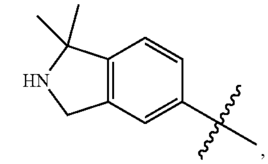,
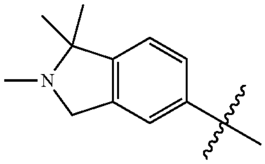,
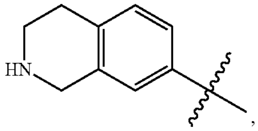,
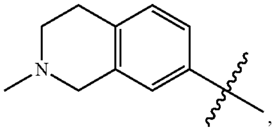,
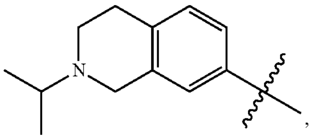,
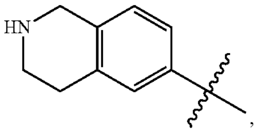,
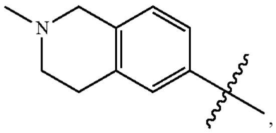,
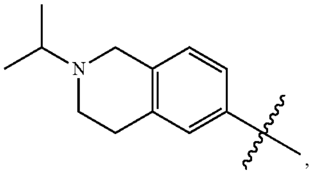,
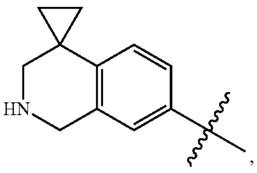,
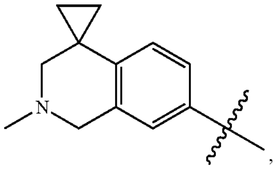,
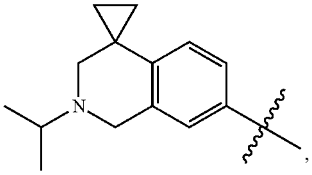,
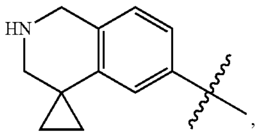,
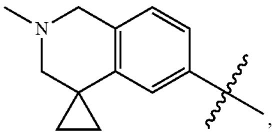,
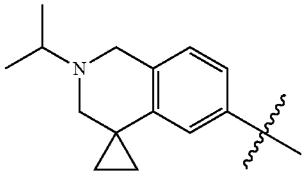,
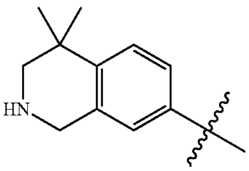,
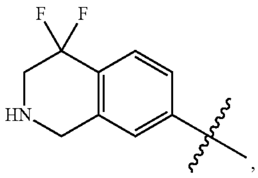,
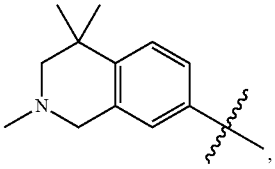, -continued
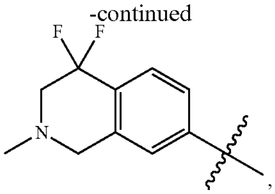,
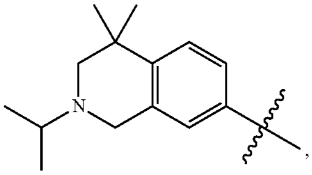,
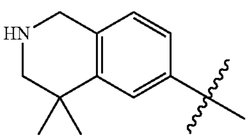, 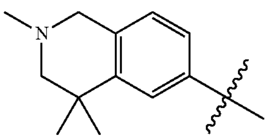,
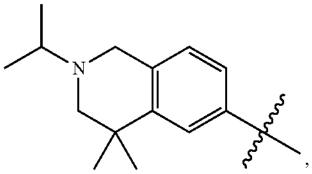,
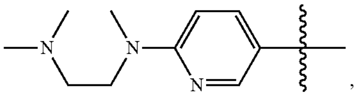,
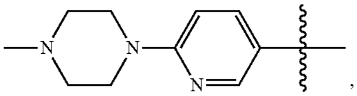,
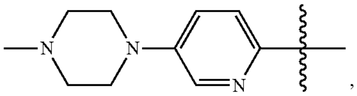,
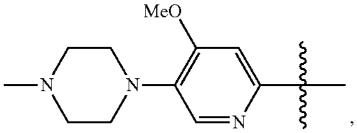,
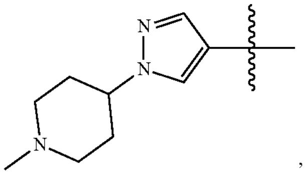,
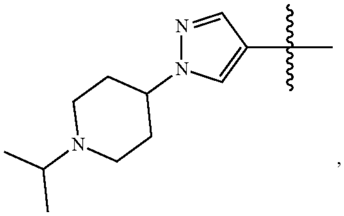,
-continued
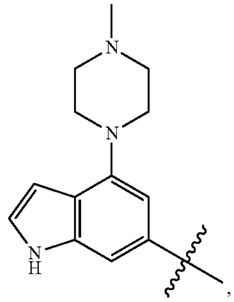, 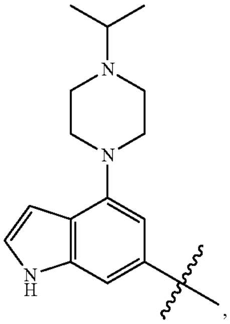,
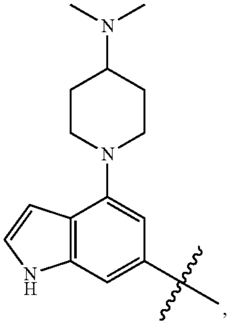, 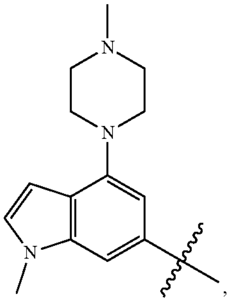,
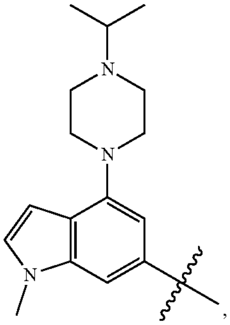, 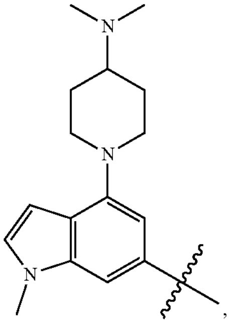,
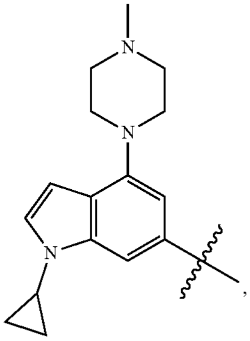, 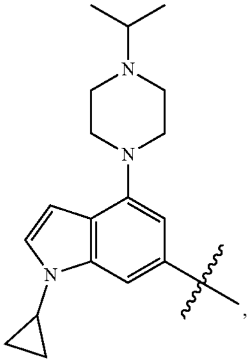,
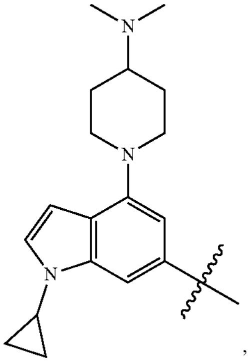, 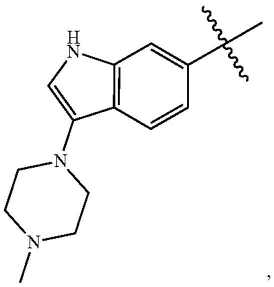, -continued
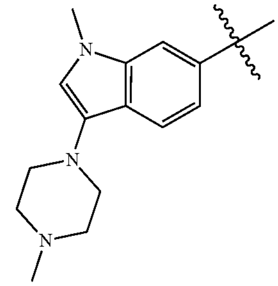
,
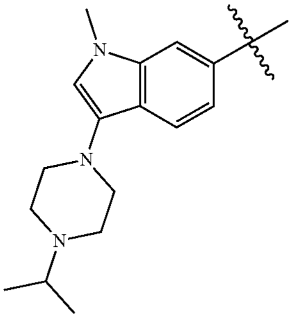
,
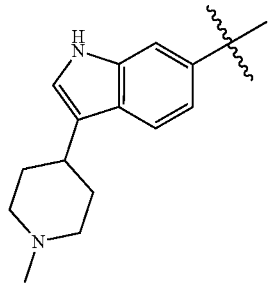
,
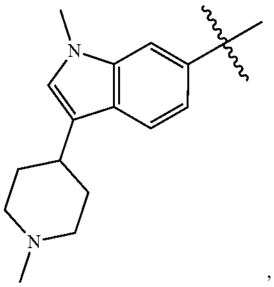
,
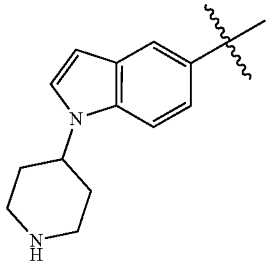
,
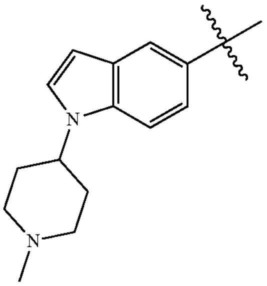
or
-continued
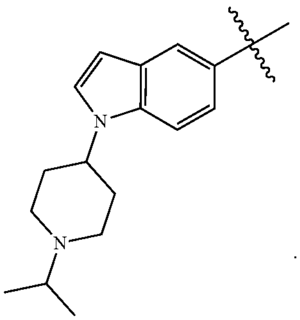 [SMILES: *c1ccc2c(ccn2C2CCN(C(C)C)CC2)c1]
.
In some embodiments of the present invention, the compound, isomers or pharmaceutically acceptable salts are selected from:
1
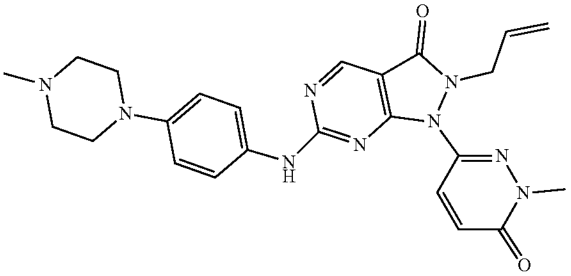
2
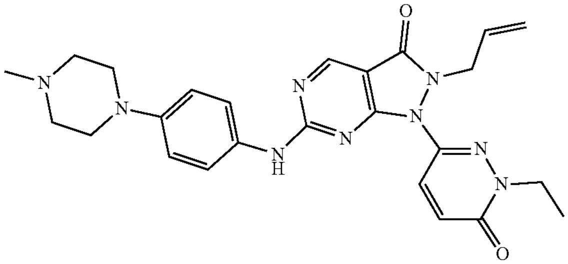
3
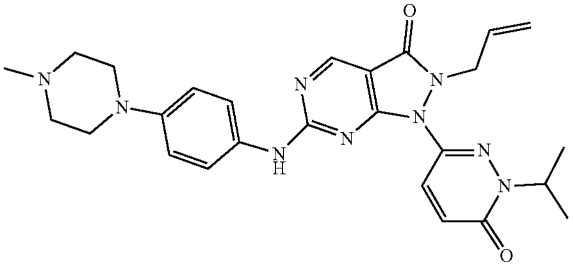
4
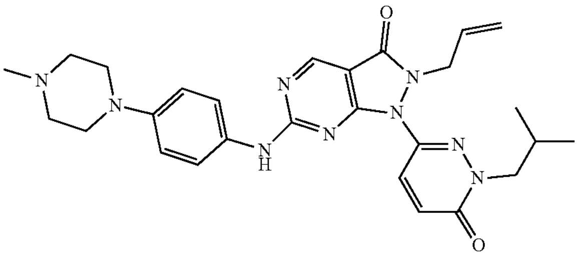

-continued
5
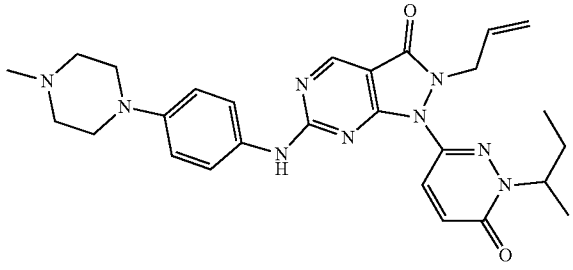
6
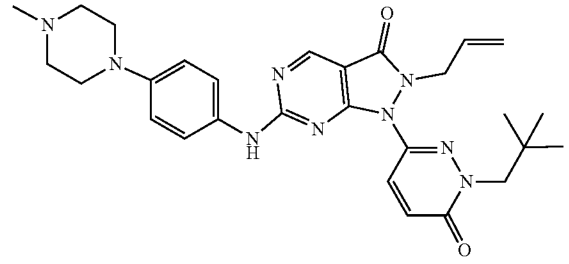
7
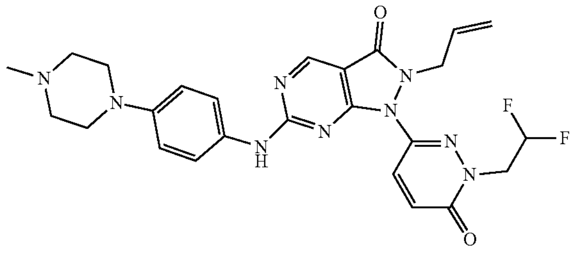
8
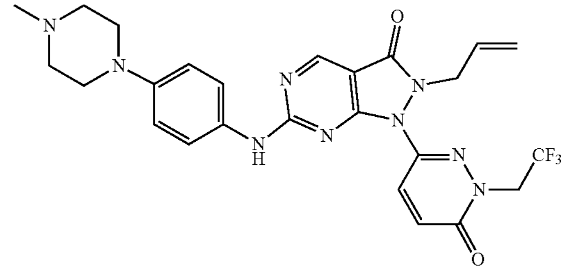
9
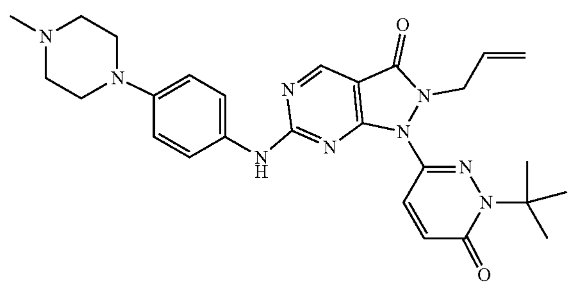
-continued
10
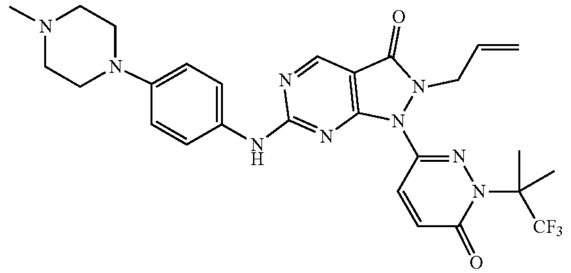
11
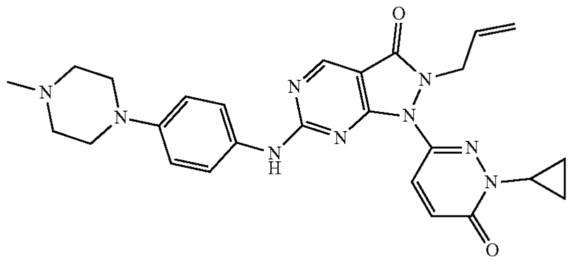
12
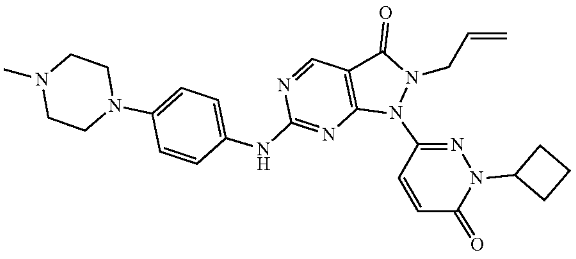
13
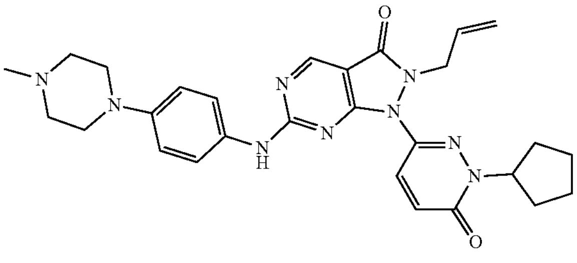
14
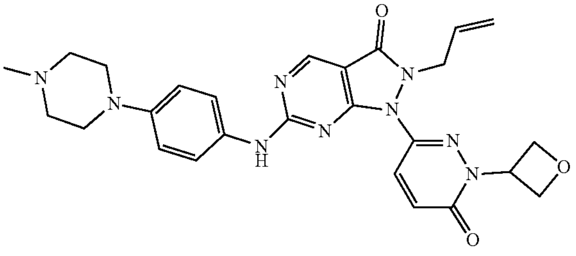

15
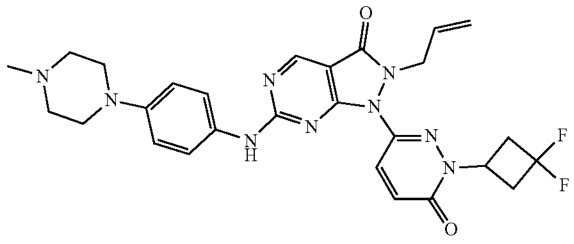
16
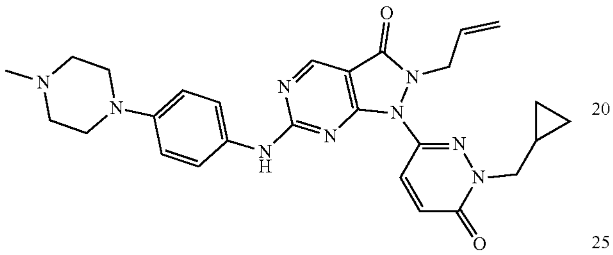
17
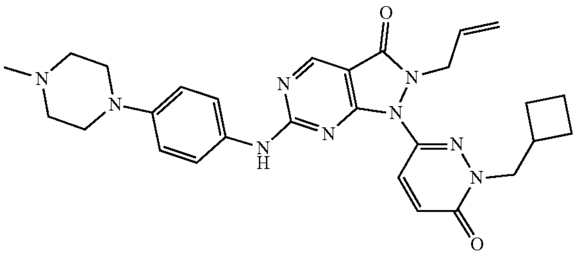
18
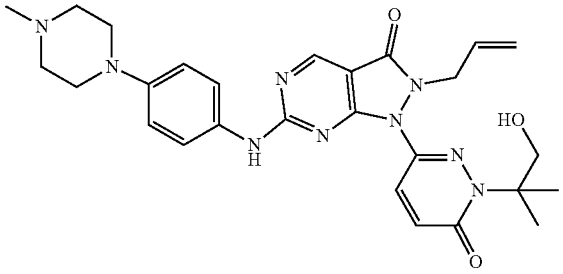
19
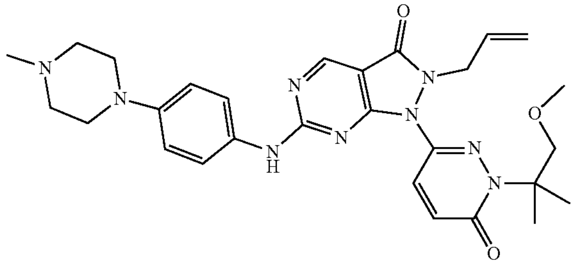
20
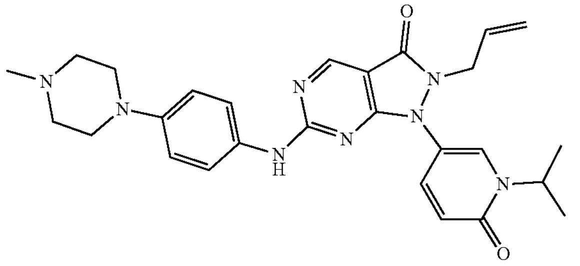
21
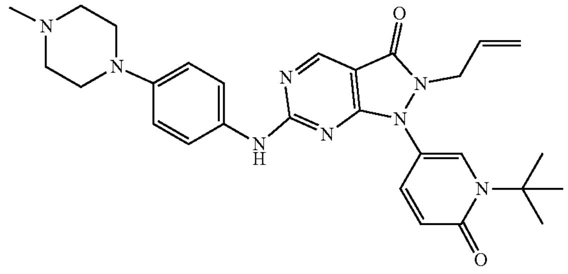
22
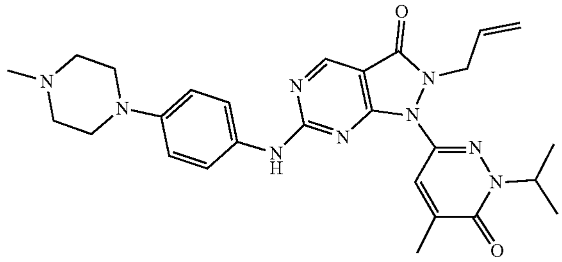
23
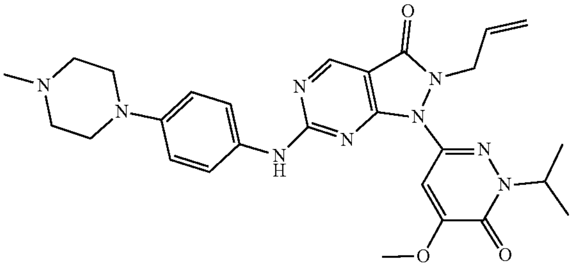
24
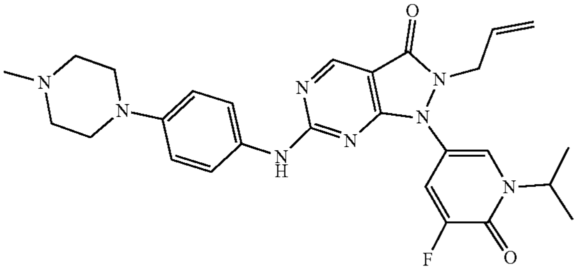

-continued
25
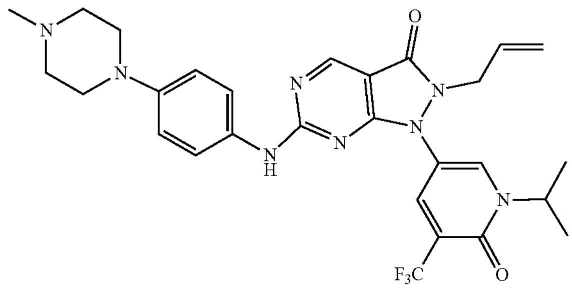
26
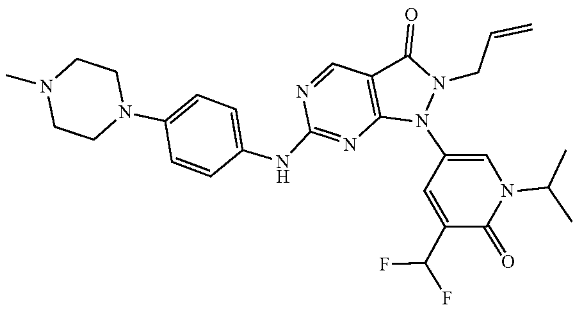
27
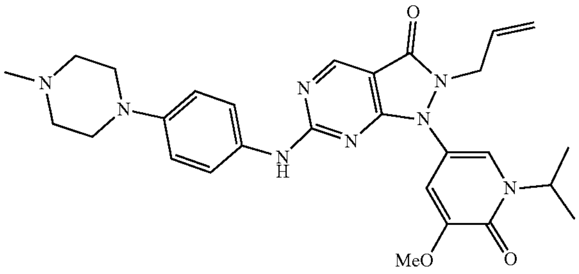
28
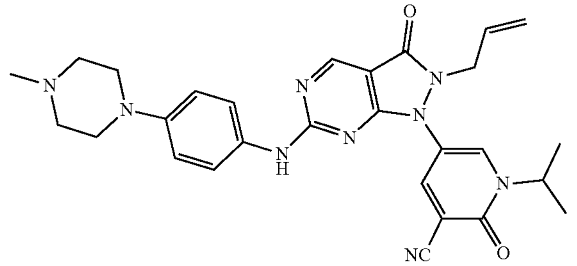
29
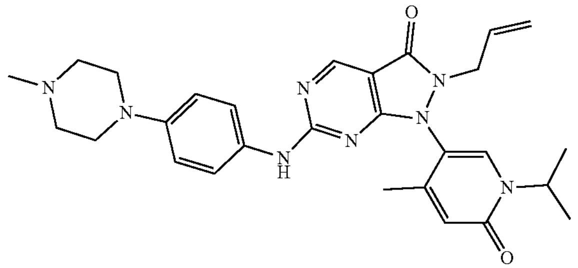
-continued
30
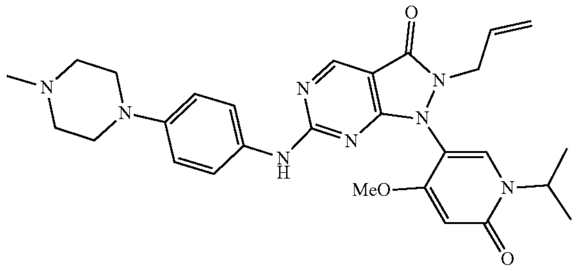
31
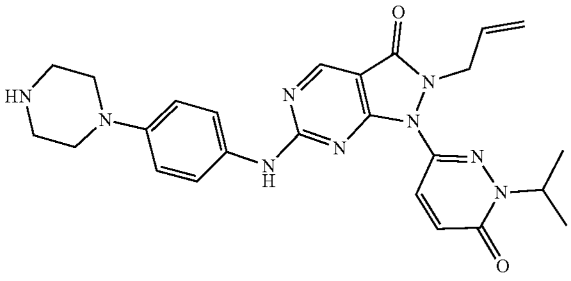
32
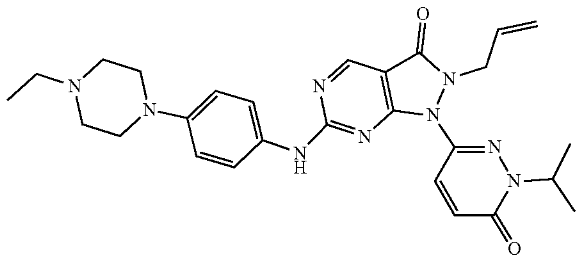
33
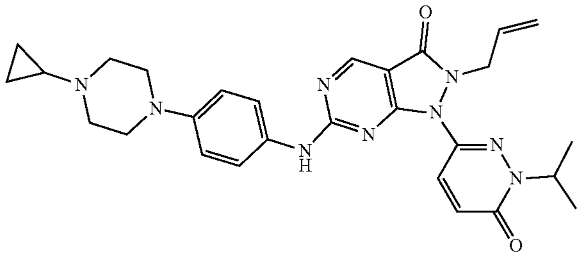
34
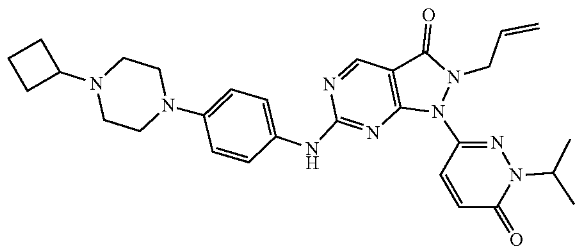

-continued
35
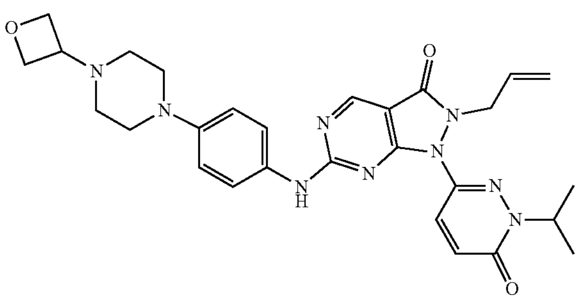
36
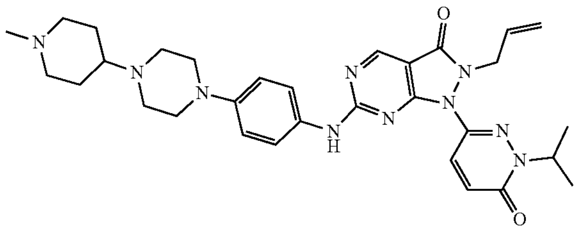
37
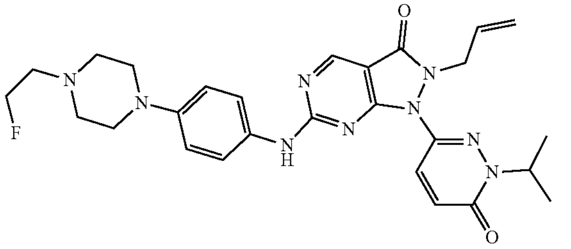
38
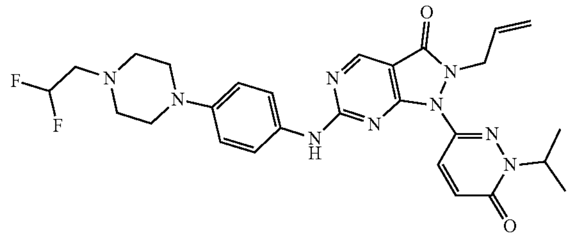
39
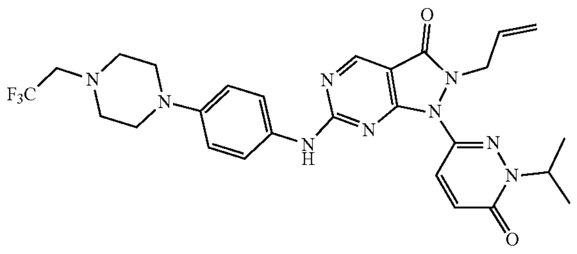
-continued
40
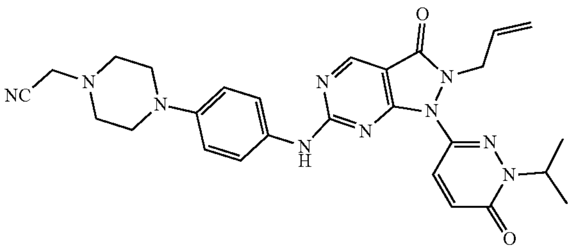
41
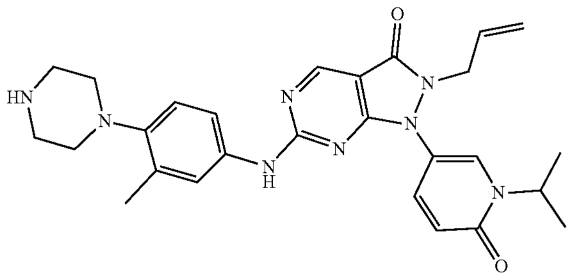
42
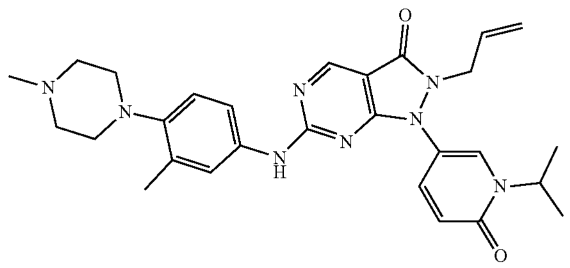
43
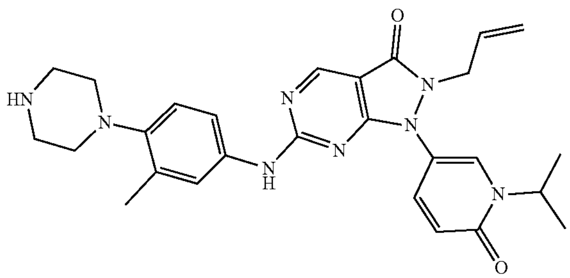
44
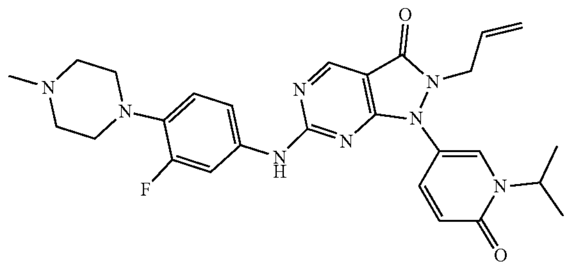

-continued
45
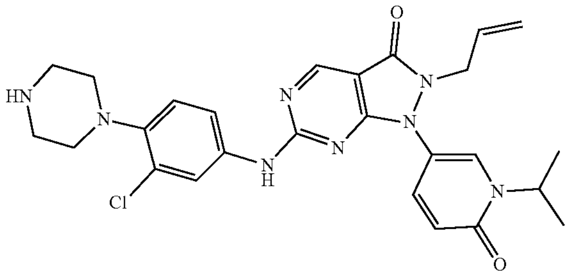
46
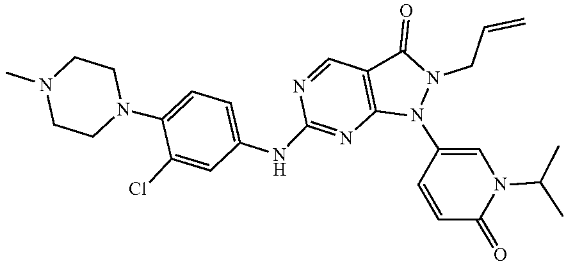
47
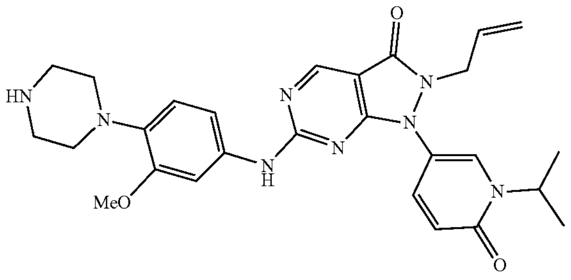
48
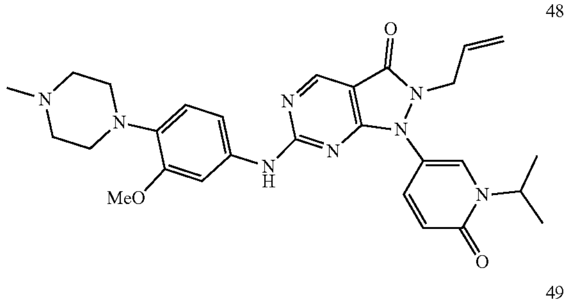
49
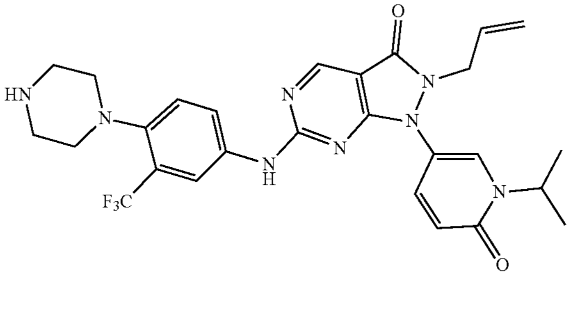
-continued
50
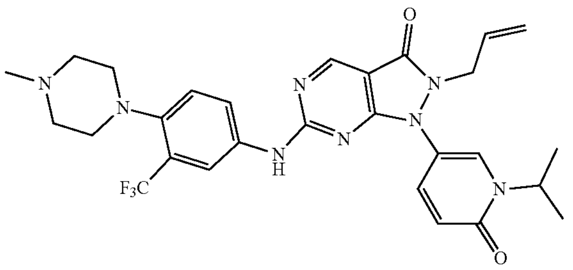
51
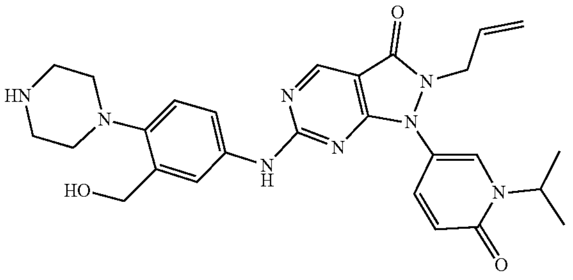
52
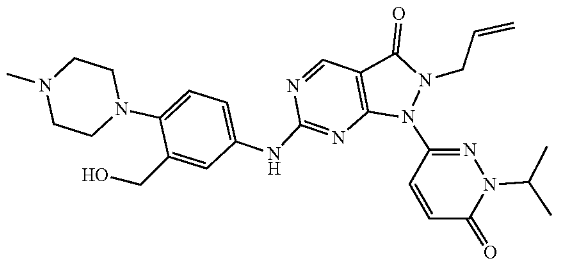
53
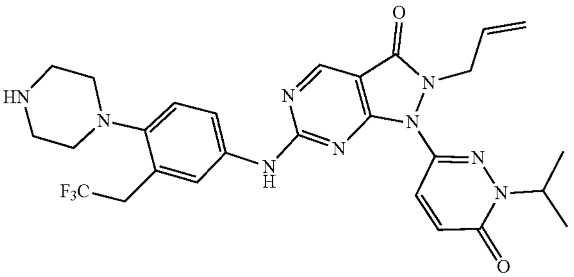
54
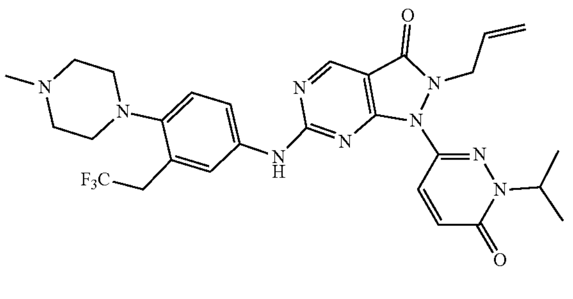

-continued
55
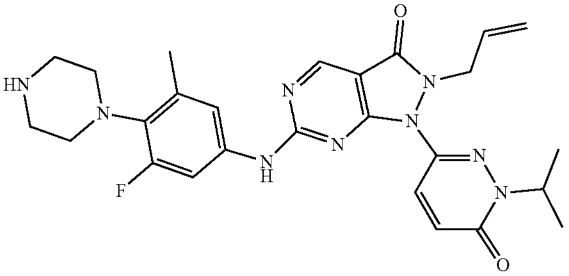
56
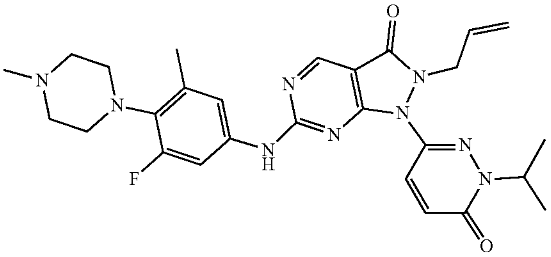
57
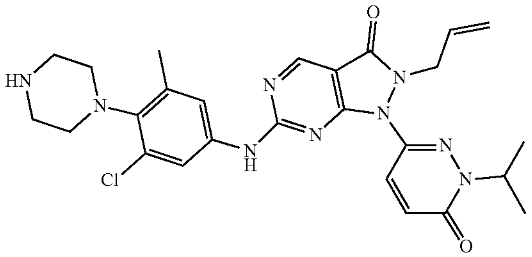
58
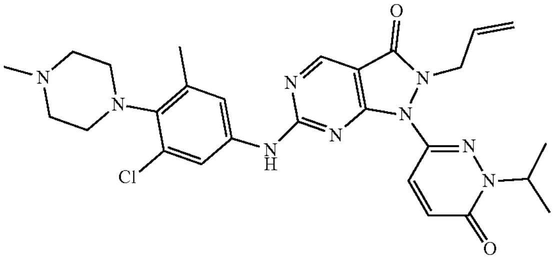
59
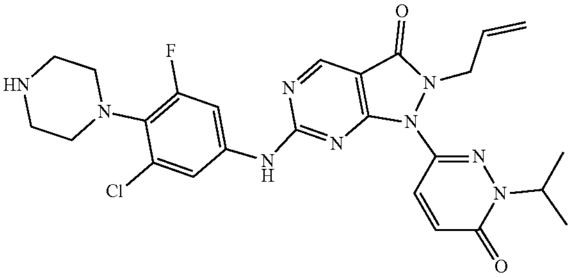
-continued
60
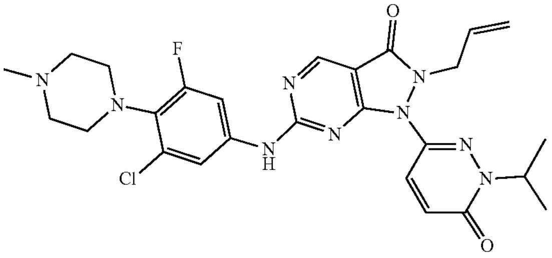
61
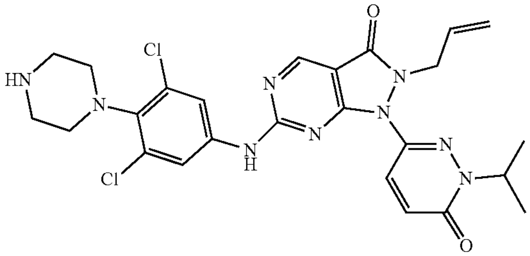
62
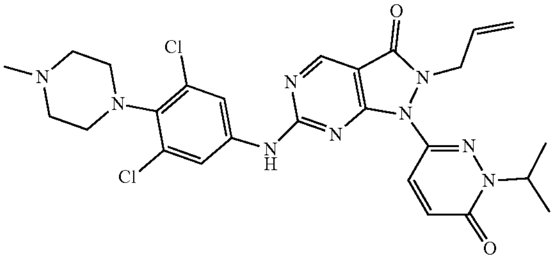
63
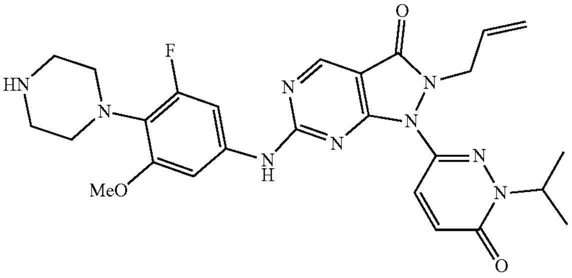
64
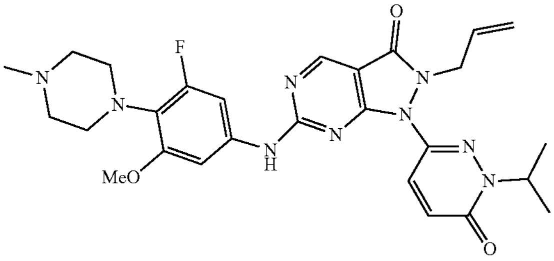

-continued
65
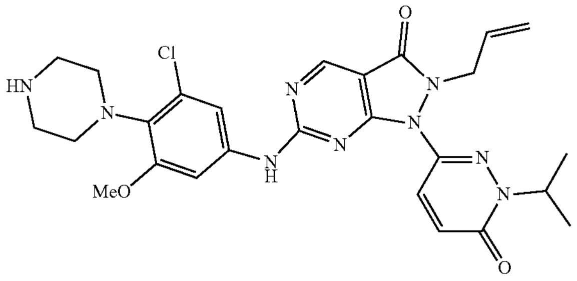
66
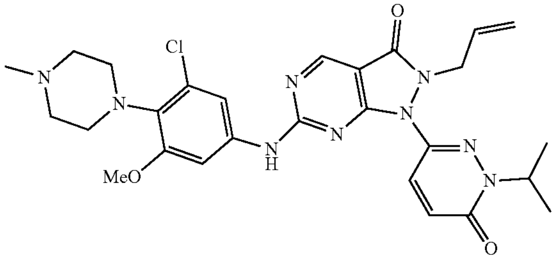
67
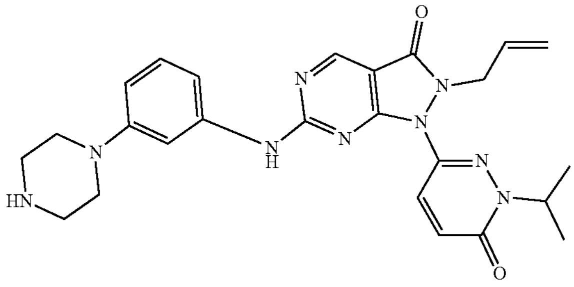
68
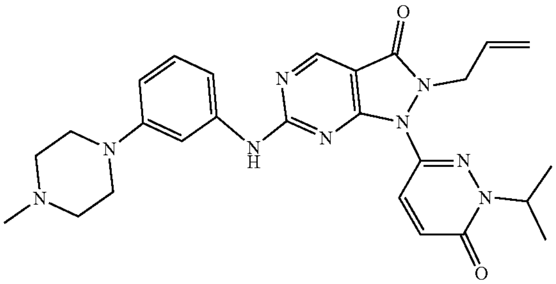
69
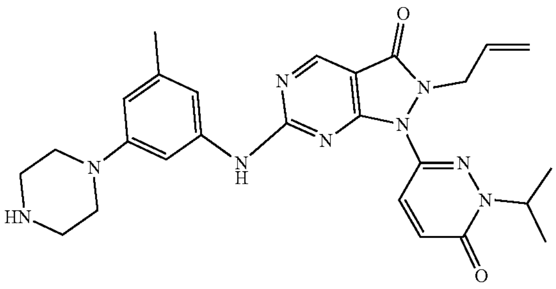
-continued
70
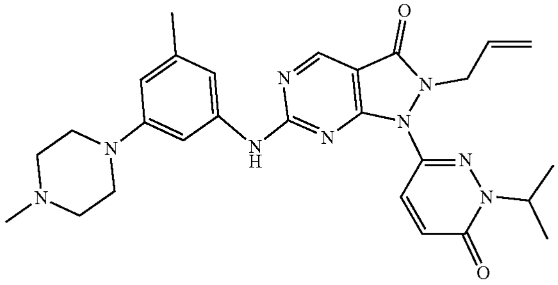
71
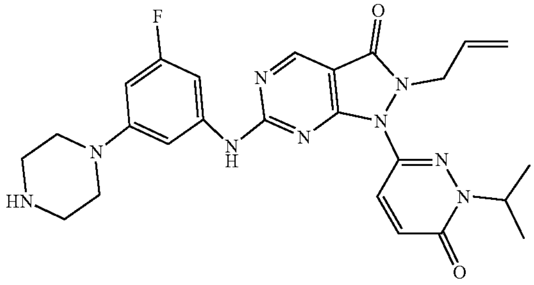
72
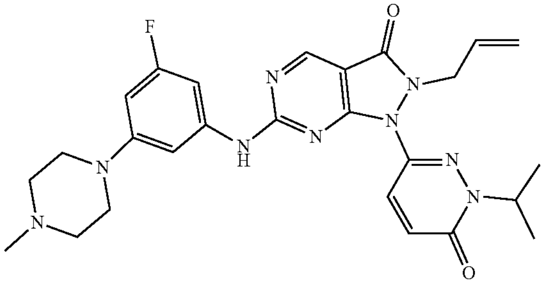
73
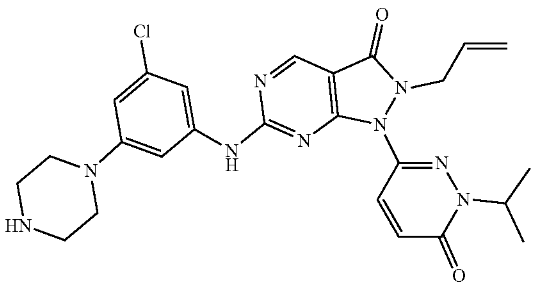
74
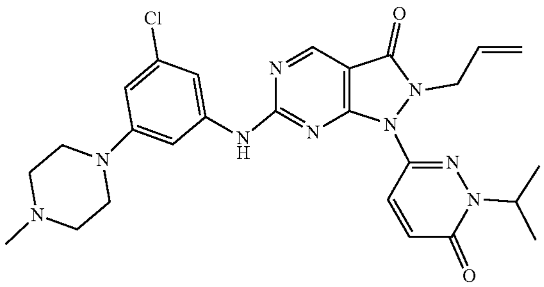

-continued
75
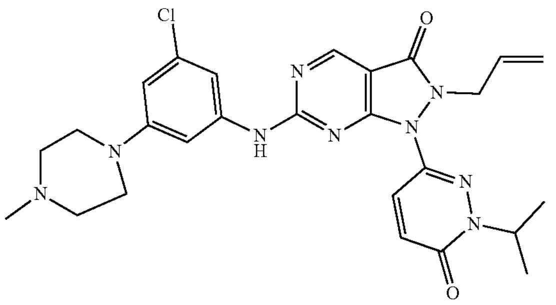
76
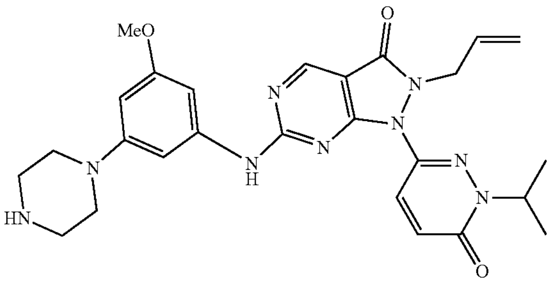
77
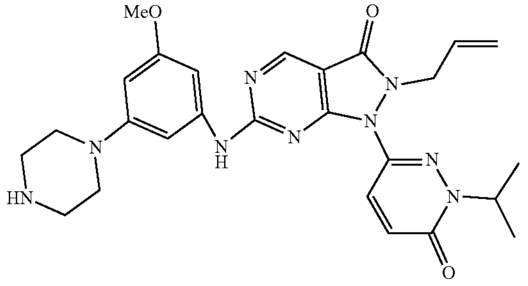
78
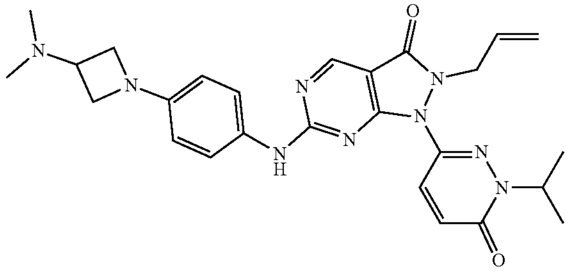
79
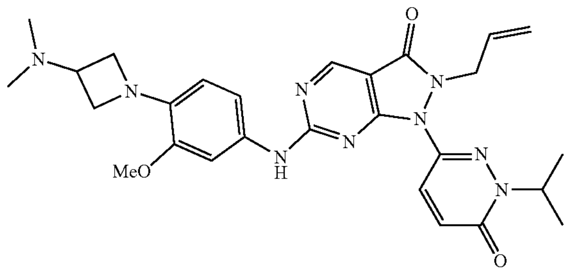
-continued
80
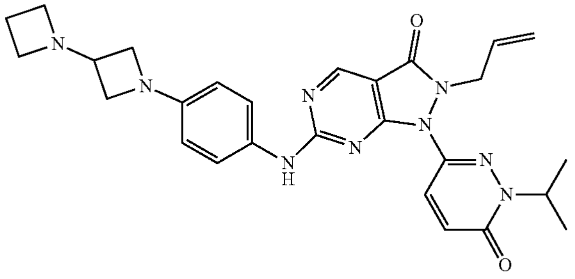
81
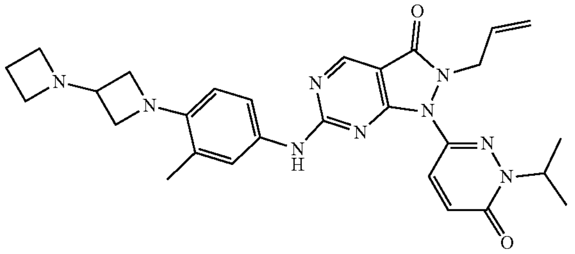
82
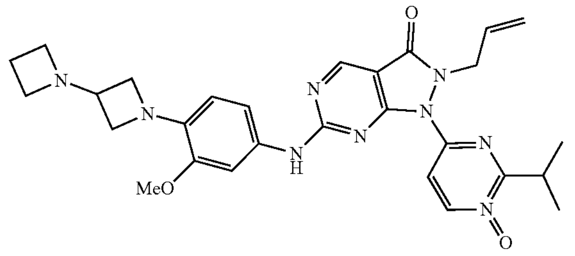
83
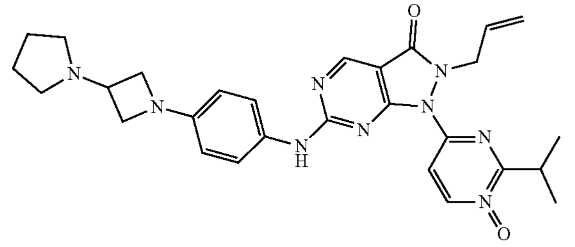
84
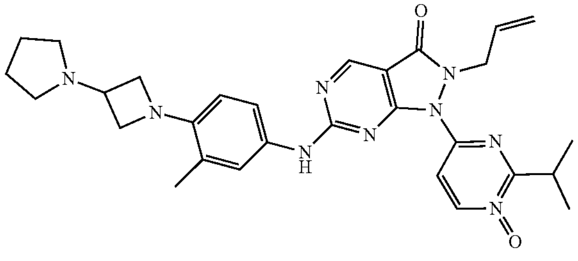

-continued
85
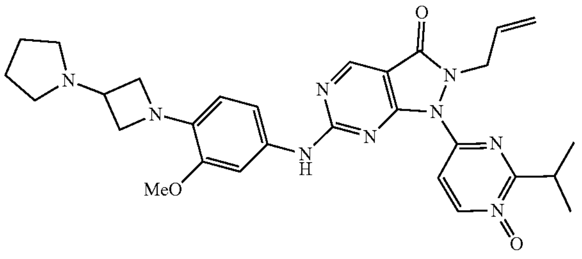
86
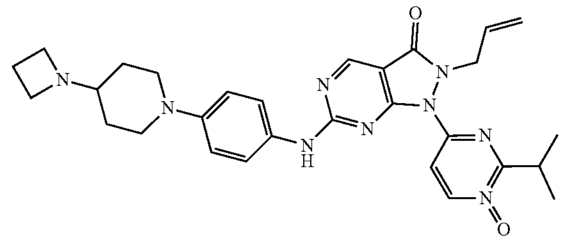
87
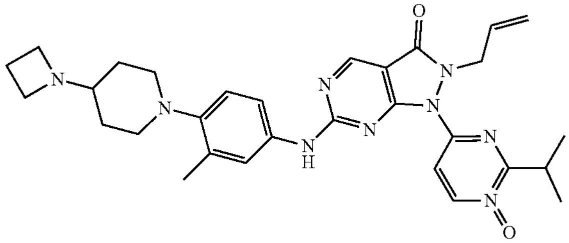
88
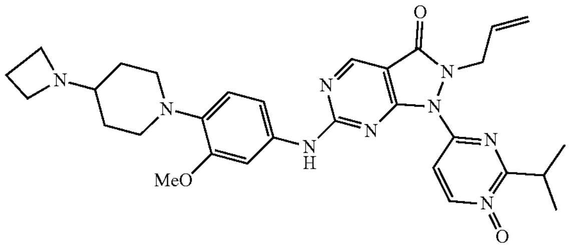
89
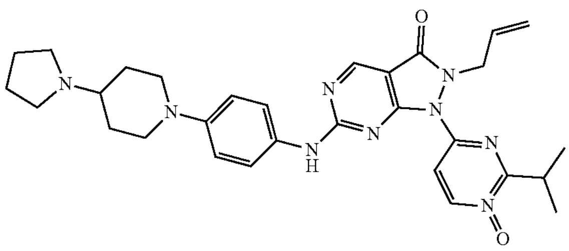
90
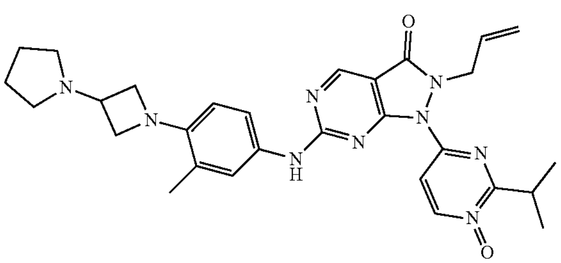
-continued
91
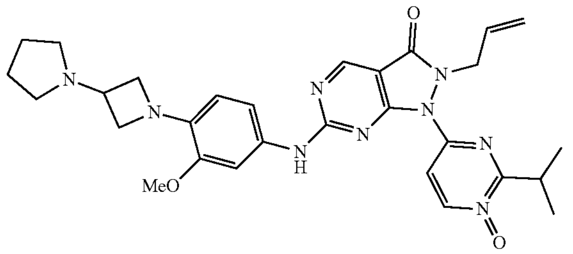
92
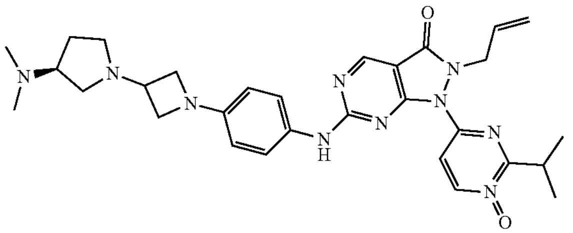
93
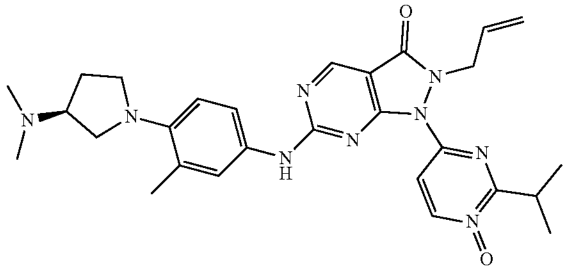
94
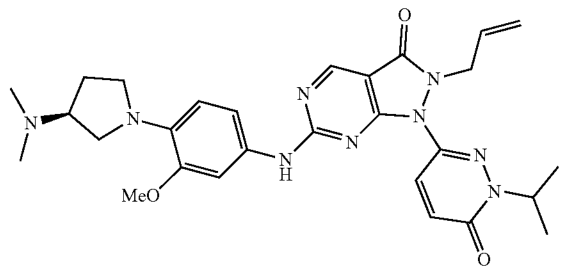
95
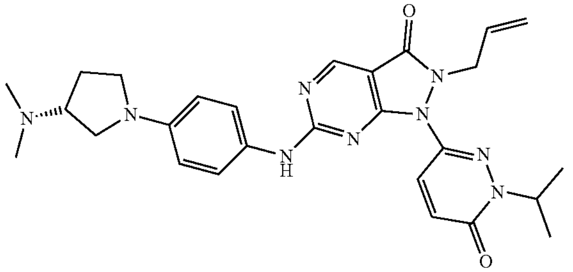

-continued
96
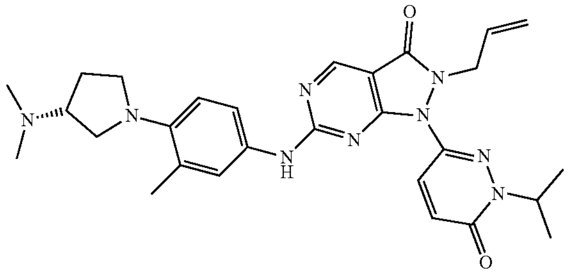
97
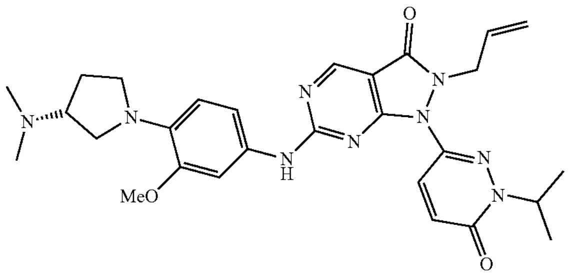
98
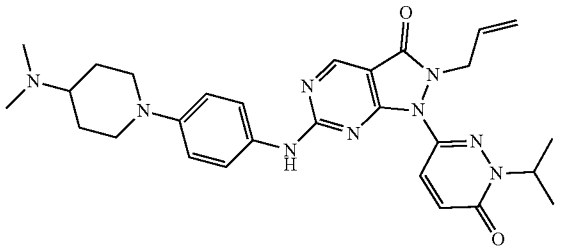
99
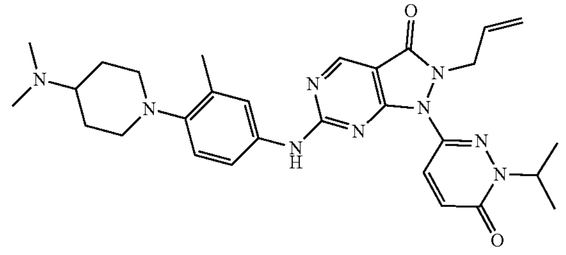
100
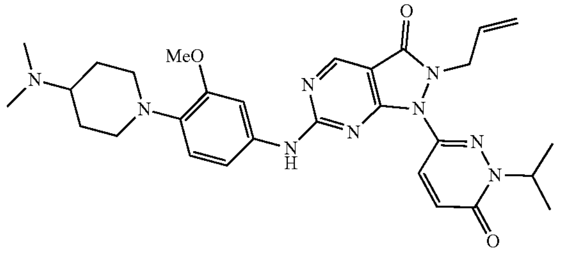
-continued
101
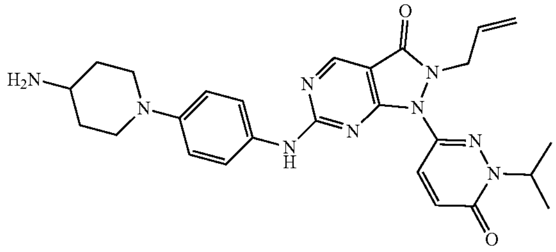
102
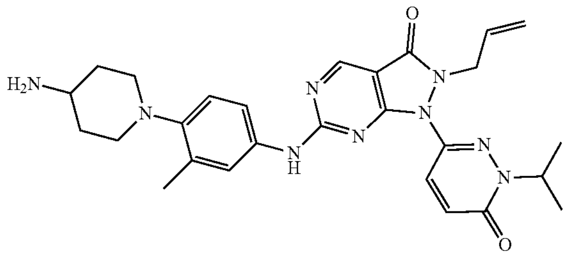
103
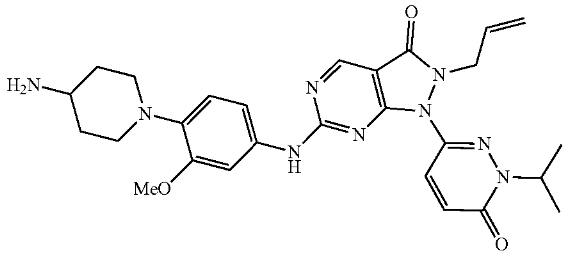
104
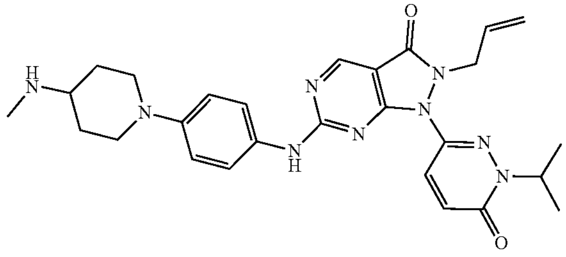
105
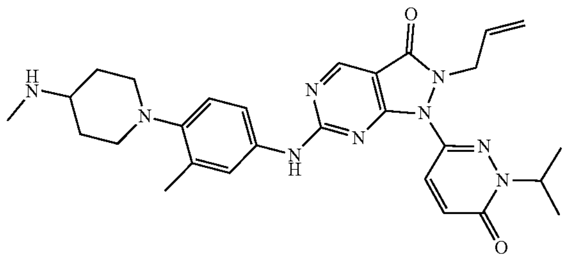

106
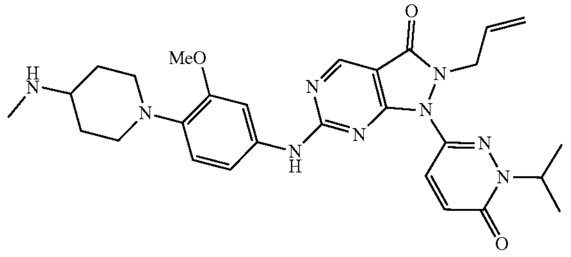
107
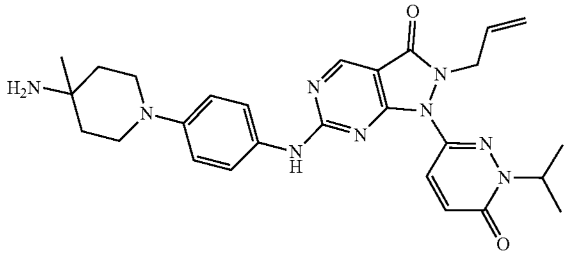
108
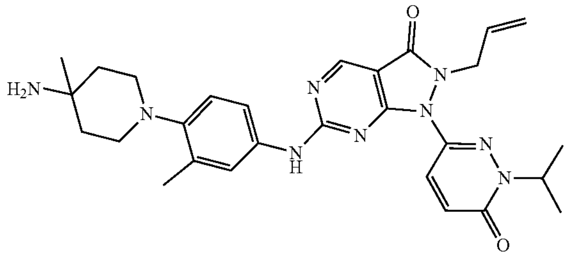
109
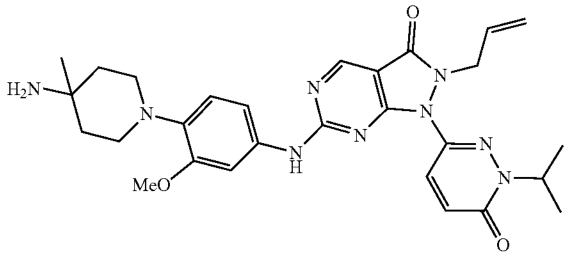
110
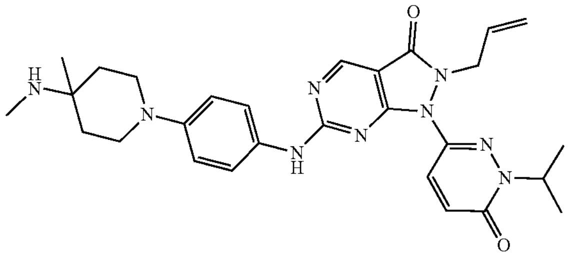
111
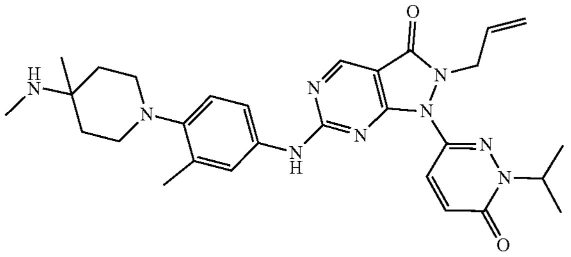
112
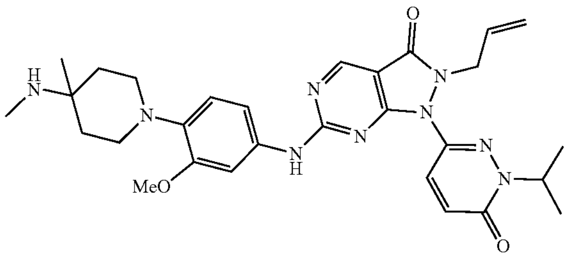
113
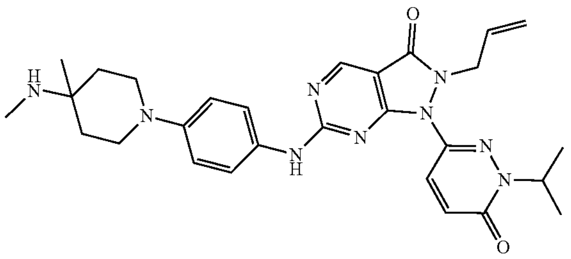
114
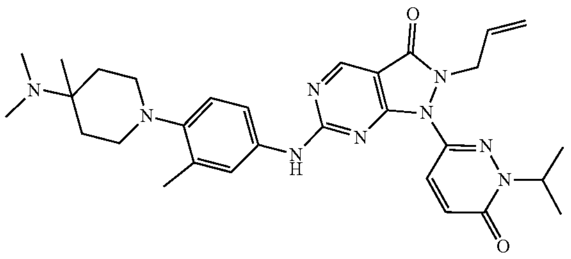
115
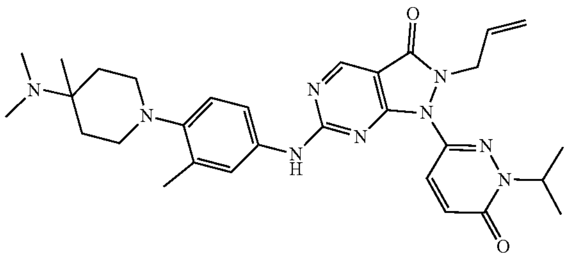

-continued
116
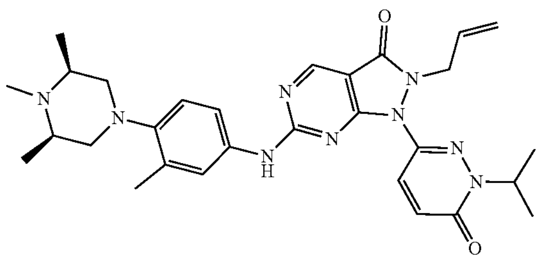
117
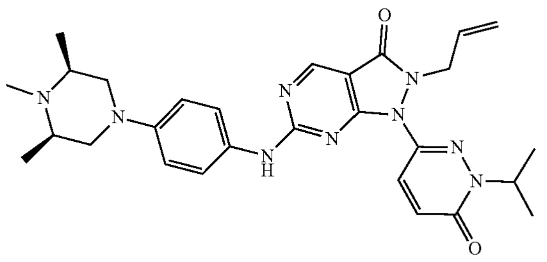
118
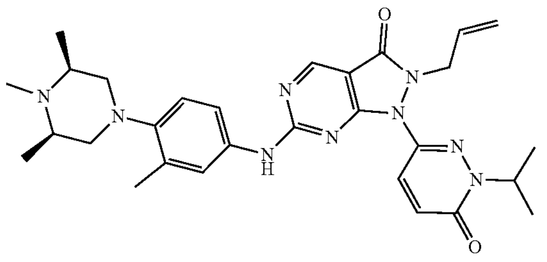
119
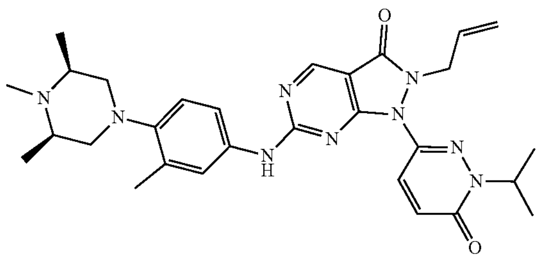
120
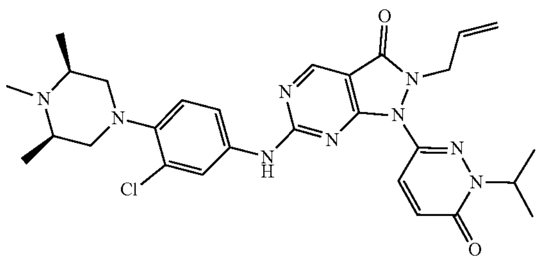
-continued
121
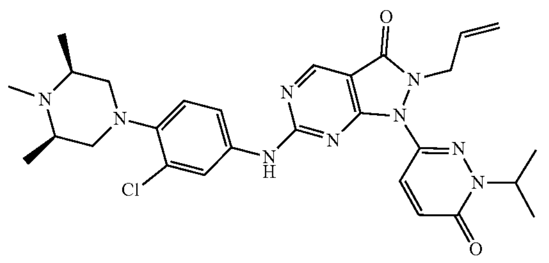
122
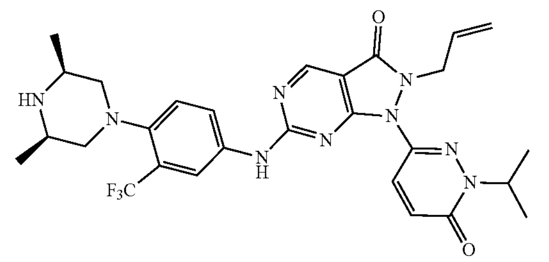
123
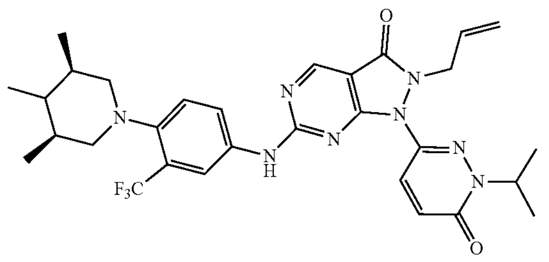
124
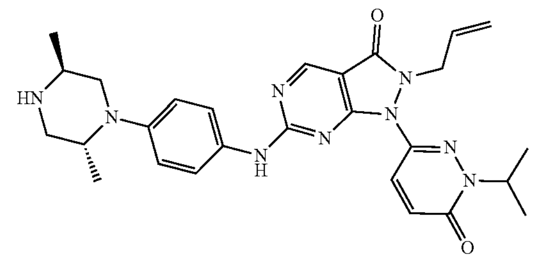
125
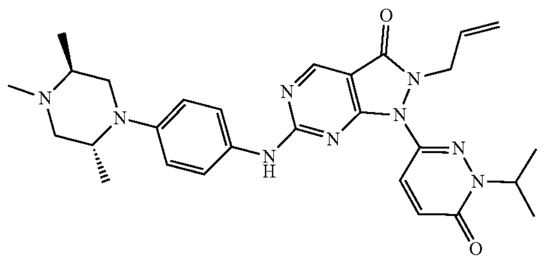

-continued
126
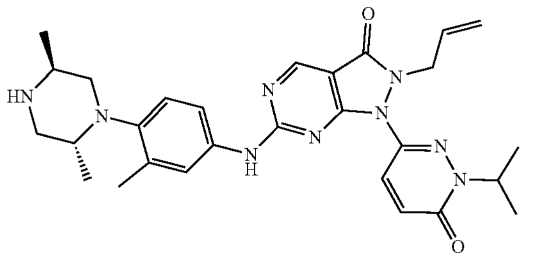
127
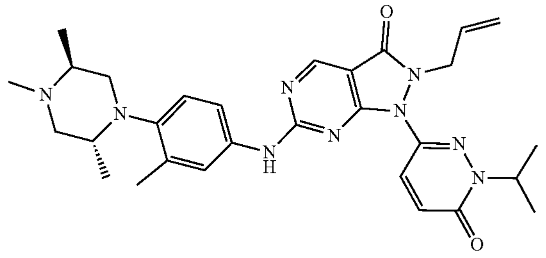
128
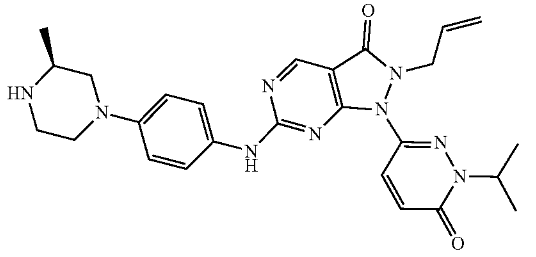
129
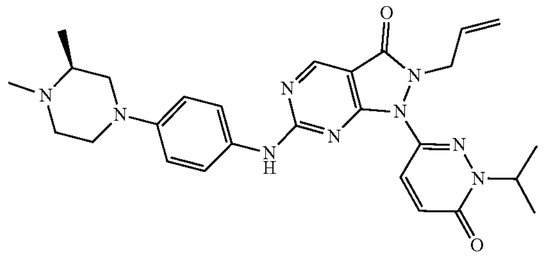
130
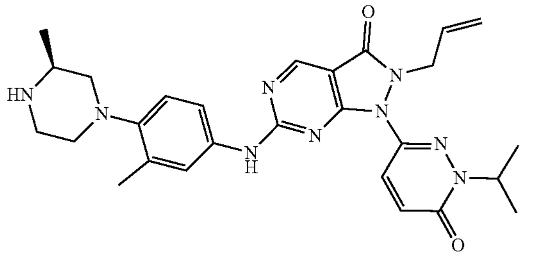
-continued
131
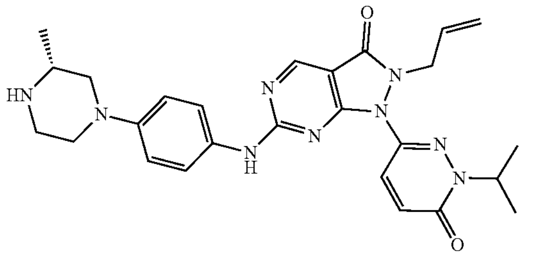
132
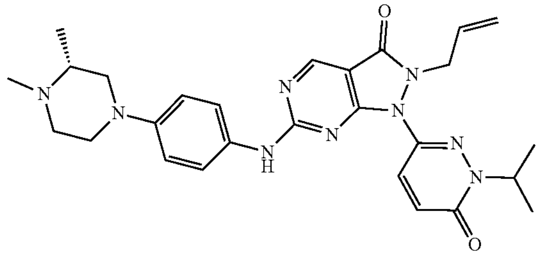
133
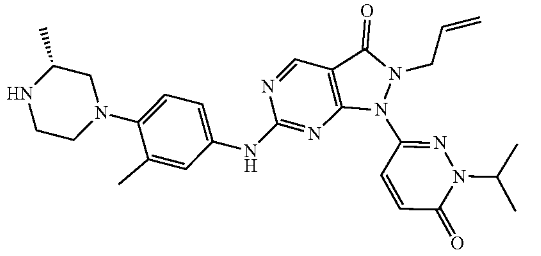
134
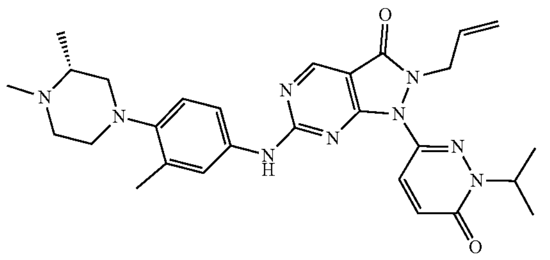
135
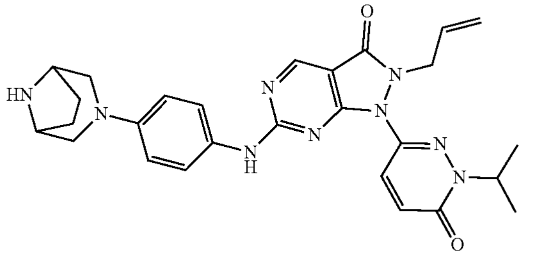

-continued
136
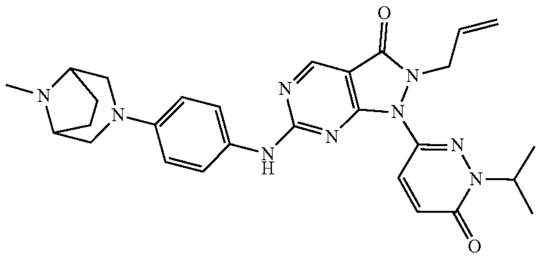
137
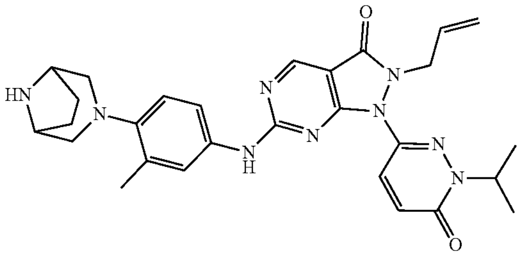
138
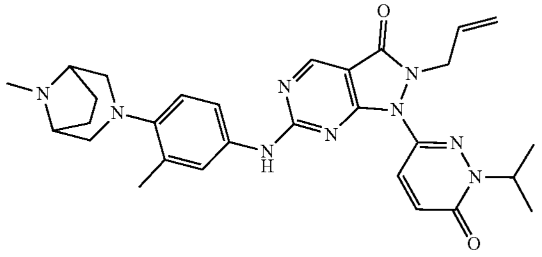
139
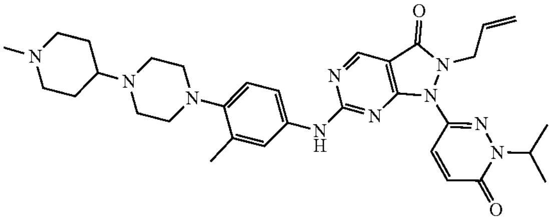
140
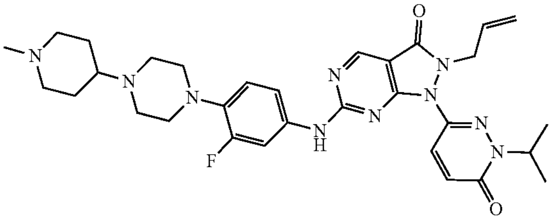
141
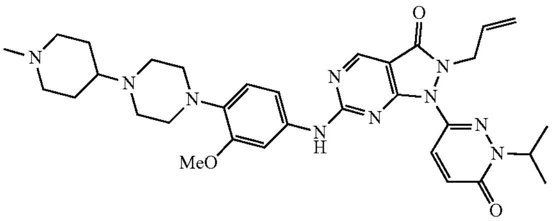
-continued
142
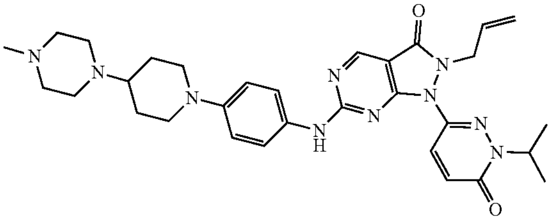
143
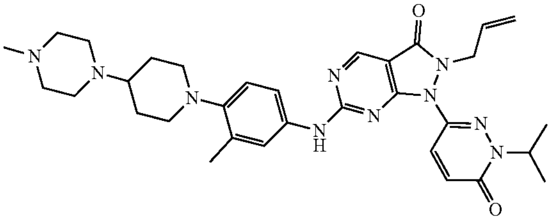
144
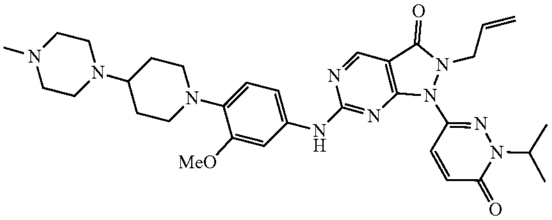
145
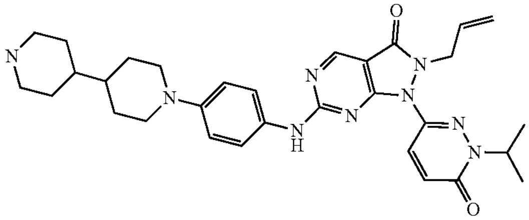
146
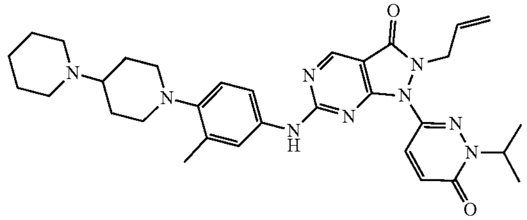
147
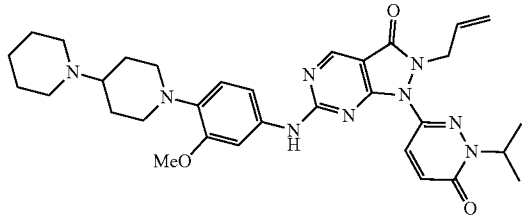

-continued
148
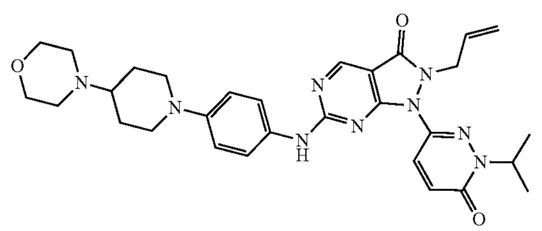
149
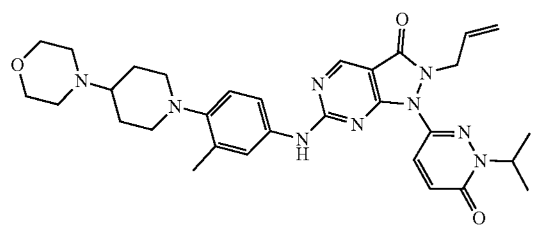
150
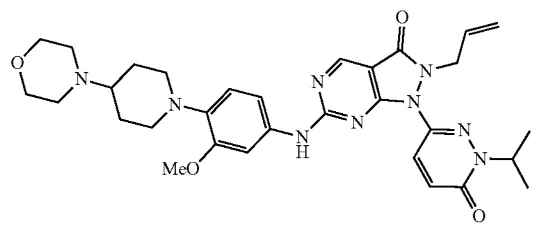
151
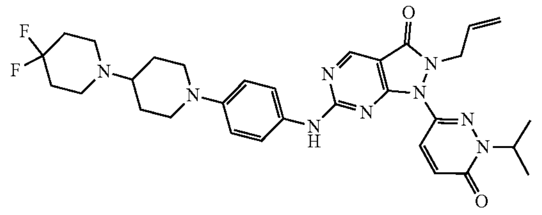
152
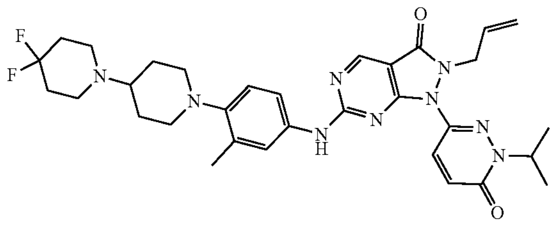
153
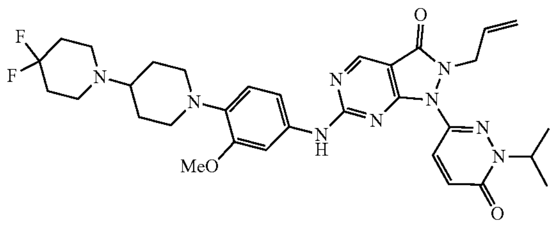
-continued
154
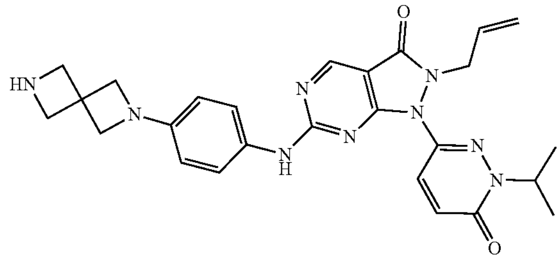
155
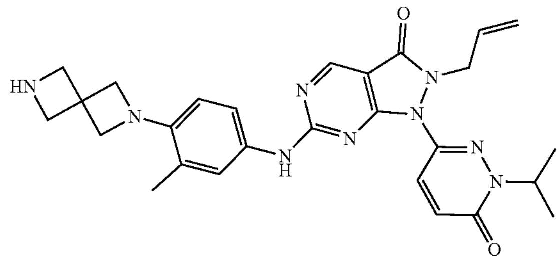
156
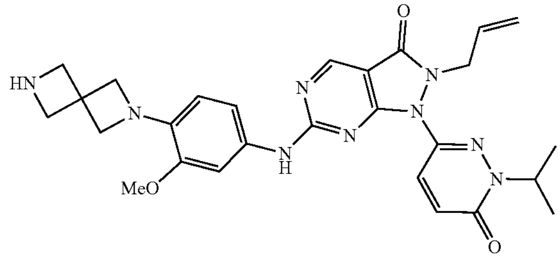
157
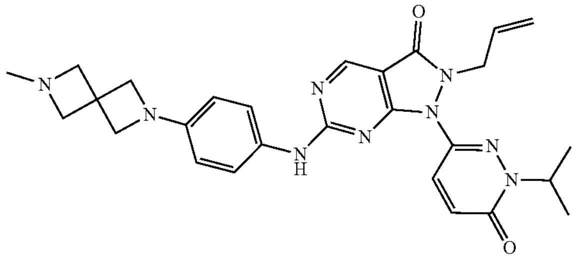
158
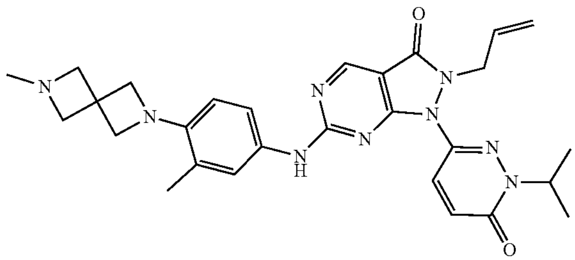

159
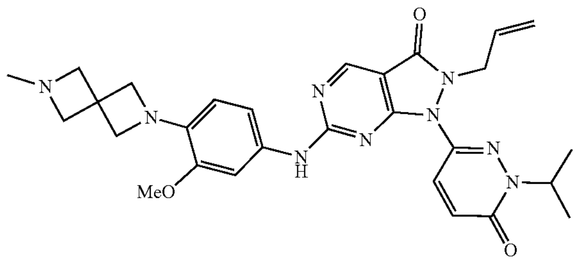
160
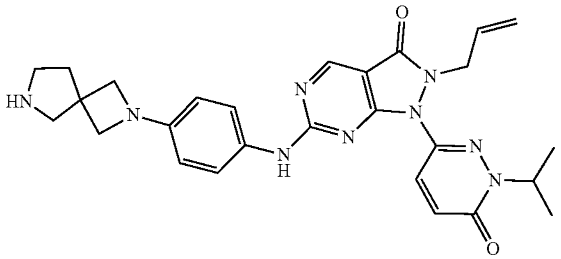
161
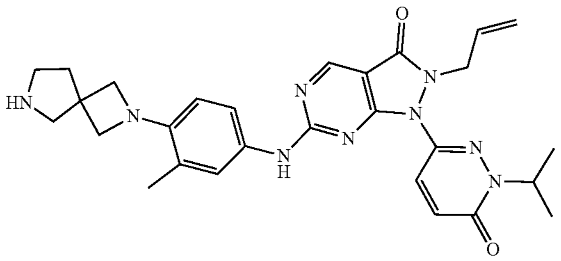
162
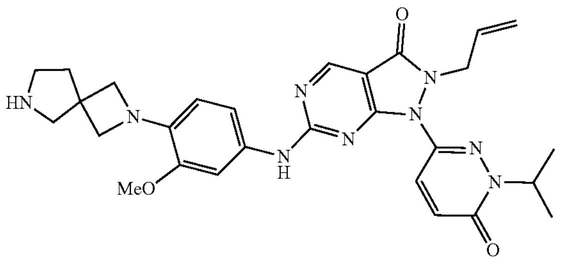
163
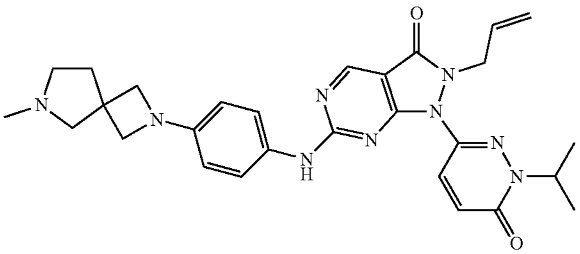
164
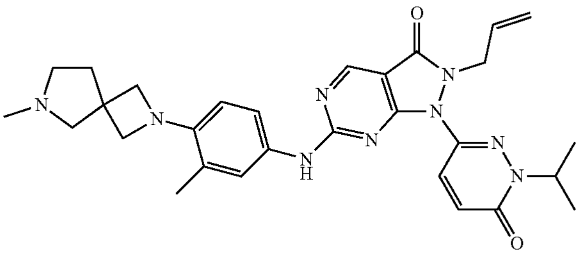
165
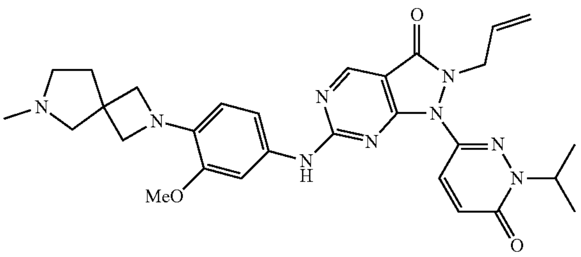
166
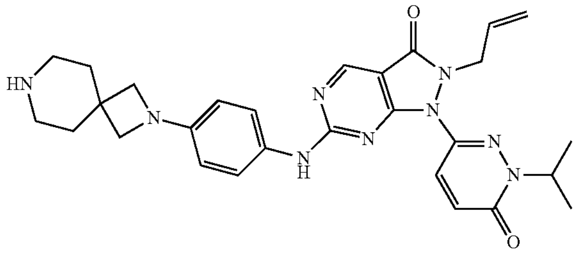
167
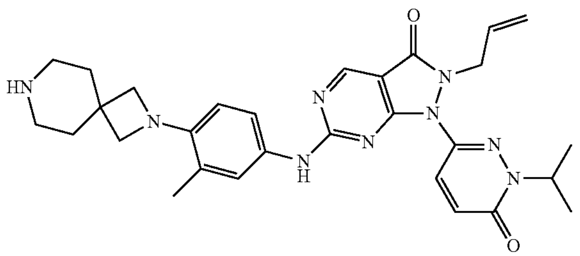
168
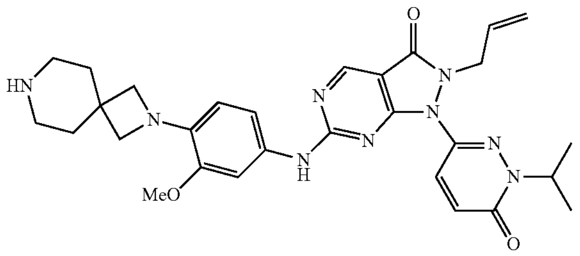

-continued
169
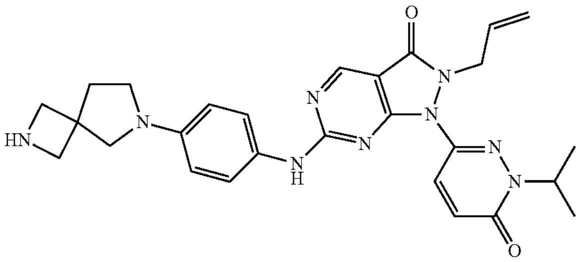
170
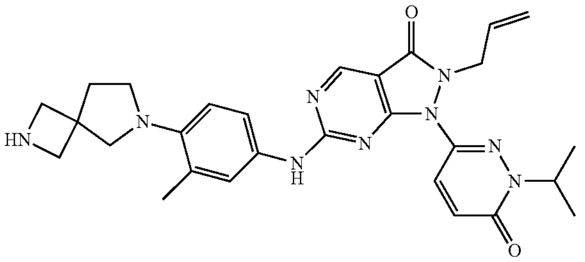
171
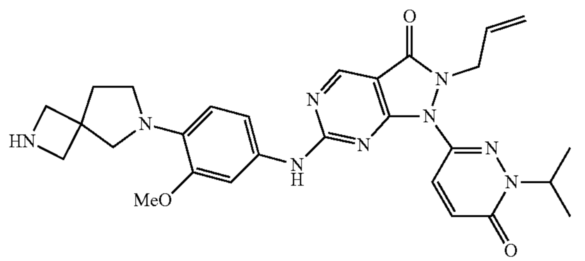
172
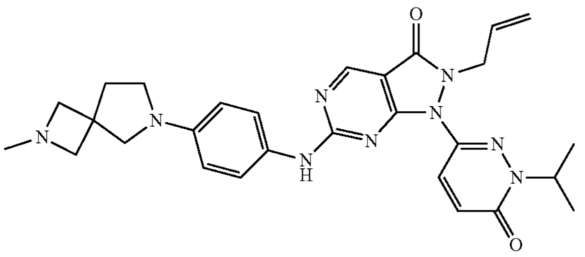
173
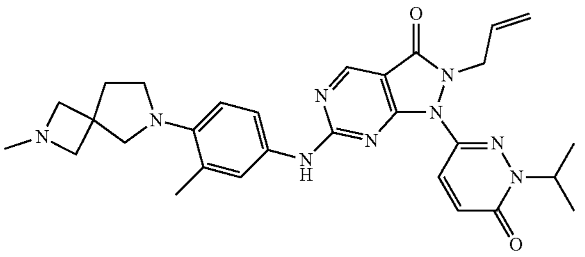
-continued
174
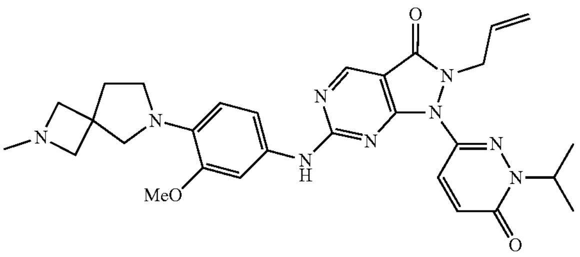
175
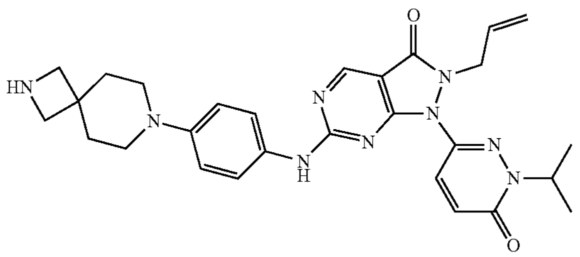
176
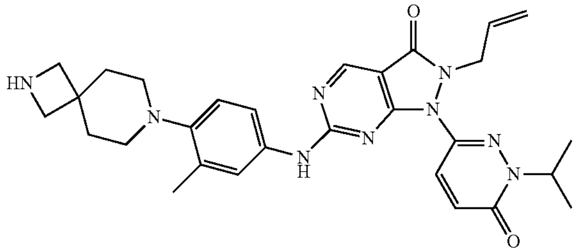
177
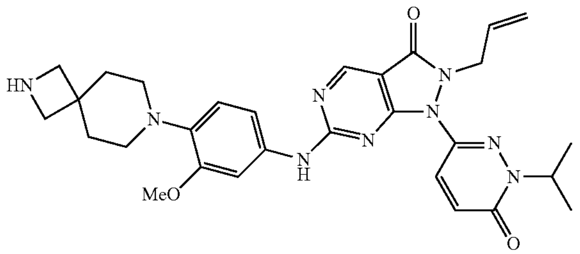
178
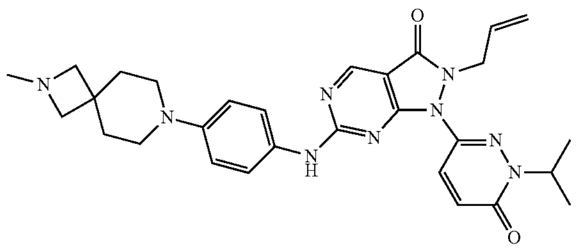

-continued
179
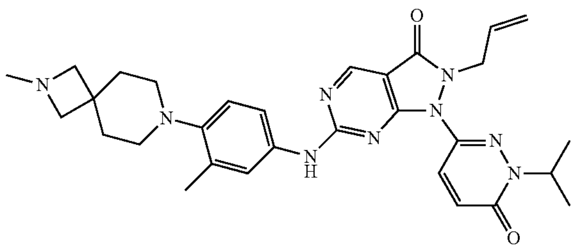
180
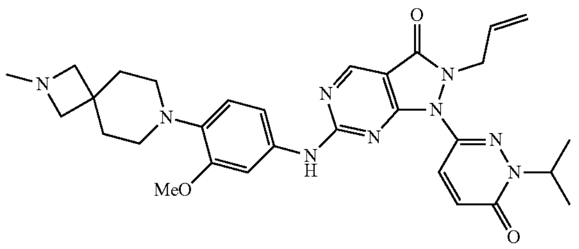
181
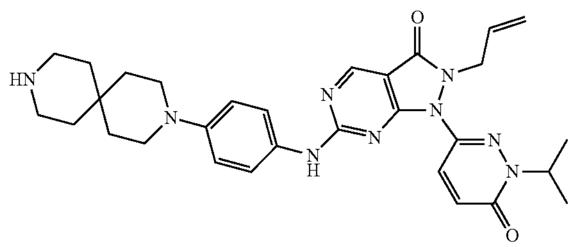
182
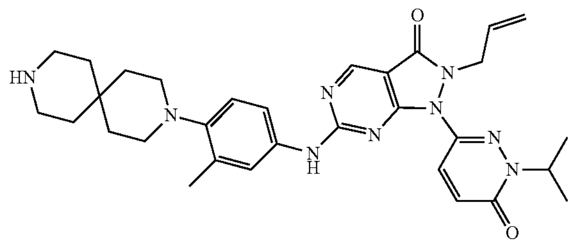
183
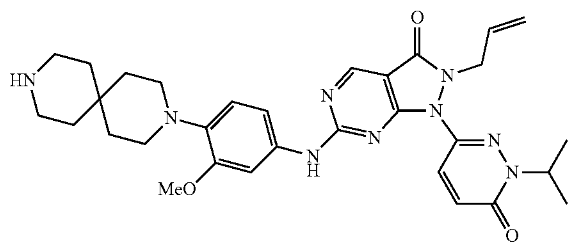
184
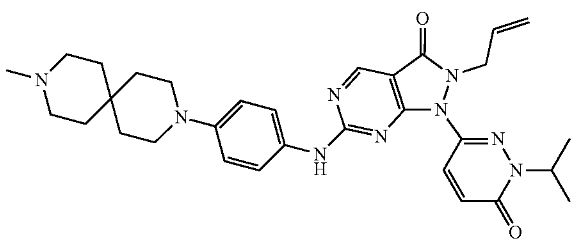
-continued
185
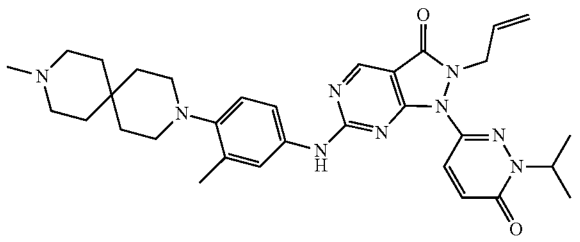
186
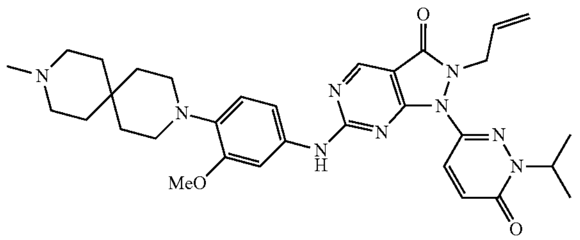
187
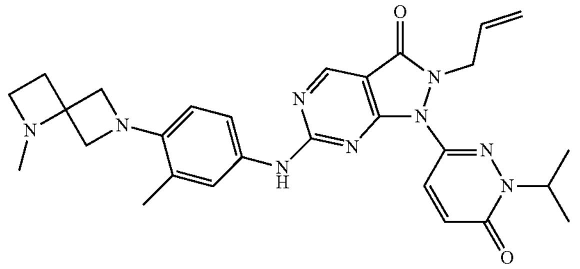
188
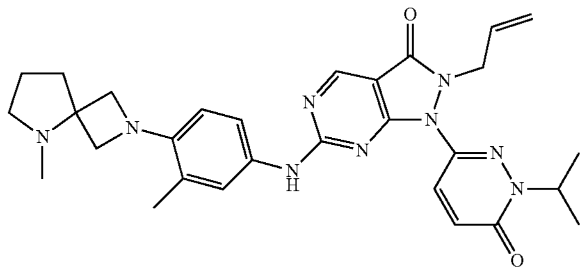
189
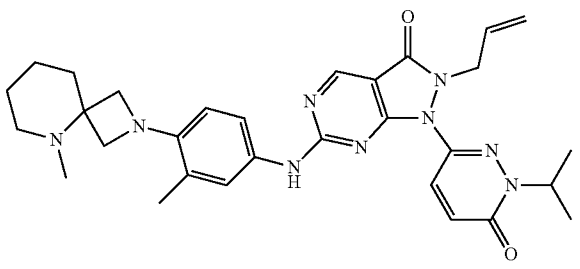

-continued
190
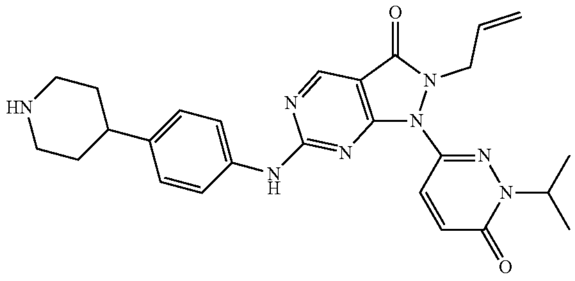
191
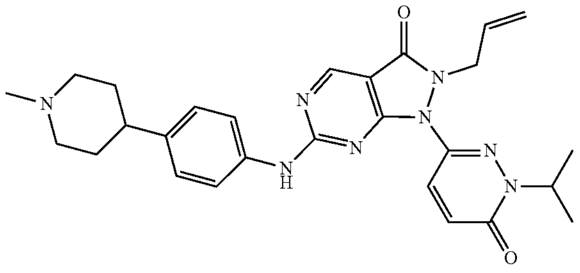
192
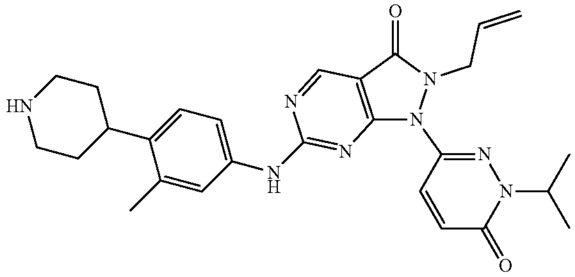
193
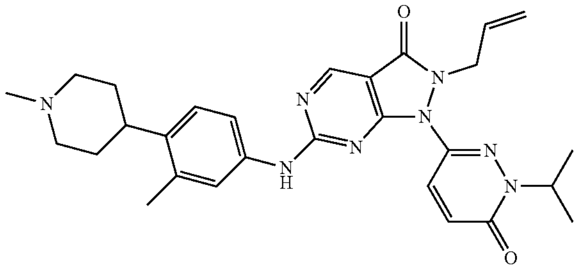
194
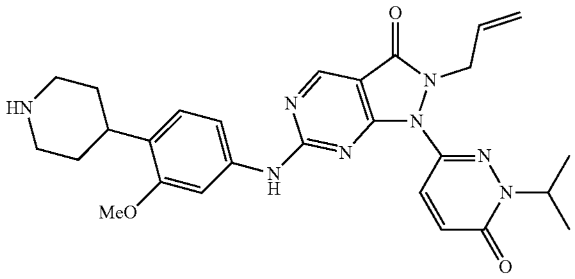
-continued
195
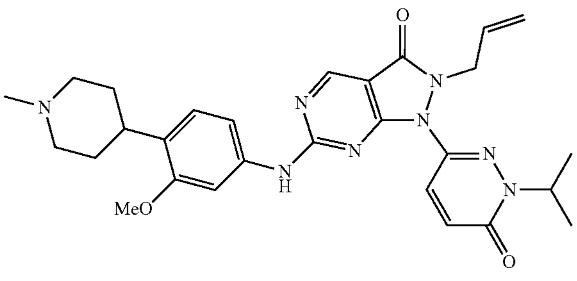
196
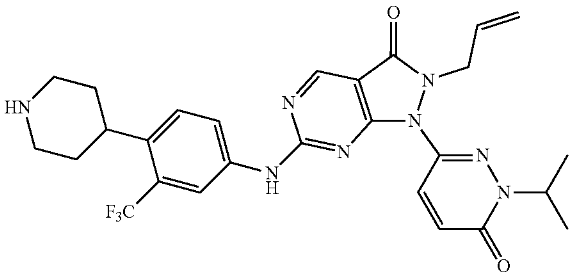
197
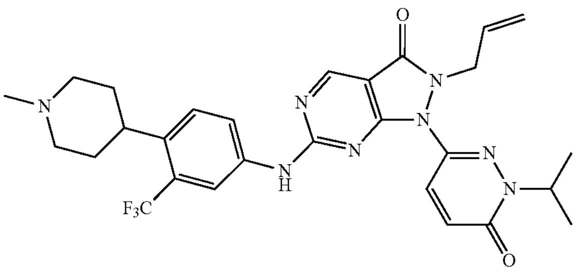
198
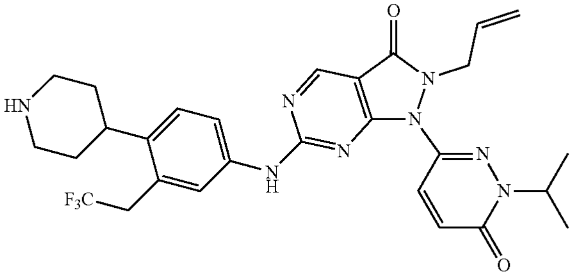
199
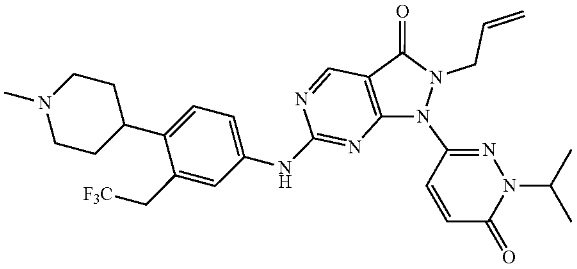

-continued
200
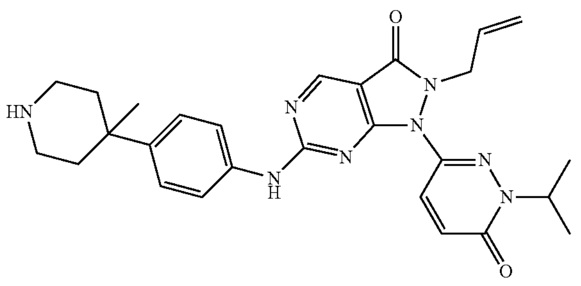
201
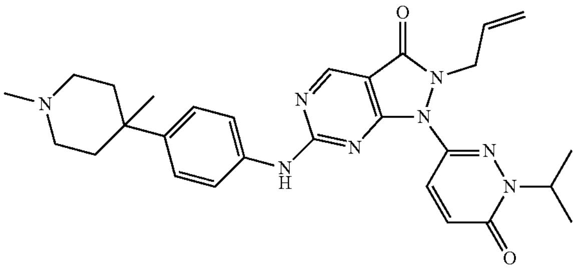
202
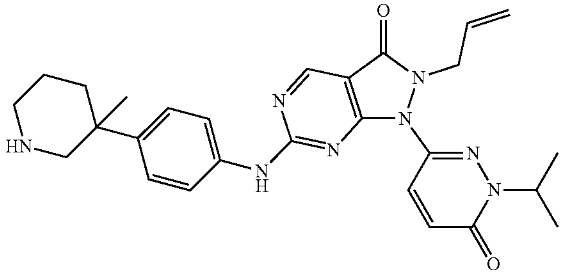
203
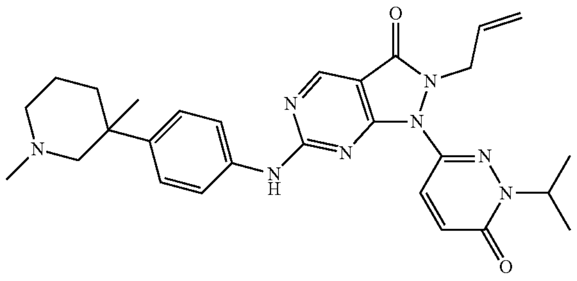
204
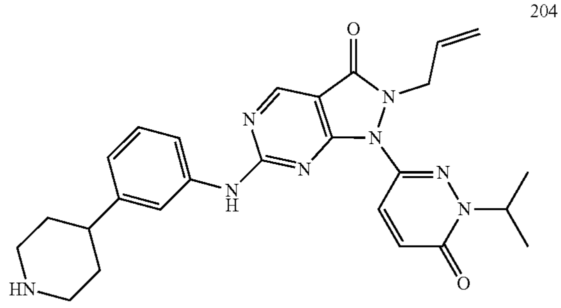
-continued
205
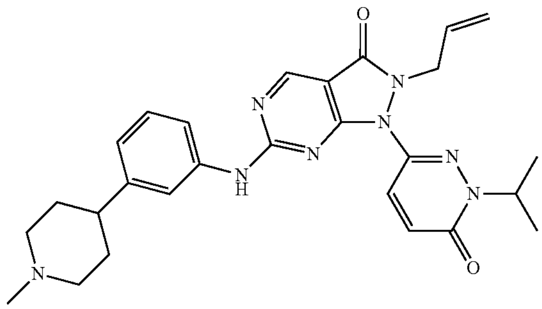
206
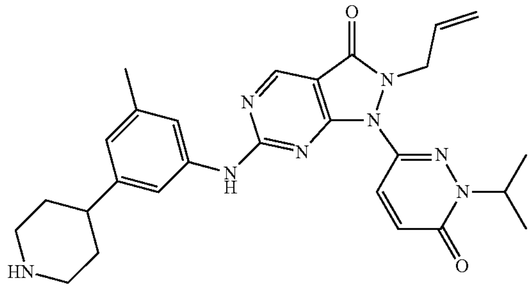
207
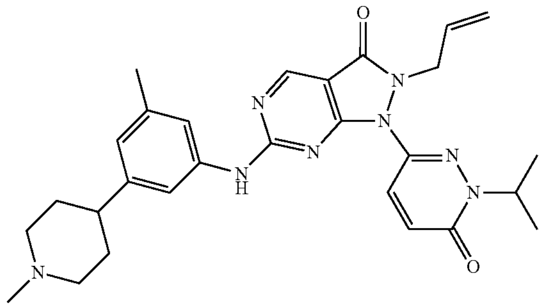
208
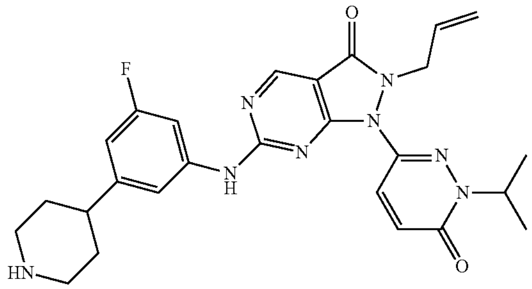
209
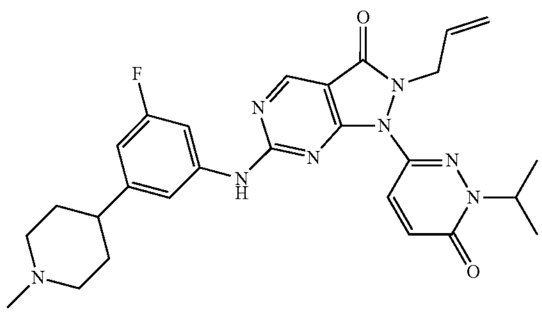

-continued
210
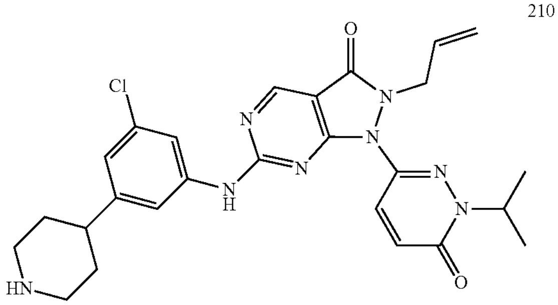
211
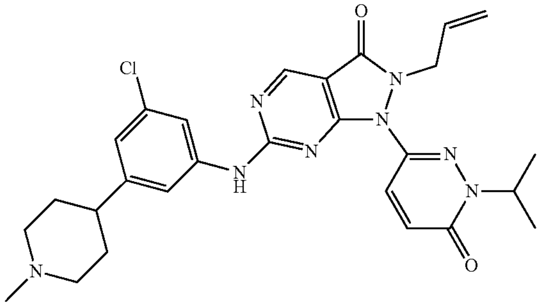
212
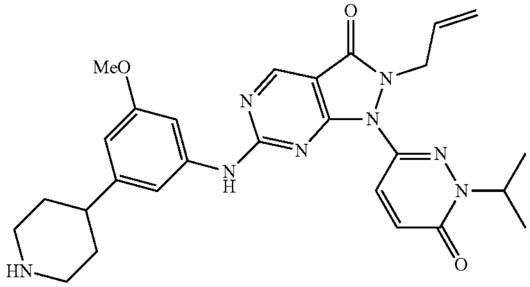
213
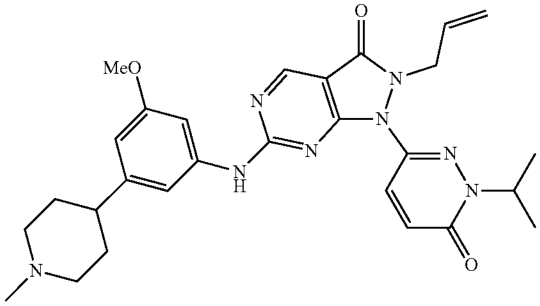
214
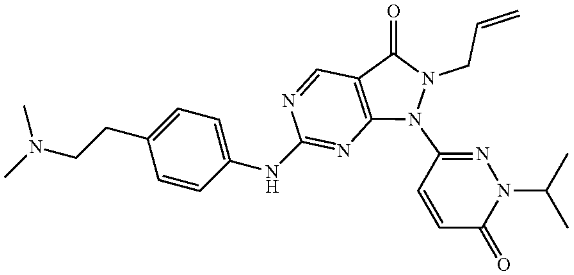
-continued
215
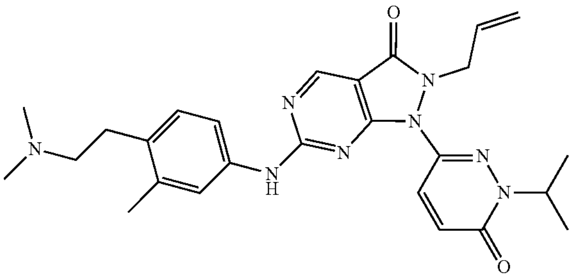
216
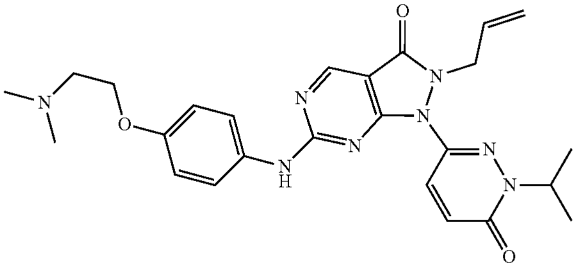
217
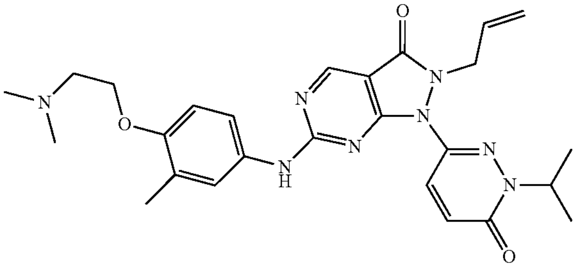
218
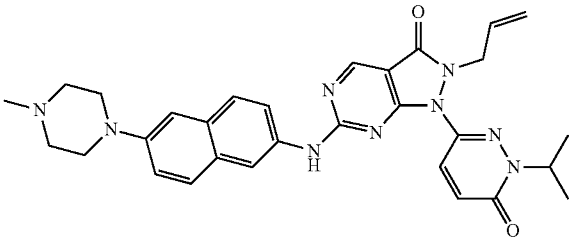
219
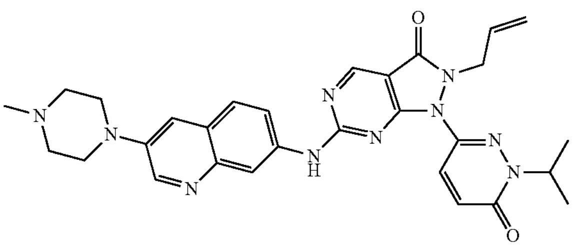

-continued
220
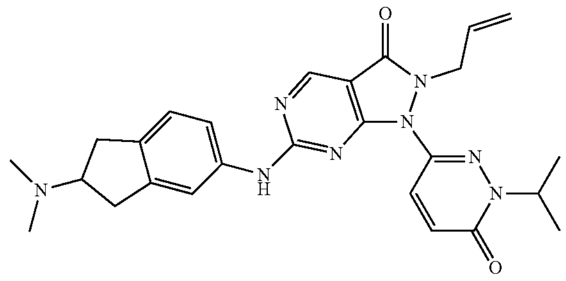
221
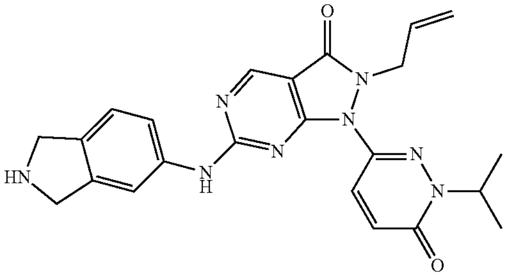
222
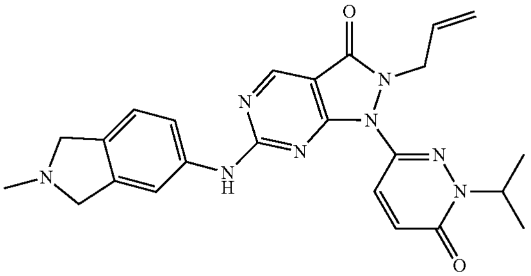
223
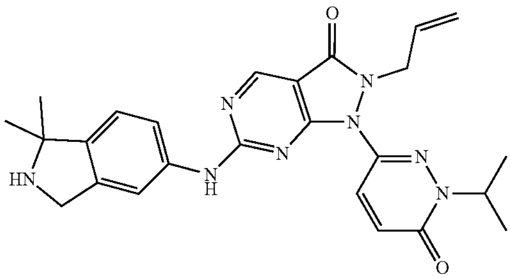
224
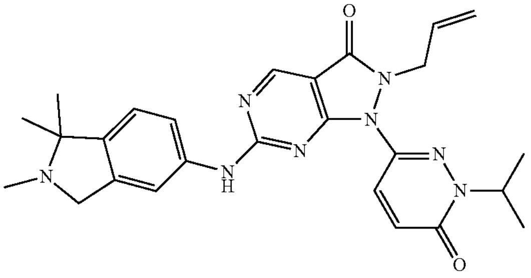
-continued
225
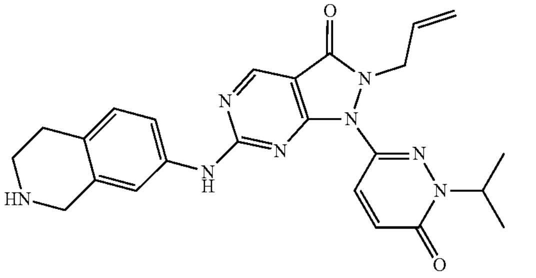
226
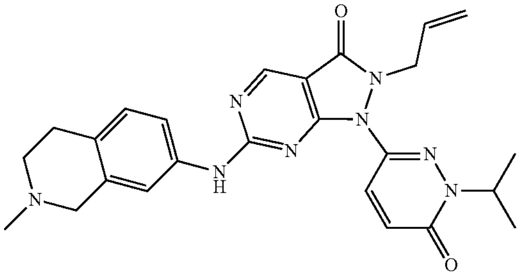
227
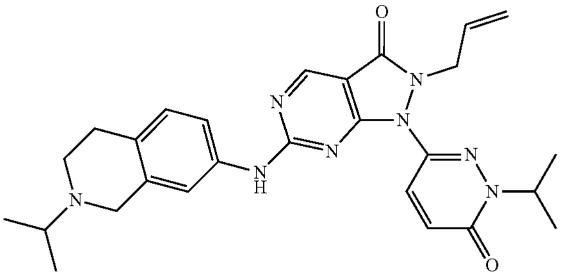
228
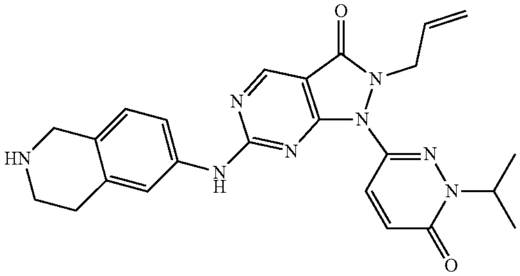
229
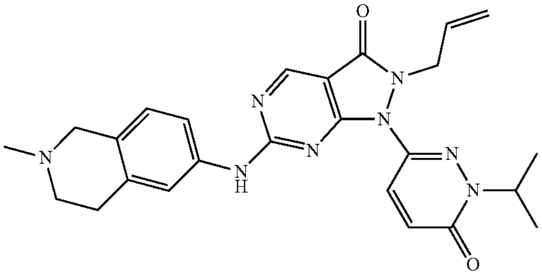

-continued
230
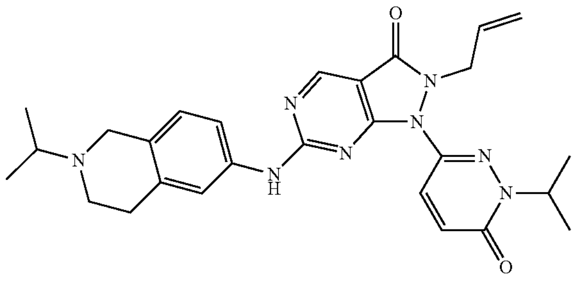
231
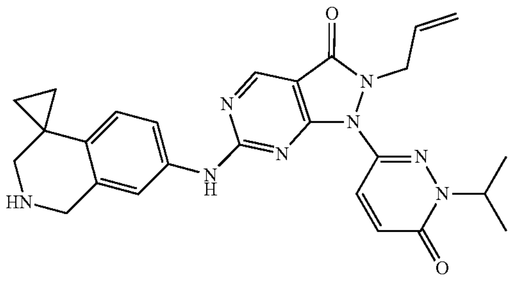
232
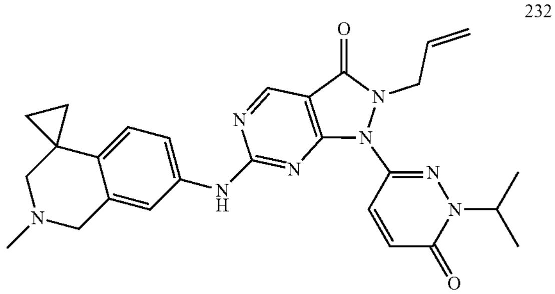
233
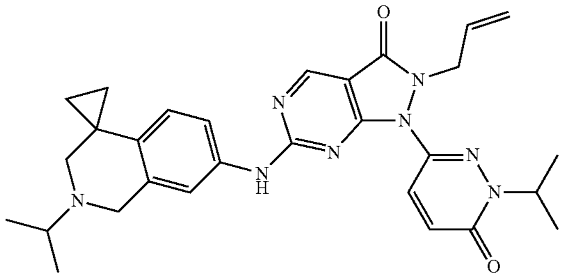
234
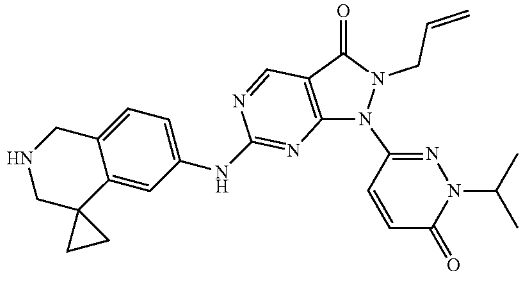
-continued
235
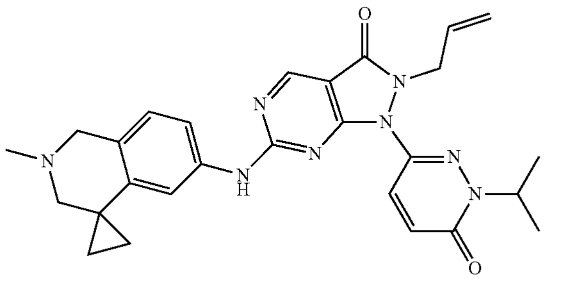
236
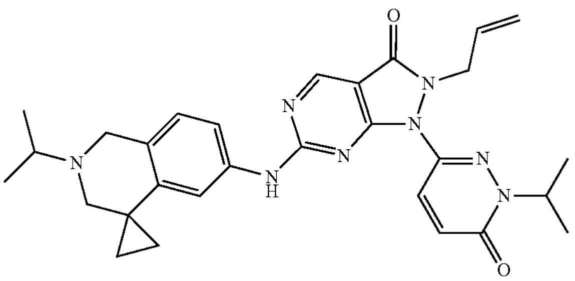
237
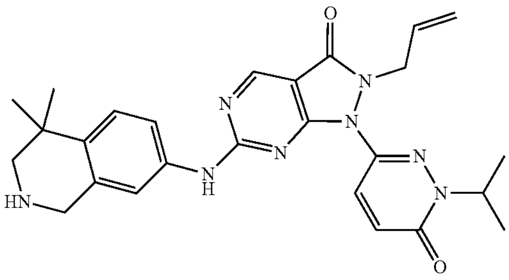
238
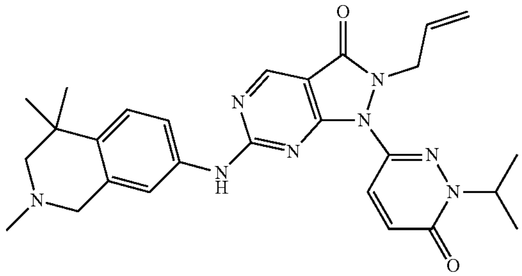
239
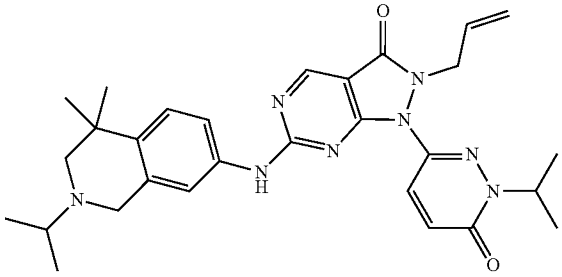

-continued
240
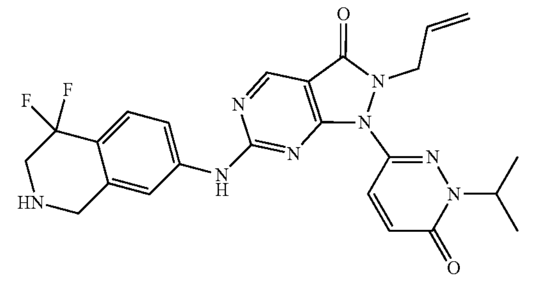
241
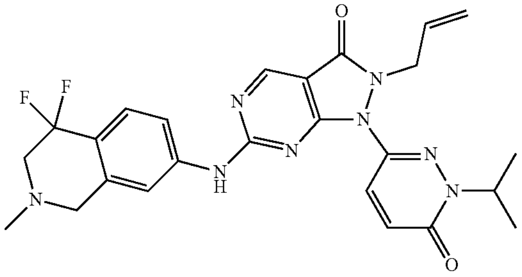
242
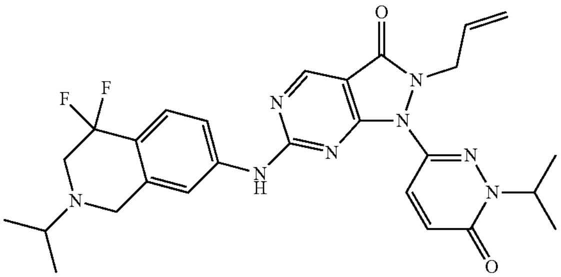
243
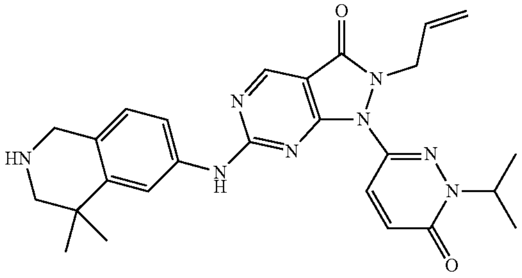
244
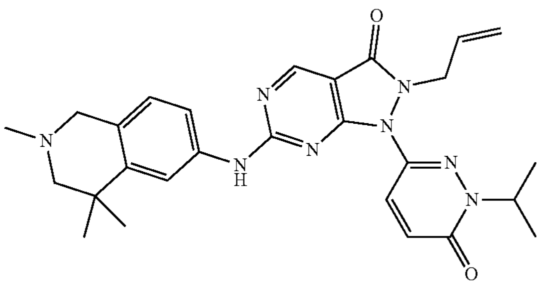
-continued
245
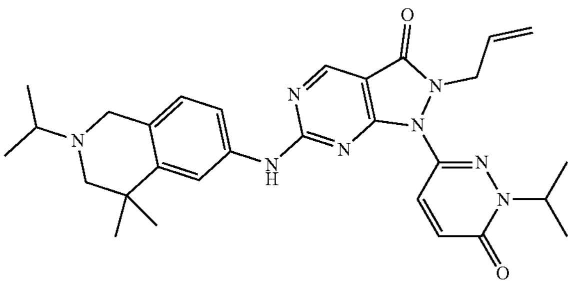
246
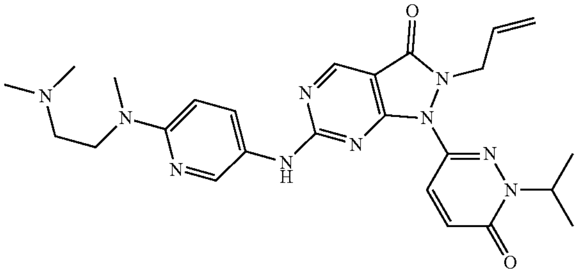
247
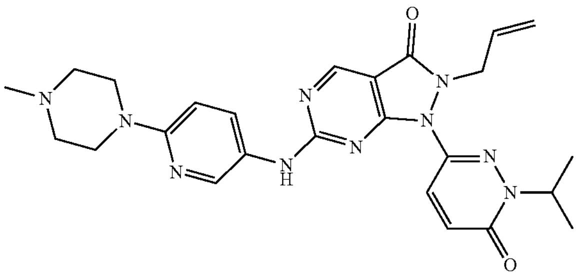
248
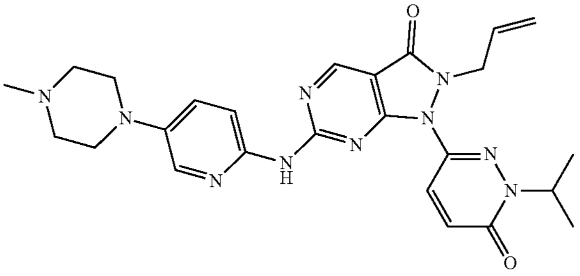
249
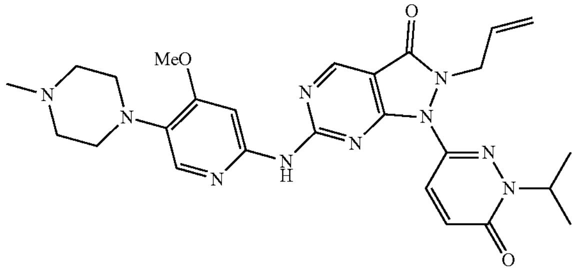

-continued
250
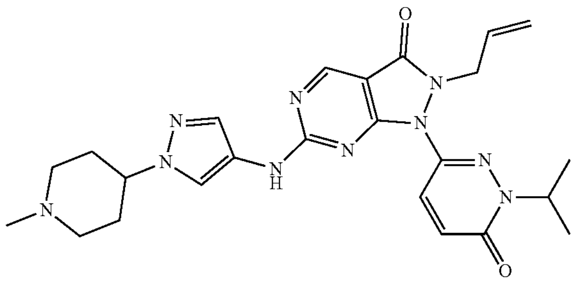
251
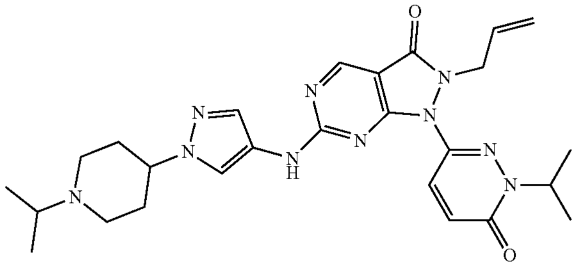
252
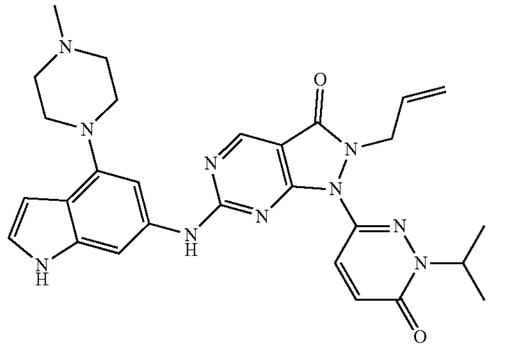
253
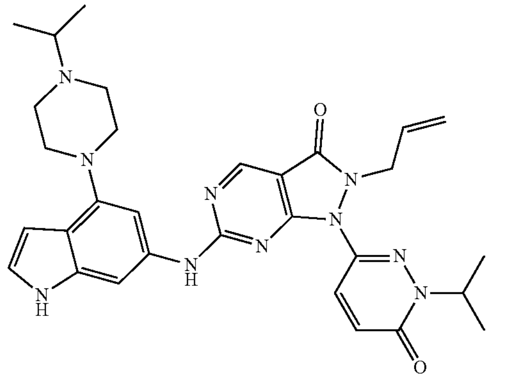
-continued
254
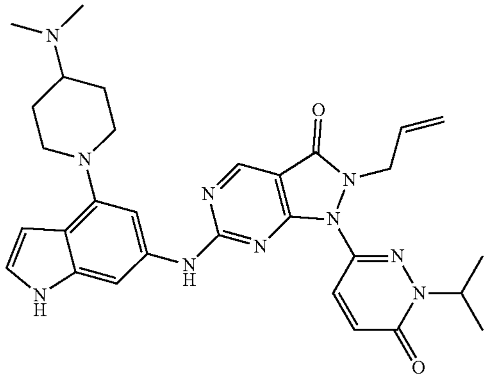
255
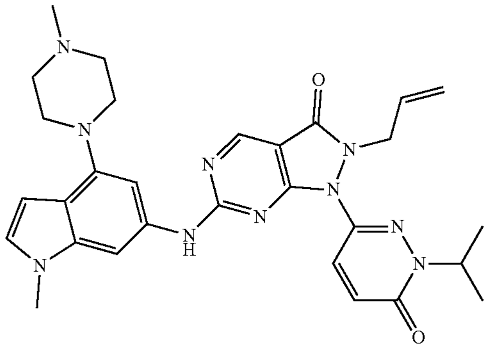
256
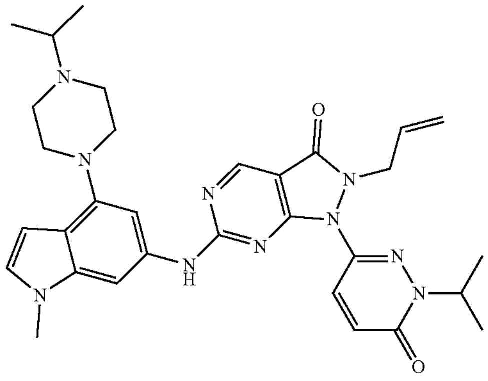
257
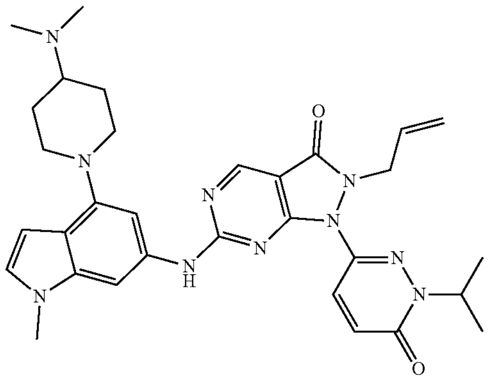

-continued
258
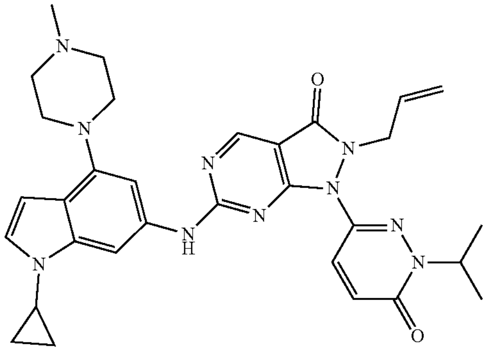
259
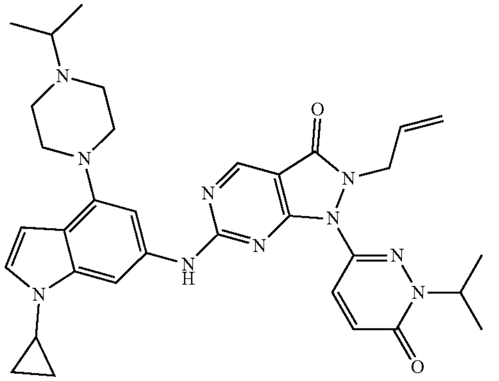
260
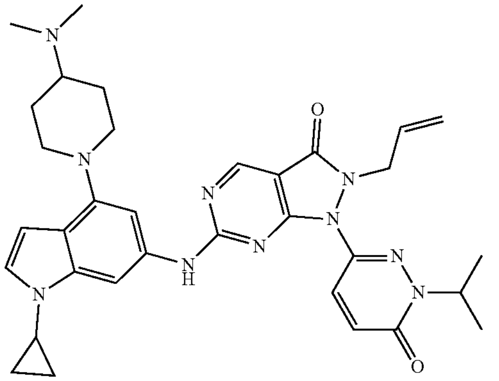
261
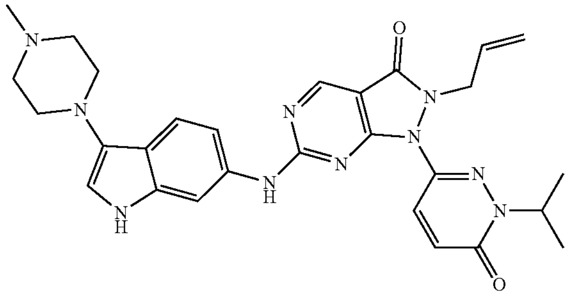
-continued
262
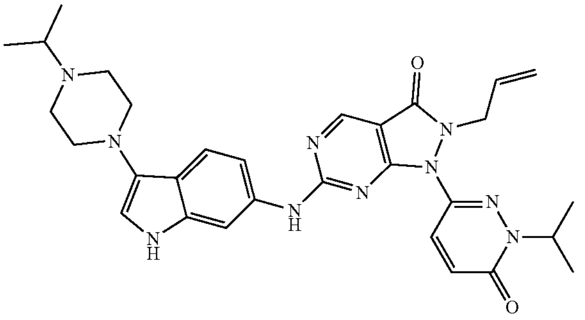
263
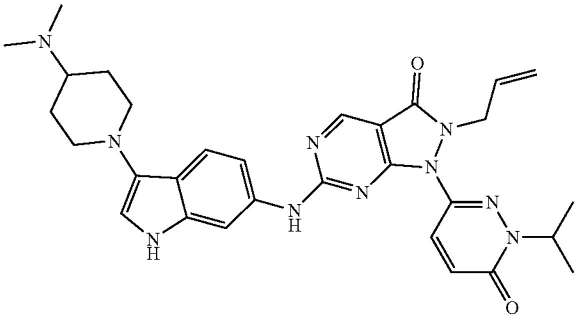
264
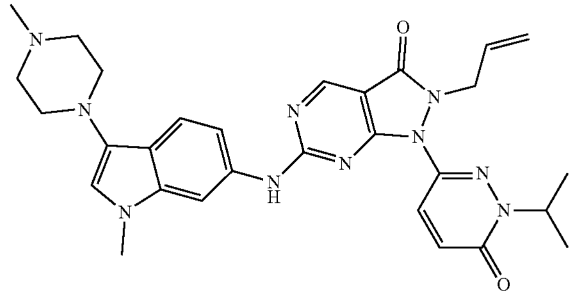
265
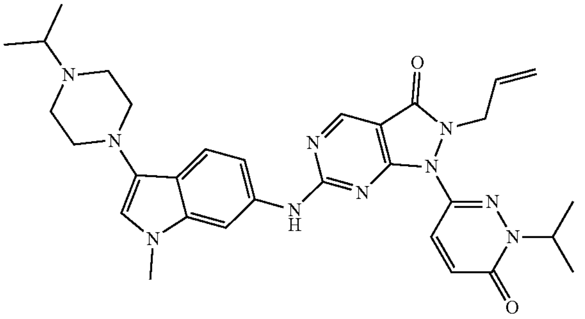

-continued
266
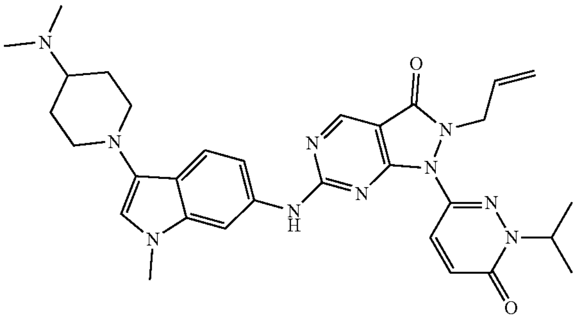
267
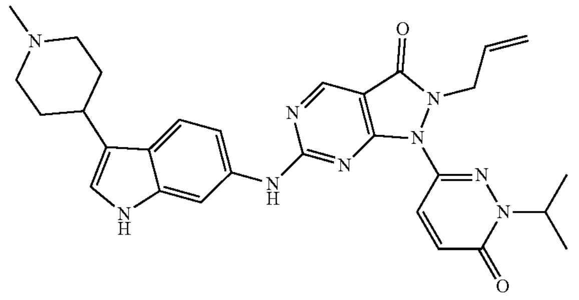
268
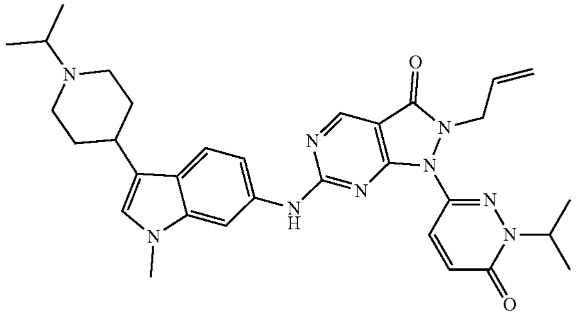
269
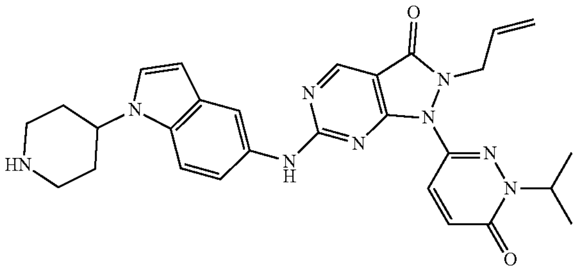
270
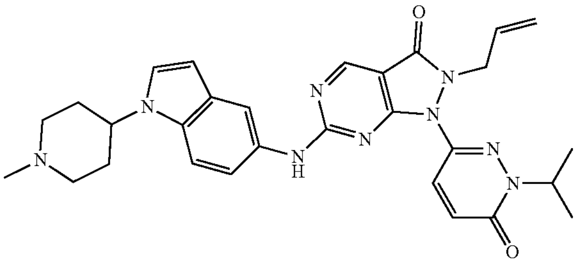
-continued
271
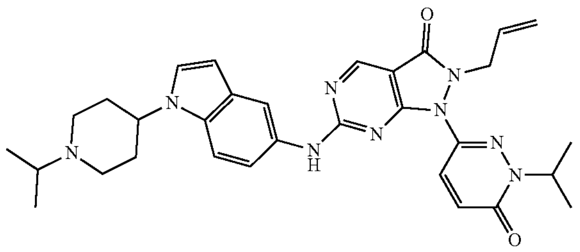
272
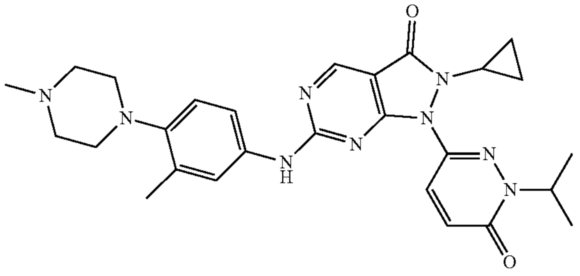
273
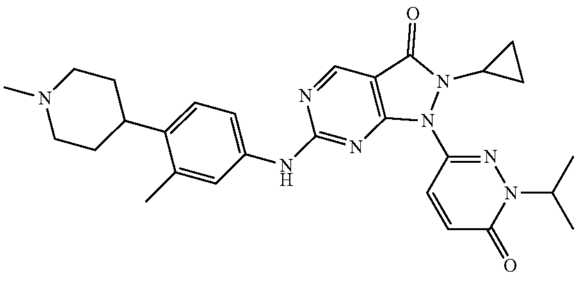
274
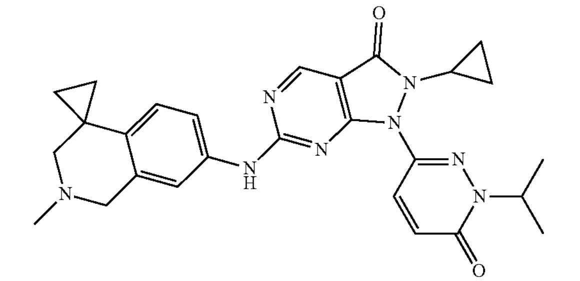
275
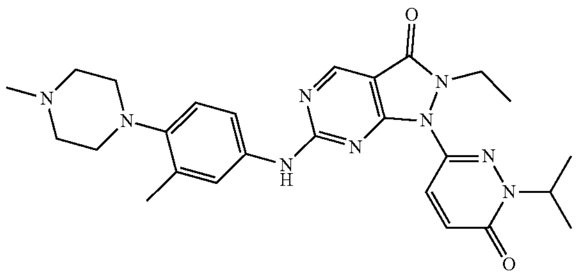

-continued
276
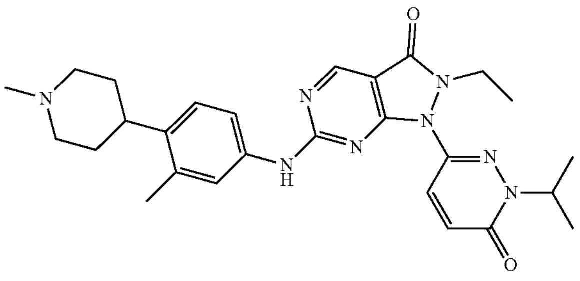
277
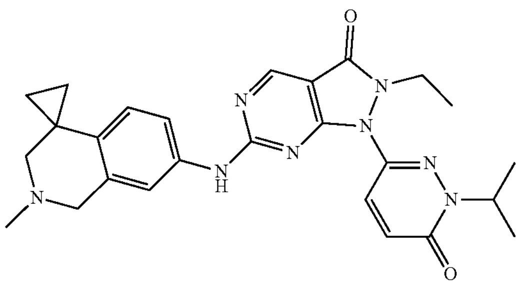
278
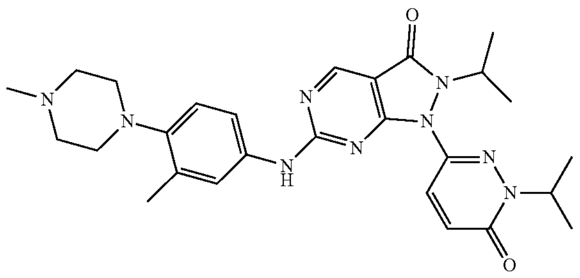
279
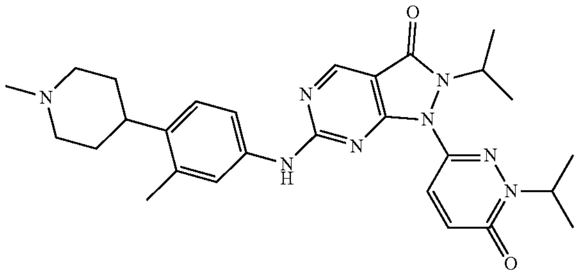
280
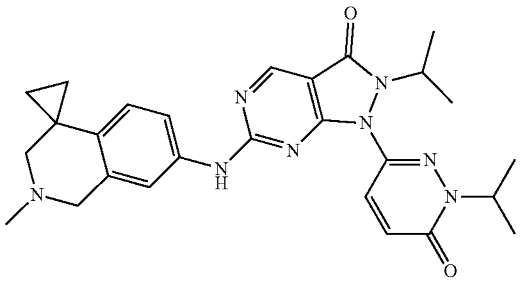
-continued
281
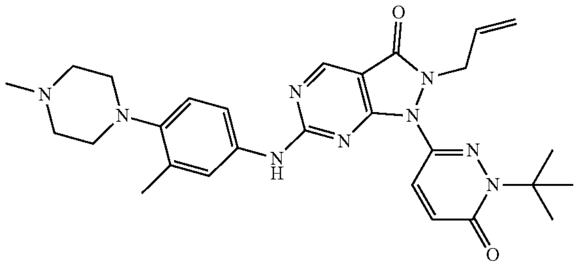
282
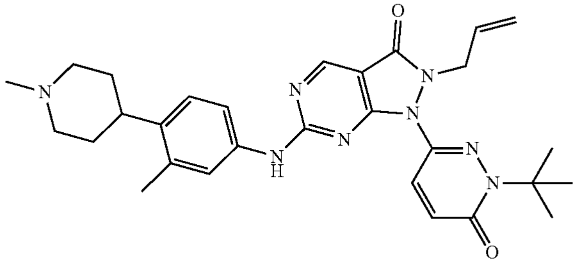
283
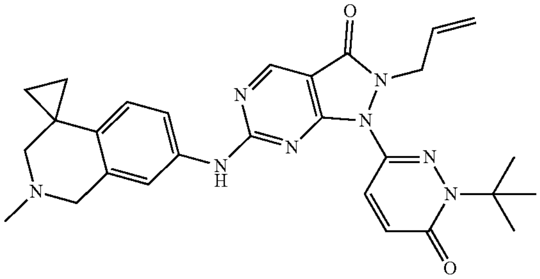
284
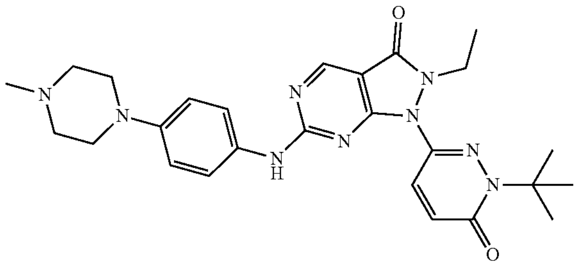
285
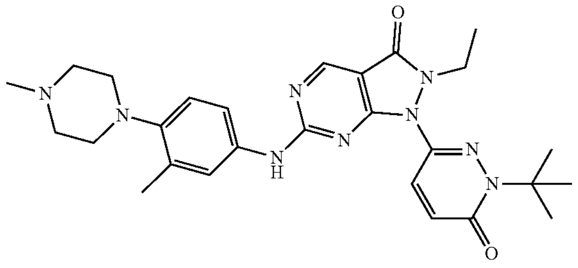

-continued
286
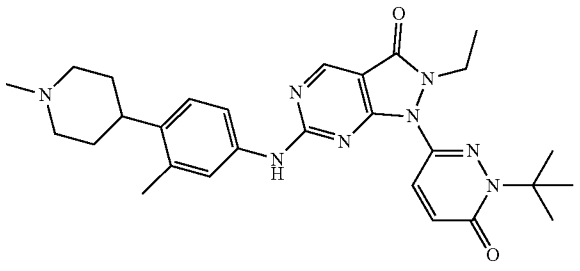
287
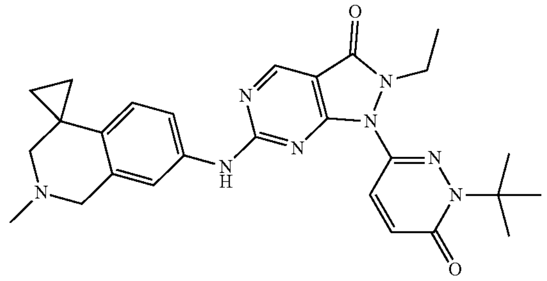
288
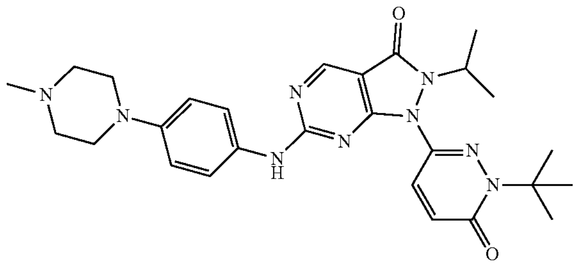
289
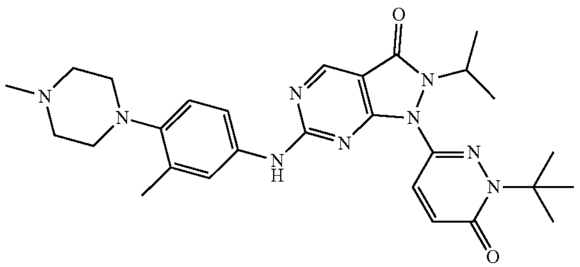
290
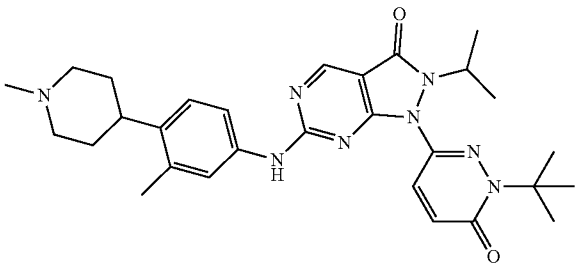
-continued
291
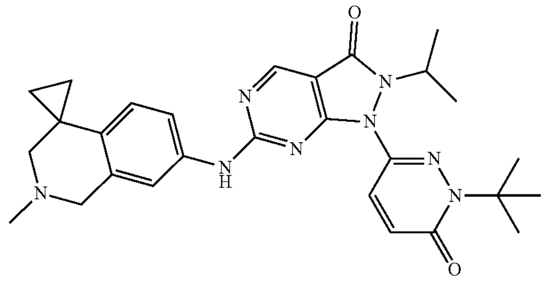
292
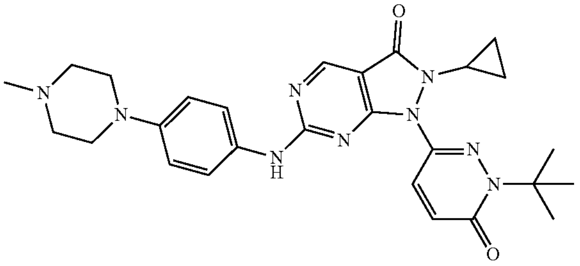
293
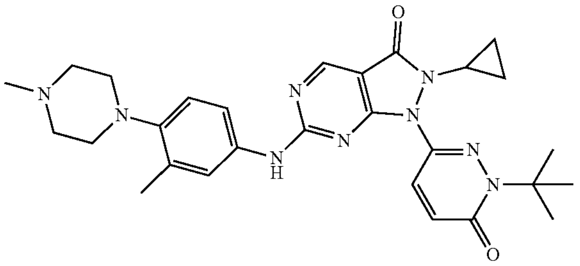
294
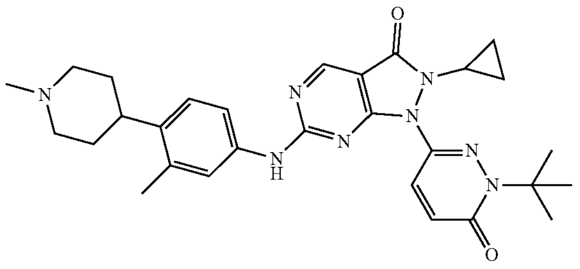
295
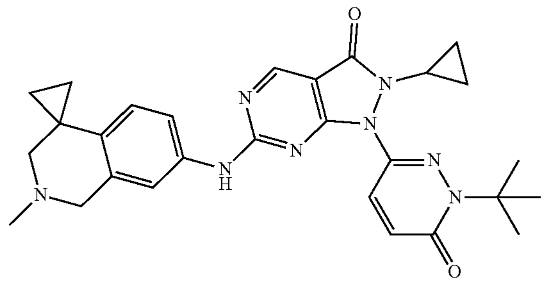

-continued
296
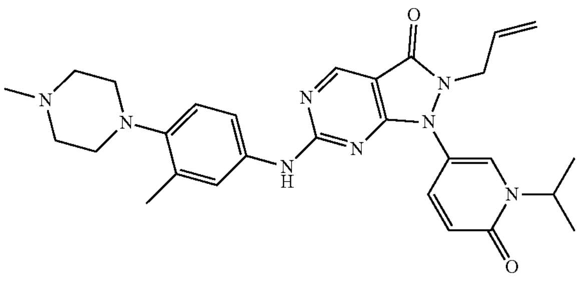
297
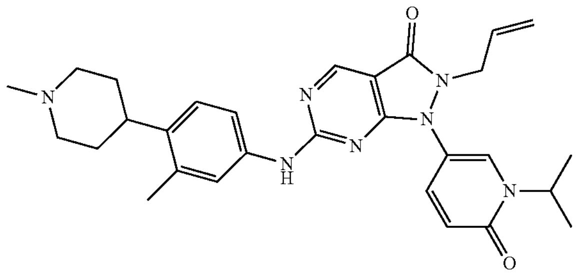
298
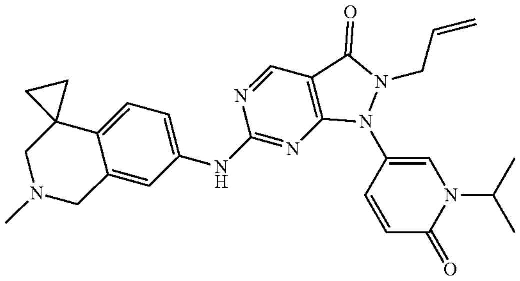
299
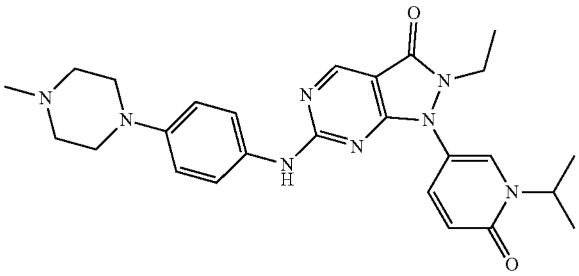
300
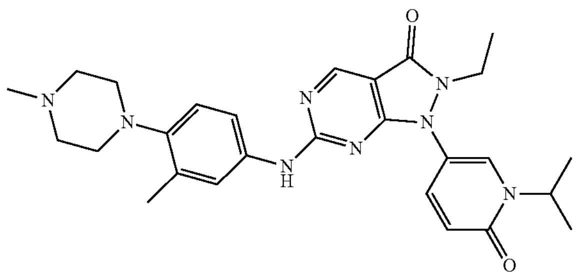
-continued
301
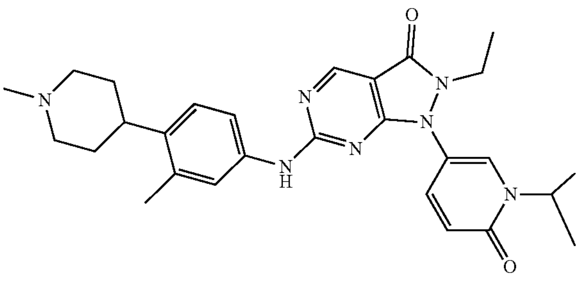
302
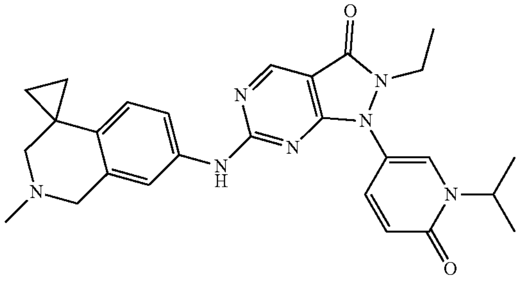
303
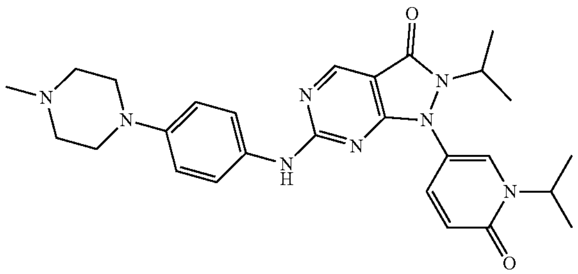
304
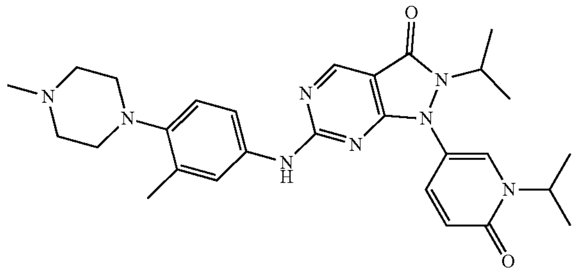
305
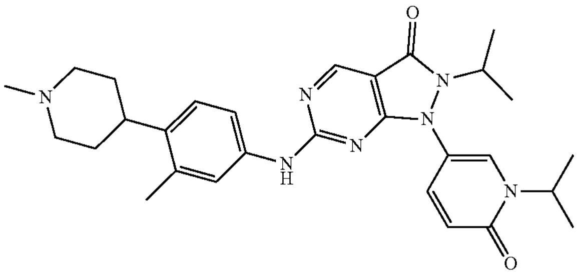

-continued
306
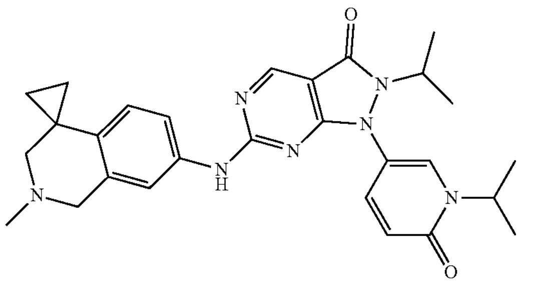
307
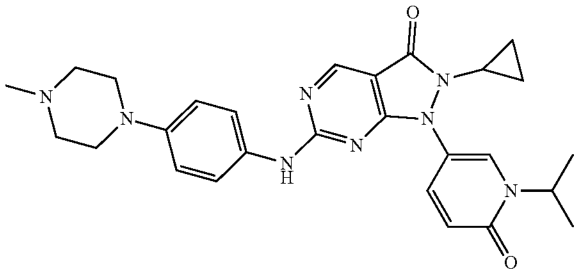
308
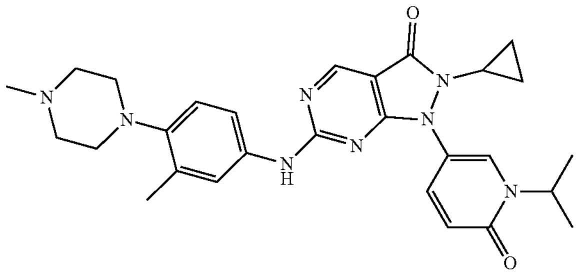
309
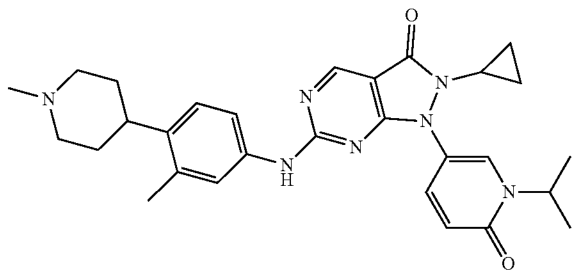
310
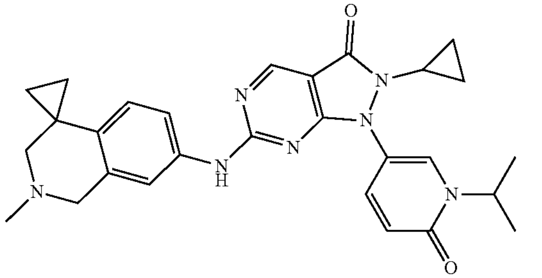
-continued
311
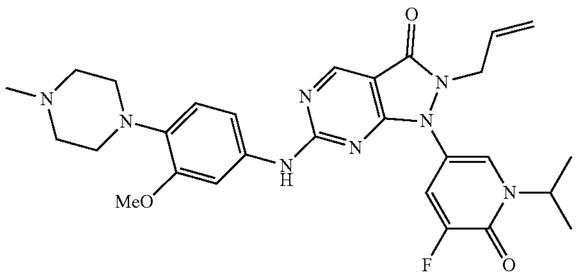
312
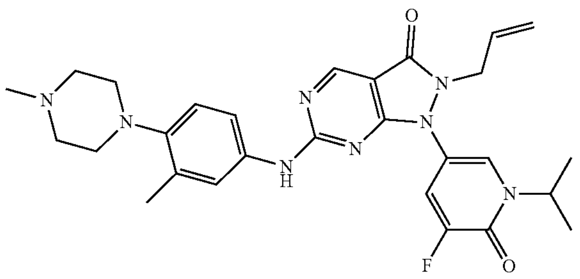
313
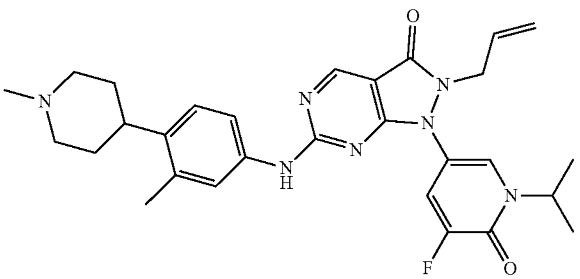
314
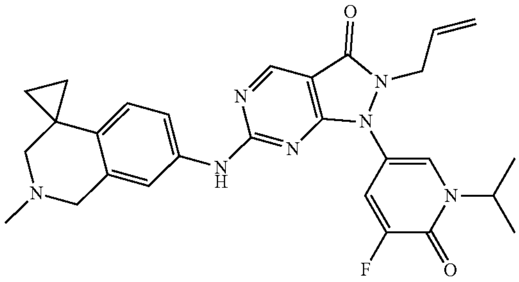
315
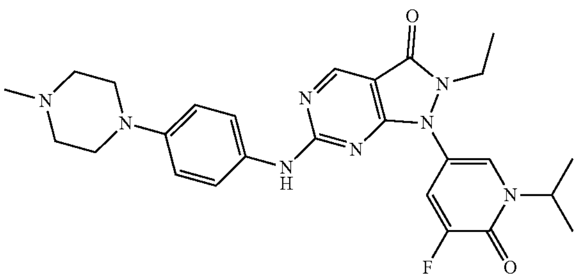

-continued
316
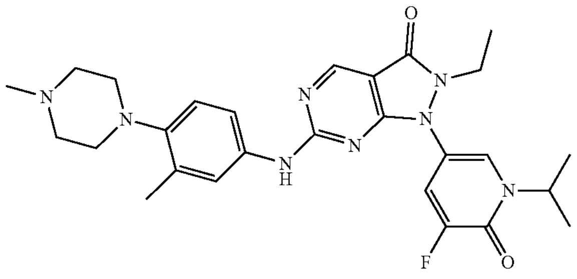
317
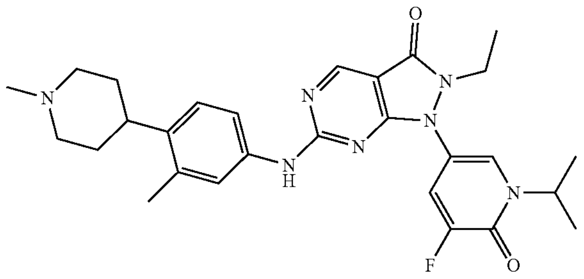
318
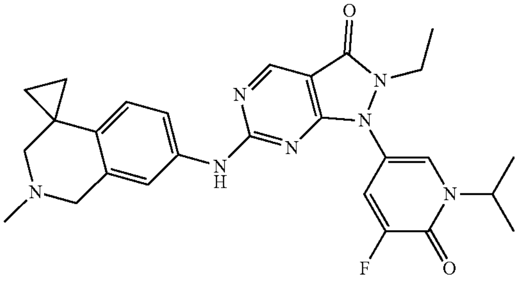
319
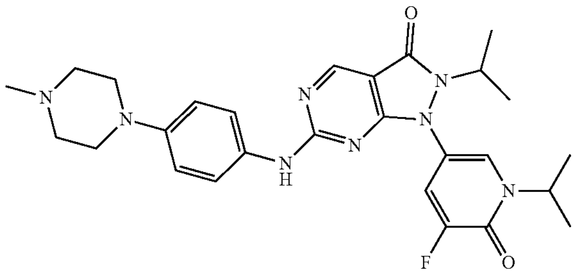
320
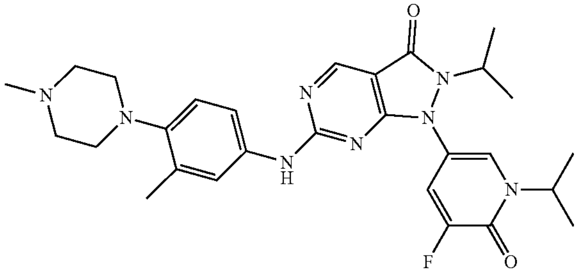
-continued
221
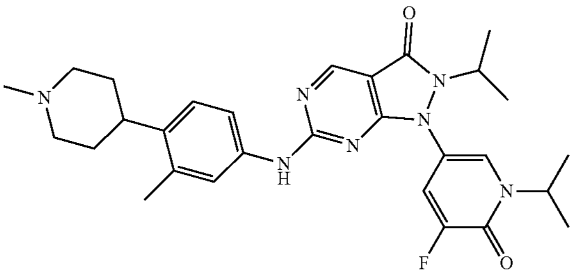
222
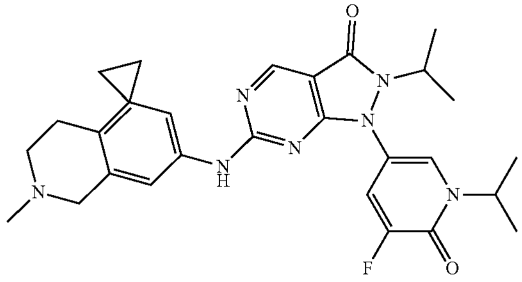
223
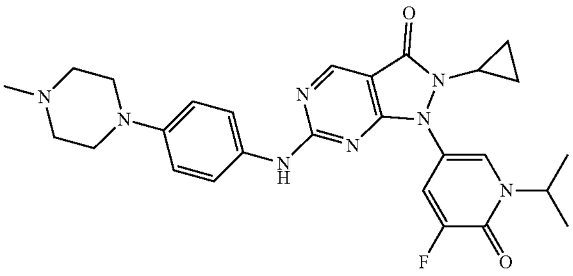
224
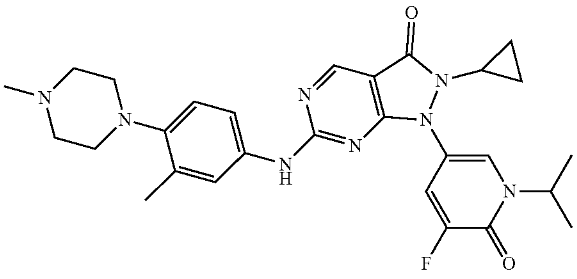
225
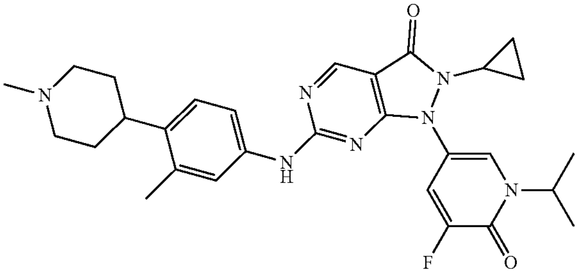

-continued
226
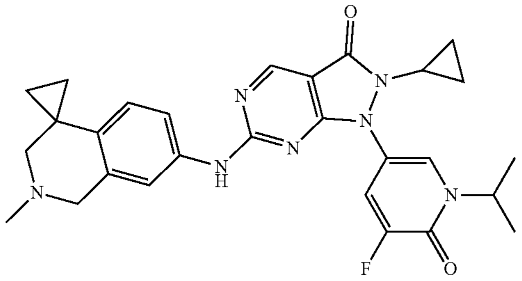
227
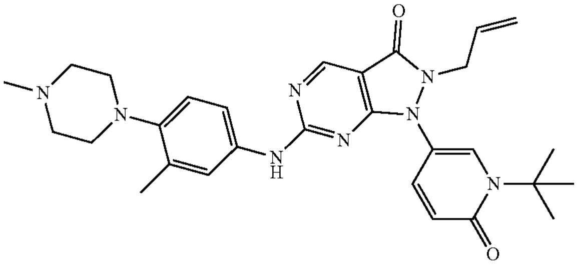
228
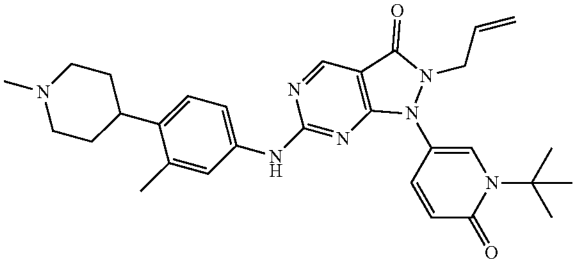
229
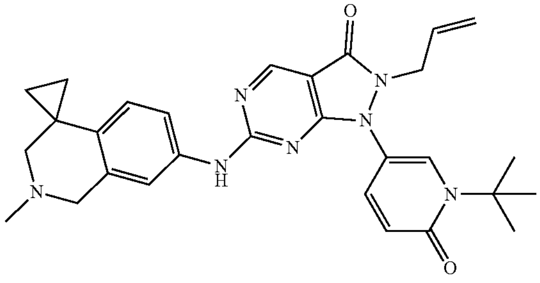
230
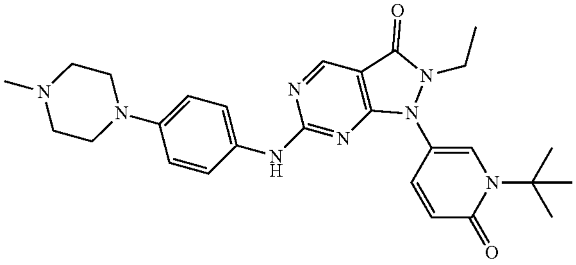
-continued
231
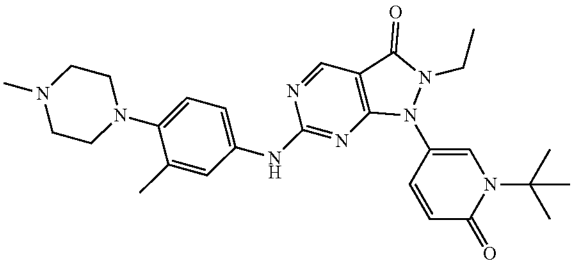
232
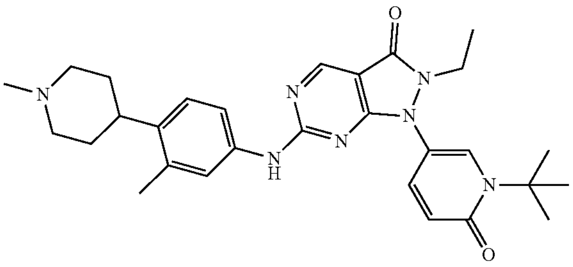
333
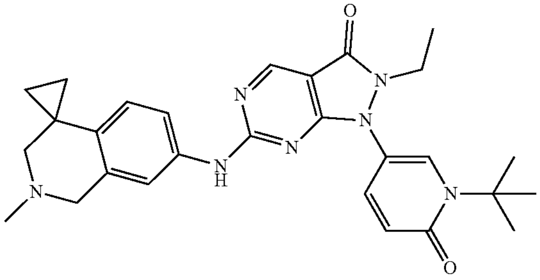
334
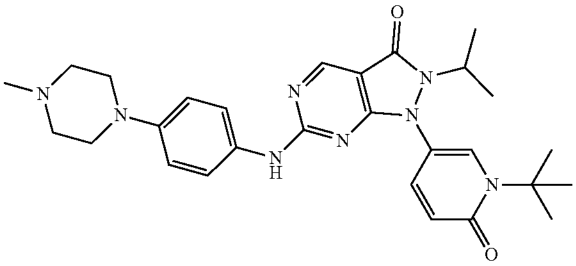
335
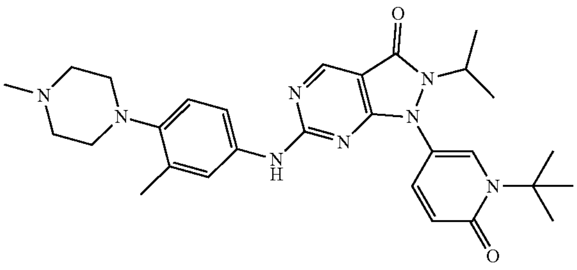

-continued

336

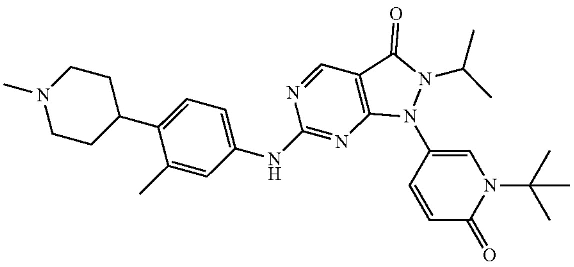

337

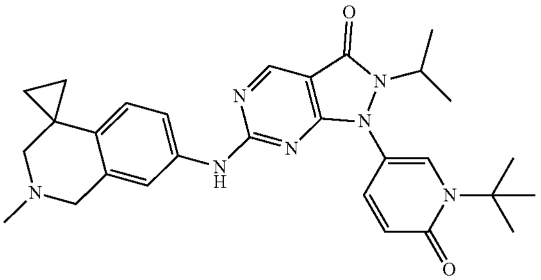

338

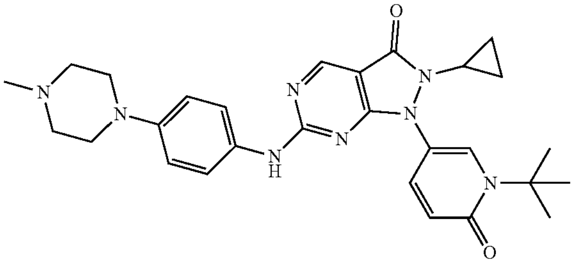

339

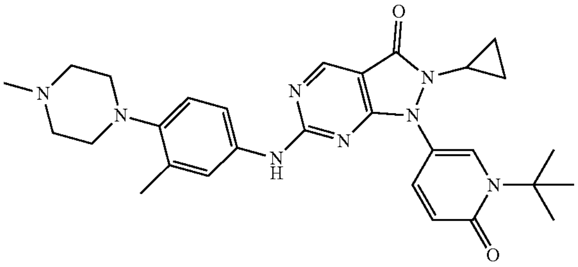

340

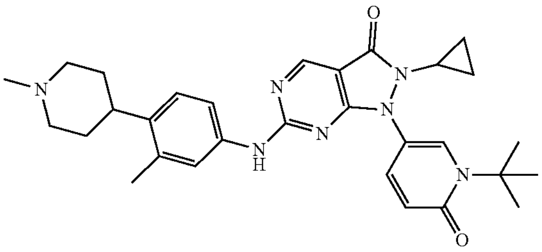

or

-continued

341

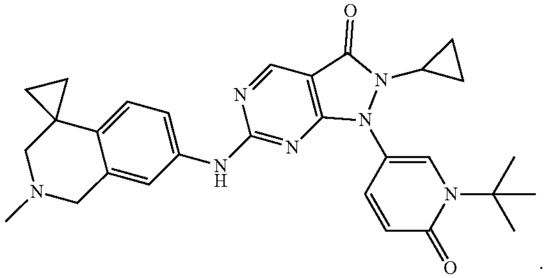

The present invention is further intended to provide a pharmaceutical composition comprising a pharmaceutically acceptable excipient or carrier, and the compound of general formula (1) or the isomers, the crystalline forms, the pharmaceutically acceptable salts, the hydrates or the solvates thereof of the present invention as an active ingredient.

The present invention is still further intended to provide use of the compound or the isomers, the crystalline forms, the pharmaceutically acceptable salts, the hydrates or the solvates thereof of the present invention in preparing a medicament for treating related diseases mediated by Wee-1.

It should be understood that both the above general description and the following detailed description of the present invention are exemplary and explanatory, and are intended to provide further explanation of the present invention claimed.

DETAILED DESCRIPTION OF THE INVENTION

Definitions and Explanations

Unless otherwise indicated, the following terms and phrases used herein are intended to have the following meanings. A particular term or phrase, unless otherwise specifically defined, should not be considered uncertain or unclear, but construed according to a common definition. When referring to a trade name herein, it is intended to refer to its corresponding commodity or its active ingredient. The term "pharmaceutically acceptable" is used herein for those compounds, compositions and/or formulations which are, within the scope of sound medical judgment, suitable for use in contact with the tissues of human beings and animals without excessive toxicity, irritation, allergic responses, or other problems or complications, commensurate with a reasonable benefit/risk ratio.

The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by subjecting the compound of general formula (1) to a reaction with acids, e.g., inorganic acids such as hydrochloric acid, hydrobromic acid, hydrofluoric acid, sulfuric acid, phosphoric acid, nitric acid, phosphoric acid and the like, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like, and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compound of general formula (1) are conveniently prepared or formed according to methods described herein. For example, the hydrates of the compound of general formula (1) are conveniently prepared by recrystallization in a mixed solvent of water/organic solvent, wherein the organic solvent used includes, but is not limited to, acetonitrile, tetrahydrofuran, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compound of general formula (1) is prepared in different forms, including but not limited to amorphous, pulverized and nanoparticle forms. In addition, the compound of general formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compound of general formula (1) has one or more stereocenters and thus occurs in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

Unless otherwise indicated, the absolute configuration of a stereocenter is represented by wedge bonds () and dashed bonds (), and wedge bonds or dashed bonds ( or ) are represented by wavy lines ().

The compound of the present invention may contain unnatural proportions of atomic isotopes at one or more of the atoms that constitute the compound. For example, the compound may be labeled with radioactive isotopes, such as tritium ($^{3}H$), iodine-125 ($^{125}I$), or carbon-14 ($^{14}C$). All isotopic variations of the compound of the present invention, whether radioactive or not, are included within the scope of the present invention.

The compound and the pharmaceutically acceptable salt thereof of the present invention can be prepared into various preparations comprising a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. Examples of pharmaceutically acceptable excipients or carriers include cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly or subcutaneously) or topically.

Unless otherwise specified, the term "alkyl" refers to a saturated aliphatic hydrocarbon group, including linear and branched chain groups containing 1 to 6 carbon atoms. Lower alkyls containing 1 to 4 carbon atoms, such as methyl, ethyl, propyl, 2-propyl, n-butyl, isobutyl or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, i-Pr, n-Pr, i-Bu, c-Pr, n-Bu and t-Bu.

Unless otherwise specified, "alkylene" refers to a divalent alkyl as defined above. Alkylene also includes spirocycloalkyl. Examples of alkylene include, but are not limited to, methylene, ethylene ( 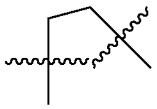 ), spirocyclopropyl ( 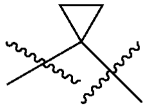 )

and spirocyclobutyl ( 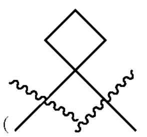 ).

Unless otherwise specified, "cycloalkyl" refers to a 3- to 14-membered all-carbon monocyclic aliphatic hydrocarbon group, wherein one or more of the rings may contain one or more double bonds, but none of them has a fully conjugated π-electron system, e.g., cyclopropyl, cyclobutyl, cyclopentyl, cyclohexane, and cyclohexadiene.

Unless otherwise specified, the term "heterocycloalkyl" refers to a saturated or partially saturated non-aromatic cyclic group consisting of carbon atoms and heteroatoms selected from nitrogen, oxygen or sulfur. The cyclic group may be monocyclic or polycyclic. In the present invention, the number of heteroatoms in the heterocycloalkyl is preferably 1, 2, 3 or 4, and the nitrogen, carbon or sulfur atom in the heterocycloalkyl may optionally be oxidized. The nitrogen atom may optionally be further substituted with other groups to form tertiary amines or quaternary ammonium salts. Examples of heterocycloalkyl include, but are not limited to: aziridinyl, azetidin-1-yl, N-alkylazetidin-3-yl, tetrahydrofuran-2-yl, tetrahydrofuran-3-yl, morpholin-4-yl, thiomorpholin-4-yl, thiomorpholin-S-oxide-4-yl, piperidin-1-yl, N-alkylpiperidin-4-yl, pyrrolidin-1-yl, N-alkylpyrrolidin-2-yl, piperazin-1-yl, 4-alkylpiperazin-1-yl and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, i-PrO, n-PrO, i-BuO, n-BuO and t-BuO.

Unless otherwise specified, "aryl" refers to an aromatic hydrocarbon group, and it is monocyclic or polycyclic; for example, a monocyclic aryl ring may be fused with one or more carbocyclic aromatic groups. Examples of aryl include, but are not limited to, phenyl, naphthyl, and phenanthryl.

Unless otherwise specified, "heteroaryl" refers to an aromatic group containing one or more heteroatoms (O, S or N), and it is monocyclic or polycyclic; for example, a monocyclic heteroaryl ring may be fused with one or more carbocyclic aromatic groups or other monocyclic heterocyclyl groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, furyl, thienyl, isoxazolyl, thiazolyl, oxazolyl, isothiazolyl, pyrrolyl, indolyl, benzimidazolyl, benzofuryl, benzothiazolyl, benzothienyl, benzoxazolyl, benzopyridyl, and pyrrolopyrimidinyl.

Unless otherwise specified, "alkenyl" refers to an unsaturated aliphatic hydrocarbon group containing carbon-carbon double bonds, including linear or branched groups containing 1 to 14 carbon atoms. Lower alkenyls containing 1 to 4 carbon atoms, such as vinyl, 1-propenyl, 1-butenyl or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkenyls containing 1 to 4 carbon atoms, such as ethynyl, 1-propynyl or 1-butynyl, are preferred.

Unless otherwise specified, the term "halogen substituted" or "halogen" by itself or as part of another substituent refers to a fluorine, chlorine, bromine or iodine atom. Further, "haloalkyl" is intended to include monohaloalkyl or polyhaloalkyl. For example, "halogenated C1-C3 alkyl" is intended to include, but is not limited to, trifluoromethyl, 2, 2, 2-trifluoroethyl, 2-chloropropyl, 3-bromopropyl, and the like.

The term "membered ring" includes any cyclic structure. The term "membered" is intended to refer to the number of backbone atoms that form a ring. For example, cyclohexyl, pyridyl, pyranyl and thiopyranyl are six-membered rings, and cyclopentyl, pyrrolyl, furanyl and thienyl are five-membered rings.

The term "moiety" refers to a specific portion or functional group of a molecule. Chemical moiety is generally considered to be a chemical entity contained in or attached to a molecule. "Optional" or "optionally" means that the subsequently described event or circumstance may, but does not necessarily, occur, and the description includes instances where the event or circumstance occurs and instances where it does not.

Synthesis of the Compounds

Methods for preparing the compounds of general formulas (1) of the present invention are hereafter described in detail, but these specific methods do not limit the present invention in any way.

The compounds of general formulas (1) described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, Advanced Organic Chemistry, 4th Ed., (Wiley 1992); Carey and Sundberg, Advanced Organic Chemistry, 4th Ed., Vols. A and B (Plenum 2000, 2001), and Green and Wuts, Protective Groups in Organic Synthesis, 3rd Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas (1), which are prepared using Method A below:

Method A comprises the following steps: firstly, subjecting a compound A1 to a reaction with $R^2$—Y to generate a compound A2; subjecting the compound A2 to a coupling reaction with a compound A3 to generate a compound A4; further subjecting the compound A4 to a reaction with a compound A5 to generate a target compound A6; and when

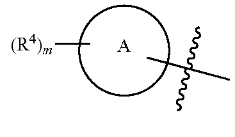

contains protective groups of primary amine and secondary amine, further removal of the protective groups is required to obtain the target compound.

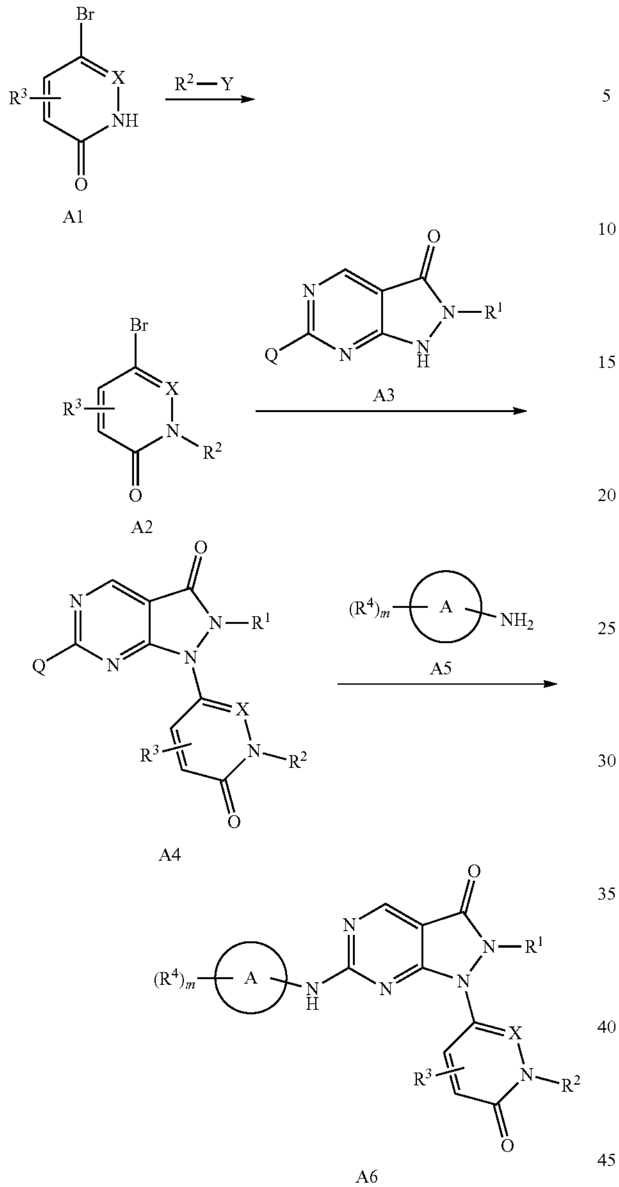

A1

A2

A4

A6

In the above reaction equation, A, $R^1$, $R^2$, $R^3$, $R^4$ and m are as defined above, Y is OH, Br or I, and Q is $CH_3S$, $CH_3SO$, $CH_3SO_2$, Br, Cl, I or the like.

Therapeutic Use

The compounds or compositions described herein are generally useful for inhibiting Wee-1 kinase, and thus may be useful for treating one or more disorders related to Wee-1 kinase activity. Therefore, in certain embodiments, the present invention provides a method for treating a Wee-1 kinase-mediated disorder, which comprises the step of administering to a patient in need thereof the compound of the present invention or a pharmaceutically acceptable composition thereof.

Cancers that can be treated with the compound of the present invention include, but are not limited to, hematological malignancies (leukemias, lymphomas, myelomas including multiple myeloma, myelodysplastic syndrome and myeloproliferative syndrome), solid tumors (carcinomas such as prostate, breast, lung, colon, pancreas, kidney, ovary and soft tissue carcinomas, osteosarcoma and interstitial tumors), and the like.

Various specific aspects, features and advantages of the compounds, methods and pharmaceutical compositions described above will be set forth in detail in the following description, which will make the content of the present invention very clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, melting points were measured using an X-4 melting point apparatus with the thermometer uncalibrated; $^1$H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was volume ratio.

In the present invention, the following abbreviations are used: $CDCl_3$ represents deuterated chloroform; CuI represents cuprous iodide; DCM represents dichloromethane; DIPEA represents diisopropylethylamine; DMF represents dimethylformamide; EA represents ethyl acetate; h represents hour; $K_2CO_3$ represents potassium carbonate; LC-MS represents liquid chromatography-mass spectrometry; m-CPBA represents m-chloroperoxybenzoic acid; MeI ($CH_3I$) represents methyl iodide; mL represents milliliter; MeOH represents methanol; min represents minute; MS represents mass spectrum; $NaHCO_3$ represents sodium bicarbonate; $Na_2SO_4$ represents sodium sulfate; NMR represents nuclear magnetic resonance; ° C. represents degree Celsius; PE represents petroleum ether; r.t. represents room temperature; TFA represents trifluoroacetic acid; and toluene represents methylbenzene.

Preparation Example 1. Preparation of 2-allyl-1-(1-methyl-6-oxo-1,6-dihydropyridazin-3-yl)-6-(methylthio)-1,2-dihydro-3H-pyrazolo[3,4-d]pyrimidin-3-one (Intermediate B1)

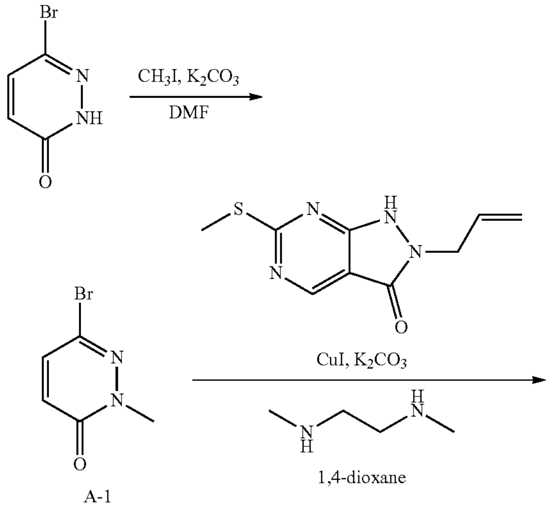

A-1

-continued

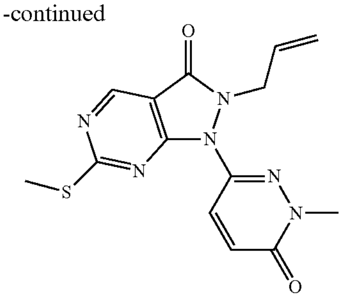

B-1

Step 1: synthesis of Compound A-1

In a 50 mL reaction flask, 6-bromo-3-pyridazinol (826 mg, 4.72 mmol) and $K_2CO_3$ (1.3 g, 9.44 mmol) were added to DMF (10 mL), followed by MeI (0.6 mL, 9.44 mmol). The mixture was stirred at r.t. The reaction was monitored by TLC (PE/EA=1/1). After completion of the reaction, water (50 mL) was added to quench the reaction. The mixture was extracted with EA (50 mL×2) to obtain an organic phase. The organic phase was washed with saturated brine (30 mL), dried over anhydrous $Na_2SO_4$, distilled under reduced pressure to remove EA, and added with cold hydrazine to remove DMF. The residue was purified by column chromatography (PE/EA=3/1) to give compound A-1 (705 mg, 79% yield). ESI-MS m/z: 189 $[M+H]^+$.

Step 2: synthesis of Compound B-1

In a 50 mL reaction flask, compound A-1 (621 mg, 3.55 mmol) and 2-propenyl-6-(methylthio)-1,2-dihydro-3H-pyrazolo[3,4-d]pyrimidin-3-one (607 mg, 2.73 mmol, refer to patent US2019106427 for synthesis) were added and dissolved in dioxane (20 mL), followed by the addition of CuI (520 mg, 2.73 mmol) and $K_2CO_3$ (528 mg, 2.73 mmol). The mixture was heated to 80° C. under nitrogen atmosphere. N,N'-dimethylethylenediamine (0.59 mL, 5.46 mmol) was added. The reaction system was heated to 95° C. and stirred. The reaction was monitored by TLC (PE/EA=1/1). After completion of the reaction, the reaction flask was cooled to room temperature. The mixture was distilled under reduced pressure and extracted with EA (50 mL×2) to obtain an organic phase. The organic phase was washed with saturated brine (50 mL), dried over anhydrous $Na_2SO_4$, and distilled under reduced pressure. The residue was purified by column chromatography (PE/EA=2/1) to give compound B-1 (309 mg, yield 34%). ESI-MS m/z: 333 $[M+H]^+$.

By the procedures similar to those in the synthesis of compound B-1, the following intermediates B2-B45 were obtained:

TABLE 1

| Structural formulas of intermediates B2-B45 | | |
|---|---|---|
| Intermediate | Compound structure | $(M + H)^+$ |
| B-2 | 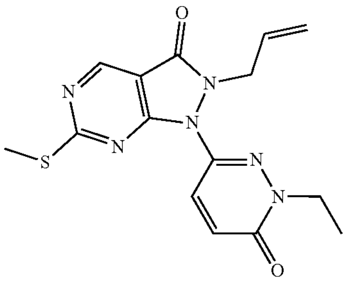 [SMILES: C=CCn1c(=O)c2cnc(SC)nc2n1-c1ccc(=O)n(CC)n1] | 345 |

TABLE 1-continued

| Structural formulas of intermediates B2-B45 | | |
|---|---|---|
| Intermediate | Compound structure | $(M + H)^+$ |
| B-3 | 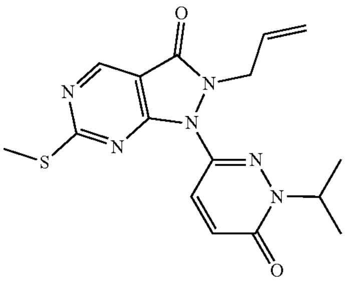 [SMILES: C=CCn1c(=O)c2cnc(SC)nc2n1-c1ccc(=O)n(C(C)C)n1] | 359 |
| B-4 | 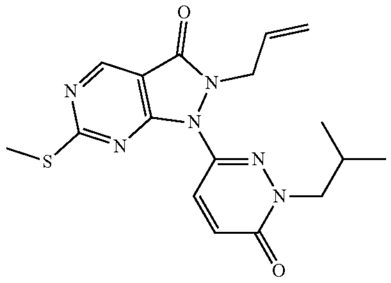 [SMILES: C=CCn1c(=O)c2cnc(SC)nc2n1-c1ccc(=O)n(CC(C)C)n1] | 373 |
| B-5 | 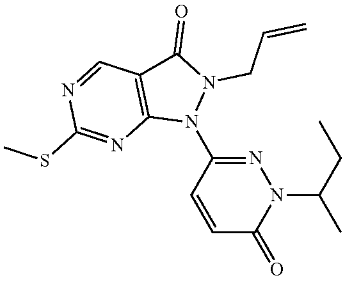 [SMILES: C=CCn1c(=O)c2cnc(SC)nc2n1-c1ccc(=O)n(C(C)CC)n1] | 373 |
| B-6 | 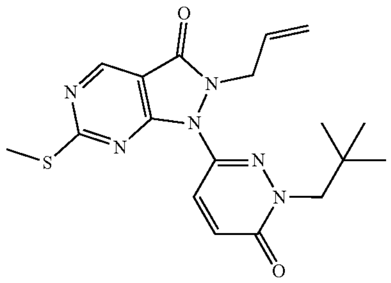 [SMILES: C=CCn1c(=O)c2cnc(SC)nc2n1-c1ccc(=O)n(CC(C)(C)C)n1] | 387 |
| B-7 | 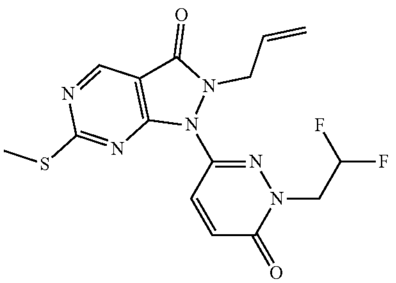 [SMILES: C=CCn1c(=O)c2cnc(SC)nc2n1-c1ccc(=O)n(CC(F)F)n1] | 381 |

TABLE 1-continued
| Structural formulas of intermediates B2-B45 | | |
|---|---|---|
| Intermediate | Compound structure | (M + H)$^+$ |
| B-8 | 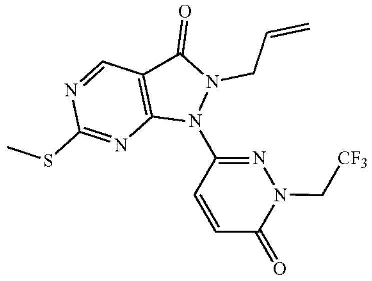 [SMILES: C=CCn1c(=O)c2cnc(SC)nc2n1-c1ccc(=O)n(CC(F)(F)F)n1] | 399 |
| B-9 | 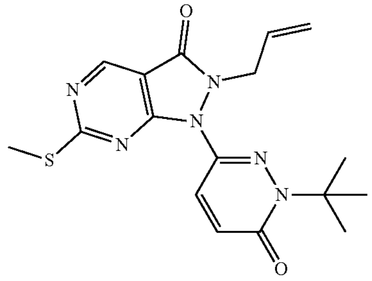 [SMILES: C=CCn1c(=O)c2cnc(SC)nc2n1-c1ccc(=O)n(C(C)(C)C)n1] | 373 |
| B-10 | 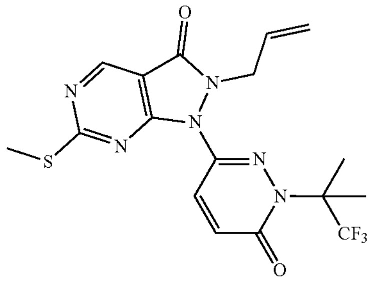 [SMILES: C=CCn1c(=O)c2cnc(SC)nc2n1-c1ccc(=O)n(C(C)(C)C(F)(F)F)n1] | 427 |
| B-11 | 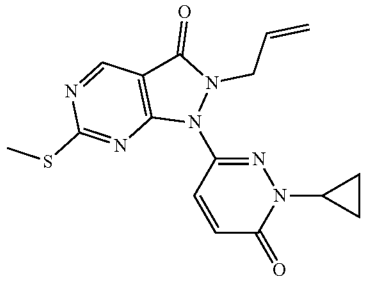 [SMILES: C=CCn1c(=O)c2cnc(SC)nc2n1-c1ccc(=O)n(C2CC2)n1] | 357 |
| B-12 | 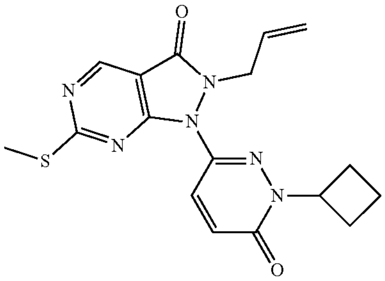 [SMILES: C=CCn1c(=O)c2cnc(SC)nc2n1-c1ccc(=O)n(C2CCC2)n1] | 371 |
TABLE 1-continued
| Structural formulas of intermediates B2-B45 | | |
|---|---|---|
| Intermediate | Compound structure | (M + H)$^+$ |
| B-13 | 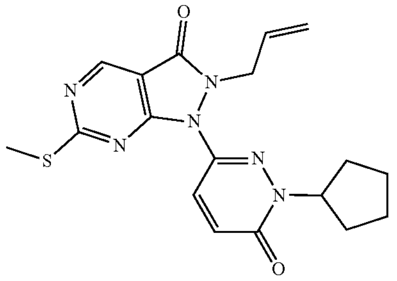 [SMILES: C=CCn1c(=O)c2cnc(SC)nc2n1-c1ccc(=O)n(C2CCCC2)n1] | 385 |
| B-14 | 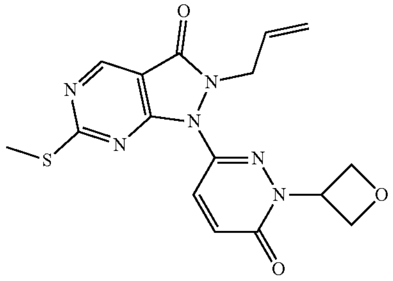 [SMILES: C=CCn1c(=O)c2cnc(SC)nc2n1-c1ccc(=O)n(C2COC2)n1] | 373 |
| B-15 | 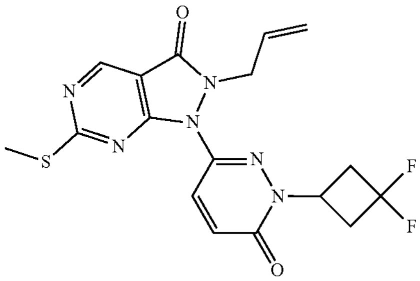 [SMILES: C=CCn1c(=O)c2cnc(SC)nc2n1-c1ccc(=O)n(C2CC(F)(F)C2)n1] | 407 |
| B-16 | 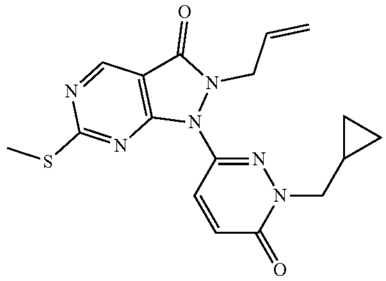 [SMILES: C=CCn1c(=O)c2cnc(SC)nc2n1-c1ccc(=O)n(CC2CC2)n1] | 371 |
| B-17 | 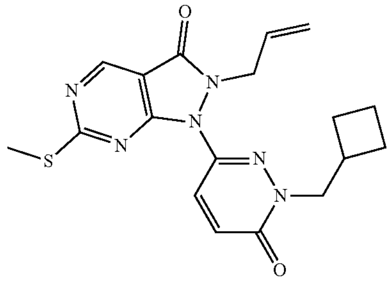 [SMILES: C=CCn1c(=O)c2cnc(SC)nc2n1-c1ccc(=O)n(CC2CCC2)n1] | 385 |

TABLE 1-continued
| Structural formulas of intermediates B2-B45 | | |
|---|---|---|
| Inter-mediate | Compound structure | $(M + H)^+$ |
| B-18 | 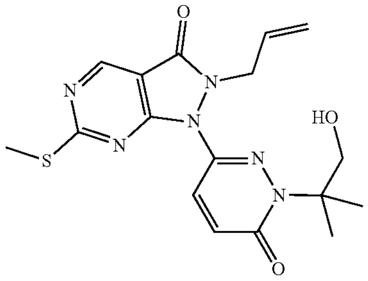 [SMILES: C=CCn1c(=O)c2cnc(SC)nc2n1-c1ccc(=O)n(C(C)(C)CO)n1] | 389 |
| B-19 | 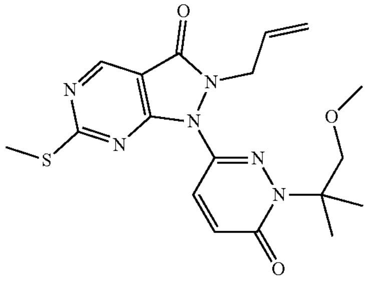 [SMILES: C=CCn1c(=O)c2cnc(SC)nc2n1-c1ccc(=O)n(C(C)(C)COC)n1] | 403 |
| B-20 | 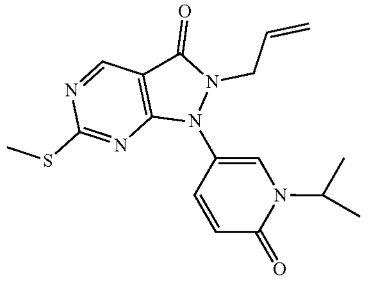 [SMILES: C=CCn1c(=O)c2cnc(SC)nc2n1-c1ccc(=O)n(C(C)C)c1] | 358 |
| B-21 | 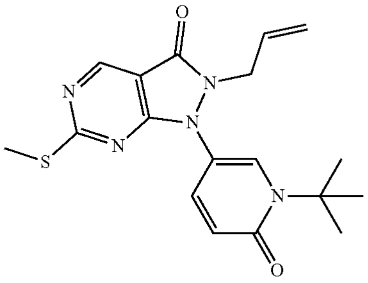 [SMILES: C=CCn1c(=O)c2cnc(SC)nc2n1-c1ccc(=O)n(C(C)(C)C)c1] | 372 |
| B-22 | 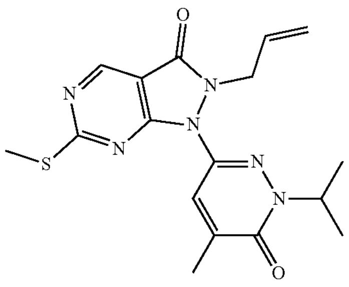 [SMILES: C=CCn1c(=O)c2cnc(SC)nc2n1-c1cc(C)c(=O)n(C(C)C)n1] | 373 |
TABLE 1-continued
| Structural formulas of intermediates B2-B45 | | |
|---|---|---|
| Inter-mediate | Compound structure | $(M + H)^+$ |
| B-23 | 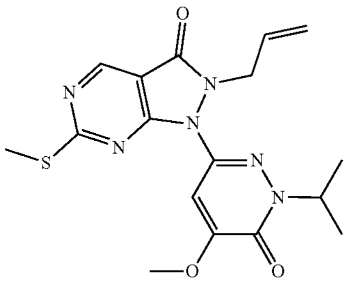 [SMILES: C=CCn1c(=O)c2cnc(SC)nc2n1-c1cc(OC)c(=O)n(C(C)C)n1] | 389 |
| B-24 | 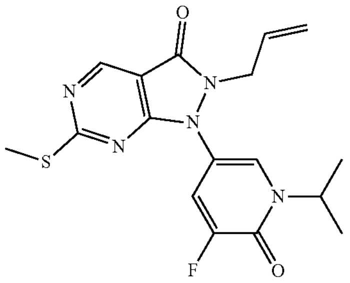 [SMILES: C=CCn1c(=O)c2cnc(SC)nc2n1-c1cc(F)c(=O)n(C(C)C)c1] | 376 |
| B-25 | 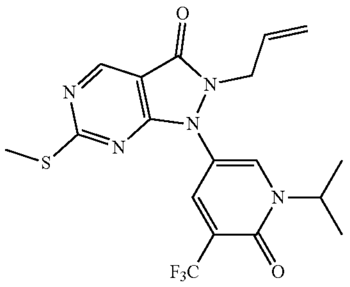 [SMILES: C=CCn1c(=O)c2cnc(SC)nc2n1-c1cc(C(F)(F)F)c(=O)n(C(C)C)c1] | 426 |
| B-26 | 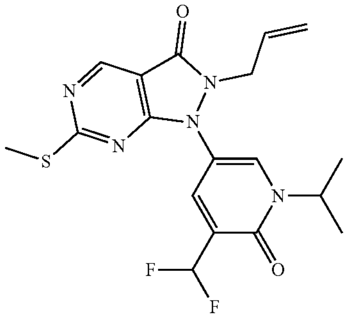 [SMILES: C=CCn1c(=O)c2cnc(SC)nc2n1-c1cc(C(F)F)c(=O)n(C(C)C)c1] | 408 |
| B-27 | 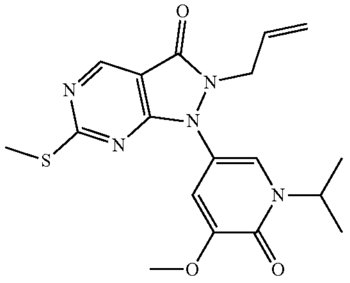 [SMILES: C=CCn1c(=O)c2cnc(SC)nc2n1-c1cc(OC)c(=O)n(C(C)C)c1] | 388 |

TABLE 1-continued
Structural formulas of intermediates B2-B45
| Intermediate | Compound structure | (M + H)+ |
| --- | --- | --- |
| B-28 | 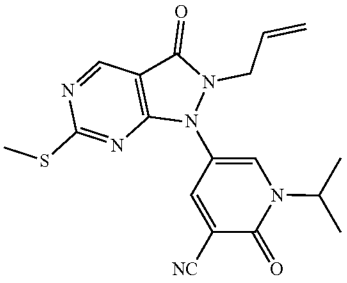 [SMILES: C=CCn1c(=O)c2cnc(SC)nc2n1-c1cc(C#N)c(=O)n(C(C)C)c1] | 383 |
| B-29 | 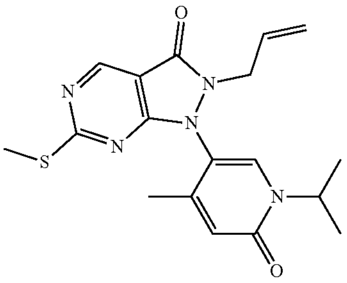 [SMILES: C=CCn1c(=O)c2cnc(SC)nc2n1-c1cn(C(C)C)c(=O)cc1C] | 372 |
| B-30 | 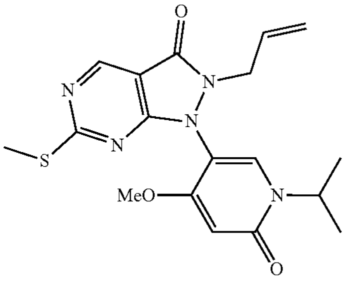 [SMILES: C=CCn1c(=O)c2cnc(SC)nc2n1-c1cn(C(C)C)c(=O)cc1OC] | 388 |
| B-31 | 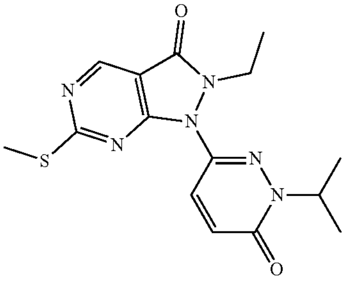 [SMILES: CCn1c(=O)c2cnc(SC)nc2n1-c1ccc(=O)n(C(C)C)n1] | 347 |
| B-32 | 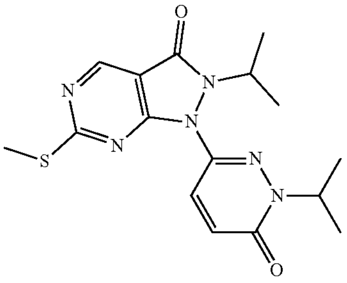 [SMILES: CSc1ncc2c(=O)n(C(C)C)n(-c3ccc(=O)n(C(C)C)n3)c2n1] | 361 |
TABLE 1-continued
Structural formulas of intermediates B2-B45
| Intermediate | Compound structure | (M + H)+ |
| --- | --- | --- |
| B-33 | 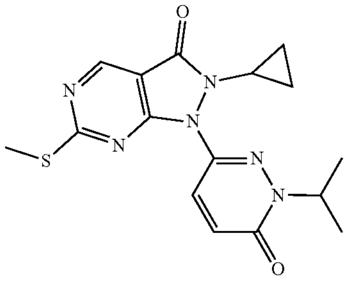 [SMILES: CSc1ncc2c(=O)n(C3CC3)n(-c3ccc(=O)n(C(C)C)n3)c2n1] | 359 |
| B-34 | 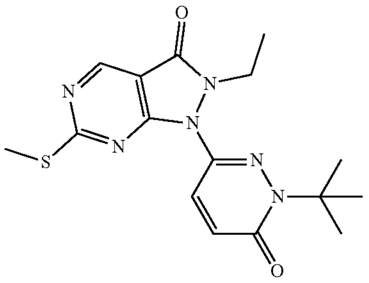 [SMILES: CCn1c(=O)c2cnc(SC)nc2n1-c1ccc(=O)n(C(C)(C)C)n1] | 361 |
| B-35 | 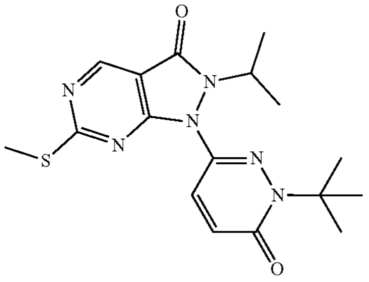 [SMILES: CSc1ncc2c(=O)n(C(C)C)n(-c3ccc(=O)n(C(C)(C)C)n3)c2n1] | 375 |
| B-36 | 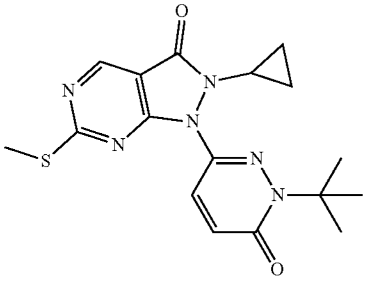 [SMILES: CSc1ncc2c(=O)n(C3CC3)n(-c3ccc(=O)n(C(C)(C)C)n3)c2n1] | 373 |
| B-37 | 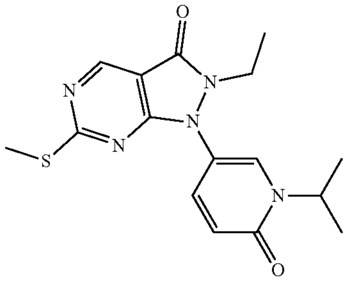 [SMILES: CCn1c(=O)c2cnc(SC)nc2n1-c1ccc(=O)n(C(C)C)c1] | 346 |

TABLE 1-continued
| Structural formulas of intermediates B2-B45 | | |
|---|---|---|
| Inter-mediate | Compound structure | (M + H)$^+$ |
| B-38 | 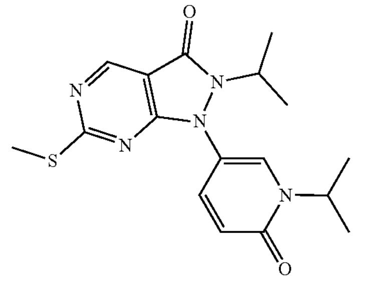 [SMILES: CSc1ncc2c(=O)n(C(C)C)n(-c3ccc(=O)n(C(C)C)c3)c2n1] | 360 |
| B-39 | 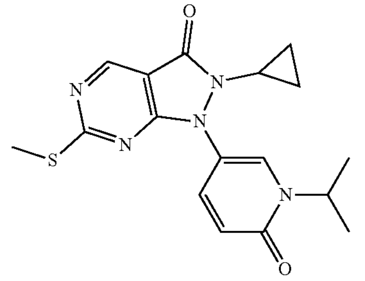 [SMILES: CSc1ncc2c(=O)n(C3CC3)n(-c3ccc(=O)n(C(C)C)c3)c2n1] | 358 |
| B-40 | 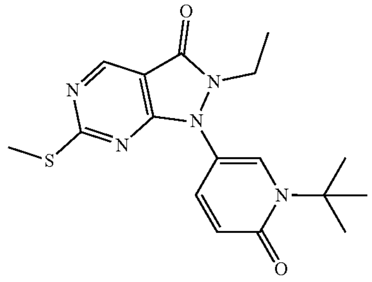 [SMILES: CCn1c(=O)c2cnc(SC)nc2n1-c1ccc(=O)n(C(C)(C)C)c1] | 360 |
| B-41 | 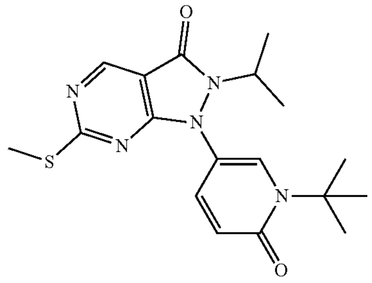 [SMILES: CSc1ncc2c(=O)n(C(C)C)n(-c3ccc(=O)n(C(C)(C)C)c3)c2n1] | 374 |
| B-42 | 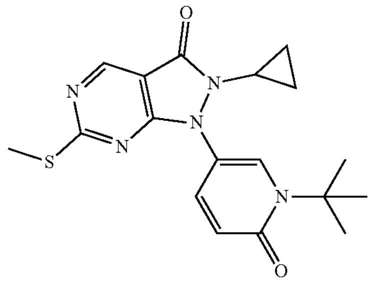 [SMILES: CSc1ncc2c(=O)n(C3CC3)n(-c3ccc(=O)n(C(C)(C)C)c3)c2n1] | 372 |
| B-43 | 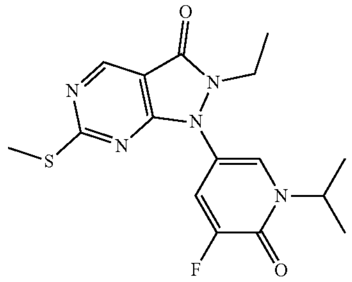 [SMILES: CCn1c(=O)c2cnc(SC)nc2n1-c1cc(F)c(=O)n(C(C)C)c1] | 364 |
| B-44 | 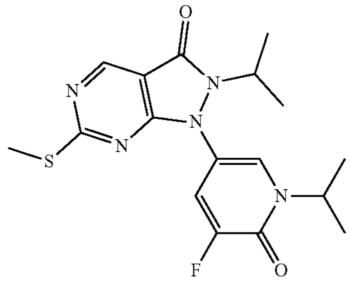 [SMILES: CSc1ncc2c(=O)n(C(C)C)n(-c3cc(F)c(=O)n(C(C)C)c3)c2n1] | 378 |
| B-45 | 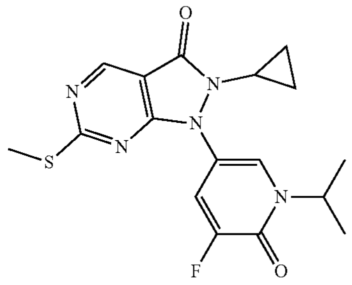 [SMILES: CSc1ncc2c(=O)n(C3CC3)n(-c3cc(F)c(=O)n(C(C)C)c3)c2n1] | 376 |
Example 1. Synthesis of 2-allyl-1-(1-methyl-6-oxo-1,6-dihydropyridazin-3-yl)-6-((4-(4-methylpiperazin-1-yl)phenyl)amino)-1,2-dihydro-3H-pyrazolo[3,4-d]pyrimidin-3-one (Compound 1)
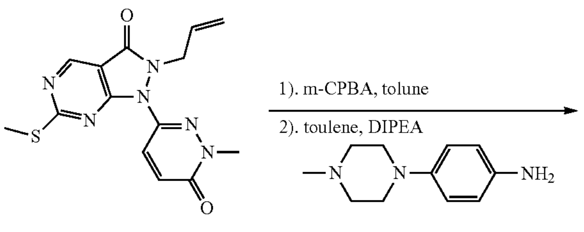
B-1

-continued

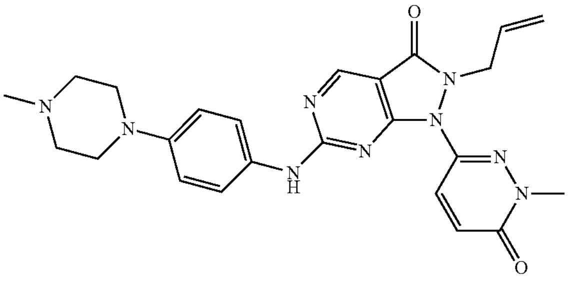

1

In a 50 mL reaction flask, compound B-1 (100 mg, 0.3 mmol) was dissolved in toluene (10 mL), followed by addition of m-CPBA (76 mg, 0.33 mmol). The mixture was stirred at r.t. for 1 h. DIPEA (0.2 mL, 1.58 mmol) and 4-(4-methylpiperazine)aniline (74.6 mg, 0.39 mmol) were added. The mixture was stirred at room temperature for 3 h. The reaction was monitored by TLC (DCM/MeOH=10/1). After completion of the reaction, the mixture was extracted with EA (30 mL×2) to obtain an organic phase. The organic phase was washed with saturated brine (30 mL), dried over anhydrous $Na_2SO_4$, and distilled under reduced pressure. The residue was purified by column chromatography (DCM/MeOH=100/1) to give compound 1 (75 mg, yield 54%).

$^1$H NMR (400 MHz, $CDCl_3$) δ 8.80 (s, 1H), 7.99 (s, 1H), 7.87 (d, J=9.8 Hz, 1H), 7.43-7.31 (m, 2H), 7.03 (d, J=9.9 Hz, 1H), 6.96-6.84 (m, 2H), 5.68 (ddt, J=16.6, 10.1, 6.3 Hz, 1H), 5.15-4.95 (m, 2H), 4.60 (d, J=6.3 Hz, 2H), 3.79 (s, 3H), 3.25-3.13 (m, 4H), 2.64-2.56 (m, 4H), 2.36 (s, 3H); ESI-MS m/z: 474 $[M+H]^+$.

Examples 2-30. Synthesis of Compounds 2-30

By the procedures similar to those in the synthesis of compound 1, the target compounds 2-30 in Table 2 can be obtained with B2-B30 as starting materials.

TABLE 2

Structures of compounds 2-30

| Compound | Compound structure | MS $(M + H)^+$ |
|---|---|---|
| 2 | 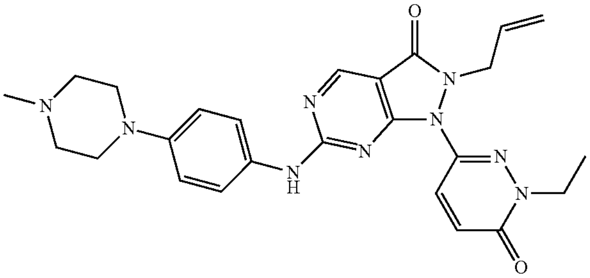 [SMILES: C=CCn1c(=O)c2cnc(Nc3ccc(N4CCN(C)CC4)cc3)nc2n1-c1ccc(=O)n(CC)n1] | 488 |
| 3 | 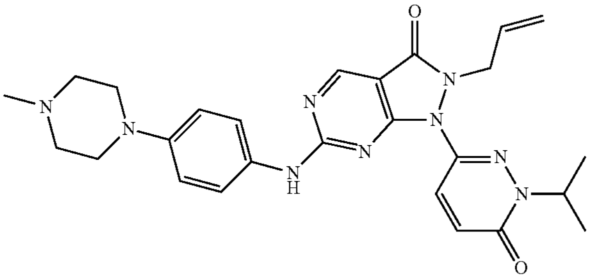 [SMILES: C=CCn1c(=O)c2cnc(Nc3ccc(N4CCN(C)CC4)cc3)nc2n1-c1ccc(=O)n(C(C)C)n1] | 571 |
| 4 | 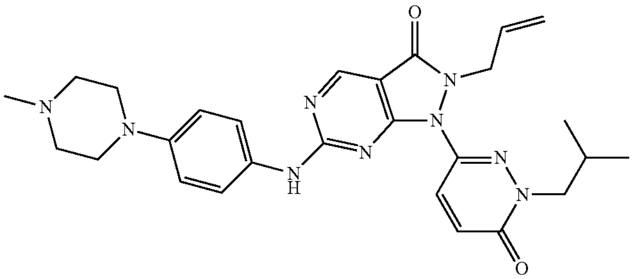 [SMILES: C=CCn1c(=O)c2cnc(Nc3ccc(N4CCN(C)CC4)cc3)nc2n1-c1ccc(=O)n(CC(C)C)n1] | 516 |

TABLE 2-continued
| Compound | Compound structure | MS $(M + H)^+$ |
|---|---|---|
| Structures of compounds 2-30 | | |
| 5 | 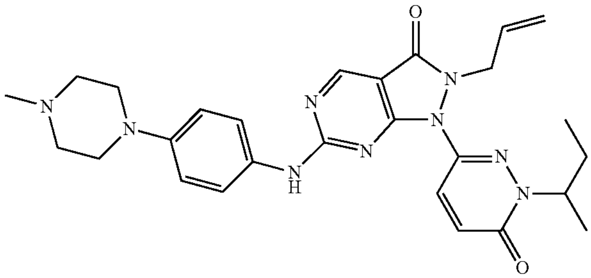 [SMILES: C=CCn1c(=O)c2cnc(Nc3ccc(N4CCN(C)CC4)cc3)nc2n1-c1ccc(=O)n(C(C)CC)n1] | 516 |
| 6 | 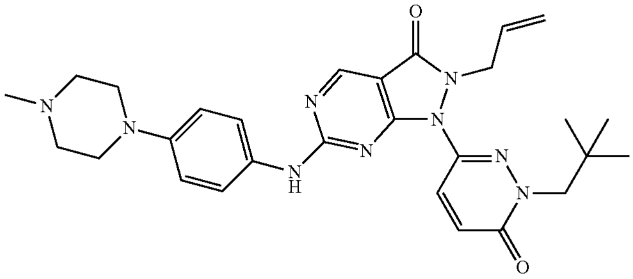 [SMILES: C=CCn1c(=O)c2cnc(Nc3ccc(N4CCN(C)CC4)cc3)nc2n1-c1ccc(=O)n(CC(C)(C)C)n1] | 530 |
| 7 | 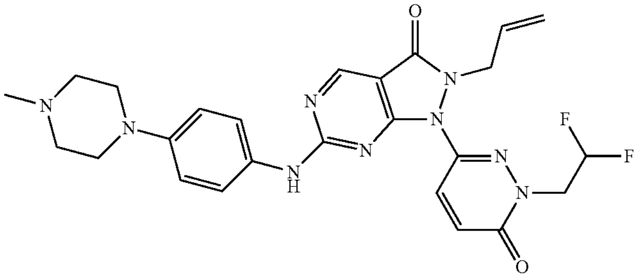 [SMILES: C=CCn1c(=O)c2cnc(Nc3ccc(N4CCN(C)CC4)cc3)nc2n1-c1ccc(=O)n(CC(F)F)n1] | 524 |
| 8 | 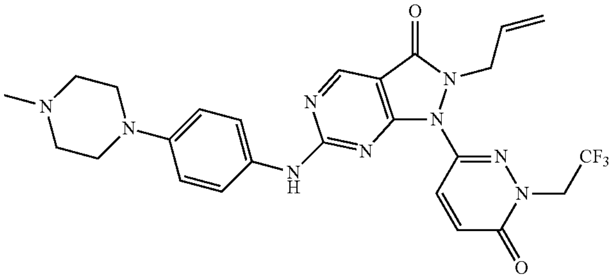 [SMILES: C=CCn1c(=O)c2cnc(Nc3ccc(N4CCN(C)CC4)cc3)nc2n1-c1ccc(=O)n(CC(F)(F)F)n1] | 542 |
| 9 | 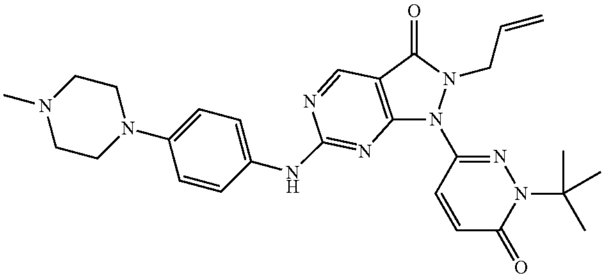 [SMILES: C=CCn1c(=O)c2cnc(Nc3ccc(N4CCN(C)CC4)cc3)nc2n1-c1ccc(=O)n(C(C)(C)C)n1] | 516 |

TABLE 2-continued
Structures of compounds 2-30
| Compound | Compound structure | MS (M + H)+ |
|---|---|---|
| 10 | 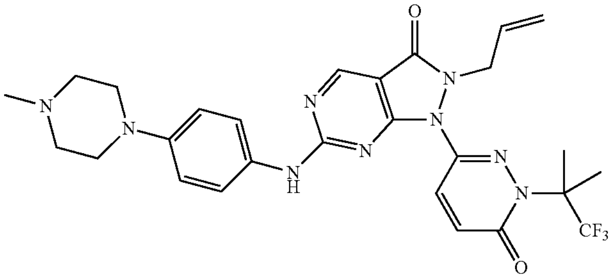 [SMILES: C=CCn1c(=O)c2cnc(Nc3ccc(N4CCN(C)CC4)cc3)nc2n1-c1ccc(=O)n(C(C)(C)C(F)(F)F)n1] | 570 |
| 11 | 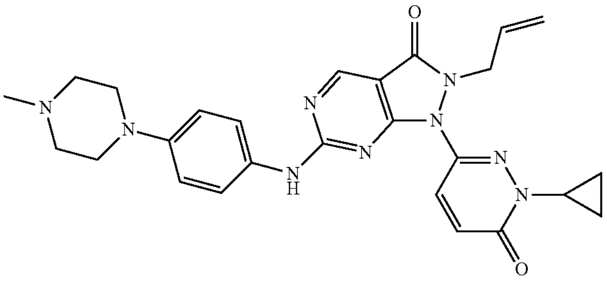 [SMILES: C=CCn1c(=O)c2cnc(Nc3ccc(N4CCN(C)CC4)cc3)nc2n1-c1ccc(=O)n(C2CC2)n1] | 500 |
| 12 | 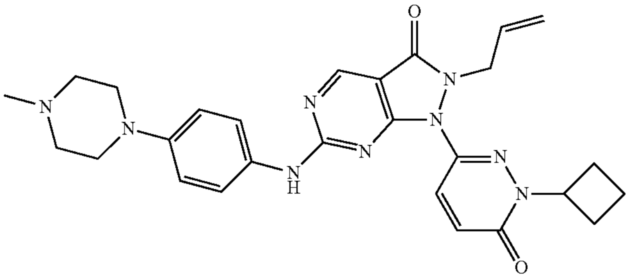 [SMILES: C=CCn1c(=O)c2cnc(Nc3ccc(N4CCN(C)CC4)cc3)nc2n1-c1ccc(=O)n(C2CCC2)n1] | 514 |
| 13 | 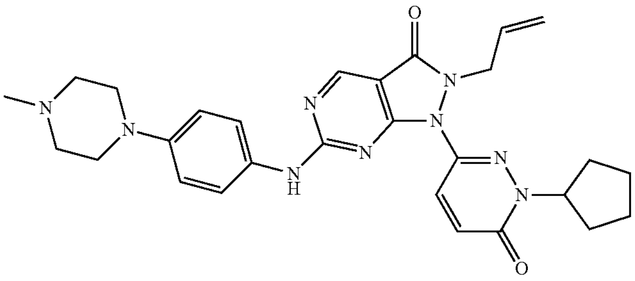 [SMILES: C=CCn1c(=O)c2cnc(Nc3ccc(N4CCN(C)CC4)cc3)nc2n1-c1ccc(=O)n(C2CCCC2)n1] | 528 |
| 14 | 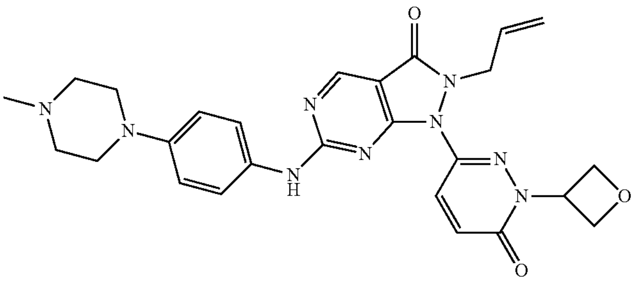 [SMILES: C=CCn1c(=O)c2cnc(Nc3ccc(N4CCN(C)CC4)cc3)nc2n1-c1ccc(=O)n(C2COC2)n1] | 516 |

TABLE 2-continued
| Structures of compounds 2-30 | | |
|---|---|---|
| Compound | Compound structure | MS (M + H)+ |
| 15 | 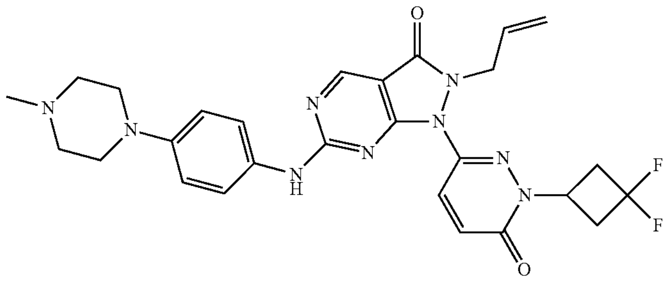 [SMILES: C=CCn1c(=O)c2cnc(Nc3ccc(N4CCN(C)CC4)cc3)nc2n1-c1ccc(=O)n(C2CC(F)(F)C2)n1] | 550 |
| 16 | 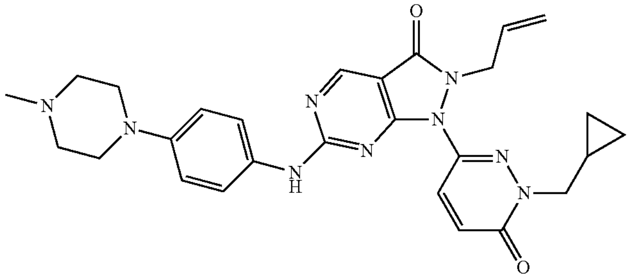 [SMILES: C=CCn1c(=O)c2cnc(Nc3ccc(N4CCN(C)CC4)cc3)nc2n1-c1ccc(=O)n(CC2CC2)n1] | 514 |
| 17 | 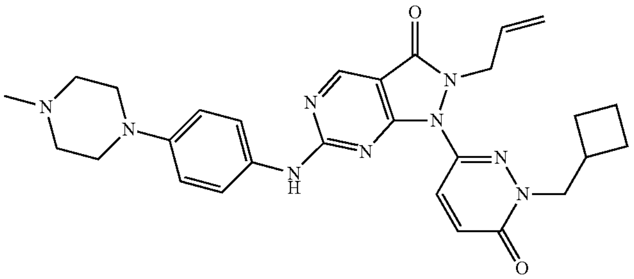 [SMILES: C=CCn1c(=O)c2cnc(Nc3ccc(N4CCN(C)CC4)cc3)nc2n1-c1ccc(=O)n(CC2CCC2)n1] | 528 |
| 18 | 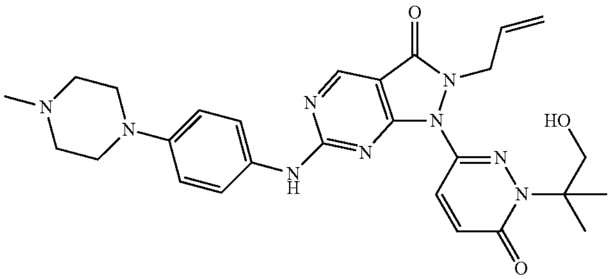 [SMILES: C=CCn1c(=O)c2cnc(Nc3ccc(N4CCN(C)CC4)cc3)nc2n1-c1ccc(=O)n(C(C)(C)CO)n1] | 532 |
| 19 | 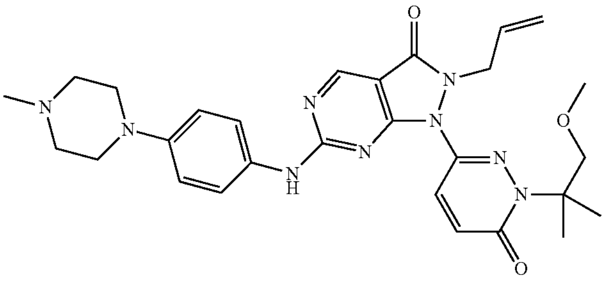 [SMILES: C=CCn1c(=O)c2cnc(Nc3ccc(N4CCN(C)CC4)cc3)nc2n1-c1ccc(=O)n(C(C)(C)COC)n1] | 546 |

TABLE 2-continued
| Structures of compounds 2-30 | | |
|---|---|---|
| Compound | Compound structure | MS (M + H)$^+$ |
| 20 | 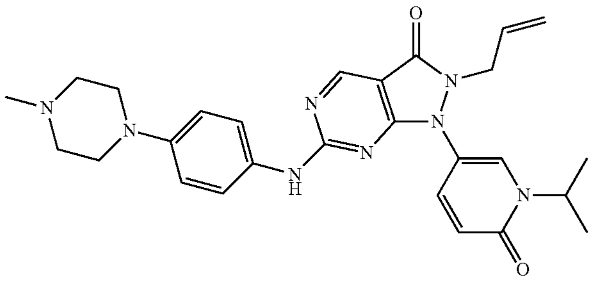 [SMILES: C=CCn1c(=O)c2cnc(Nc3ccc(N4CCN(C)CC4)cc3)nc2n1-c1ccc(=O)n(C(C)C)c1] | 501 |
| 21 | 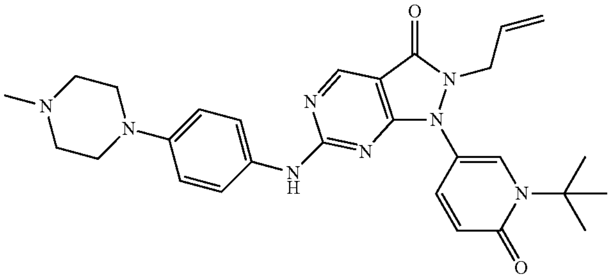 [SMILES: C=CCn1c(=O)c2cnc(Nc3ccc(N4CCN(C)CC4)cc3)nc2n1-c1ccc(=O)n(C(C)(C)C)c1] | 515 |
| 22 | 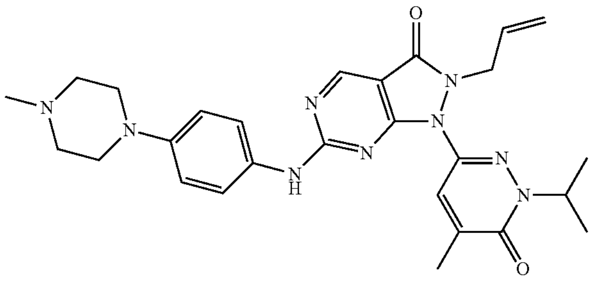 [SMILES: C=CCn1c(=O)c2cnc(Nc3ccc(N4CCN(C)CC4)cc3)nc2n1-c1cc(C)c(=O)n(C(C)C)n1] | 516 |
| 23 | 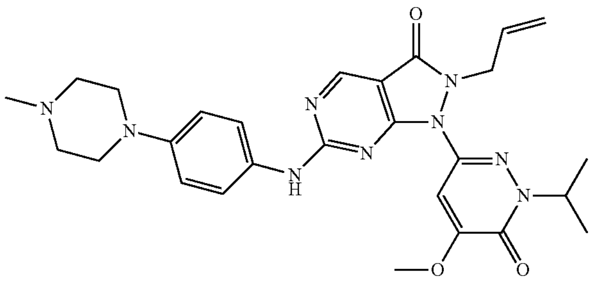 [SMILES: C=CCn1c(=O)c2cnc(Nc3ccc(N4CCN(C)CC4)cc3)nc2n1-c1cc(OC)c(=O)n(C(C)C)n1] | 532 |
| 24 | 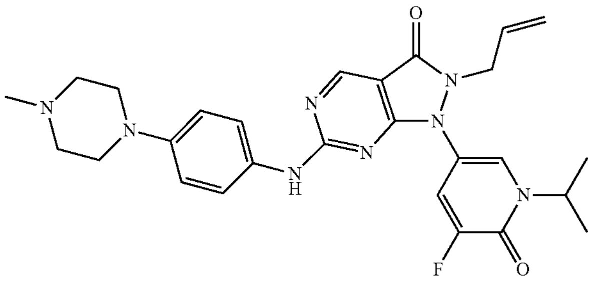 [SMILES: C=CCn1c(=O)c2cnc(Nc3ccc(N4CCN(C)CC4)cc3)nc2n1-c1cc(F)c(=O)n(C(C)C)c1] | 519 |

TABLE 2-continued
| Compound | Compound structure | MS (M + H)+ |
| --- | --- | --- |
| Structures of compounds 2-30 | | |
| 25 | 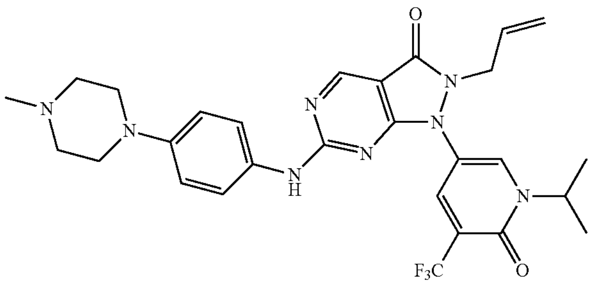 [SMILES: C=CCn1c(=O)c2cnc(Nc3ccc(N4CCN(C)CC4)cc3)nc2n1-c1cc(C(F)(F)F)c(=O)n(C(C)C)c1] | 569 |
| 26 | 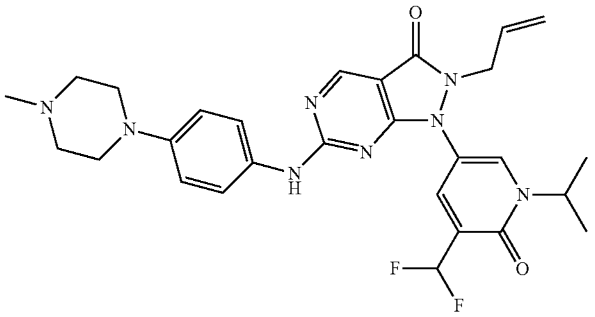 [SMILES: C=CCn1c(=O)c2cnc(Nc3ccc(N4CCN(C)CC4)cc3)nc2n1-c1cc(C(F)F)c(=O)n(C(C)C)c1] | 551 |
| 27 | 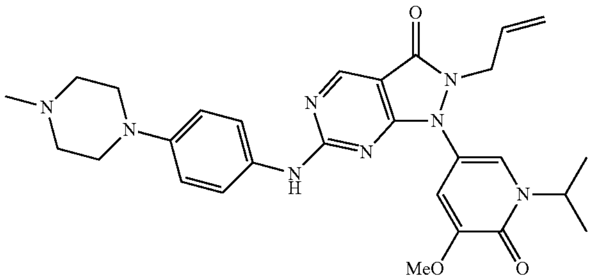 [SMILES: C=CCn1c(=O)c2cnc(Nc3ccc(N4CCN(C)CC4)cc3)nc2n1-c1cc(OC)c(=O)n(C(C)C)c1] | 531 |
| 28 | 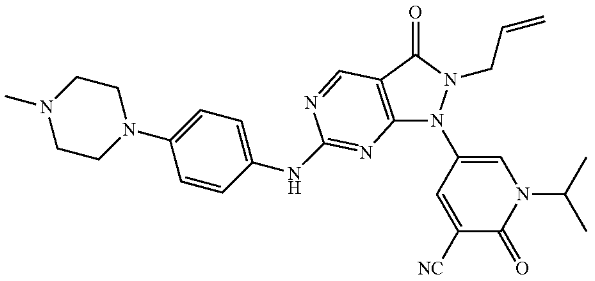 [SMILES: C=CCn1c(=O)c2cnc(Nc3ccc(N4CCN(C)CC4)cc3)nc2n1-c1cc(C#N)c(=O)n(C(C)C)c1] | 526 |
| 29 | 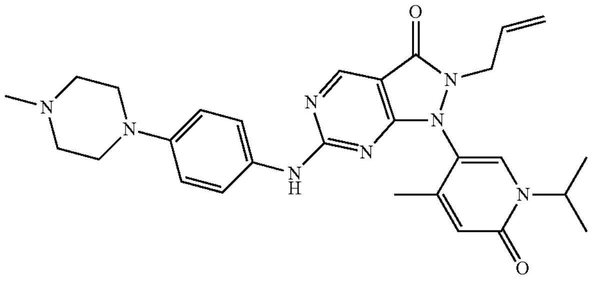 [SMILES: C=CCn1c(=O)c2cnc(Nc3ccc(N4CCN(C)CC4)cc3)nc2n1-c1cn(C(C)C)c(=O)cc1C] | 515 |

TABLE 2-continued

Structures of compounds 2-30

| Compound | Compound structure | MS (M + H)$^+$ |
| --- | --- | --- |
| 30 | 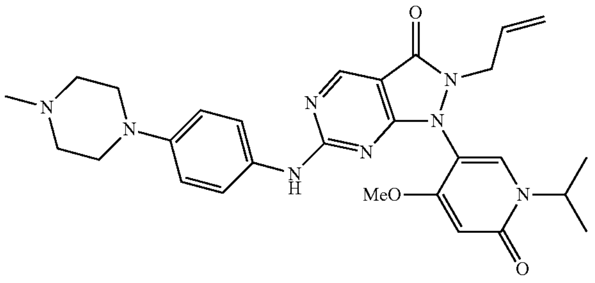 [SMILES: C=CCn1c(=O)c2cnc(Nc3ccc(N4CCN(C)CC4)cc3)nc2n1-c1cn(C(C)C)c(=O)cc1OC] | 531 |

Example 31

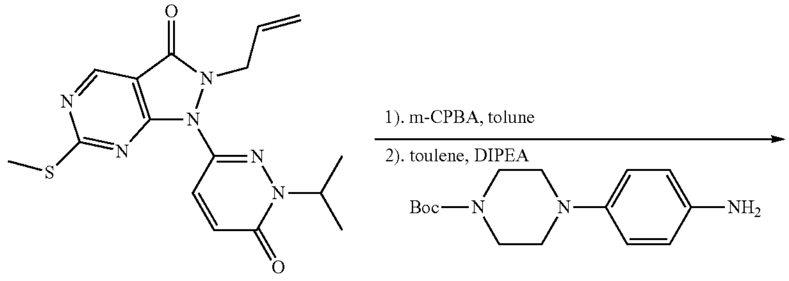

B-3

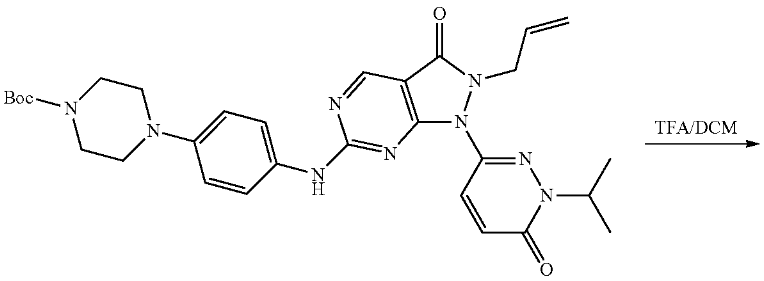

C-1

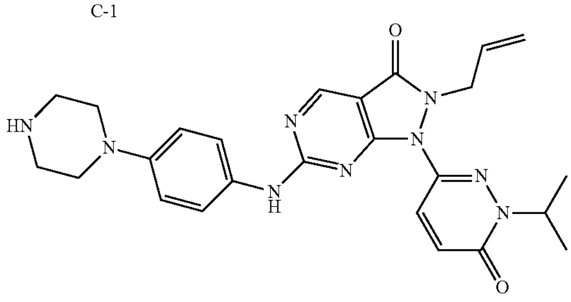

31

Step 1: Synthesis of Compound C-1

In a 50 mL reaction flask, compound B-3 (107 mg, 0.3 mmol) was dissolved in toluene (10 mL), followed by addition of M-CPBA (76 mg, 0.33 mmol). The mixture was stirred at r.t. for 1 h. DIPEA (0.2 mL, 1.58 mmol) and tert-butyl 4-(4-aminobenzene)piperazine-1-carboxylate (100 mg, 0.36 mmol) were added. The mixture was stirred at r.t. for 3 h. The reaction was monitored by TLC (DCM/MeOH=20/1). After completion of the reaction, the mixture was extracted with EA (30 mL×2) to obtain an organic phase. The organic phase was washed with saturated brine (30 mL), dried over anhydrous $Na_2SO_4$, and distilled under reduced pressure. The residue was purified by column chromatography (DCM/MeOH=100/1) to give compound C1 (135 mg, 77% yield). ESI-MS m/z: 588 [M+H]$^+$.

Step 1: synthesis of Compound 31

In a 20 mL reaction flask, compound C-1 (117 mg, 0.2 mmol) was dissolved in DCM (5 mL), followed by the addition of TFA (1 mL) while cooling in an ice salt bath. After addition, the mixture was stirred at r.t. for 3 h. The reaction was monitored by TLC (DCM/MeOH=20/1). After completion of the reaction, the mixture was diluted with DCM (50 mL), adjusted to alkalinity with a saturated $NaHCO_3$ solution, followed by liquid separation. The organic phase was washed with saturated brine (30 mL), dried over anhydrous $Na_2SO_4$, and distilled under reduced pressure. The residue was purified by column chromatography (DCM/MeOH=50/1) to give compound 31 (58 mg, 59% yield).

$^1$H NMR (400 MHz, $CDCl_3$) δ: 8.80 (s, 1H), 7.99 (s, 1H), 7.84 (d, J=9.8 Hz, 1H), 7.43-7.34 (m, 2H), 7.00 (d, J=9.8 Hz, 1H), 6.94-6.87 (m, 2H), 5.66 (ddt, J=16.7, 10.1, 6.4 Hz, 1H), 5.40-5.28 (m, 1H), 5.08 (dd, J=10.1, 1.3 Hz, 1H), 5.00 (dd, J=17.1, 1.4 Hz, 1H), 4.66 (d, J=6.4 Hz, 2H), 3.25-3.14 (m, 4H), 2.60 (t, J=5.0 Hz, 4H), 1.38 (d, J=6.7 Hz, 6H); ESI-MS m/z: 488 [M+H]+.

Examples 32-341: Synthesis of Compounds 32-341

By the procedures similar to those in the synthesis of compounds 1 and 31, the target compounds 32-341 in Table 3 can be obtained with different intermediates in Table 1 as starting materials.

TABLE 3

Structures of compounds 32-34

| Compound | Compound structure | MS $(M + H)^+$ |
| --- | --- | --- |
| 32 | 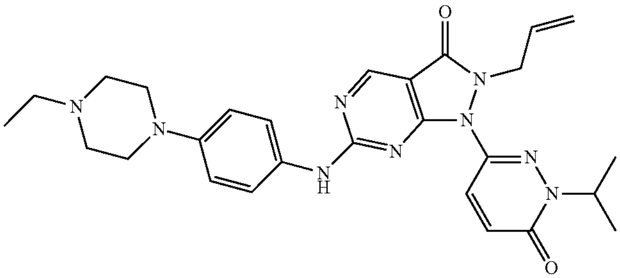 [SMILES: C=CCn1c(=O)c2cnc(Nc3ccc(N4CCN(CC)CC4)cc3)nc2n1-c1ccc(=O)n(C(C)C)n1] | 516 |
| 33 | 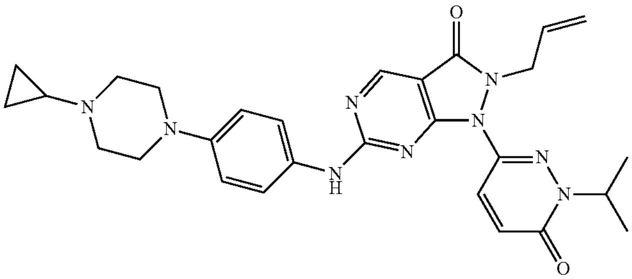 [SMILES: C=CCn1c(=O)c2cnc(Nc3ccc(N4CCN(C5CC5)CC4)cc3)nc2n1-c1ccc(=O)n(C(C)C)n1] | 528 |
| 34 | 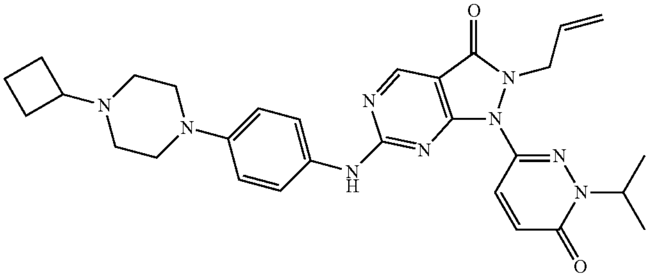 [SMILES: C=CCn1c(=O)c2cnc(Nc3ccc(N4CCN(C5CCC5)CC4)cc3)nc2n1-c1ccc(=O)n(C(C)C)n1] | 542 |
| 35 | 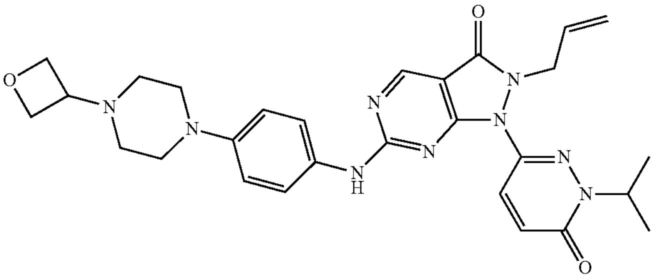 [SMILES: C=CCn1c(=O)c2cnc(Nc3ccc(N4CCN(C5COC5)CC4)cc3)nc2n1-c1ccc(=O)n(C(C)C)n1] | 544 |

TABLE 3-continued
Structures of compounds 32-34
| Compound | Compound structure | MS (M + H)+ |
| --- | --- | --- |
| 36 | 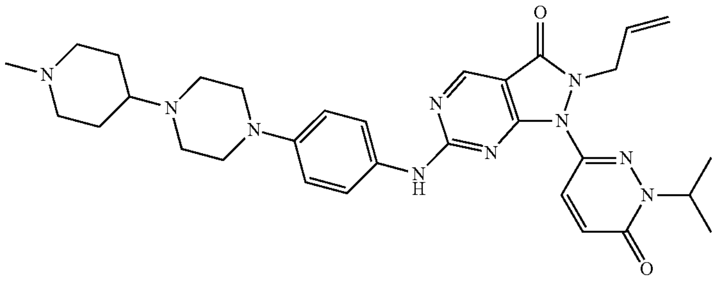 | 585 |
| 37 | 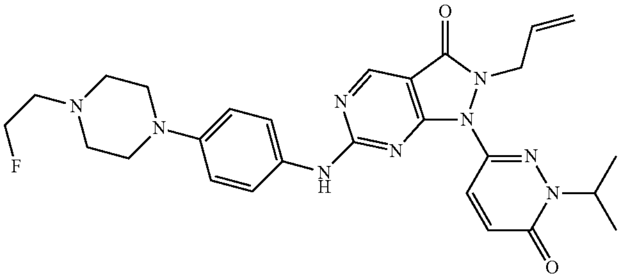 [SMILES: C=CCn1c(=O)c2cnc(Nc3ccc(N4CCN(CCF)CC4)cc3)nc2n1-c1ccc(=O)n(C(C)C)n1] | 534 |
| 38 | 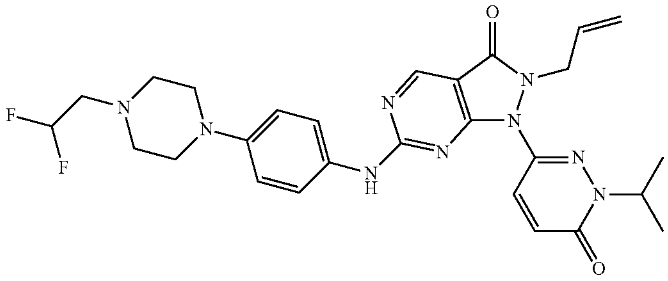 [SMILES: C=CCn1c(=O)c2cnc(Nc3ccc(N4CCN(CC(F)F)CC4)cc3)nc2n1-c1ccc(=O)n(C(C)C)n1] | 552 |
| 39 | 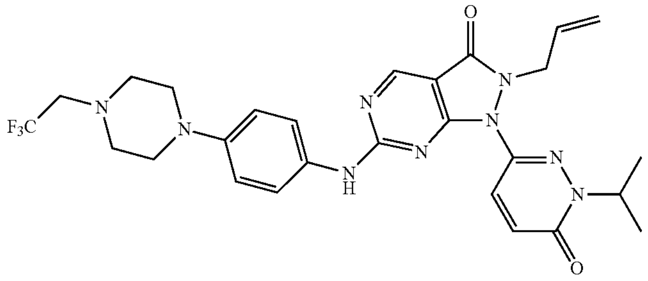 [SMILES: C=CCn1c(=O)c2cnc(Nc3ccc(N4CCN(CC(F)(F)F)CC4)cc3)nc2n1-c1ccc(=O)n(C(C)C)n1] | 570 |
| 40 | 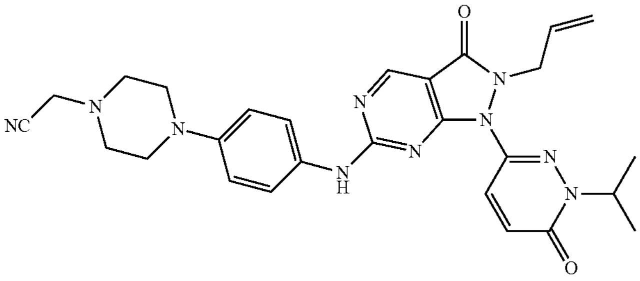 [SMILES: C=CCn1c(=O)c2cnc(Nc3ccc(N4CCN(CC#N)CC4)cc3)nc2n1-c1ccc(=O)n(C(C)C)n1] | 527 |

TABLE 3-continued
| Structures of compounds 32-34 | | |
|---|---|---|
| Compound | Compound structure | MS (M + H)$^+$ |
| 41 | 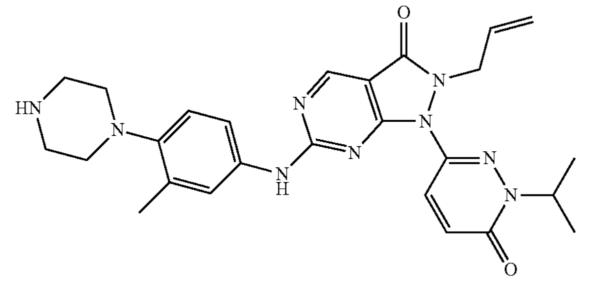 | 502 |
| 42 | 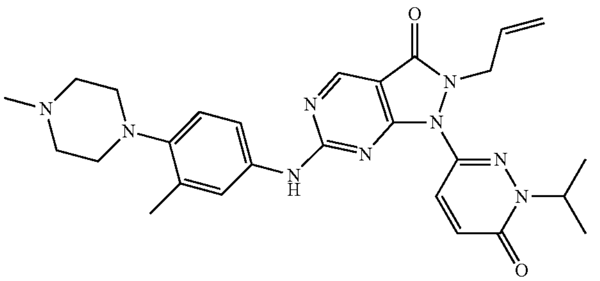 [SMILES: C=CCn1c(=O)c2cnc(Nc3ccc(N4CCN(C)CC4)c(C)c3)nc2n1-c1ccc(=O)n(C(C)C)n1] | 516 |
| 43 | 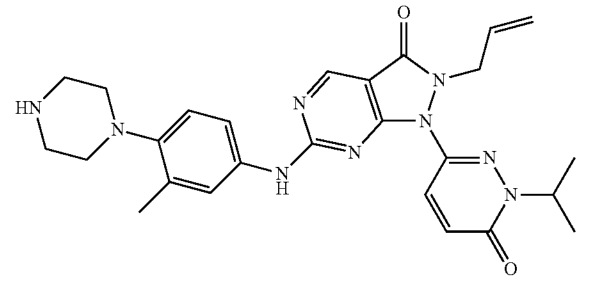 | 502 |
| 44 | 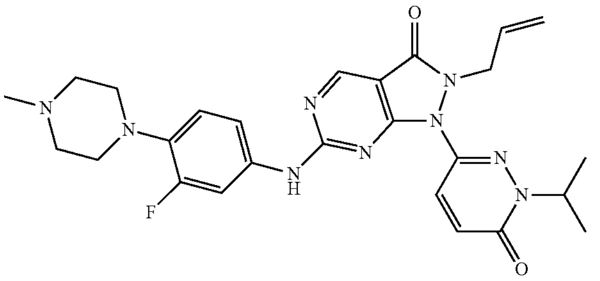 [SMILES: C=CCn1c(=O)c2cnc(Nc3ccc(N4CCN(C)CC4)c(F)c3)nc2n1-c1ccc(=O)n(C(C)C)n1] | 520 |
| 45 | 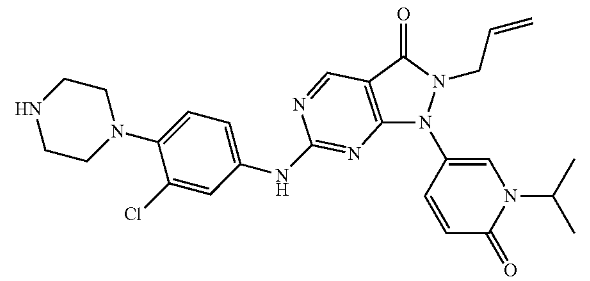 | 521 |

TABLE 3-continued
| Structures of compounds 32-34 | | |
|---|---|---|
| Compound | Compound structure | MS (M + H)$^+$ |
| 46 | 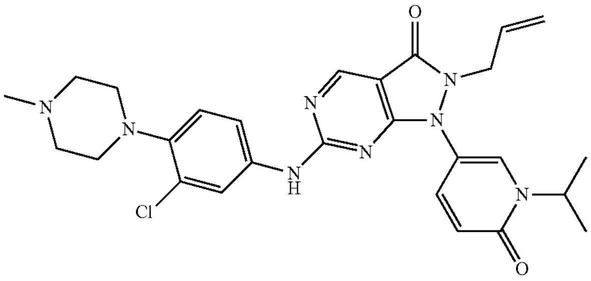 | 535 |
| 47 | 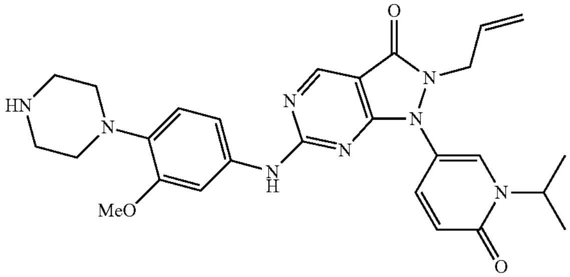 [SMILES: C=CCn1c(=O)c2cnc(Nc3ccc(N4CCNCC4)c(OC)c3)nc2n1-c1ccc(=O)n(C(C)C)c1] | 517 |
| 48 | 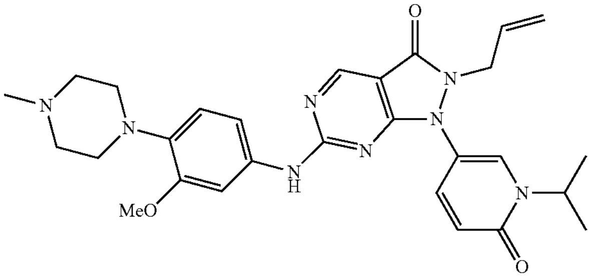 [SMILES: C=CCn1c(=O)c2cnc(Nc3ccc(N4CCN(C)CC4)c(OC)c3)nc2n1-c1ccc(=O)n(C(C)C)c1] | 531 |
| 49 | 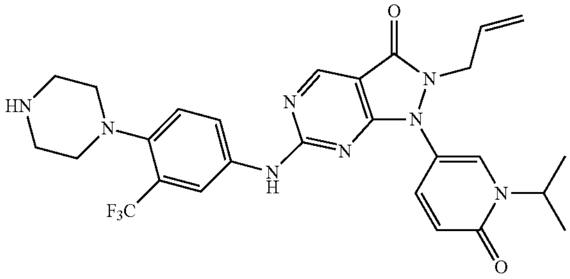 [SMILES: C=CCn1c(=O)c2cnc(Nc3ccc(N4CCNCC4)c(C(F)(F)F)c3)nc2n1-c1ccc(=O)n(C(C)C)c1] | 555 |
| 50 | 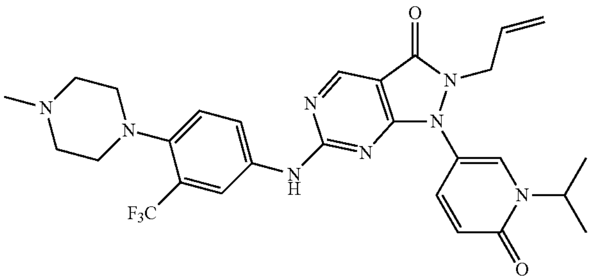 | 569 |

TABLE 3-continued
| Structures of compounds 32-34 | | |
|---|---|---|
| Compound | Compound structure | MS (M + H)$^+$ |
| 51 | 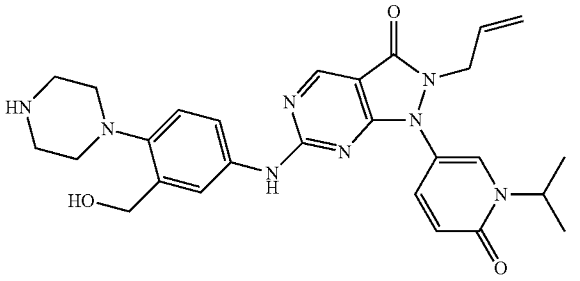 [SMILES: C=CCn1c(=O)c2cnc(Nc3ccc(N4CCNCC4)c(CO)c3)nc2n1-c1ccc(=O)n(C(C)C)c1] | 517 |
| 52 | 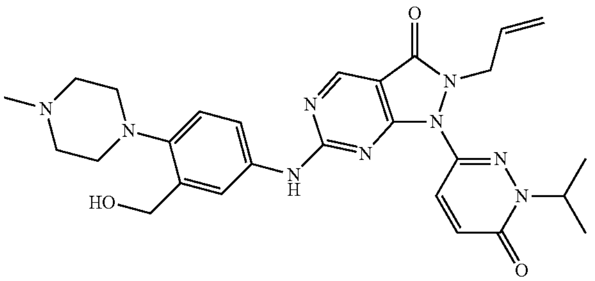 | 532 |
| 53 | 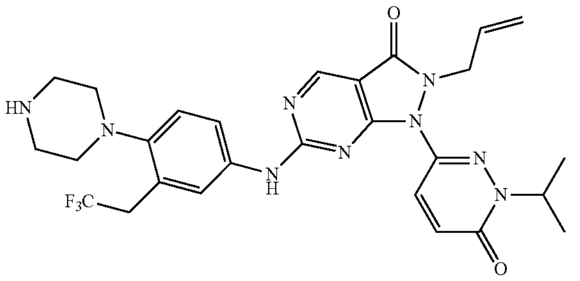 [SMILES: C=CCn1c(=O)c2cnc(Nc3ccc(N4CCNCC4)c(CC(F)(F)F)c3)nc2n1-c1ccc(=O)n(C(C)C)n1] | 570 |
| 54 | 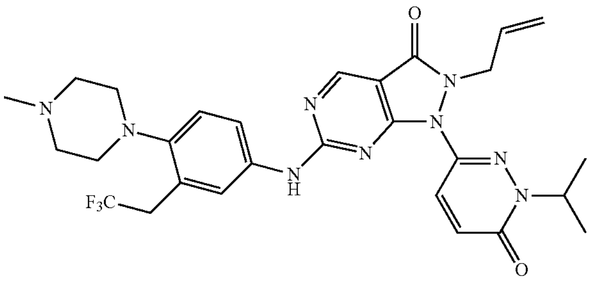 [SMILES: C=CCn1c(=O)c2cnc(Nc3ccc(N4CCN(C)CC4)c(CC(F)(F)F)c3)nc2n1-c1ccc(=O)n(C(C)C)n1] | 584 |
| 55 | 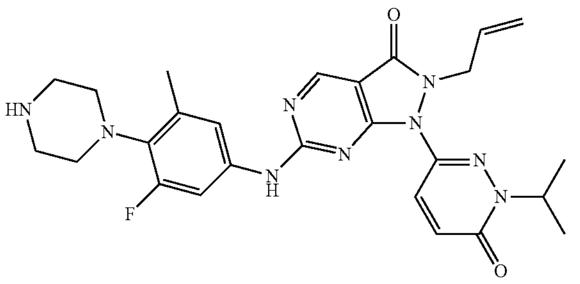 [SMILES: C=CCn1c(=O)c2cnc(Nc3cc(C)c(N4CCNCC4)c(F)c3)nc2n1-c1ccc(=O)n(C(C)C)n1] | 520 |

TABLE 3-continued
| Structures of compounds 32-34 | | |
|---|---|---|
| Compound | Compound structure | MS (M + H)+ |
| 56 | 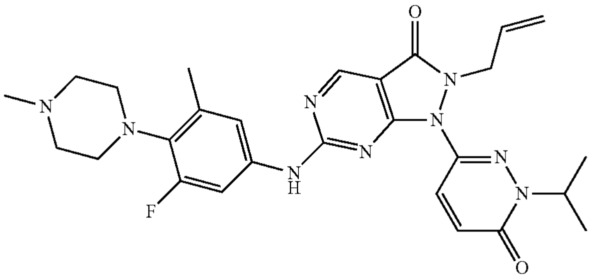 [SMILES: C=CCn1c(=O)c2cnc(Nc3cc(C)c(N4CCN(C)CC4)c(F)c3)nc2n1-c1ccc(=O)n(C(C)C)n1] | 534 |
| 57 | 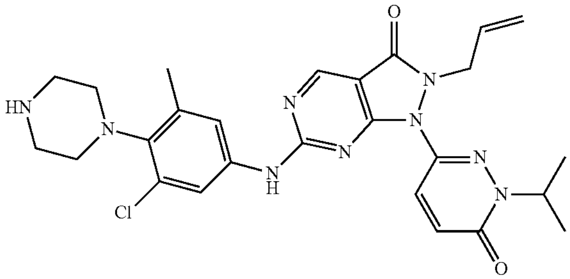 [SMILES: C=CCn1c(=O)c2cnc(Nc3cc(C)c(N4CCNCC4)c(Cl)c3)nc2n1-c1ccc(=O)n(C(C)C)n1] | 536 |
| 58 | 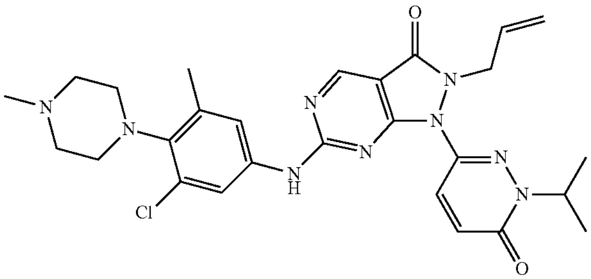 | 550 |
| 59 | 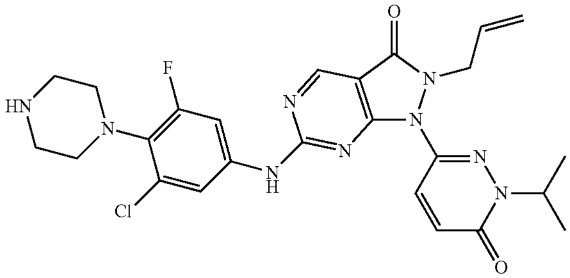 | 540 |
| 60 | 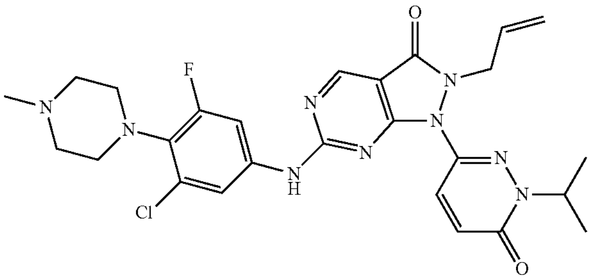 | 554 |

TABLE 3-continued
| Structures of compounds 32-34 | | |
|---|---|---|
| Compound | Compound structure | MS (M + H)$^+$ |
| 61 | 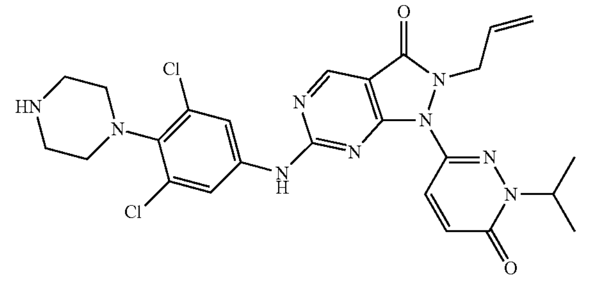 [SMILES: C=CCn1c(=O)c2cnc(Nc3cc(Cl)c(N4CCNCC4)c(Cl)c3)nc2n1-c1ccc(=O)n(C(C)C)n1] | 556 |
| 62 | 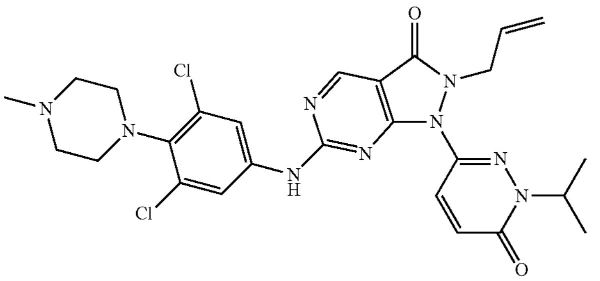 [SMILES: C=CCn1c(=O)c2cnc(Nc3cc(Cl)c(N4CCN(C)CC4)c(Cl)c3)nc2n1-c1ccc(=O)n(C(C)C)n1] | 570 |
| 63 | 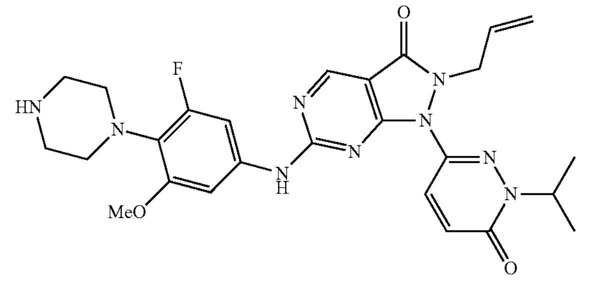 [SMILES: C=CCn1c(=O)c2cnc(Nc3cc(F)c(N4CCNCC4)c(OC)c3)nc2n1-c1ccc(=O)n(C(C)C)n1] | 536 |
| 64 | 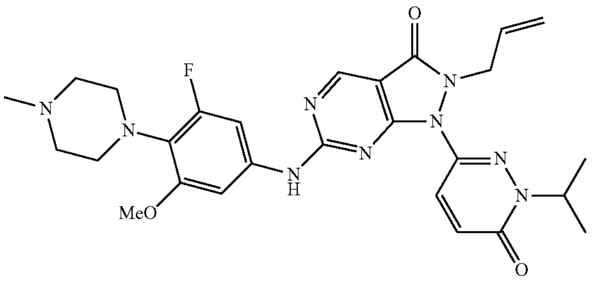 [SMILES: C=CCn1c(=O)c2cnc(Nc3cc(F)c(N4CCN(C)CC4)c(OC)c3)nc2n1-c1ccc(=O)n(C(C)C)n1] | 550 |
| 65 | 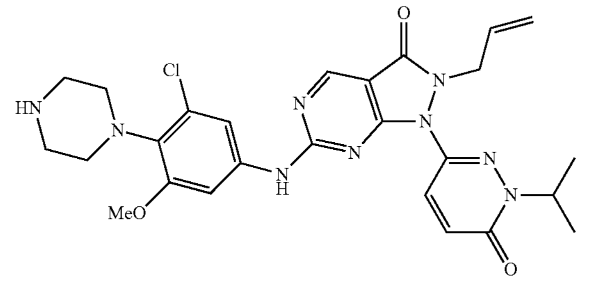 [SMILES: C=CCn1c(=O)c2cnc(Nc3cc(Cl)c(N4CCNCC4)c(OC)c3)nc2n1-c1ccc(=O)n(C(C)C)n1] | 552 |

TABLE 3-continued
| Structures of compounds 32-34 | | |
|---|---|---|
| Compound | Compound structure | MS (M + H)$^+$ |
| 66 | 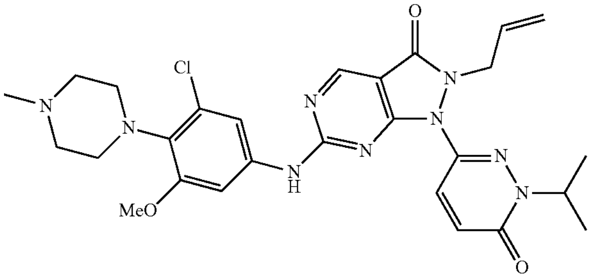 | 566 |
| 67 | 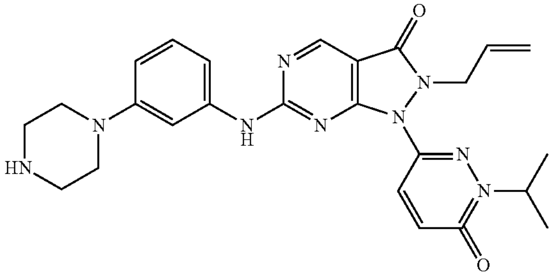 | 488 |
| 68 | 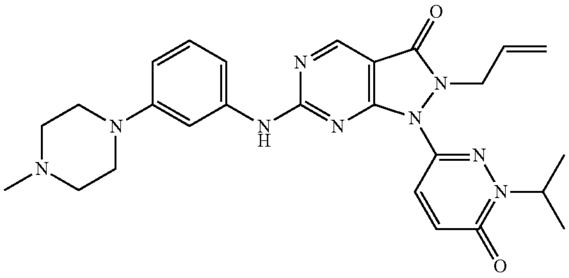 | 502 |
| 69 | 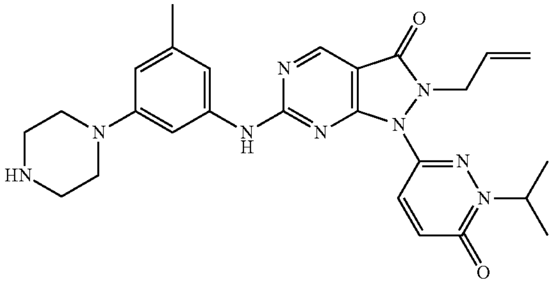 | 502 |
| 70 | 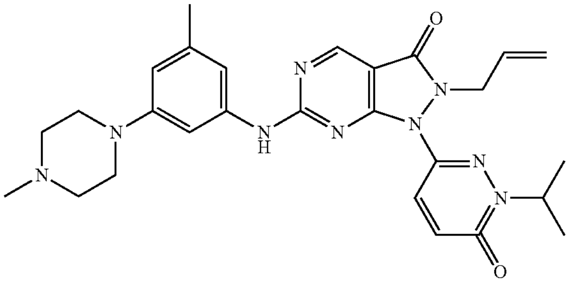 | 516 |

TABLE 3-continued
| Structures of compounds 32-34 | | |
|---|---|---|
| Compound | Compound structure | MS (M + H)$^+$ |
| 71 | 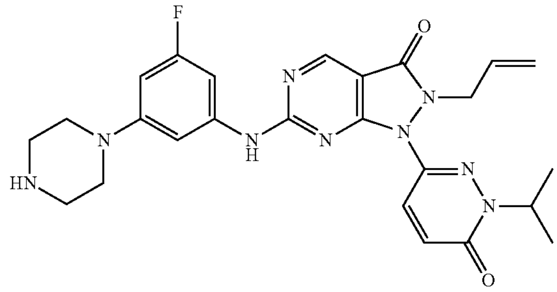 [SMILES: C=CCn1c(=O)c2cnc(Nc3cc(F)cc(N4CCNCC4)c3)nc2n1-c1ccc(=O)n(C(C)C)n1] | 506 |
| 72 | 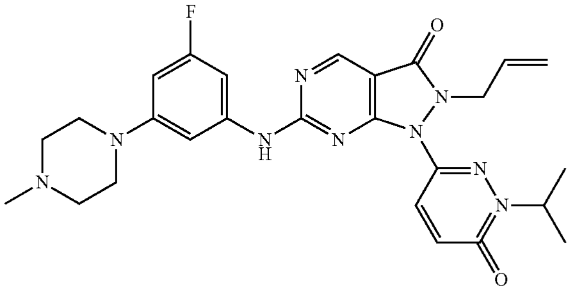 | 520 |
| 73 | 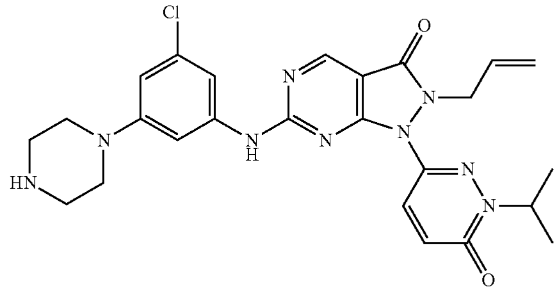 | 522 |
| 74 | 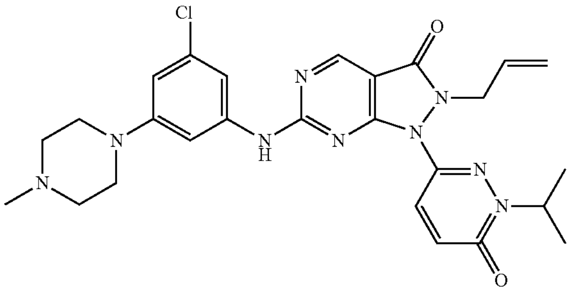 | 536 |
| 75 | 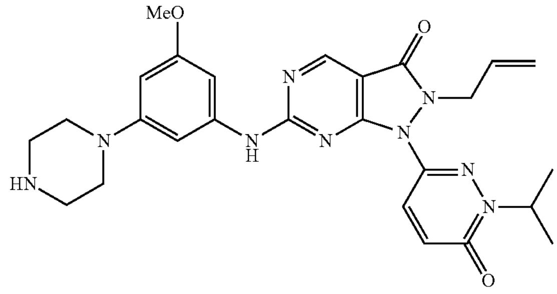 | 518 |

TABLE 3-continued
| Compound | Compound structure | MS (M + H)+ |
|---|---|---|
| Structures of compounds 32-34 | | |
| 76 | 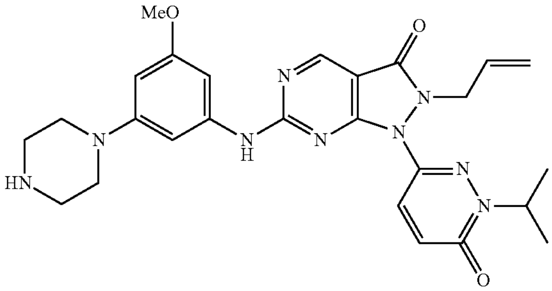 | 518 |
| 77 | 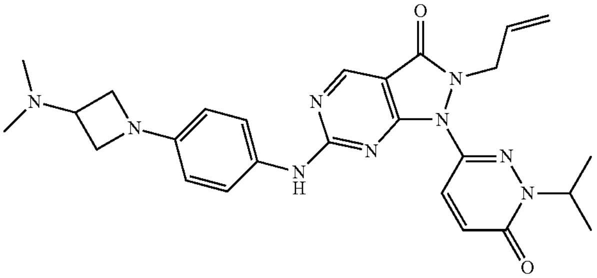 [SMILES: C=CCn1c(=O)c2cnc(Nc3ccc(N4CC(N(C)C)C4)cc3)nc2n1-c1ccc(=O)n(C(C)C)n1] | 502 |
| 78 | 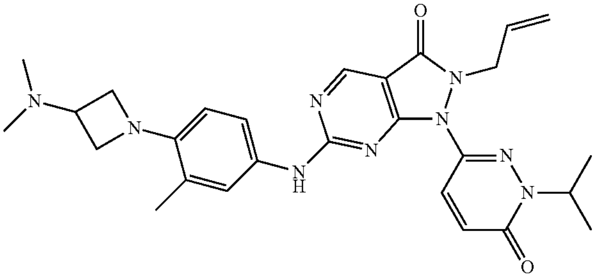 | 516 |
| 79 | 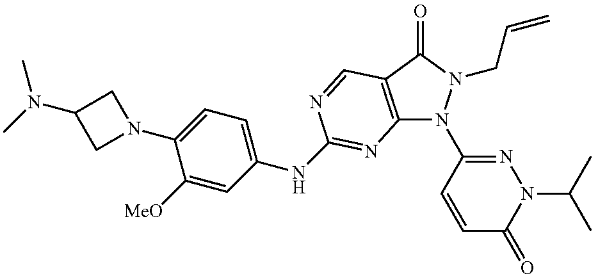 [SMILES: C=CCn1c(=O)c2cnc(Nc3ccc(N4CC(N(C)C)C4)c(OC)c3)nc2n1-c1ccc(=O)n(C(C)C)n1] | 532 |
| 80 | 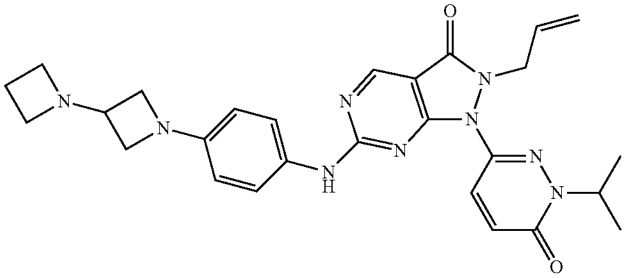 [SMILES: C=CCn1c(=O)c2cnc(Nc3ccc(N4CC(N5CCC5)C4)cc3)nc2n1-c1ccc(=O)n(C(C)C)n1] | 514 |

TABLE 3-continued
| Structures of compounds 32-34 | | |
|---|---|---|
| Compound | Compound structure | MS (M + H)$^+$ |
| 81 | 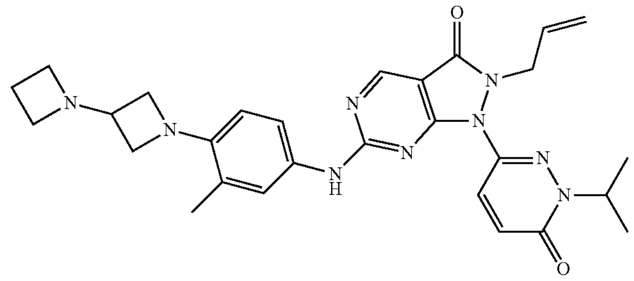 [SMILES: C=CCn1c(=O)c2cnc(Nc3ccc(N4CC(N5CCC5)C4)c(C)c3)nc2n1-c1ccc(=O)n(C(C)C)n1] | 528 |
| 82 | 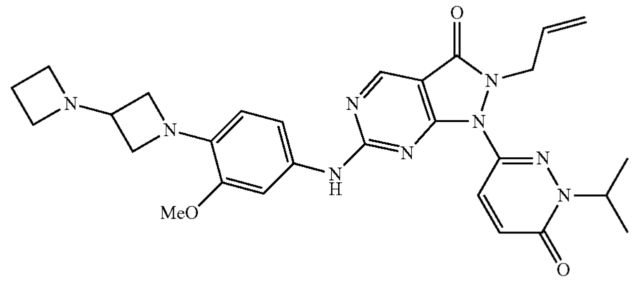 [SMILES: C=CCn1c(=O)c2cnc(Nc3ccc(N4CC(N5CCC5)C4)c(OC)c3)nc2n1-c1ccc(=O)n(C(C)C)n1] | 544 |
| 83 | 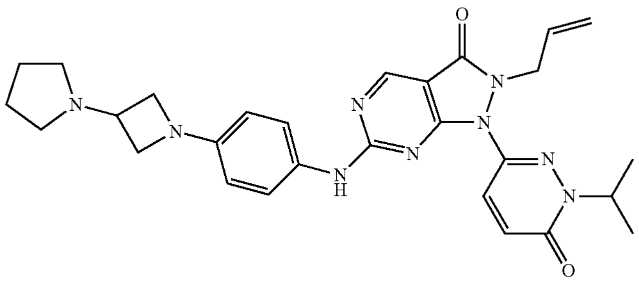 [SMILES: C=CCn1c(=O)c2cnc(Nc3ccc(N4CC(N5CCCC5)C4)cc3)nc2n1-c1ccc(=O)n(C(C)C)n1] | 528 |
| 84 | 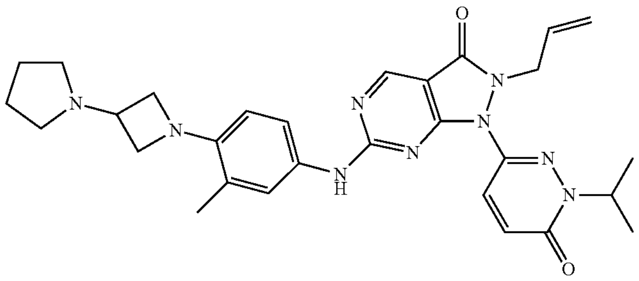 | 542 |
| 85 | 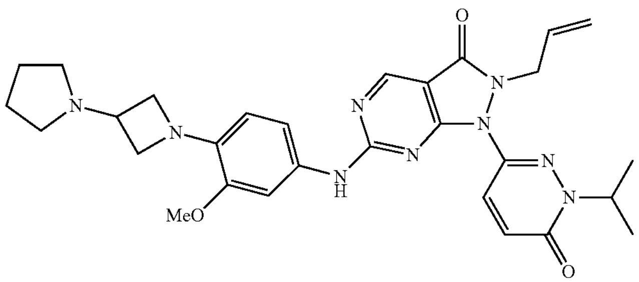 [SMILES: C=CCn1c(=O)c2cnc(Nc3ccc(N4CC(N5CCCC5)C4)c(OC)c3)nc2n1-c1ccc(=O)n(C(C)C)n1] | 558 |

TABLE 3-continued
Structures of compounds 32-34
| Compound | Compound structure | MS (M + H)+ |
|---|---|---|
| 86 | 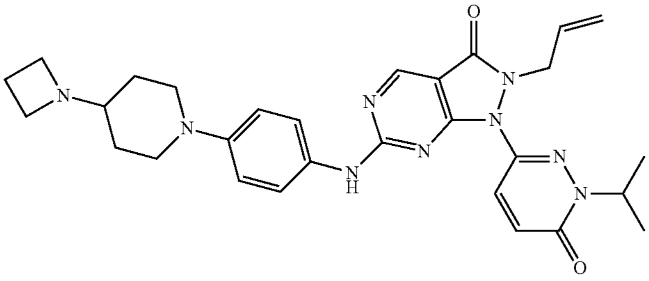 [SMILES: C=CCn1c(=O)c2cnc(Nc3ccc(N4CCC(N5CCC5)CC4)cc3)nc2n1-c1ccc(=O)n(C(C)C)n1] | 542 |
| 87 | 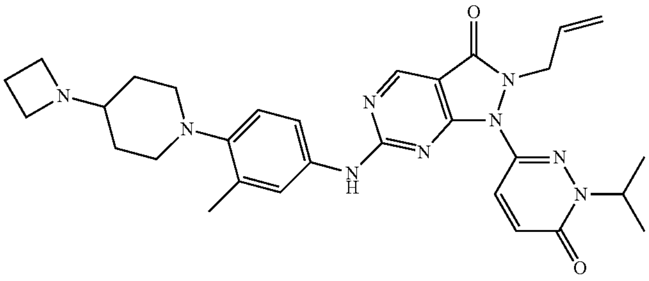 [SMILES: C=CCn1c(=O)c2cnc(Nc3ccc(N4CCC(N5CCC5)CC4)c(C)c3)nc2n1-c1ccc(=O)n(C(C)C)n1] | 556 |
| 88 | 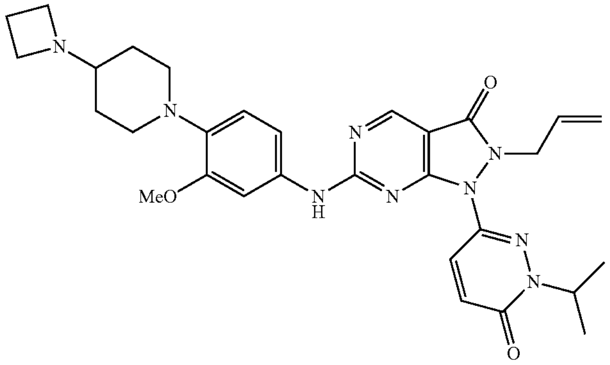 [SMILES: C=CCn1c(=O)c2cnc(Nc3ccc(N4CCC(N5CCC5)CC4)c(OC)c3)nc2n1-c1ccc(=O)n(C(C)C)n1] | 572 |
| 89 | 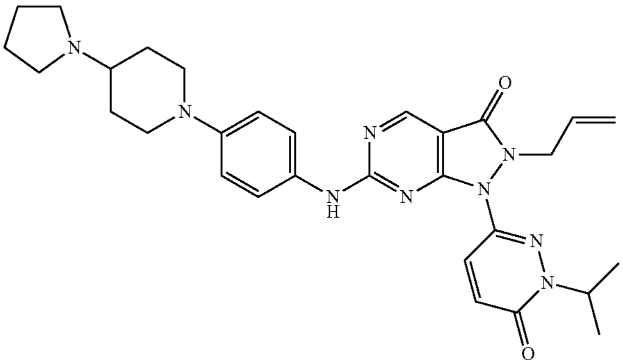 [SMILES: C=CCn1c(=O)c2cnc(Nc3ccc(N4CCC(N5CCCC5)CC4)cc3)nc2n1-c1ccc(=O)n(C(C)C)n1] | 556 |

TABLE 3-continued
| Structures of compounds 32-34 | | |
|---|---|---|
| Compound | Compound structure | MS (M + H)+ |
| 90 | 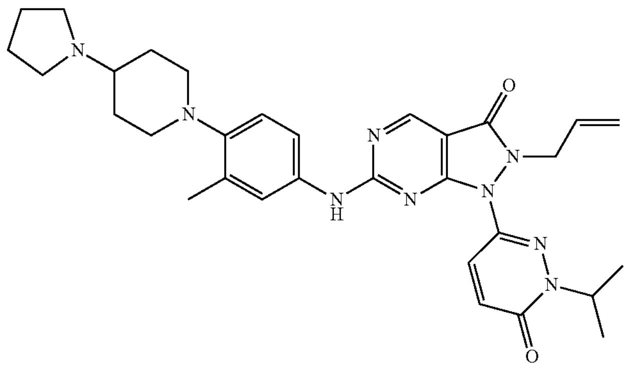 [SMILES: C=CCn1c(=O)c2cnc(Nc3ccc(N4CCC(N5CCCC5)CC4)c(C)c3)nc2n1-c1ccc(=O)n(C(C)C)n1] | 570 |
| 91 | 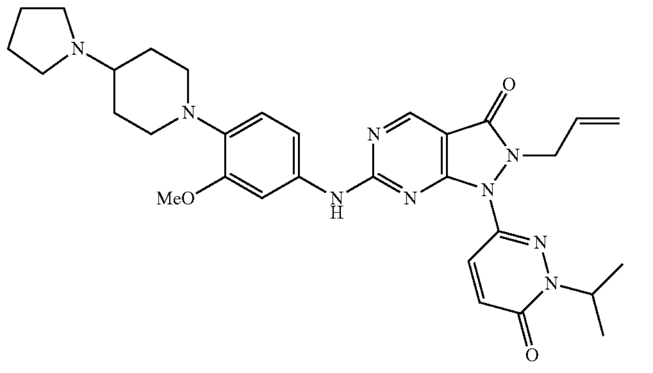 [SMILES: C=CCn1c(=O)c2cnc(Nc3ccc(N4CCC(N5CCCC5)CC4)c(OC)c3)nc2n1-c1ccc(=O)n(C(C)C)n1] | 586 |
| 92 | 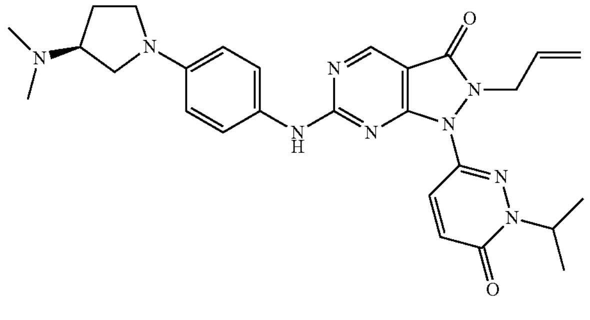 [SMILES: C=CCn1c(=O)c2cnc(Nc3ccc(N4CC[C@H](N(C)C)C4)cc3)nc2n1-c1ccc(=O)n(C(C)C)n1] | 516 |
| 93 | 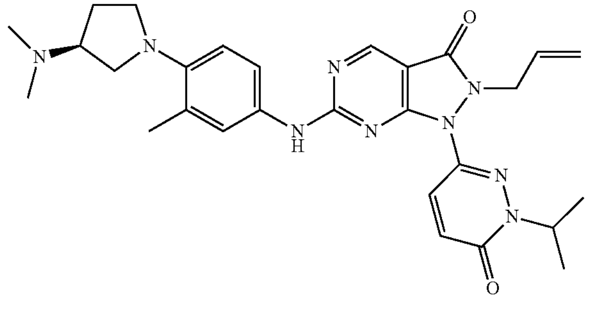 [SMILES: C=CCn1c(=O)c2cnc(Nc3ccc(N4CC[C@H](N(C)C)C4)c(C)c3)nc2n1-c1ccc(=O)n(C(C)C)n1] | 530 |

TABLE 3-continued
| Structures of compounds 32-34 | | |
|---|---|---|
| Compound | Compound structure | MS (M + H)+ |
| 94 | 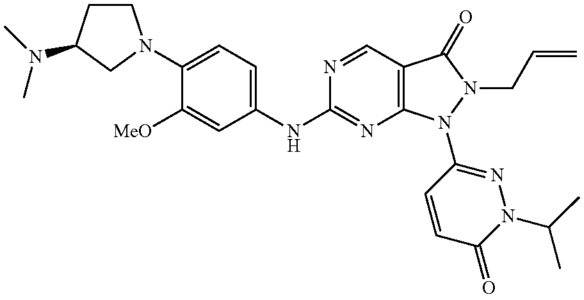 [SMILES: C=CCn1c(=O)c2cnc(Nc3ccc(N4CC[C@H](N(C)C)C4)c(OC)c3)nc2n1-c1ccc(=O)n(C(C)C)n1] | 546 |
| 95 | 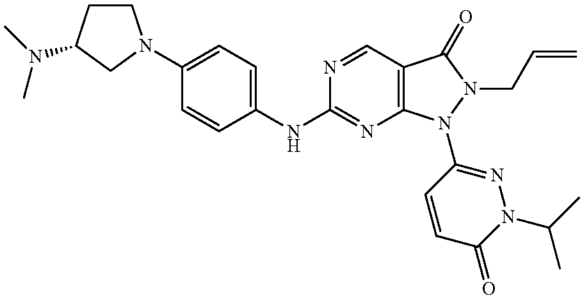 [SMILES: C=CCn1c(=O)c2cnc(Nc3ccc(N4CC[C@@H](N(C)C)C4)cc3)nc2n1-c1ccc(=O)n(C(C)C)n1] | 516 |
| 96 | 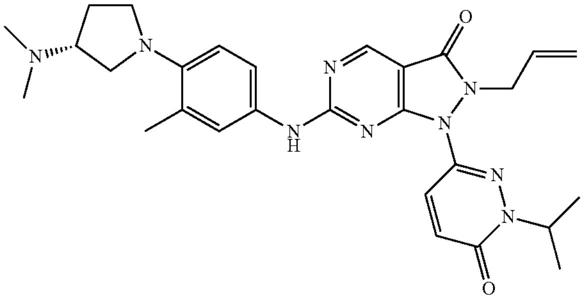 [SMILES: C=CCn1c(=O)c2cnc(Nc3ccc(N4CC[C@@H](N(C)C)C4)c(C)c3)nc2n1-c1ccc(=O)n(C(C)C)n1] | 530 |
| 97 | 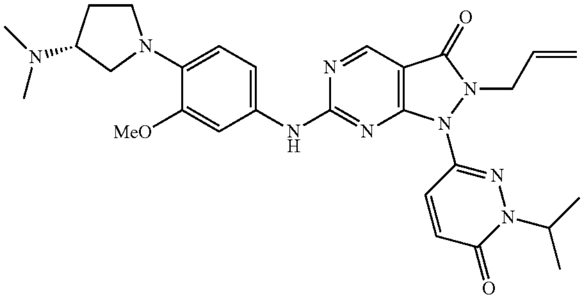 [SMILES: C=CCn1c(=O)c2cnc(Nc3ccc(N4CC[C@@H](N(C)C)C4)c(OC)c3)nc2n1-c1ccc(=O)n(C(C)C)n1] | 546 |
| 98 | 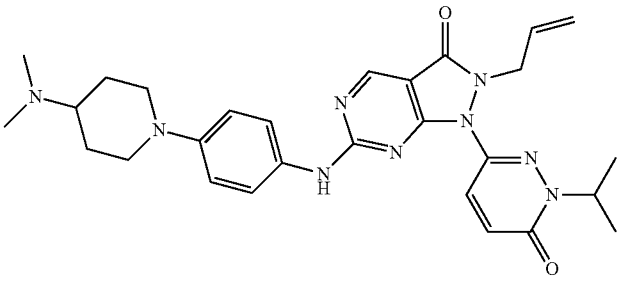 [SMILES: C=CCn1c(=O)c2cnc(Nc3ccc(N4CCC(N(C)C)CC4)cc3)nc2n1-c1ccc(=O)n(C(C)C)n1] | 530 |

TABLE 3-continued
| Structures of compounds 32-34 | | |
| --- | --- | --- |
| Compound | Compound structure | MS (M + H)$^+$ |
| 99 | 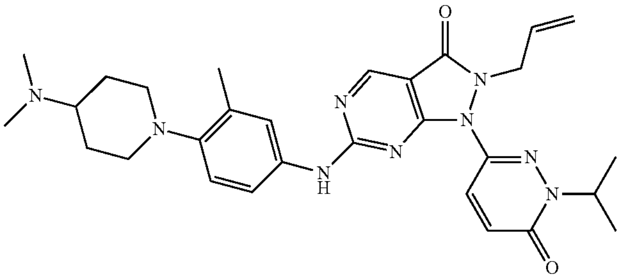 [SMILES: C=CCn1c(=O)c2cnc(Nc3ccc(N4CCC(N(C)C)CC4)c(C)c3)nc2n1-c1ccc(=O)n(C(C)C)n1] | 544 |
| 100 | 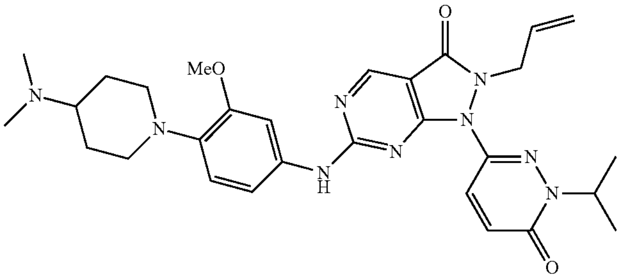 [SMILES: C=CCn1c(=O)c2cnc(Nc3ccc(N4CCC(N(C)C)CC4)c(OC)c3)nc2n1-c1ccc(=O)n(C(C)C)n1] | 560 |
| 101 | 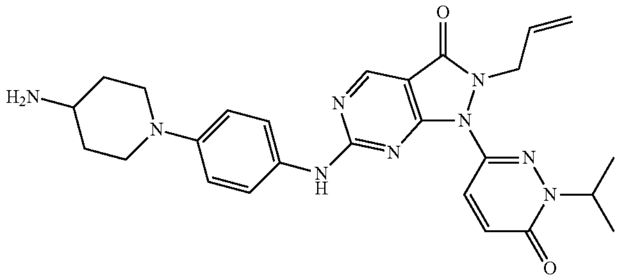 [SMILES: C=CCn1c(=O)c2cnc(Nc3ccc(N4CCC(N)CC4)cc3)nc2n1-c1ccc(=O)n(C(C)C)n1] | 502 |
| 102 | 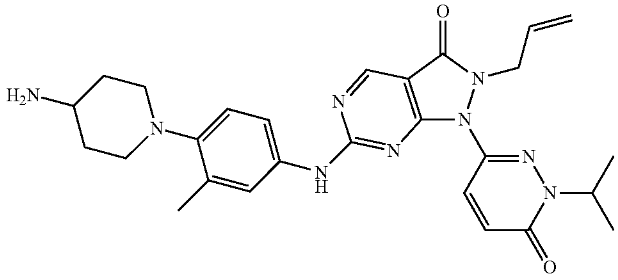 [SMILES: C=CCn1c(=O)c2cnc(Nc3ccc(N4CCC(N)CC4)c(C)c3)nc2n1-c1ccc(=O)n(C(C)C)n1] | 516 |
| 103 | 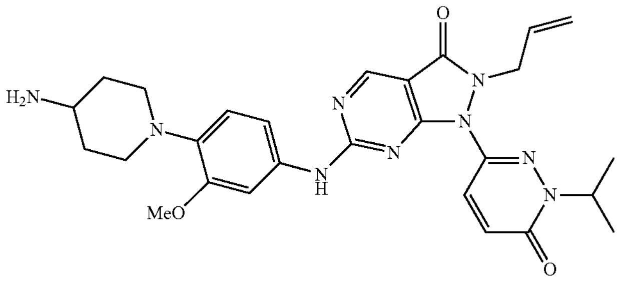 [SMILES: C=CCn1c(=O)c2cnc(Nc3ccc(N4CCC(N)CC4)c(OC)c3)nc2n1-c1ccc(=O)n(C(C)C)n1] | 532 |

TABLE 3-continued
| Structures of compounds 32-34 | | |
|---|---|---|
| Compound | Compound structure | MS (M + H)$^+$ |
| 104 | 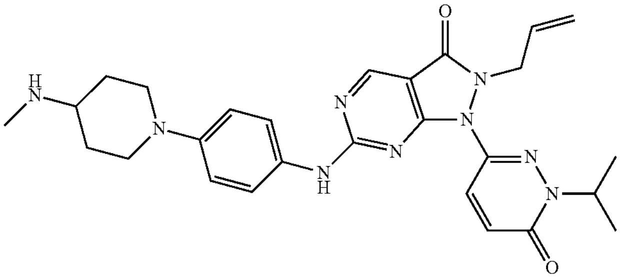 [SMILES: C=CCn1c(=O)c2cnc(Nc3ccc(N4CCC(NC)CC4)cc3)nc2n1-c1ccc(=O)n(C(C)C)n1] | 516 |
| 105 | 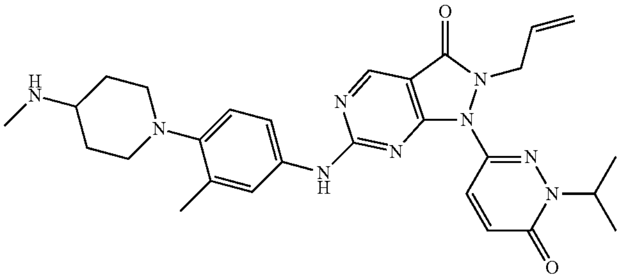 | 530 |
| 106 | 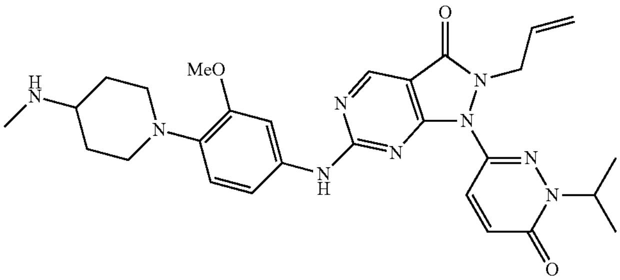 [SMILES: C=CCn1c(=O)c2cnc(Nc3ccc(N4CCC(NC)CC4)c(OC)c3)nc2n1-c1ccc(=O)n(C(C)C)n1] | 546 |
| 107 | 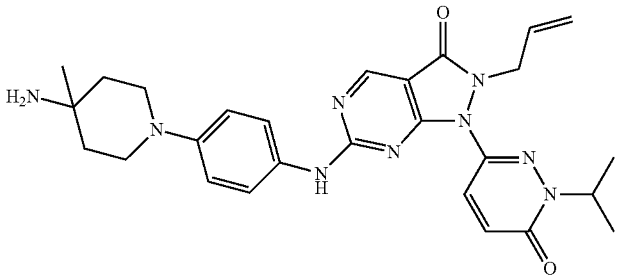 [SMILES: C=CCn1c(=O)c2cnc(Nc3ccc(N4CCC(C)(N)CC4)cc3)nc2n1-c1ccc(=O)n(C(C)C)n1] | 516 |
| 108 | 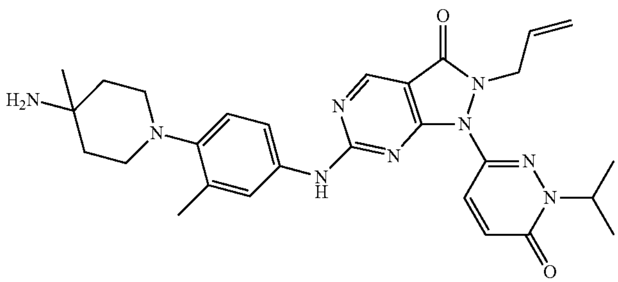 [SMILES: C=CCn1c(=O)c2cnc(Nc3ccc(N4CCC(C)(N)CC4)c(C)c3)nc2n1-c1ccc(=O)n(C(C)C)n1] | 530 |

TABLE 3-continued
| Structures of compounds 32-34 | | |
|---|---|---|
| Compound | Compound structure | MS (M + H)+ |
| 109 | 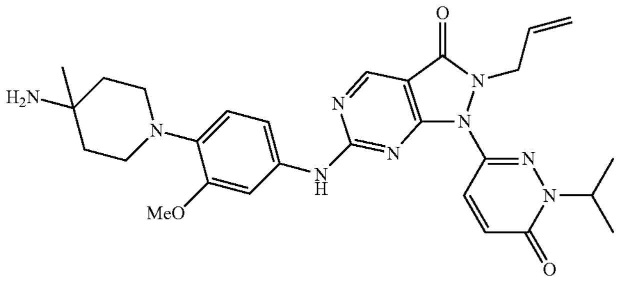 [SMILES: C=CCn1c(=O)c2cnc(Nc3ccc(N4CCC(C)(N)CC4)c(OC)c3)nc2n1-c1ccc(=O)n(C(C)C)n1] | 546 |
| 110 | 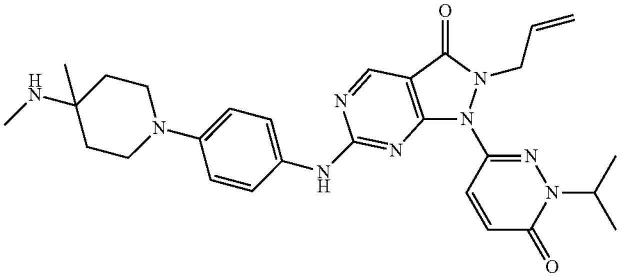 | 530 |
| 111 | 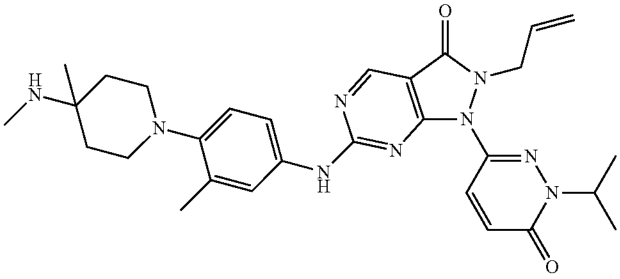 [SMILES: C=CCn1c(=O)c2cnc(Nc3ccc(N4CCC(C)(NC)CC4)c(C)c3)nc2n1-c1ccc(=O)n(C(C)C)n1] | 544 |
| 112 | 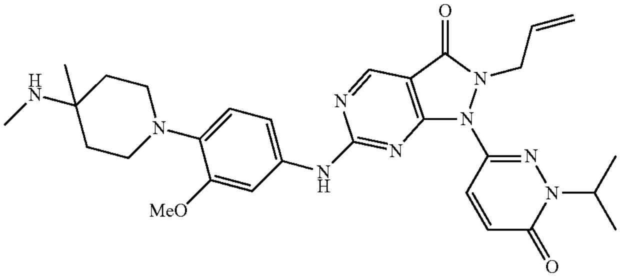 [SMILES: C=CCn1c(=O)c2cnc(Nc3ccc(N4CCC(C)(NC)CC4)c(OC)c3)nc2n1-c1ccc(=O)n(C(C)C)n1] | 560 |
| 113 | 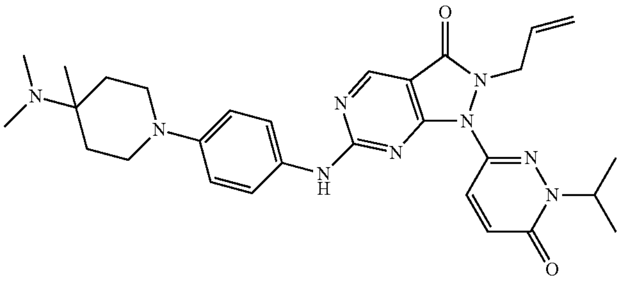 [SMILES: C=CCn1c(=O)c2cnc(Nc3ccc(N4CCC(C)(N(C)C)CC4)cc3)nc2n1-c1ccc(=O)n(C(C)C)n1] | 544 |

TABLE 3-continued
| Structures of compounds 32-34 | | |
|---|---|---|
| Compound | Compound structure | MS (M + H)$^+$ |
| 114 | 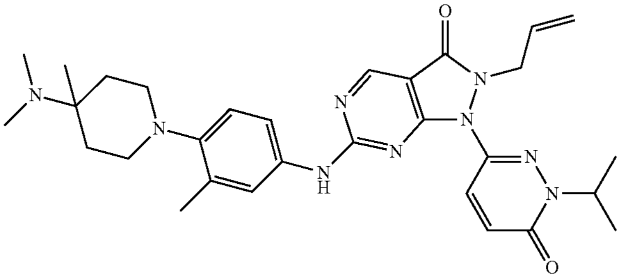 [SMILES: C=CCn1c(=O)c2cnc(Nc3ccc(N4CCC(C)(N(C)C)CC4)c(C)c3)nc2n1-c1ccc(=O)n(C(C)C)n1] | 558 |
| 115 | 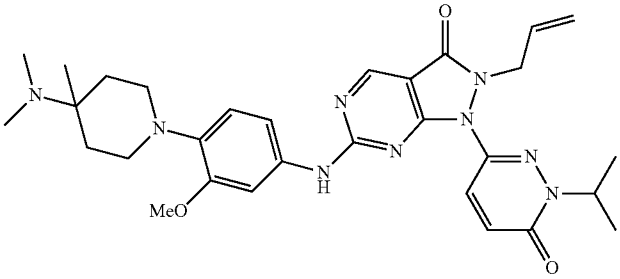 [SMILES: C=CCn1c(=O)c2cnc(Nc3ccc(N4CCC(C)(N(C)C)CC4)c(OC)c3)nc2n1-c1ccc(=O)n(C(C)C)n1] | 574 |
| 116 | 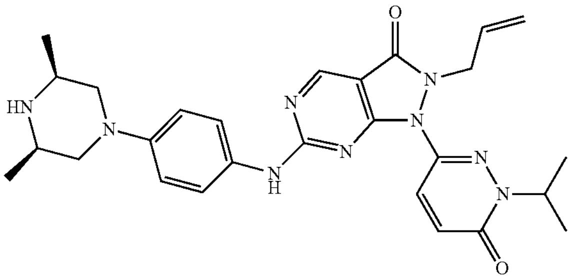 | 516 |
| 117 | 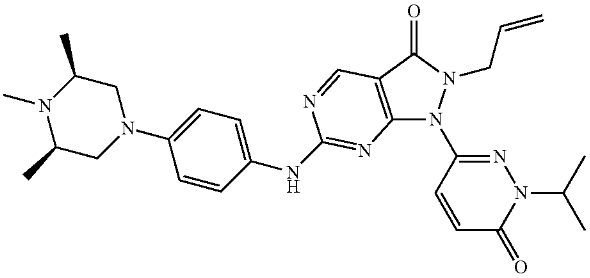 [SMILES: C=CCn1c(=O)c2cnc(Nc3ccc(N4C[C@@H](C)N(C)[C@@H](C)C4)cc3)nc2n1-c1ccc(=O)n(C(C)C)n1] | 530 |
| 118 | 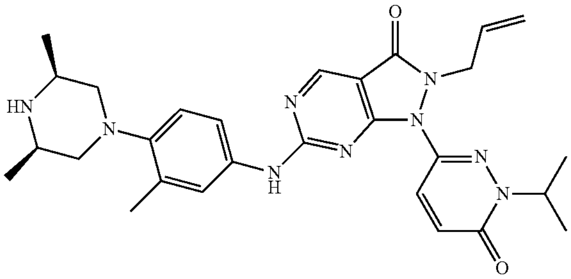 [SMILES: C=CCn1c(=O)c2cnc(Nc3ccc(N4C[C@@H](C)N[C@@H](C)C4)c(C)c3)nc2n1-c1ccc(=O)n(C(C)C)n1] | 530 |

TABLE 3-continued
| Structures of compounds 32-34 | | |
|---|---|---|
| Compound | Compound structure | MS (M + H)$^+$ |
| 119 | 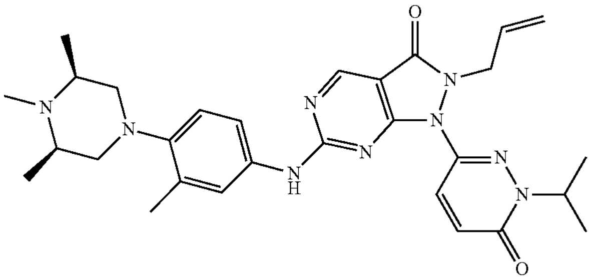 [SMILES: C=CCn1c(=O)c2cnc(Nc3ccc(N4C[C@@H](C)N(C)[C@@H](C)C4)c(C)c3)nc2n1-c1ccc(=O)n(C(C)C)n1] | 544 |
| 120 | 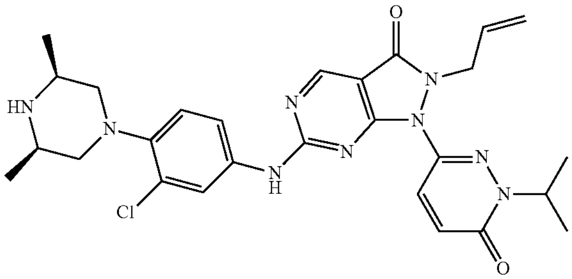 [SMILES: C=CCn1c(=O)c2cnc(Nc3ccc(N4C[C@@H](C)N[C@@H](C)C4)c(Cl)c3)nc2n1-c1ccc(=O)n(C(C)C)n1] | 550 |
| 121 | 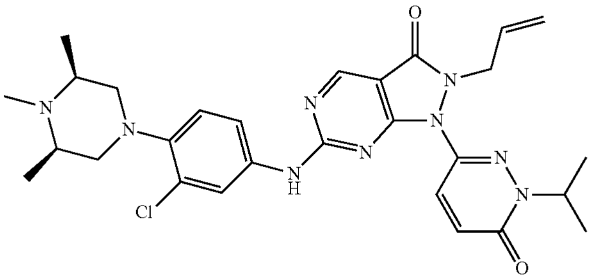 | 564 |
| 122 | 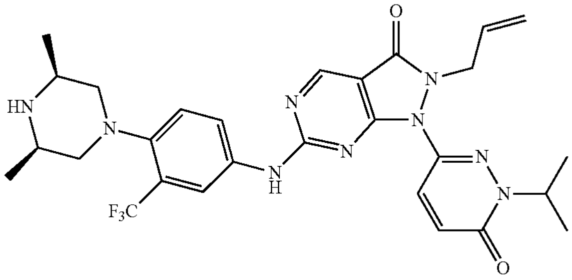 [SMILES: C=CCn1c(=O)c2cnc(Nc3ccc(N4C[C@@H](C)N[C@@H](C)C4)c(C(F)(F)F)c3)nc2n1-c1ccc(=O)n(C(C)C)n1] | 574 |
| 123 | 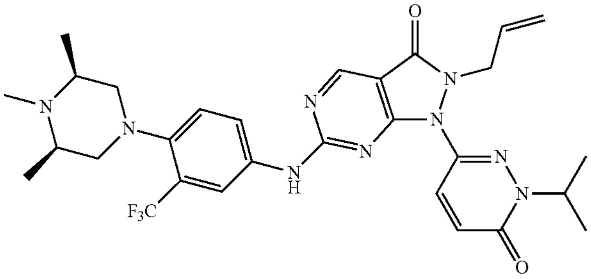 [SMILES: C=CCn1c(=O)c2cnc(Nc3ccc(N4C[C@@H](C)N(C)[C@@H](C)C4)c(C(F)(F)F)c3)nc2n1-c1ccc(=O)n(C(C)C)n1] | 598 |

TABLE 3-continued
| Structures of compounds 32-34 | | |
|---|---|---|
| Compound | Compound structure | MS (M + H)+ |
| 124 | 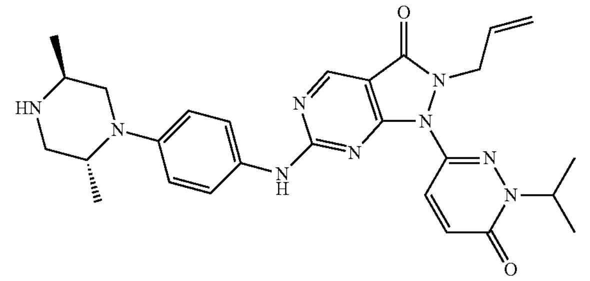 [SMILES: C=CCn1c(=O)c2cnc(Nc3ccc(N4C[C@H](C)NC[C@H]4C)cc3)nc2n1-c1ccc(=O)n(C(C)C)n1] | 516 |
| 125 | 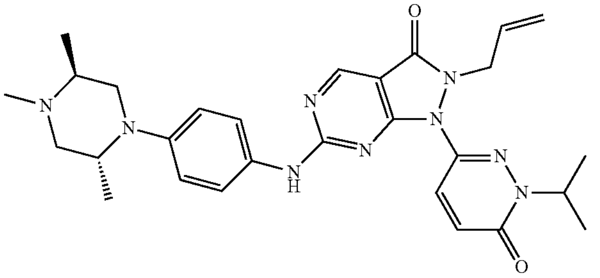 [SMILES: C=CCn1c(=O)c2cnc(Nc3ccc(N4C[C@H](C)N(C)C[C@H]4C)cc3)nc2n1-c1ccc(=O)n(C(C)C)n1] | 530 |
| 126 | 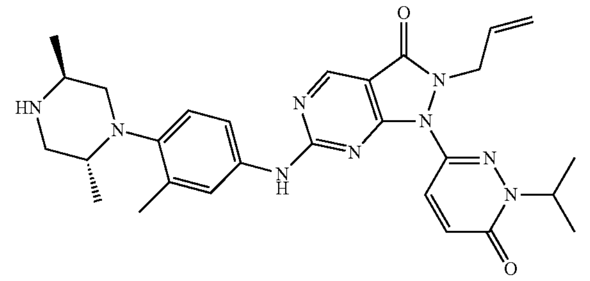 [SMILES: C=CCn1c(=O)c2cnc(Nc3ccc(N4C[C@H](C)NC[C@H]4C)c(C)c3)nc2n1-c1ccc(=O)n(C(C)C)n1] | 530 |
| 127 | 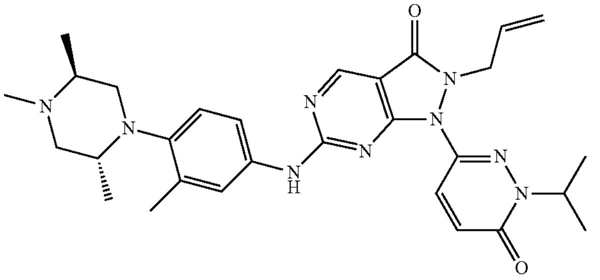 [SMILES: C=CCn1c(=O)c2cnc(Nc3ccc(N4C[C@H](C)N(C)C[C@H]4C)c(C)c3)nc2n1-c1ccc(=O)n(C(C)C)n1] | 544 |
| 128 | 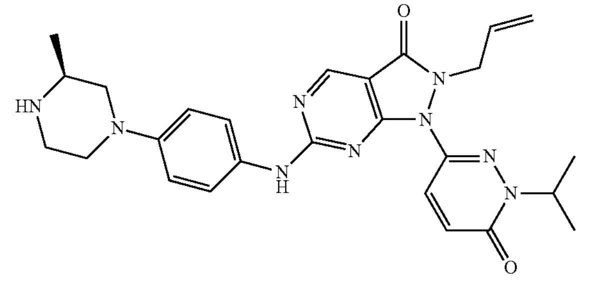 [SMILES: C=CCn1c(=O)c2cnc(Nc3ccc(N4CCN[C@@H](C)C4)cc3)nc2n1-c1ccc(=O)n(C(C)C)n1] | 502 |

TABLE 3-continued
| Structures of compounds 32-34 | | |
| --- | --- | --- |
| Compound | Compound structure | MS (M + H)$^+$ |
| 129 | 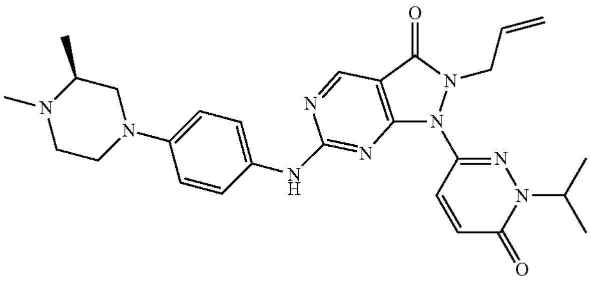 [SMILES: C=CCn1c(=O)c2cnc(Nc3ccc(N4CCN(C)[C@@H](C)C4)cc3)nc2n1-c1ccc(=O)n(C(C)C)n1] | 516 |
| 130 | 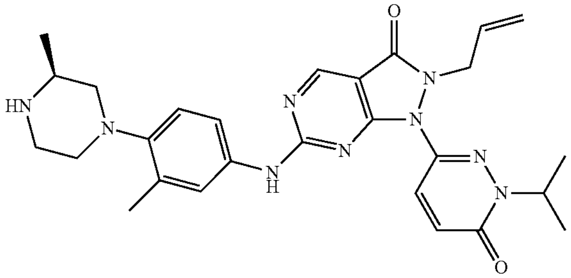 [SMILES: C=CCn1c(=O)c2cnc(Nc3ccc(N4CCN[C@@H](C)C4)c(C)c3)nc2n1-c1ccc(=O)n(C(C)C)n1] | 516 |
| 131 | 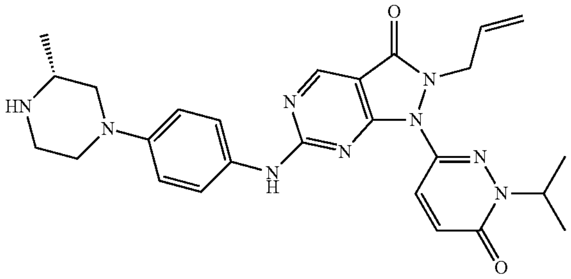 [SMILES: C=CCn1c(=O)c2cnc(Nc3ccc(N4CCN[C@H](C)C4)cc3)nc2n1-c1ccc(=O)n(C(C)C)n1] | 502 |
| 132 | 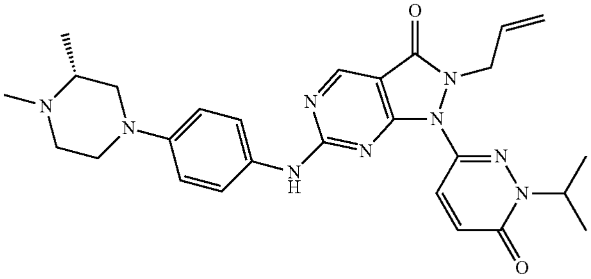 [SMILES: C=CCn1c(=O)c2cnc(Nc3ccc(N4CCN(C)[C@H](C)C4)cc3)nc2n1-c1ccc(=O)n(C(C)C)n1] | 516 |
| 133 | 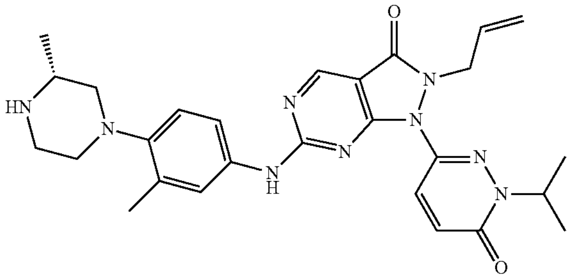 [SMILES: C=CCn1c(=O)c2cnc(Nc3ccc(N4CCN[C@H](C)C4)c(C)c3)nc2n1-c1ccc(=O)n(C(C)C)n1] | 516 |

TABLE 3-continued
| Structures of compounds 32-34 | | |
|---|---|---|
| Compound | Compound structure | MS (M + H)+ |
| 134 | 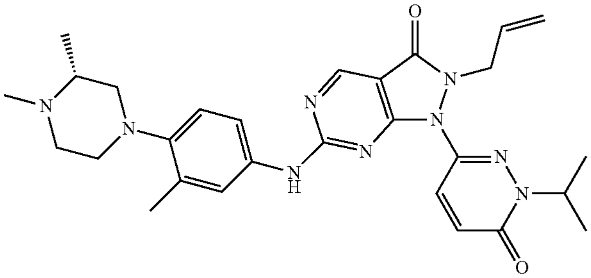 [SMILES: C=CCn1c(=O)c2cnc(Nc3ccc(N4CCN(C)[C@H](C)C4)c(C)c3)nc2n1-c1ccc(=O)n(C(C)C)n1] | 530 |
| 135 | 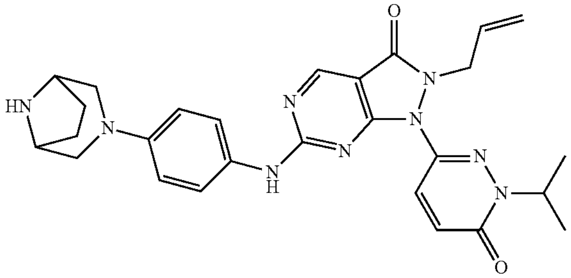 [SMILES: C=CCn1c(=O)c2cnc(Nc3ccc(N4CC5CCC(C4)N5)cc3)nc2n1-c1ccc(=O)n(C(C)C)n1] | 514 |
| 136 | 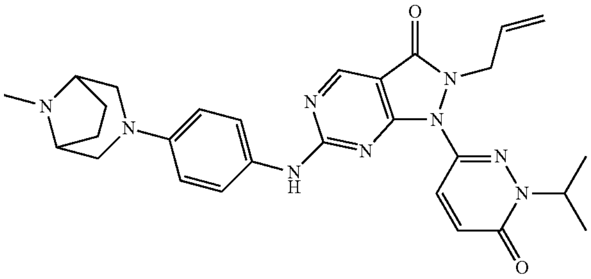 | 528 |
| 137 | 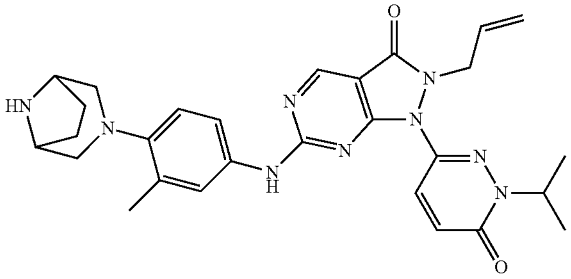 [SMILES: C=CCn1c(=O)c2cnc(Nc3ccc(N4CC5CCC(C4)N5)c(C)c3)nc2n1-c1ccc(=O)n(C(C)C)n1] | 528 |
| 138 | 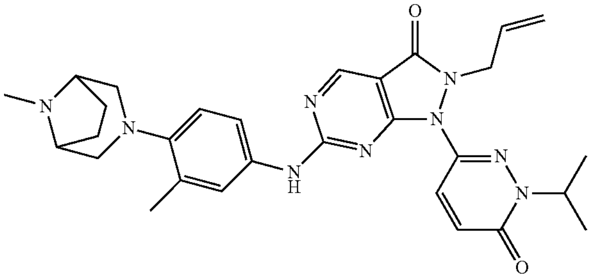 [SMILES: C=CCn1c(=O)c2cnc(Nc3ccc(N4CC5CCC(C4)N5C)c(C)c3)nc2n1-c1ccc(=O)n(C(C)C)n1] | 542 |

TABLE 3-continued
| Structures of compounds 32-34 | | |
|---|---|---|
| Compound | Compound structure | MS (M + H)$^+$ |
| 139 | 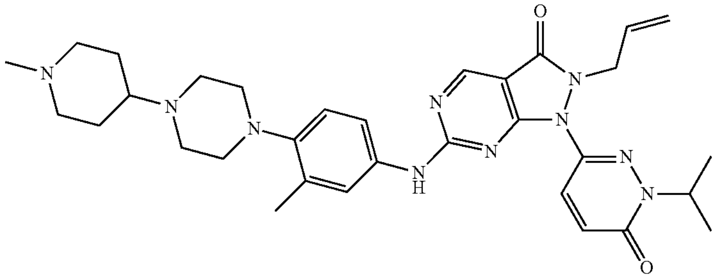 [SMILES: C=CCn1c(=O)c2cnc(Nc3ccc(N4CCN(C5CCN(C)CC5)CC4)c(C)c3)nc2n1-c1ccc(=O)n(C(C)C)n1] | 599 |
| 140 | 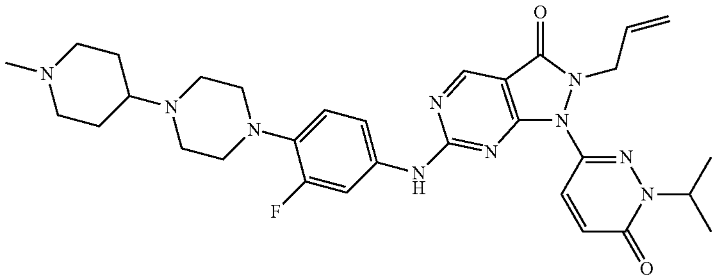 [SMILES: C=CCn1c(=O)c2cnc(Nc3ccc(N4CCN(C5CCN(C)CC5)CC4)c(F)c3)nc2n1-c1ccc(=O)n(C(C)C)n1] | 603 |
| 141 | 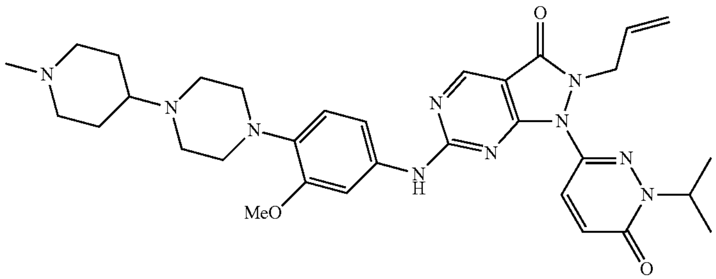 [SMILES: C=CCn1c(=O)c2cnc(Nc3ccc(N4CCN(C5CCN(C)CC5)CC4)c(OC)c3)nc2n1-c1ccc(=O)n(C(C)C)n1] | 615 |
| 142 | 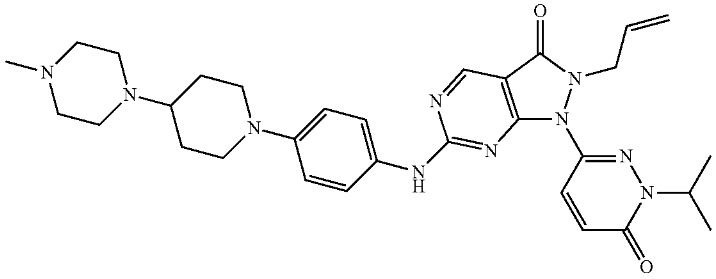 [SMILES: C=CCn1c(=O)c2cnc(Nc3ccc(N4CCC(N5CCN(C)CC5)CC4)cc3)nc2n1-c1ccc(=O)n(C(C)C)n1] | 585 |
| 143 | 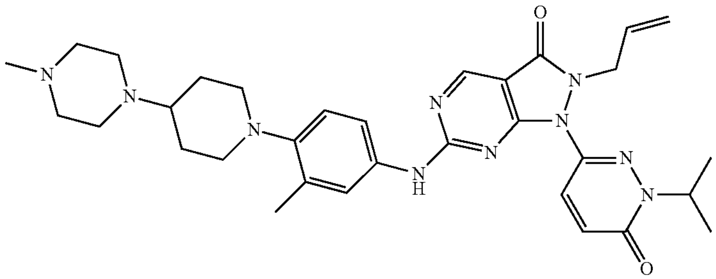 [SMILES: C=CCn1c(=O)c2cnc(Nc3ccc(N4CCC(N5CCN(C)CC5)CC4)c(C)c3)nc2n1-c1ccc(=O)n(C(C)C)n1] | 599 |

TABLE 3-continued
| Structures of compounds 32-34 | | |
|---|---|---|
| Compound | Compound structure | MS (M + H)$^+$ |
| 144 | 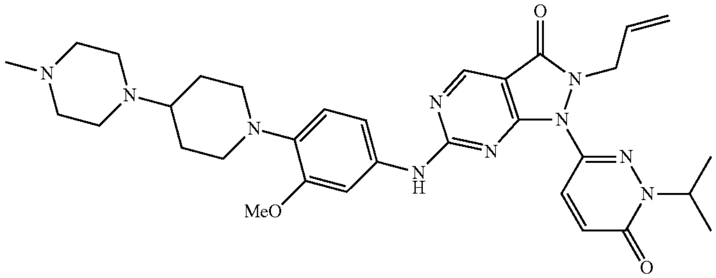 [SMILES: C=CCn1c(=O)c2cnc(Nc3ccc(N4CCC(N5CCN(C)CC5)CC4)c(OC)c3)nc2n1-c1ccc(=O)n(C(C)C)n1] | 615 |
| 145 | 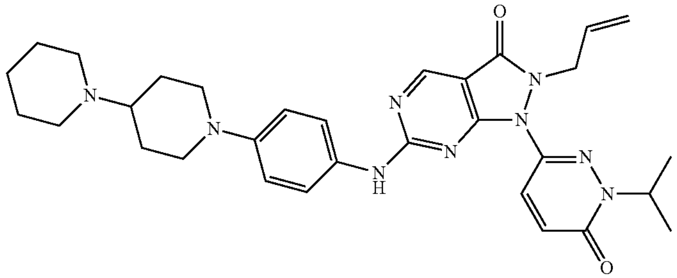 [SMILES: C=CCn1c(=O)c2cnc(Nc3ccc(N4CCC(N5CCCCC5)CC4)cc3)nc2n1-c1ccc(=O)n(C(C)C)n1] | 570 |
| 146 | 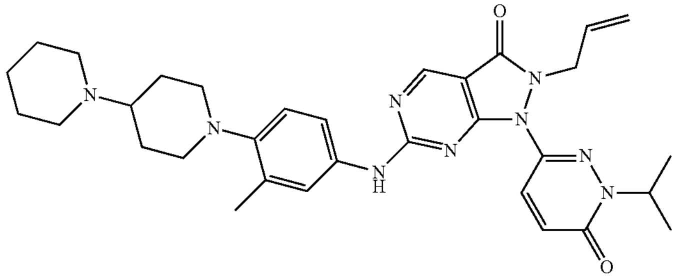 [SMILES: C=CCn1c(=O)c2cnc(Nc3ccc(N4CCC(N5CCCCC5)CC4)c(C)c3)nc2n1-c1ccc(=O)n(C(C)C)n1] | 584 |
| 147 | 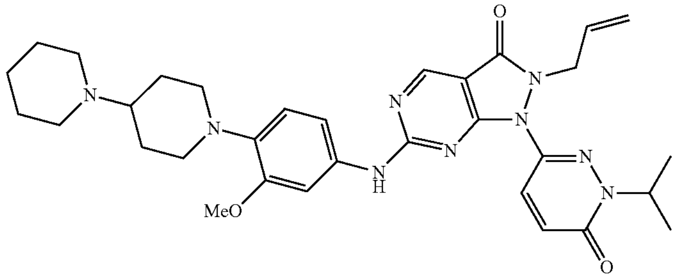 [SMILES: C=CCn1c(=O)c2cnc(Nc3ccc(N4CCC(N5CCCCC5)CC4)c(OC)c3)nc2n1-c1ccc(=O)n(C(C)C)n1] | 600 |
| 148 | 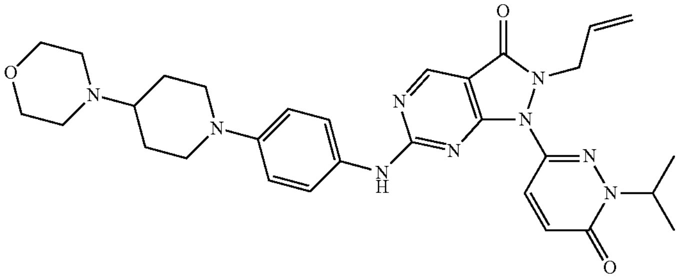 [SMILES: C=CCn1c(=O)c2cnc(Nc3ccc(N4CCC(N5CCOCC5)CC4)cc3)nc2n1-c1ccc(=O)n(C(C)C)n1] | 572 |

TABLE 3-continued
| Structures of compounds 32-34 | | |
|---|---|---|
| Compound | Compound structure | MS (M + H)+ |
| 149 | 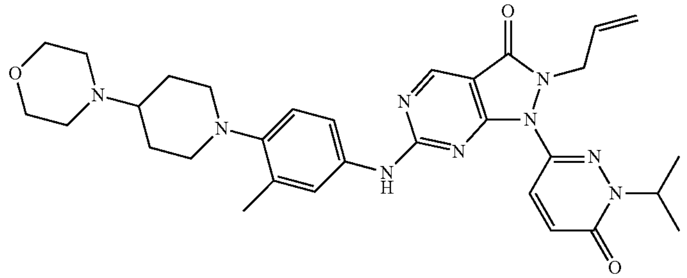 [SMILES: C=CCn1c(=O)c2cnc(Nc3ccc(N4CCC(N5CCOCC5)CC4)c(C)c3)nc2n1-c1ccc(=O)n(C(C)C)n1] | 586 |
| 150 | 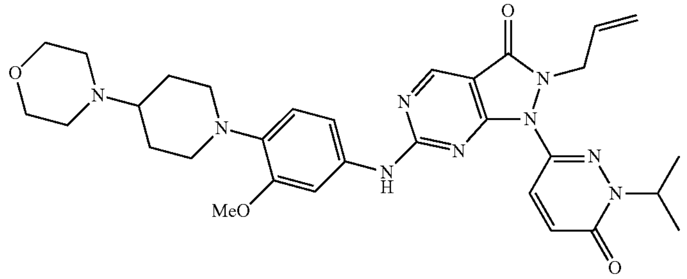 [SMILES: C=CCn1c(=O)c2cnc(Nc3ccc(N4CCC(N5CCOCC5)CC4)c(OC)c3)nc2n1-c1ccc(=O)n(C(C)C)n1] | 602 |
| 151 | 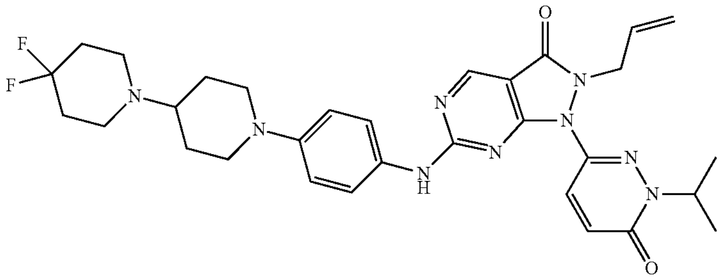 [SMILES: C=CCn1c(=O)c2cnc(Nc3ccc(N4CCC(N5CCC(F)(F)CC5)CC4)cc3)nc2n1-c1ccc(=O)n(C(C)C)n1] | 606 |
| 152 | 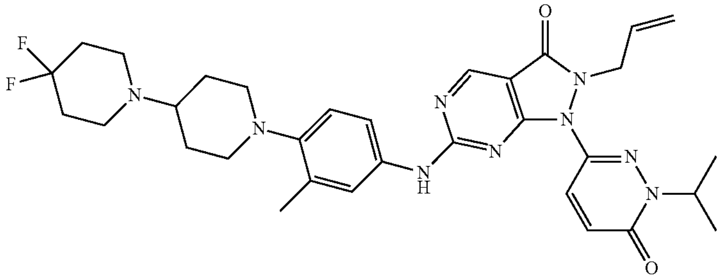 [SMILES: C=CCn1c(=O)c2cnc(Nc3ccc(N4CCC(N5CCC(F)(F)CC5)CC4)c(C)c3)nc2n1-c1ccc(=O)n(C(C)C)n1] | 620 |
| 153 | 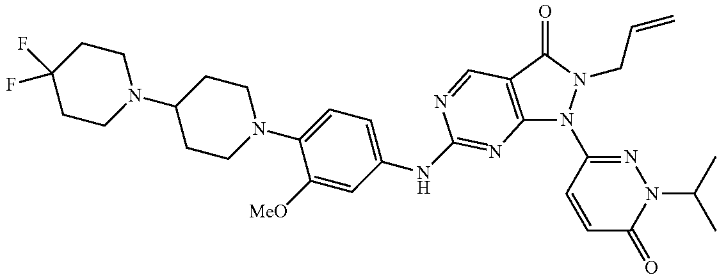 [SMILES: C=CCn1c(=O)c2cnc(Nc3ccc(N4CCC(N5CCC(F)(F)CC5)CC4)c(OC)c3)nc2n1-c1ccc(=O)n(C(C)C)n1] | 636 |

TABLE 3-continued
| Structures of compounds 32-34 | | |
|---|---|---|
| Compound | Compound structure | MS (M + H)$^+$ |
| 154 | 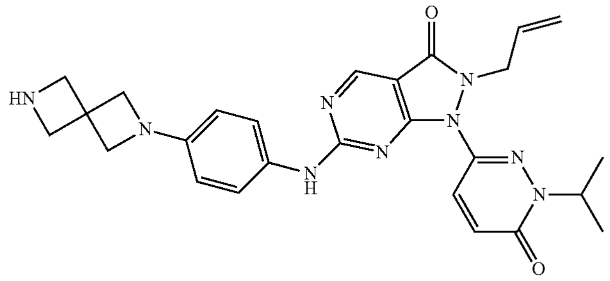 [SMILES: C=CCn1c(=O)c2cnc(Nc3ccc(N4CC5(CNC5)C4)cc3)nc2n1-c1ccc(=O)n(C(C)C)n1] | 500 |
| 155 | 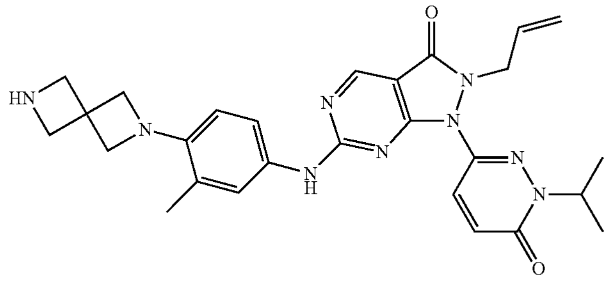 [SMILES: C=CCn1c(=O)c2cnc(Nc3ccc(N4CC5(CNC5)C4)c(C)c3)nc2n1-c1ccc(=O)n(C(C)C)n1] | 514 |
| 156 | 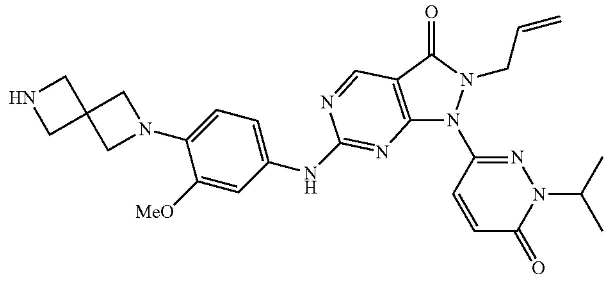 [SMILES: C=CCn1c(=O)c2cnc(Nc3ccc(N4CC5(CNC5)C4)c(OC)c3)nc2n1-c1ccc(=O)n(C(C)C)n1] | 530 |
| 157 | 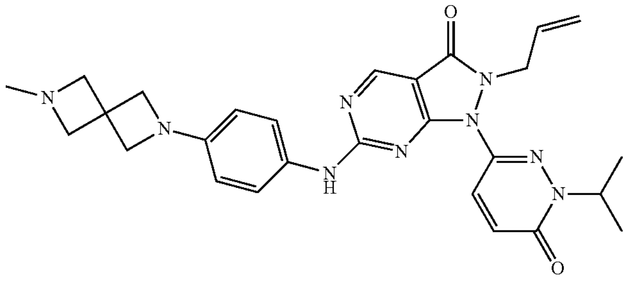 [SMILES: C=CCn1c(=O)c2cnc(Nc3ccc(N4CC5(CN(C)C5)C4)cc3)nc2n1-c1ccc(=O)n(C(C)C)n1] | 514 |
| 158 | 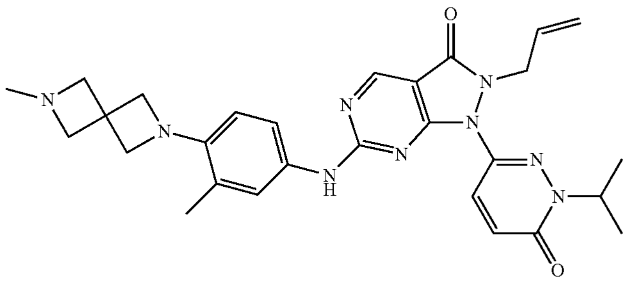 [SMILES: C=CCn1c(=O)c2cnc(Nc3ccc(N4CC5(CN(C)C5)C4)c(C)c3)nc2n1-c1ccc(=O)n(C(C)C)n1] | 528 |

TABLE 3-continued
| Compound | Compound structure | MS (M + H)+ |
|---|---|---|
| | Structures of compounds 32-34 | |
| 159 | 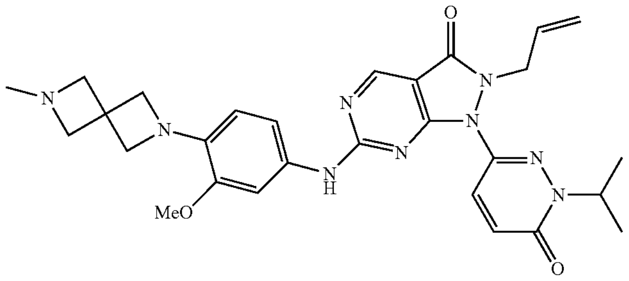 [SMILES: C=CCn1c(=O)c2cnc(Nc3ccc(N4CC5(CN(C)C5)C4)c(OC)c3)nc2n1-c1ccc(=O)n(C(C)C)n1] | 544 |
| 160 | 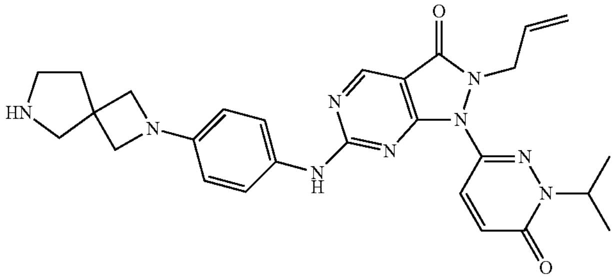 [SMILES: C=CCn1c(=O)c2cnc(Nc3ccc(N4CC5(CCNC5)C4)cc3)nc2n1-c1ccc(=O)n(C(C)C)n1] | 514 |
| 161 | 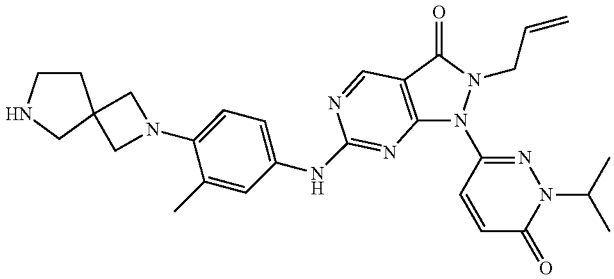 [SMILES: C=CCn1c(=O)c2cnc(Nc3ccc(N4CC5(CCNC5)C4)c(C)c3)nc2n1-c1ccc(=O)n(C(C)C)n1] | 528 |
| 162 | 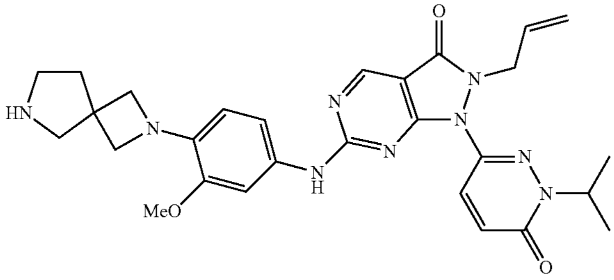 [SMILES: C=CCn1c(=O)c2cnc(Nc3ccc(N4CC5(CCNC5)C4)c(OC)c3)nc2n1-c1ccc(=O)n(C(C)C)n1] | 544 |
| 163 | 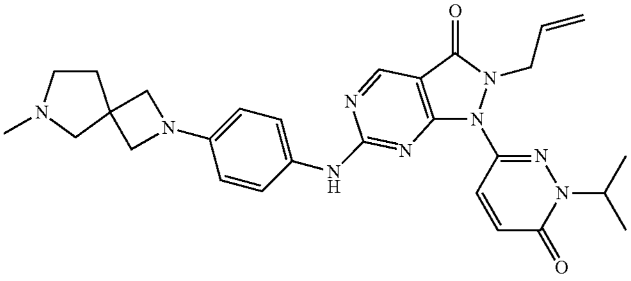 [SMILES: C=CCn1c(=O)c2cnc(Nc3ccc(N4CC5(CCN(C)C5)C4)cc3)nc2n1-c1ccc(=O)n(C(C)C)n1] | 528 |

TABLE 3-continued
| Structures of compounds 32-34 | | |
|---|---|---|
| Compound | Compound structure | MS (M + H)+ |
| 164 | 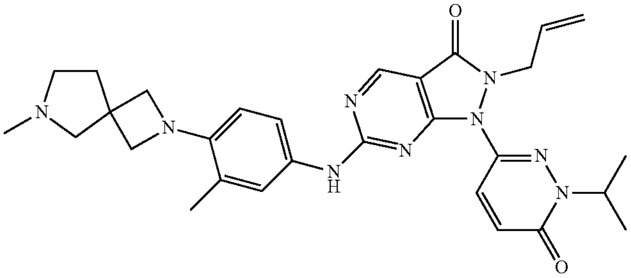 [SMILES: C=CCn1c(=O)c2cnc(Nc3ccc(N4CC5(CCN(C)C5)C4)c(C)c3)nc2n1-c1ccc(=O)n(C(C)C)n1] | 542 |
| 165 | 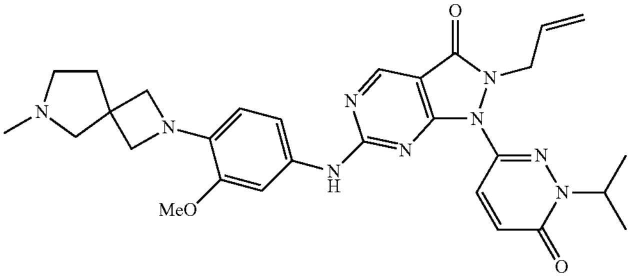 [SMILES: C=CCn1c(=O)c2cnc(Nc3ccc(N4CC5(CCN(C)C5)C4)c(OC)c3)nc2n1-c1ccc(=O)n(C(C)C)n1] | 558 |
| 166 | 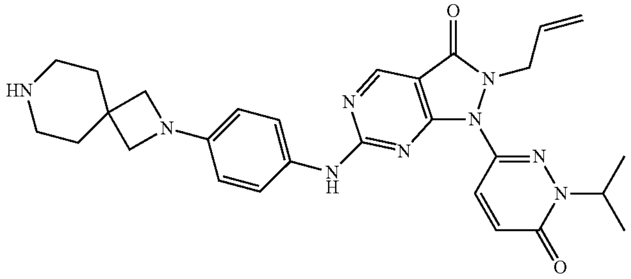 | 528 |
| 167 | 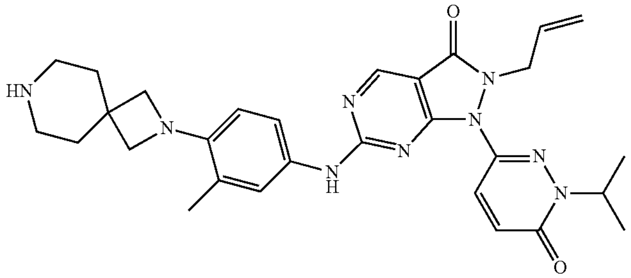 [SMILES: C=CCn1c(=O)c2cnc(Nc3ccc(N4CC5(CCNCC5)C4)c(C)c3)nc2n1-c1ccc(=O)n(C(C)C)n1] | 542 |
| 168 | 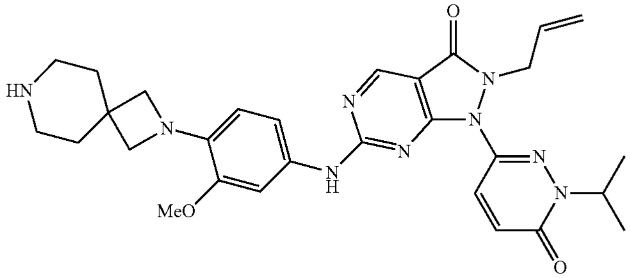 [SMILES: C=CCn1c(=O)c2cnc(Nc3ccc(N4CC5(CCNCC5)C4)c(OC)c3)nc2n1-c1ccc(=O)n(C(C)C)n1] | 558 |

TABLE 3-continued
| Structures of compounds 32-34 | | |
|---|---|---|
| Compound | Compound structure | MS (M + H)$^+$ |
| 169 | 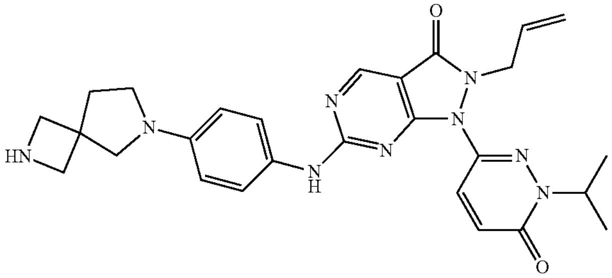 [SMILES: C=CCn1c(=O)c2cnc(Nc3ccc(N4CCC5(CNC5)C4)cc3)nc2n1-c1ccc(=O)n(C(C)C)n1] | 514 |
| 170 | 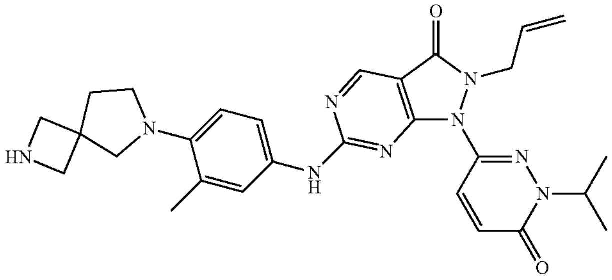 [SMILES: C=CCn1c(=O)c2cnc(Nc3ccc(N4CCC5(CNC5)C4)c(C)c3)nc2n1-c1ccc(=O)n(C(C)C)n1] | 528 |
| 171 | 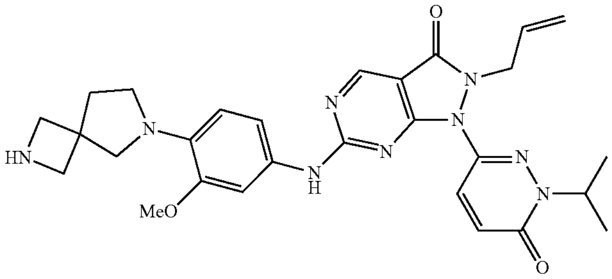 [SMILES: C=CCn1c(=O)c2cnc(Nc3ccc(N4CCC5(CNC5)C4)c(OC)c3)nc2n1-c1ccc(=O)n(C(C)C)n1] | 544 |
| 172 | 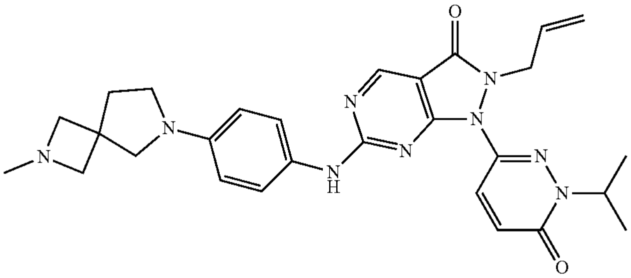 [SMILES: C=CCn1c(=O)c2cnc(Nc3ccc(N4CCC5(CN(C)C5)C4)cc3)nc2n1-c1ccc(=O)n(C(C)C)n1] | 528 |
| 173 | 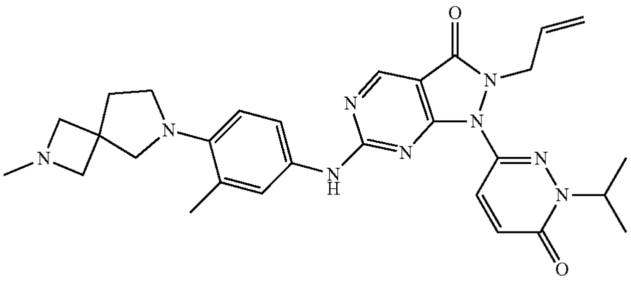 [SMILES: C=CCn1c(=O)c2cnc(Nc3ccc(N4CCC5(CN(C)C5)C4)c(C)c3)nc2n1-c1ccc(=O)n(C(C)C)n1] | 542 |

TABLE 3-continued
| Structures of compounds 32-34 | | |
|---|---|---|
| Compound | Compound structure | MS (M + H)+ |
| 174 | 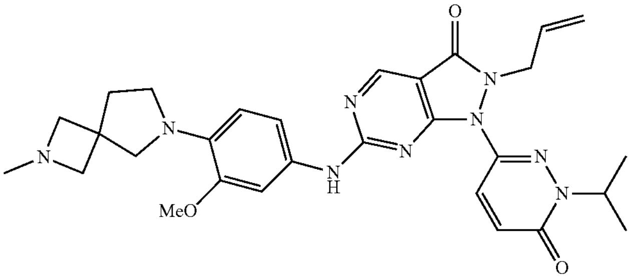 [SMILES: C=CCn1c(=O)c2cnc(Nc3ccc(N4CCC5(CN(C)C5)C4)c(OC)c3)nc2n1-c1ccc(=O)n(C(C)C)n1] | 558 |
| 175 | 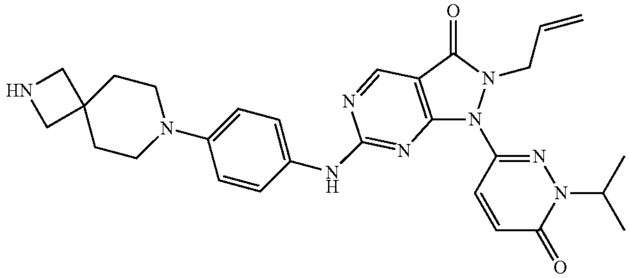 [SMILES: C=CCn1c(=O)c2cnc(Nc3ccc(N4CCC5(CC4)CNC5)cc3)nc2n1-c1ccc(=O)n(C(C)C)n1] | 528 |
| 176 | 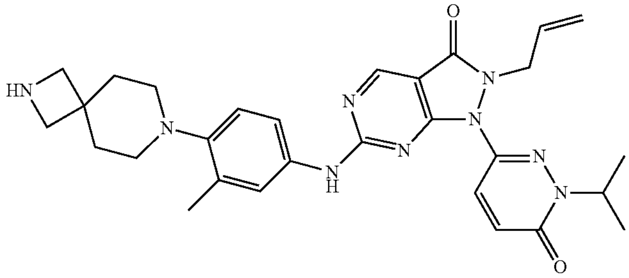 [SMILES: C=CCn1c(=O)c2cnc(Nc3ccc(N4CCC5(CC4)CNC5)c(C)c3)nc2n1-c1ccc(=O)n(C(C)C)n1] | 542 |
| 177 | 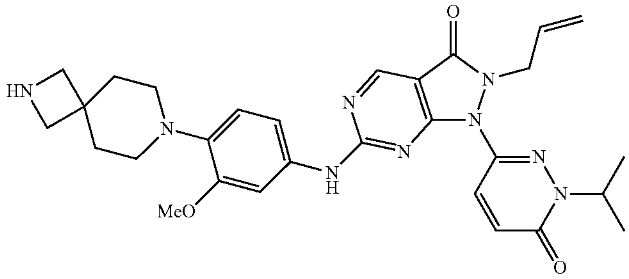 [SMILES: C=CCn1c(=O)c2cnc(Nc3ccc(N4CCC5(CC4)CNC5)c(OC)c3)nc2n1-c1ccc(=O)n(C(C)C)n1] | 558 |
| 178 | 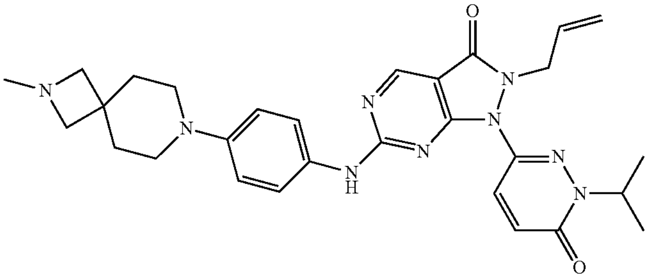 [SMILES: C=CCn1c(=O)c2cnc(Nc3ccc(N4CCC5(CC4)CN(C)C5)cc3)nc2n1-c1ccc(=O)n(C(C)C)n1] | 542 |

TABLE 3-continued
| Structures of compounds 32-34 | | |
|---|---|---|
| Compound | Compound structure | MS $(M + H)^+$ |
| 179 | 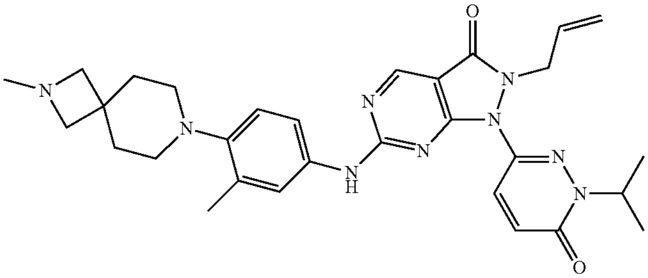 [SMILES: C=CCn1c(=O)c2cnc(Nc3ccc(N4CCC5(CC4)CN(C)C5)c(C)c3)nc2n1-c1ccc(=O)n(C(C)C)n1] | 556 |
| 180 | 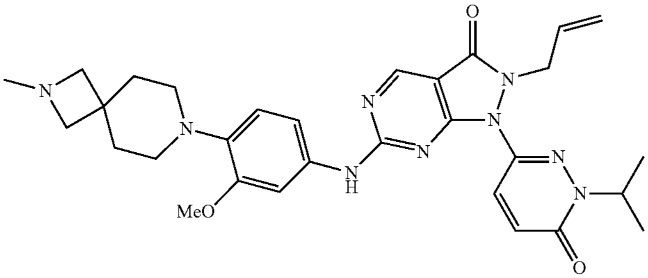 [SMILES: C=CCn1c(=O)c2cnc(Nc3ccc(N4CCC5(CC4)CN(C)C5)c(OC)c3)nc2n1-c1ccc(=O)n(C(C)C)n1] | 572 |
| 181 | 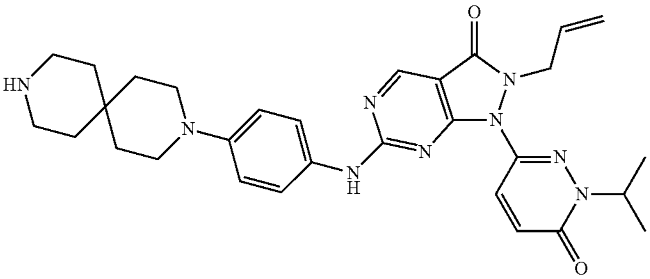 | 556 |
| 182 | 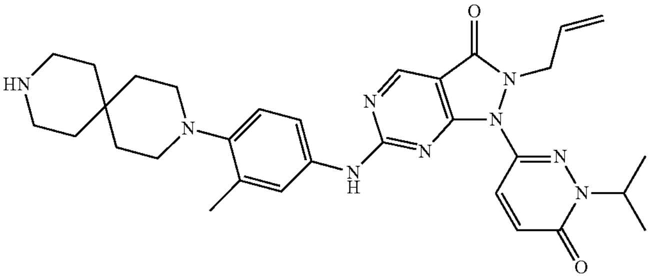 [SMILES: C=CCn1c(=O)c2cnc(Nc3ccc(N4CCC5(CCNCC5)CC4)c(C)c3)nc2n1-c1ccc(=O)n(C(C)C)n1] | 570 |
| 183 | 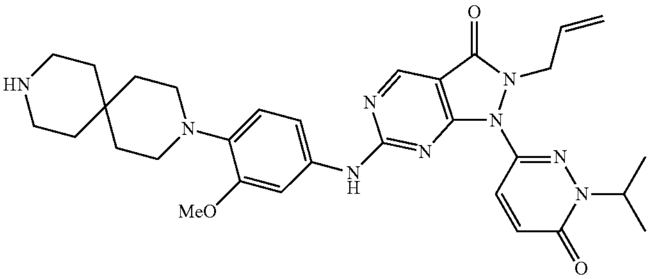 [SMILES: C=CCn1c(=O)c2cnc(Nc3ccc(N4CCC5(CCNCC5)CC4)c(OC)c3)nc2n1-c1ccc(=O)n(C(C)C)n1] | 586 |

TABLE 3-continued
| Structures of compounds 32-34 | | |
|---|---|---|
| Compound | Compound structure | MS (M + H)+ |
| 184 | 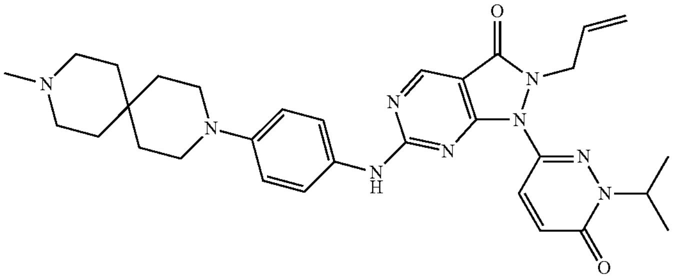 [SMILES: C=CCn1c(=O)c2cnc(Nc3ccc(N4CCC5(CCN(C)CC5)CC4)cc3)nc2n1-c1ccc(=O)n(C(C)C)n1] | 570 |
| 185 | 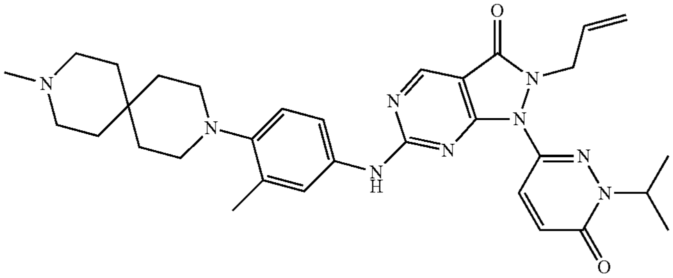 [SMILES: C=CCn1c(=O)c2cnc(Nc3ccc(N4CCC5(CCN(C)CC5)CC4)c(C)c3)nc2n1-c1ccc(=O)n(C(C)C)n1] | 584 |
| 186 | 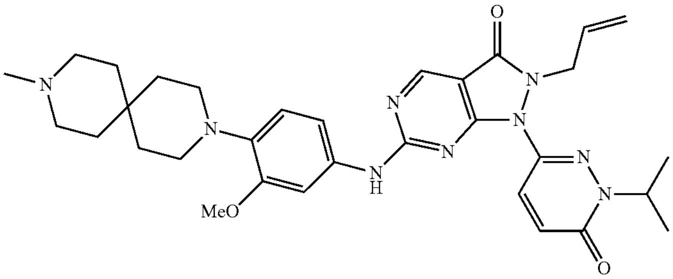 [SMILES: C=CCn1c(=O)c2cnc(Nc3ccc(N4CCC5(CCN(C)CC5)CC4)c(OC)c3)nc2n1-c1ccc(=O)n(C(C)C)n1] | 600 |
| 187 | 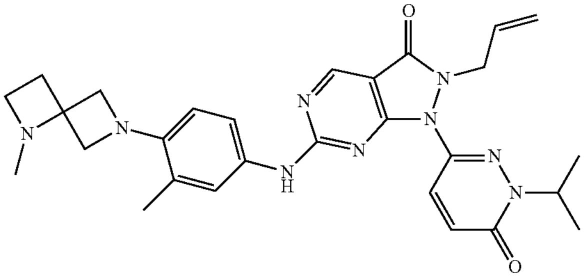 [SMILES: C=CCn1c(=O)c2cnc(Nc3ccc(N4CC5(CCN5C)C4)c(C)c3)nc2n1-c1ccc(=O)n(C(C)C)n1] | 528 |
| 188 | 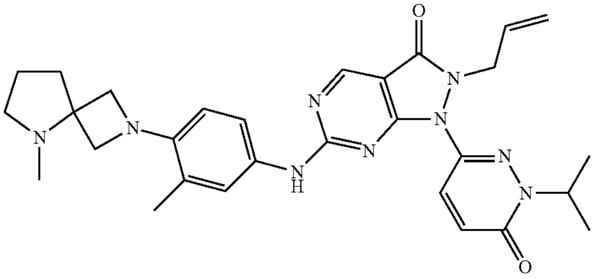 [SMILES: C=CCn1c(=O)c2cnc(Nc3ccc(N4CC5(CCCN5C)C4)c(C)c3)nc2n1-c1ccc(=O)n(C(C)C)n1] | 542 |

TABLE 3-continued
| Compound | Compound structure | MS (M + H)+ |
| --- | --- | --- |
| Structures of compounds 32-34 | | |
| 189 | 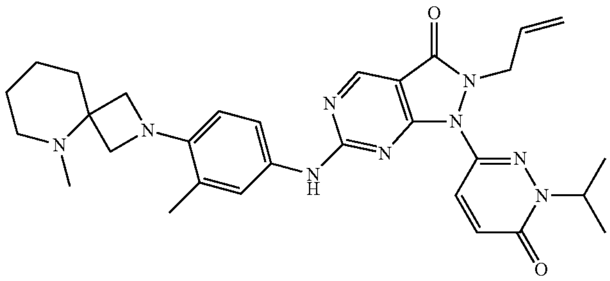 [SMILES: C=CCn1c(=O)c2cnc(Nc3ccc(N4CC5(CCCCN5C)C4)c(C)c3)nc2n1-c1ccc(=O)n(C(C)C)n1] | 556 |
| 190 | 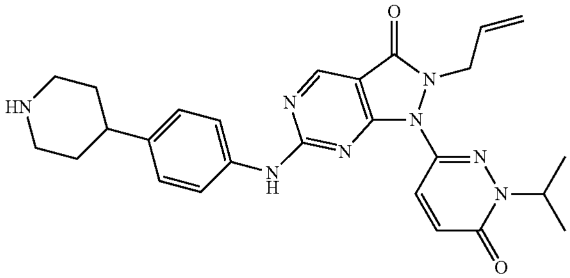 [SMILES: C=CCn1c(=O)c2cnc(Nc3ccc(C4CCNCC4)cc3)nc2n1-c1ccc(=O)n(C(C)C)n1] | 487 |
| 191 | 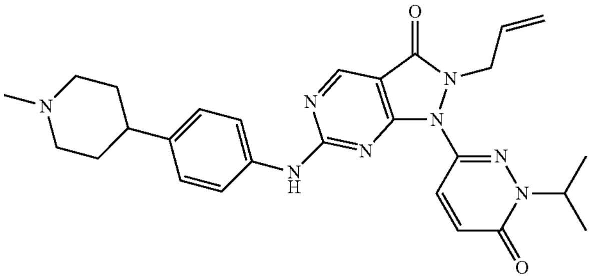 | 501 |
| 192 | 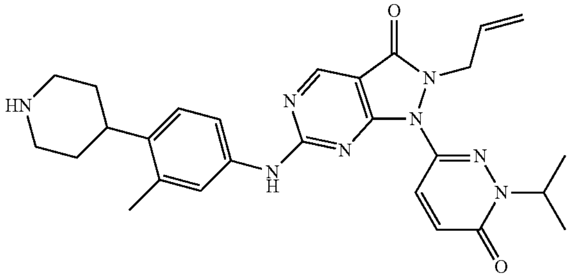 [SMILES: C=CCn1c(=O)c2cnc(Nc3ccc(C4CCNCC4)c(C)c3)nc2n1-c1ccc(=O)n(C(C)C)n1] | 501 |
| 193 | 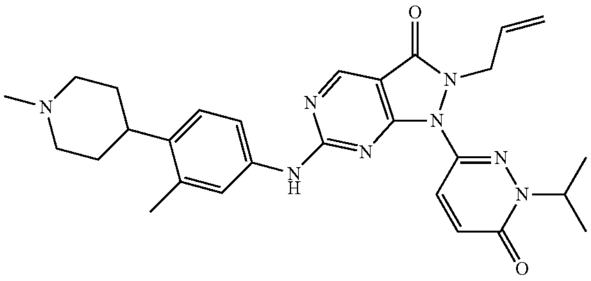 [SMILES: C=CCn1c(=O)c2cnc(Nc3ccc(C4CCN(C)CC4)c(C)c3)nc2n1-c1ccc(=O)n(C(C)C)n1] | 515 |

TABLE 3-continued
| Structures of compounds 32-34 | | |
|---|---|---|
| Compound | Compound structure | MS (M + H)$^+$ |
| 194 | 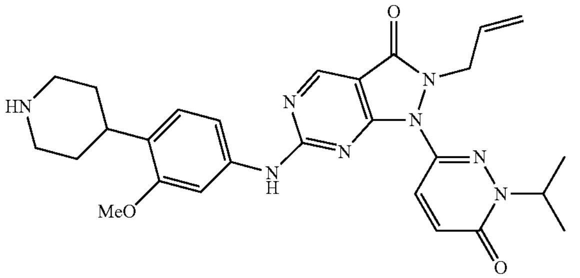 [SMILES: C=CCn1c(=O)c2cnc(Nc3ccc(C4CCNCC4)c(OC)c3)nc2n1-c1ccc(=O)n(C(C)C)n1] | 517 |
| 195 | 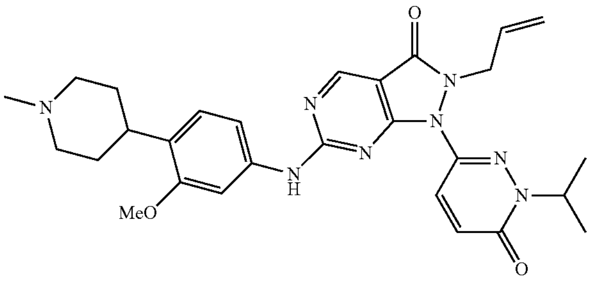 [SMILES: C=CCn1c(=O)c2cnc(Nc3ccc(C4CCN(C)CC4)c(OC)c3)nc2n1-c1ccc(=O)n(C(C)C)n1] | 531 |
| 196 | 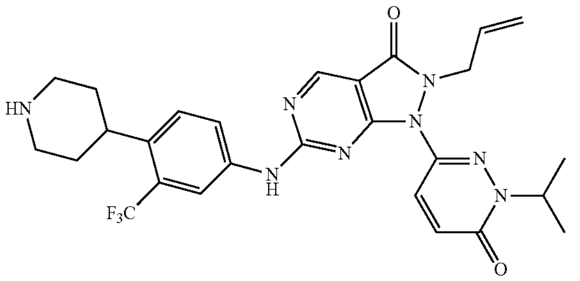 [SMILES: C=CCn1c(=O)c2cnc(Nc3ccc(C4CCNCC4)c(C(F)(F)F)c3)nc2n1-c1ccc(=O)n(C(C)C)n1] | 555 |
| 197 | 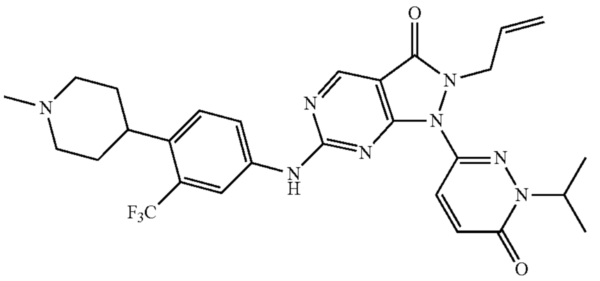 [SMILES: C=CCn1c(=O)c2cnc(Nc3ccc(C4CCN(C)CC4)c(C(F)(F)F)c3)nc2n1-c1ccc(=O)n(C(C)C)n1] | 569 |
| 198 | 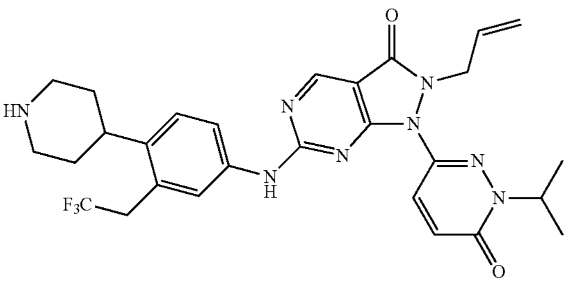 [SMILES: C=CCn1c(=O)c2cnc(Nc3ccc(C4CCNCC4)c(CC(F)(F)F)c3)nc2n1-c1ccc(=O)n(C(C)C)n1] | 569 |

TABLE 3-continued
| Structures of compounds 32-34 | | |
|---|---|---|
| Compound | Compound structure | MS (M + H)+ |
| 199 | 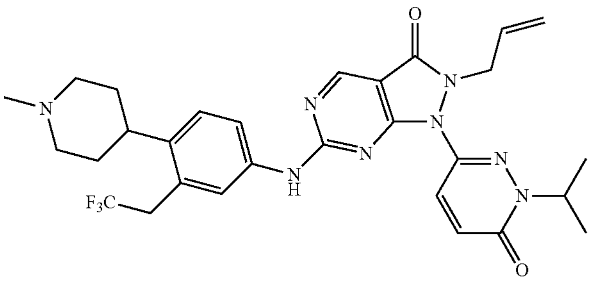 | 583 |
| 200 | 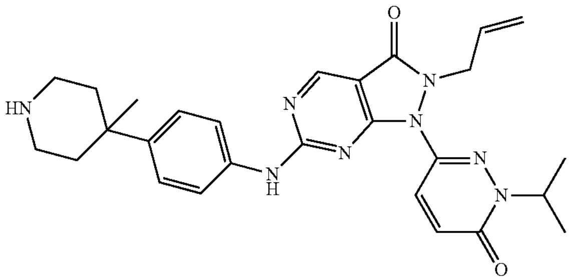 | 501 |
| 201 | 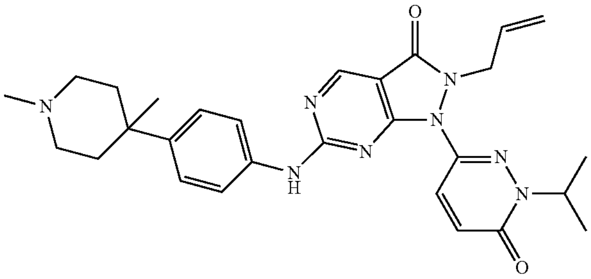 [SMILES: C=CCn1c(=O)c2cnc(Nc3ccc(C4(C)CCN(C)CC4)cc3)nc2n1-c1ccc(=O)n(C(C)C)n1] | 515 |
| 202 | 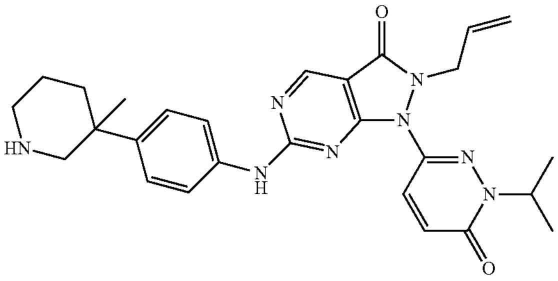 [SMILES: C=CCn1c(=O)c2cnc(Nc3ccc(C4(C)CCCNC4)cc3)nc2n1-c1ccc(=O)n(C(C)C)n1] | 501 |
| 203 | 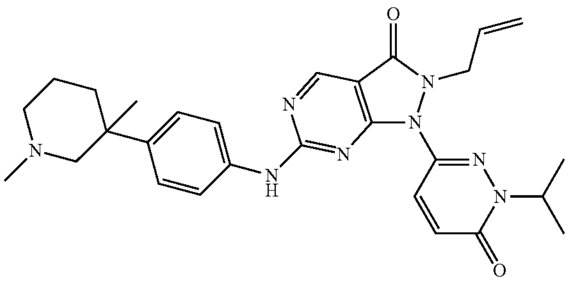 [SMILES: C=CCn1c(=O)c2cnc(Nc3ccc(C4(C)CCCN(C)C4)cc3)nc2n1-c1ccc(=O)n(C(C)C)n1] | 515 |

TABLE 3-continued
| Structures of compounds 32-34 | | |
|---|---|---|
| Compound | Compound structure | MS (M + H)$^+$ |
| 204 | 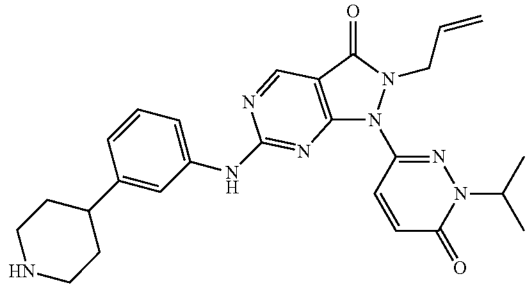 [SMILES: C=CCn1c(=O)c2cnc(Nc3cccc(C4CCNCC4)c3)nc2n1-c1ccc(=O)n(C(C)C)n1] | 487 |
| 205 | 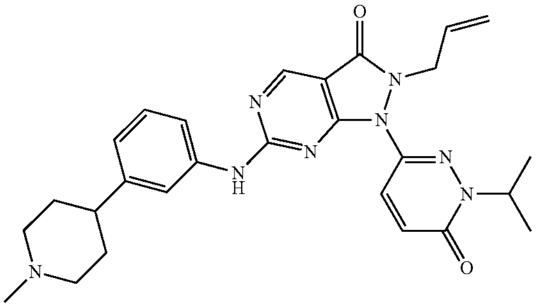 [SMILES: C=CCn1c(=O)c2cnc(Nc3cccc(C4CCN(C)CC4)c3)nc2n1-c1ccc(=O)n(C(C)C)n1] | 501 |
| 206 | 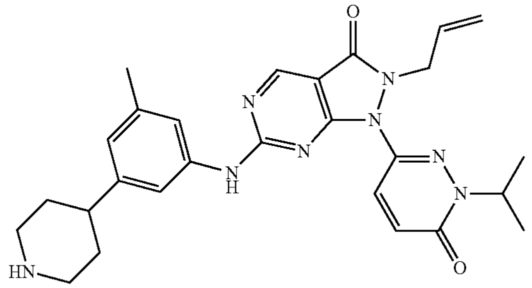 | 501 |
| 207 | 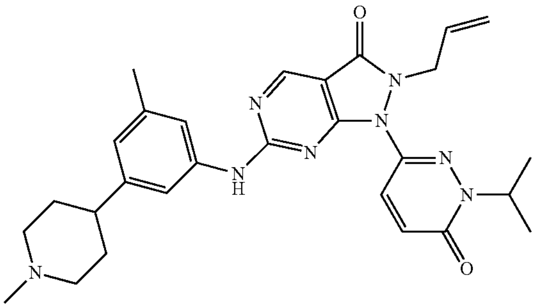 | 515 |
| 208 | 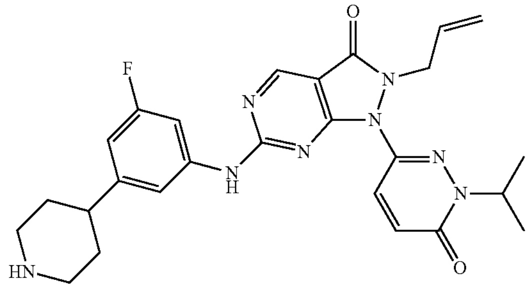 [SMILES: C=CCn1c(=O)c2cnc(Nc3cc(F)cc(C4CCNCC4)c3)nc2n1-c1ccc(=O)n(C(C)C)n1] | 505 |

TABLE 3-continued
Structures of compounds 32-34
| Compound | Compound structure | MS (M + H)$^+$ |
| --- | --- | --- |
| 209 | 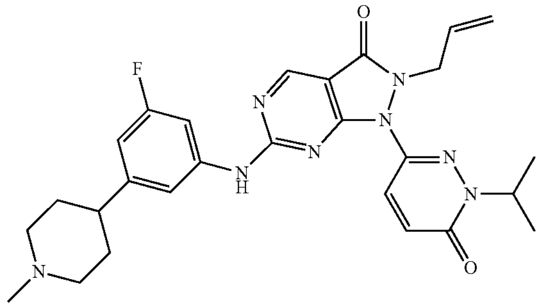 [SMILES: C=CCn1c(=O)c2cnc(Nc3cc(F)cc(C4CCN(C)CC4)c3)nc2n1-c1ccc(=O)n(C(C)C)n1] | 519 |
| 210 | 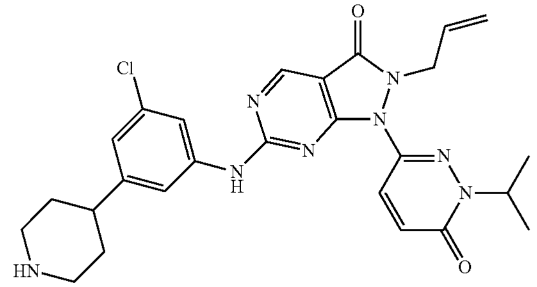 [SMILES: C=CCn1c(=O)c2cnc(Nc3cc(Cl)cc(C4CCNCC4)c3)nc2n1-c1ccc(=O)n(C(C)C)n1] | 521 |
| 211 | 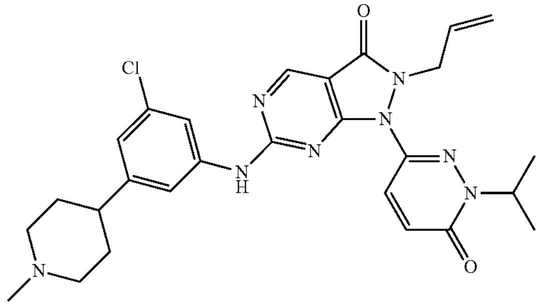 [SMILES: C=CCn1c(=O)c2cnc(Nc3cc(Cl)cc(C4CCN(C)CC4)c3)nc2n1-c1ccc(=O)n(C(C)C)n1] | 535 |
| 212 | 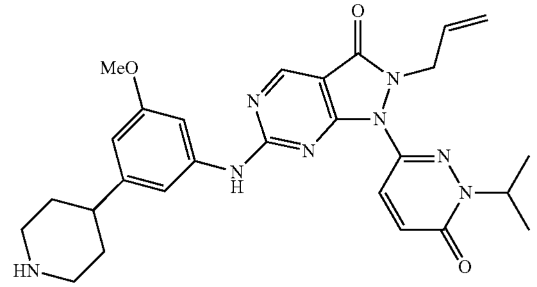 [SMILES: C=CCn1c(=O)c2cnc(Nc3cc(OC)cc(C4CCNCC4)c3)nc2n1-c1ccc(=O)n(C(C)C)n1] | 517 |
| 213 | 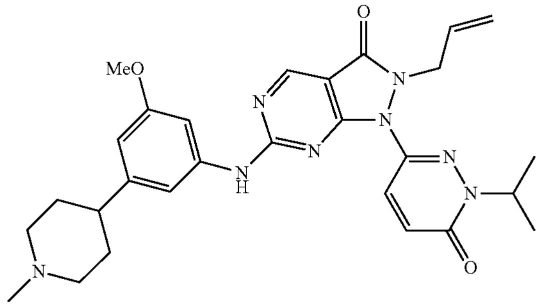 [SMILES: C=CCn1c(=O)c2cnc(Nc3cc(OC)cc(C4CCN(C)CC4)c3)nc2n1-c1ccc(=O)n(C(C)C)n1] | 531 |

TABLE 3-continued
| Structures of compounds 32-34 | | |
|---|---|---|
| Compound | Compound structure | MS (M + H)+ |
| 214 | 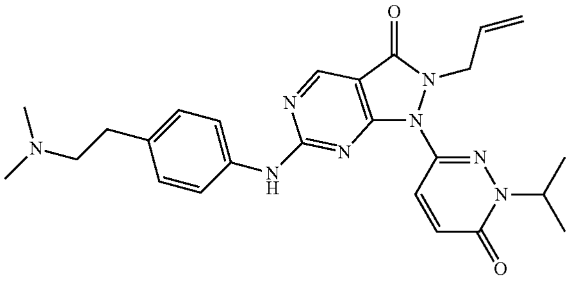 [SMILES: C=CCn1c(=O)c2cnc(Nc3ccc(CCN(C)C)cc3)nc2n1-c1ccc(=O)n(C(C)C)n1] | 475 |
| 215 | 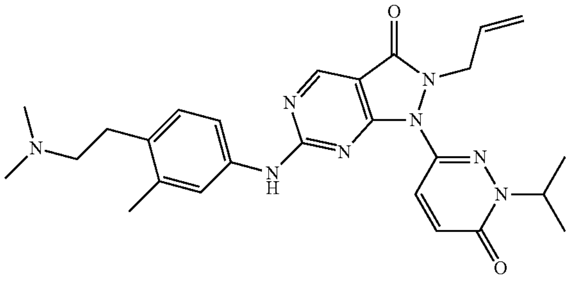 [SMILES: C=CCn1c(=O)c2cnc(Nc3ccc(CCN(C)C)c(C)c3)nc2n1-c1ccc(=O)n(C(C)C)n1] | 489 |
| 216 | 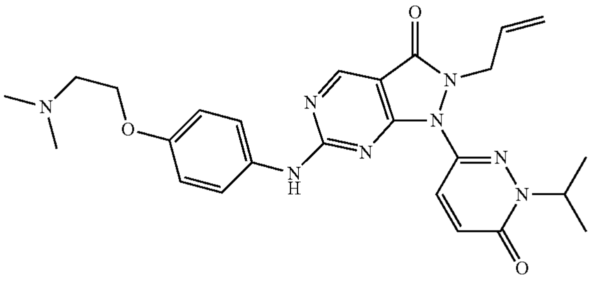 [SMILES: C=CCn1c(=O)c2cnc(Nc3ccc(OCCN(C)C)cc3)nc2n1-c1ccc(=O)n(C(C)C)n1] | 491 |
| 217 | 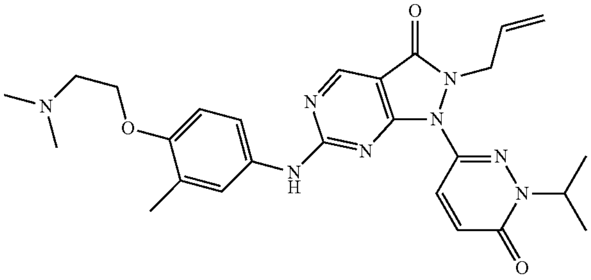 [SMILES: C=CCn1c(=O)c2cnc(Nc3ccc(OCCN(C)C)c(C)c3)nc2n1-c1ccc(=O)n(C(C)C)n1] | 505 |
| 218 | 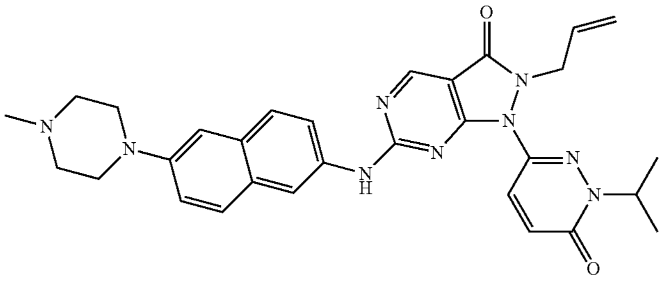 [SMILES: C=CCn1c(=O)c2cnc(Nc3ccc4cc(N5CCN(C)CC5)ccc4c3)nc2n1-c1ccc(=O)n(C(C)C)n1] | 552 |

TABLE 3-continued
| Structures of compounds 32-34 | | |
|---|---|---|
| Compound | Compound structure | MS (M + H)+ |
| 219 | 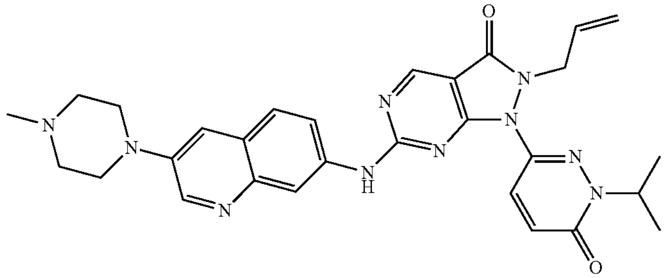 | 553 |
| 220 | 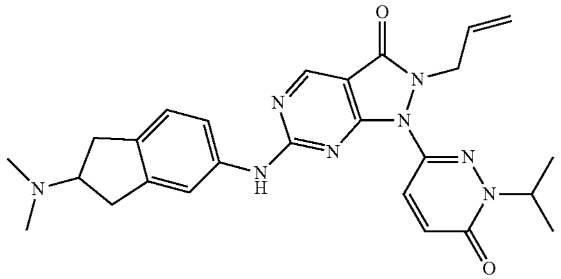 [SMILES: C=CCn1c(=O)c2cnc(Nc3ccc4c(c3)CC(N(C)C)C4)nc2n1-c1ccc(=O)n(C(C)C)n1] | 487 |
| 221 | 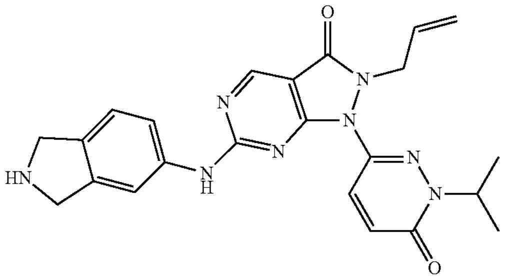 [SMILES: C=CCn1c(=O)c2cnc(Nc3ccc4c(c3)CNC4)nc2n1-c1ccc(=O)n(C(C)C)n1] | 445 |
| 222 | 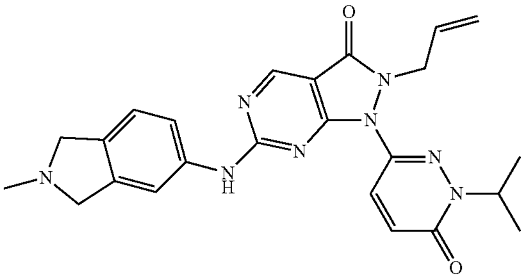 [SMILES: C=CCn1c(=O)c2cnc(Nc3ccc4c(c3)CN(C)C4)nc2n1-c1ccc(=O)n(C(C)C)n1] | 459 |
| 223 | 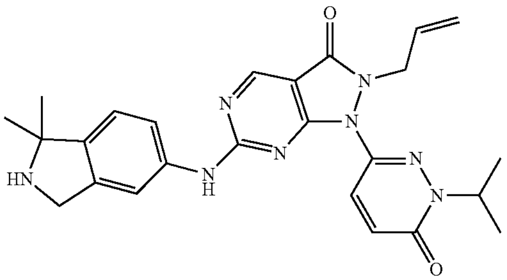 [SMILES: C=CCn1c(=O)c2cnc(Nc3ccc4c(c3)CNC4(C)C)nc2n1-c1ccc(=O)n(C(C)C)n1] | 473 |

TABLE 3-continued
| Structures of compounds 32-34 | | |
|---|---|---|
| Compound | Compound structure | MS (M + H)$^+$ |
| 224 | 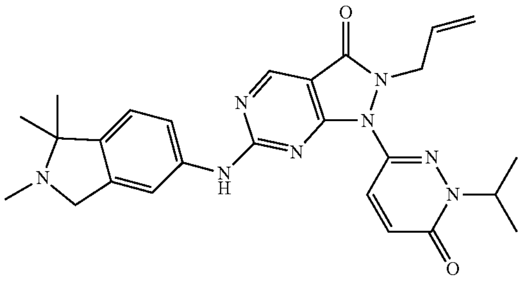 [SMILES: C=CCn1c(=O)c2cnc(Nc3ccc4c(c3)CN(C)C4(C)C)nc2n1-c1ccc(=O)n(C(C)C)n1] | 487 |
| 225 | 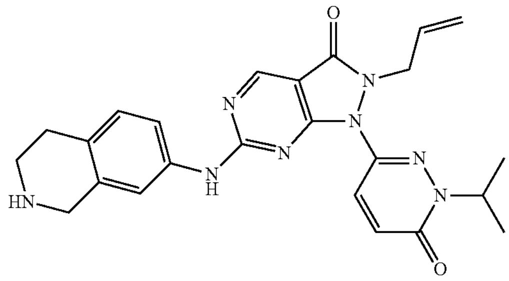 [SMILES: C=CCn1c(=O)c2cnc(Nc3ccc4c(c3)CNCC4)nc2n1-c1ccc(=O)n(C(C)C)n1] | 459 |
| 226 | 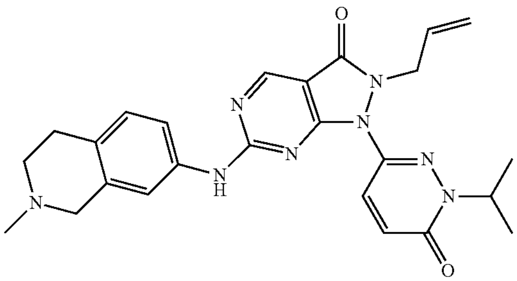 [SMILES: C=CCn1c(=O)c2cnc(Nc3ccc4c(c3)CN(C)CC4)nc2n1-c1ccc(=O)n(C(C)C)n1] | 473 |
| 227 | 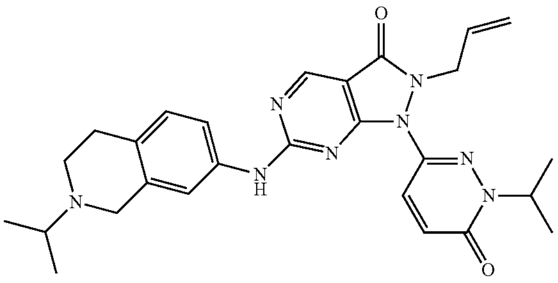 [SMILES: C=CCn1c(=O)c2cnc(Nc3ccc4c(c3)CN(C(C)C)CC4)nc2n1-c1ccc(=O)n(C(C)C)n1] | 501 |
| 228 | 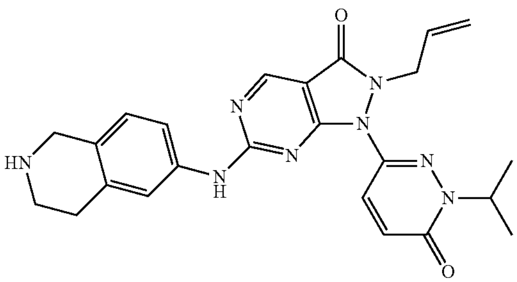 [SMILES: C=CCn1c(=O)c2cnc(Nc3ccc4c(c3)CCNC4)nc2n1-c1ccc(=O)n(C(C)C)n1] | 459 |

TABLE 3-continued
| Structures of compounds 32-34 | | |
|---|---|---|
| Compound | Compound structure | MS (M + H)+ |
| 229 | 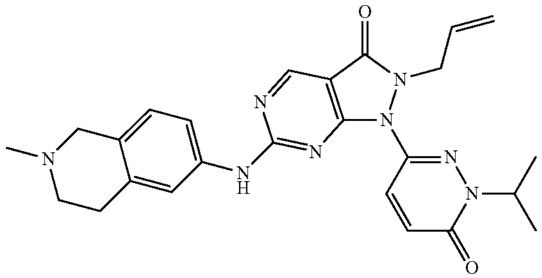 [SMILES: C=CCn1c(=O)c2cnc(Nc3ccc4c(c3)CCN(C)C4)nc2n1-c1ccc(=O)n(C(C)C)n1] | 473 |
| 230 | 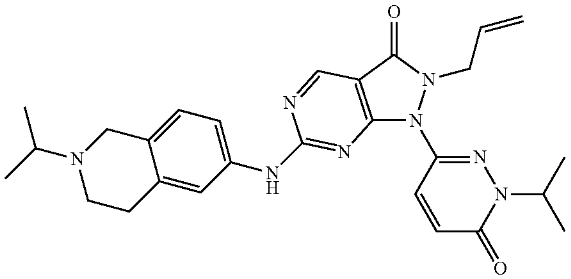 [SMILES: C=CCn1c(=O)c2cnc(Nc3ccc4c(c3)CCN(C(C)C)C4)nc2n1-c1ccc(=O)n(C(C)C)n1] | 501 |
| 231 | 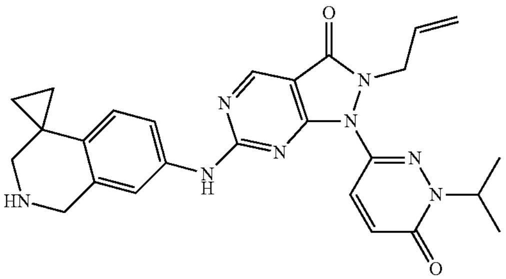 [SMILES: C=CCn1c(=O)c2cnc(Nc3ccc4c(c3)CNCC43CC3)nc2n1-c1ccc(=O)n(C(C)C)n1] | 485 |
| 232 | 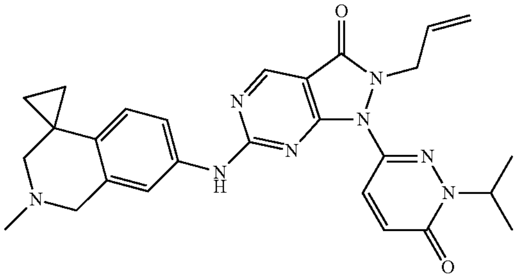 [SMILES: C=CCn1c(=O)c2cnc(Nc3ccc4c(c3)CN(C)CC43CC3)nc2n1-c1ccc(=O)n(C(C)C)n1] | 499 |
| 233 | 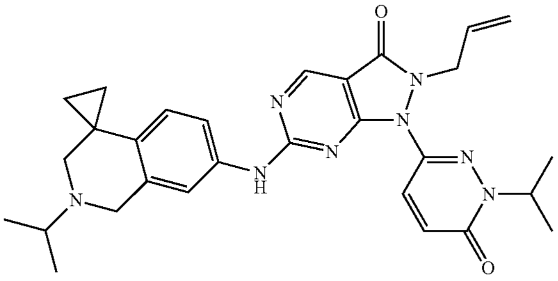 [SMILES: C=CCn1c(=O)c2cnc(Nc3ccc4c(c3)CN(C(C)C)CC43CC3)nc2n1-c1ccc(=O)n(C(C)C)n1] | 527 |

TABLE 3-continued
Structures of compounds 32-34
| Compound | Compound structure | MS (M + H)+ |
| --- | --- | --- |
| 234 | 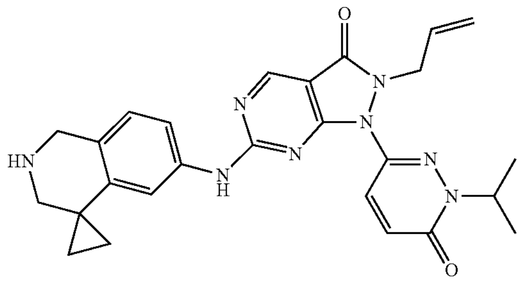 [SMILES: C=CCn1c(=O)c2cnc(Nc3ccc4c(c3)C3(CC3)CNC4)nc2n1-c1ccc(=O)n(C(C)C)n1] | 485 |
| 235 | 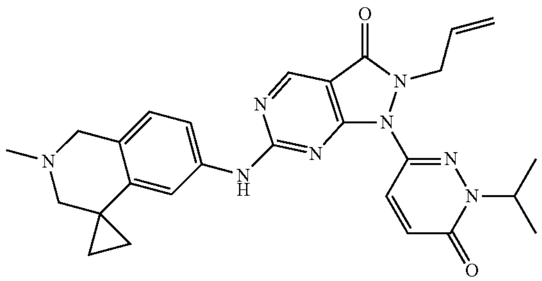 [SMILES: C=CCn1c(=O)c2cnc(Nc3ccc4c(c3)C3(CC3)CN(C)C4)nc2n1-c1ccc(=O)n(C(C)C)n1] | 499 |
| 236 | 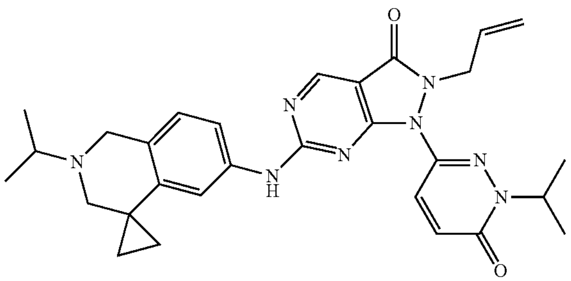 [SMILES: C=CCn1c(=O)c2cnc(Nc3ccc4c(c3)C3(CC3)CN(C(C)C)C4)nc2n1-c1ccc(=O)n(C(C)C)n1] | 527 |
| 237 | 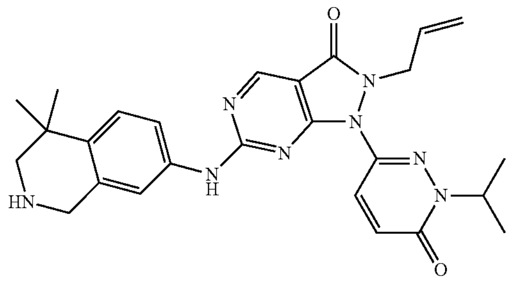 [SMILES: C=CCn1c(=O)c2cnc(Nc3ccc4c(c3)CNCC4(C)C)nc2n1-c1ccc(=O)n(C(C)C)n1] | 487 |
| 238 | 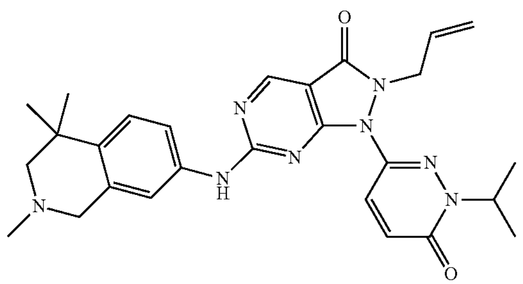 [SMILES: C=CCn1c(=O)c2cnc(Nc3ccc4c(c3)CN(C)CC4(C)C)nc2n1-c1ccc(=O)n(C(C)C)n1] | 501 |

TABLE 3-continued
| Structures of compounds 32-34 | | |
|---|---|---|
| Compound | Compound structure | MS (M + H)+ |
| 239 | 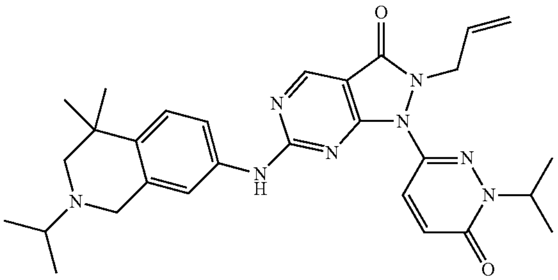 | 529 |
| 240 | 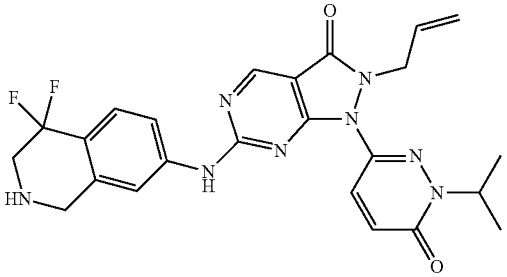 | 495 |
| 241 | 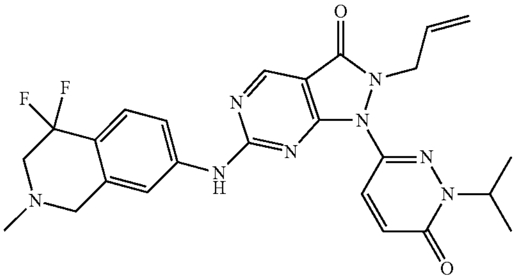 | 509 |
| 242 | 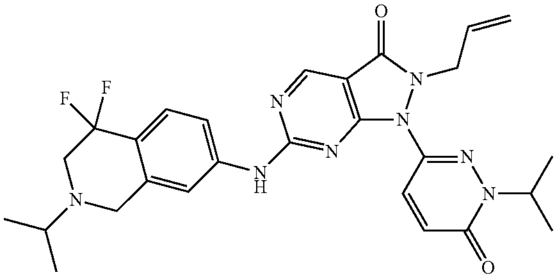 [SMILES: C=CCn1c(=O)c2cnc(Nc3ccc4c(c3)CN(C(C)C)CC4(C)C)nc2n1-c1ccc(=O)n(C(C)C)n1] | 537 |
| 243 | 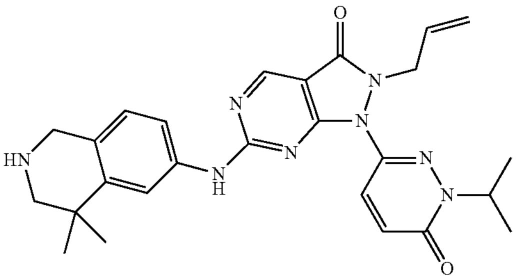 [SMILES: C=CCn1c(=O)c2cnc(Nc3ccc4c(c3)C(C)(C)CNC4)nc2n1-c1ccc(=O)n(C(C)C)n1] | 487 |

TABLE 3-continued
| Structures of compounds 32-34 | | |
|---|---|---|
| Compound | Compound structure | MS $(M + H)^+$ |
| 244 | 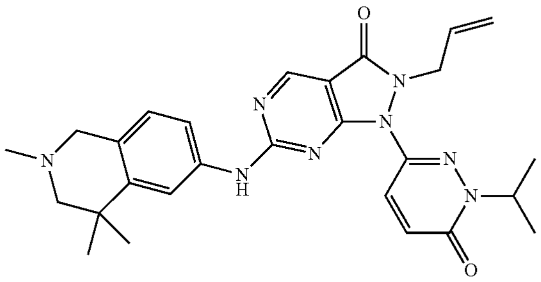 [SMILES: C=CCn1c(=O)c2cnc(Nc3ccc4c(c3)C(C)(C)CN(C)C4)nc2n1-c1ccc(=O)n(C(C)C)n1] | 501 |
| 245 | 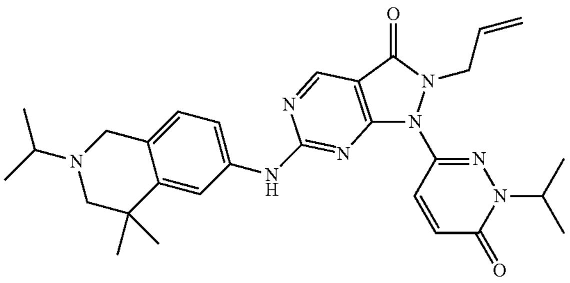 [SMILES: C=CCn1c(=O)c2cnc(Nc3ccc4c(c3)C(C)(C)CN(C(C)C)C4)nc2n1-c1ccc(=O)n(C(C)C)n1] | 529 |
| 246 | 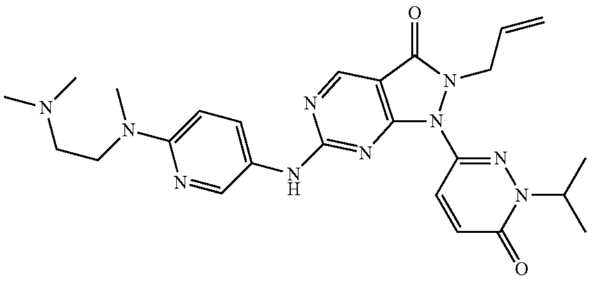 [SMILES: C=CCn1c(=O)c2cnc(Nc3ccc(N(C)CCN(C)C)nc3)nc2n1-c1ccc(=O)n(C(C)C)n1] | 505 |
| 247 | 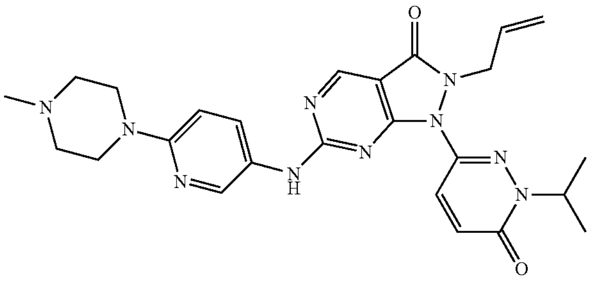 | 503 |
| 248 | 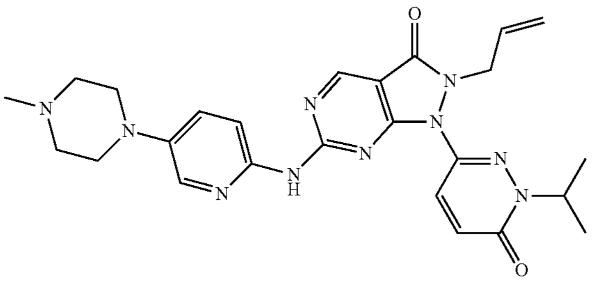 | 503 |

TABLE 3-continued
| Structures of compounds 32-34 | | |
|---|---|---|
| Compound | Compound structure | MS (M + H)$^+$ |
| 249 | 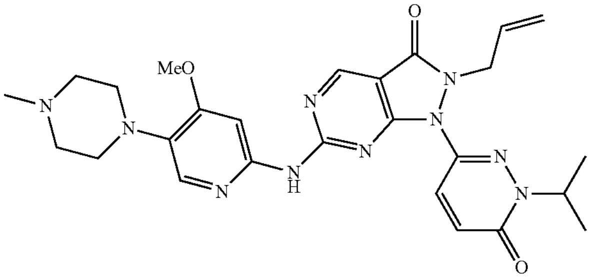 [SMILES: C=CCn1c(=O)c2cnc(Nc3cc(OC)c(N4CCN(C)CC4)cn3)nc2n1-c1ccc(=O)n(C(C)C)n1] | 533 |
| 250 | 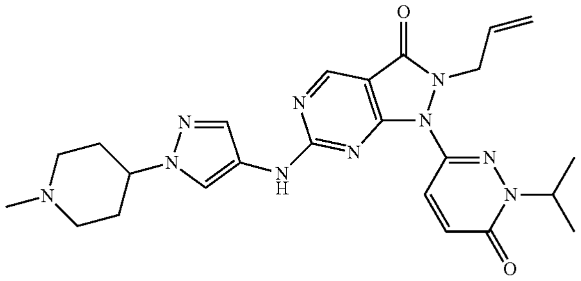 [SMILES: C=CCn1c(=O)c2cnc(Nc3cnn(C4CCN(C)CC4)c3)nc2n1-c1ccc(=O)n(C(C)C)n1] | 491 |
| 251 | 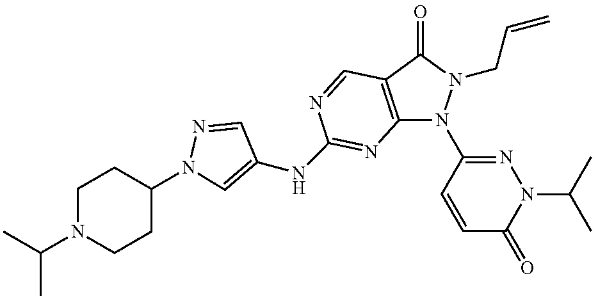 [SMILES: C=CCn1c(=O)c2cnc(Nc3cnn(C4CCN(C(C)C)CC4)c3)nc2n1-c1ccc(=O)n(C(C)C)n1] | 519 |
| 252 | 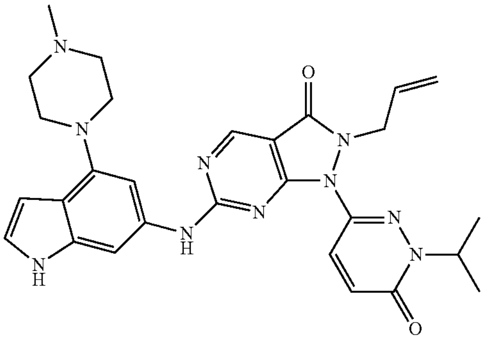 [SMILES: C=CCn1c(=O)c2cnc(Nc3cc(N4CCN(C)CC4)c4cc[nH]c4c3)nc2n1-c1ccc(=O)n(C(C)C)n1] | 541 |

TABLE 3-continued
| Compound | Compound structure | MS (M + H)⁺ |
|---|---|---|
| Structures of compounds 32-34 | | |
| 253 | 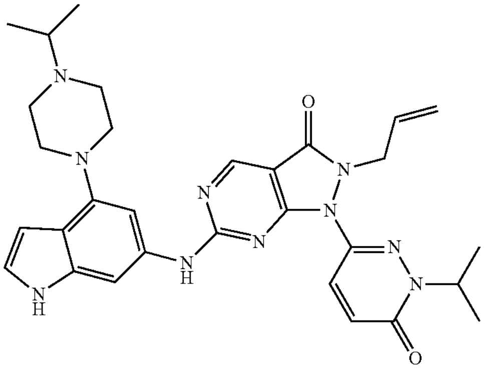 [SMILES: C=CCn1c(=O)c2cnc(Nc3cc(N4CCN(C(C)C)CC4)c4cc[nH]c4c3)nc2n1-c1ccc(=O)n(C(C)C)n1] | 569 |
| 254 | 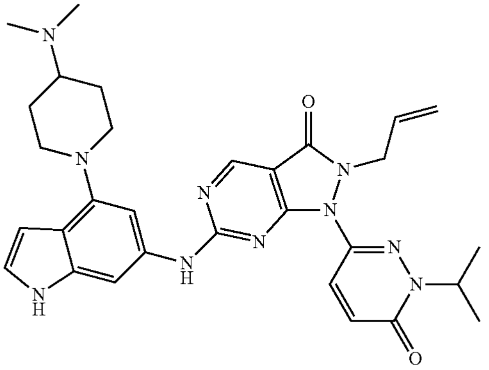 [SMILES: C=CCn1c(=O)c2cnc(Nc3cc(N4CCC(N(C)C)CC4)c4cc[nH]c4c3)nc2n1-c1ccc(=O)n(C(C)C)n1] | 569 |
| 255 | 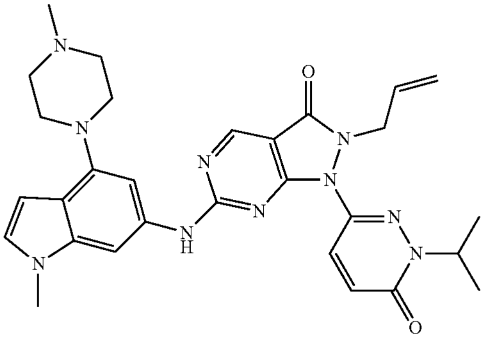 [SMILES: C=CCn1c(=O)c2cnc(Nc3cc(N4CCN(C)CC4)c4ccn(C)c4c3)nc2n1-c1ccc(=O)n(C(C)C)n1] | 555 |
| 256 | 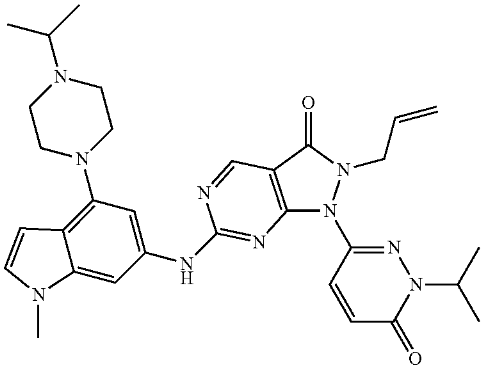 [SMILES: C=CCn1c(=O)c2cnc(Nc3cc(N4CCN(C(C)C)CC4)c4ccn(C)c4c3)nc2n1-c1ccc(=O)n(C(C)C)n1] | 583 |

TABLE 3-continued
| Structures of compounds 32-34 | | |
|---|---|---|
| Compound | Compound structure | MS (M + H)+ |
| 257 | 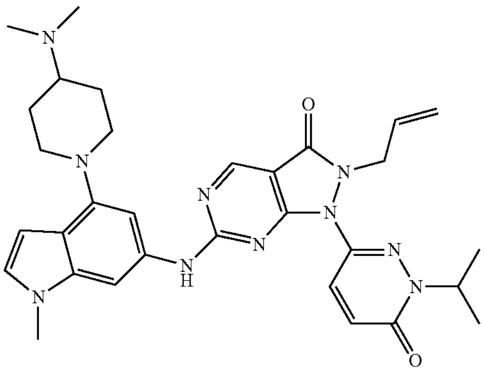 [SMILES: C=CCn1c(=O)c2cnc(Nc3cc(N4CCC(N(C)C)CC4)c4ccn(C)c4c3)nc2n1-c1ccc(=O)n(C(C)C)n1] | 583 |
| 258 | 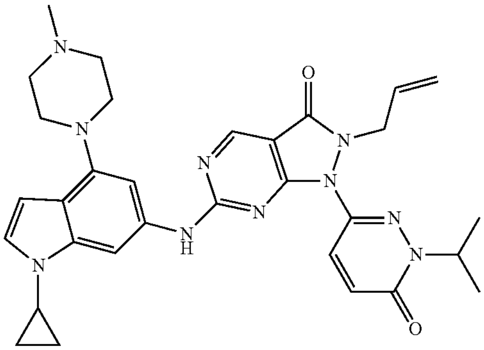 [SMILES: C=CCn1c(=O)c2cnc(Nc3cc(N4CCN(C)CC4)c4ccn(C5CC5)c4c3)nc2n1-c1ccc(=O)n(C(C)C)n1] | 581 |
| 259 | 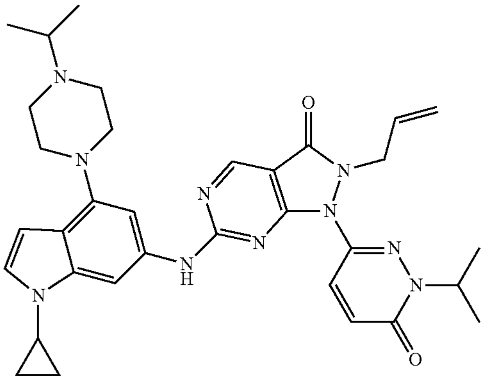 [SMILES: C=CCn1c(=O)c2cnc(Nc3cc(N4CCN(C(C)C)CC4)c4ccn(C5CC5)c4c3)nc2n1-c1ccc(=O)n(C(C)C)n1] | 609 |
| 260 | 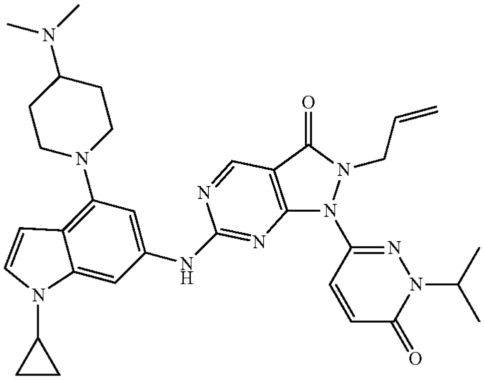 | 609 |

TABLE 3-continued
| Compound | Compound structure | MS (M + H)$^+$ |
|---|---|---|
| Structures of compounds 32-34 | | |
| 261 | 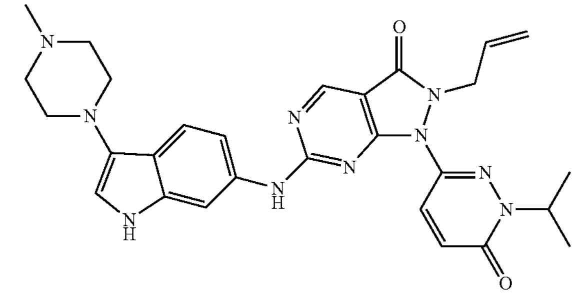 [SMILES: C=CCn1c(=O)c2cnc(Nc3ccc4c(N5CCN(C)CC5)c[nH]c4c3)nc2n1-c1ccc(=O)n(C(C)C)n1] | 541 |
| 262 | 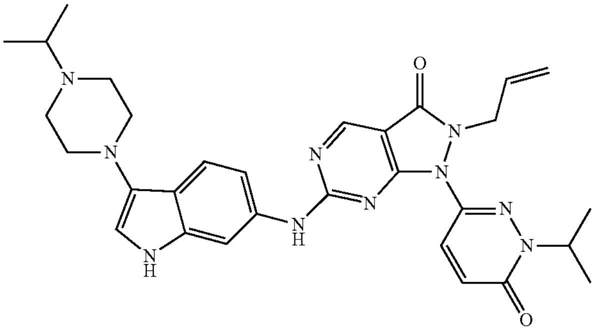 [SMILES: C=CCn1c(=O)c2cnc(Nc3ccc4c(N5CCN(C(C)C)CC5)c[nH]c4c3)nc2n1-c1ccc(=O)n(C(C)C)n1] | 569 |
| 263 | 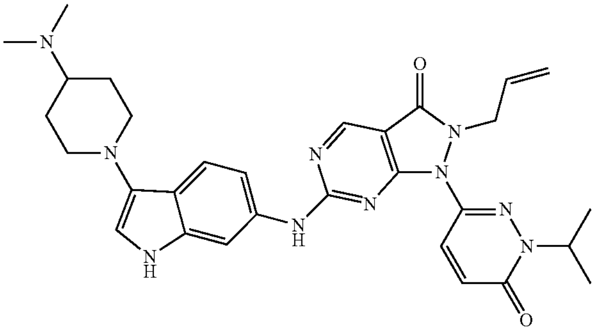 | 569 |
| 264 | 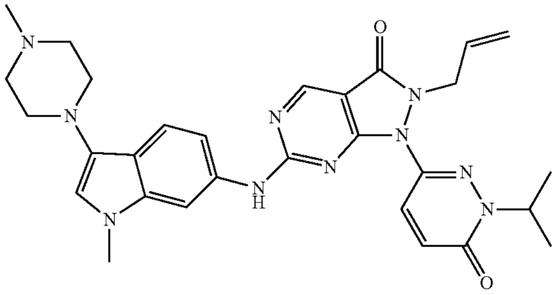 | 555 |

TABLE 3-continued
| Structures of compounds 32-34 | | |
|---|---|---|
| Compound | Compound structure | MS (M + H)$^+$ |
| 265 | 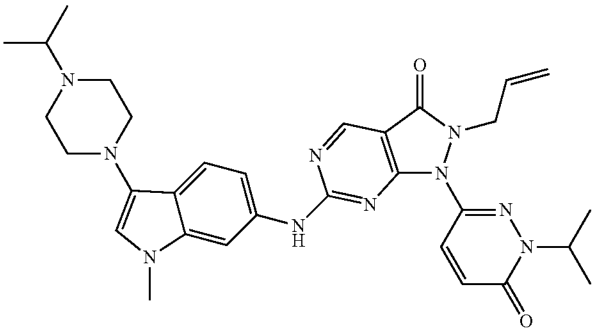 | 583 |
| 266 | 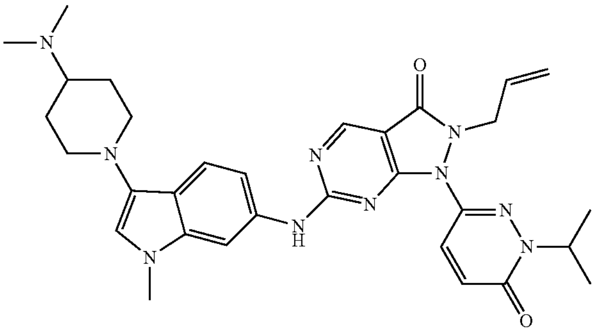 | 583 |
| 267 | 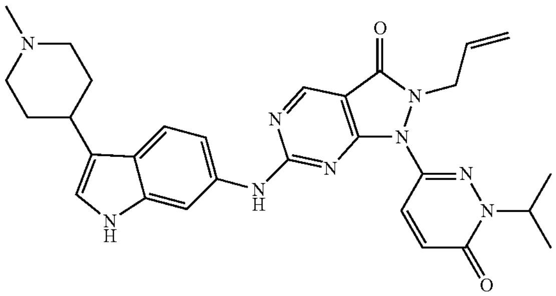 [SMILES: C=CCn1c(=O)c2cnc(Nc3ccc4c(C5CCN(C)CC5)c[nH]c4c3)nc2n1-c1ccc(=O)n(C(C)C)n1] | 540 |
| 268 | 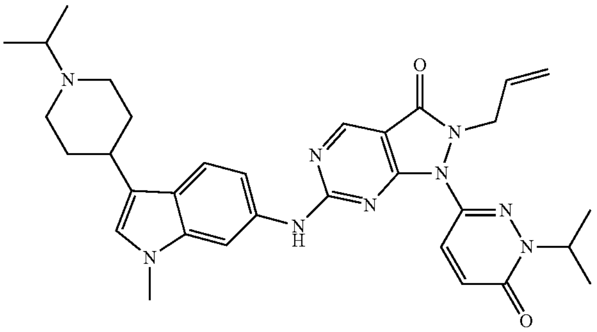 [SMILES: C=CCn1c(=O)c2cnc(Nc3ccc4c(C5CCN(C(C)C)CC5)cn(C)c4c3)nc2n1-c1ccc(=O)n(C(C)C)n1] | 582 |

TABLE 3-continued
| Structures of compounds 32-34 | | |
|---|---|---|
| Compound | Compound structure | MS (M + H)$^+$ |
| 269 | 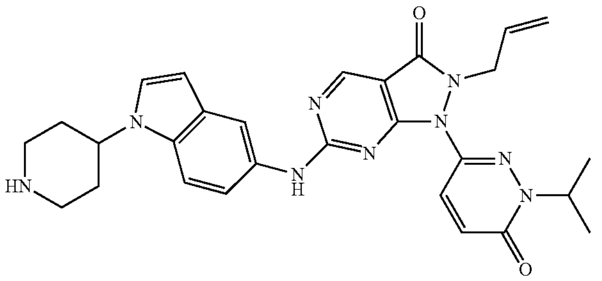 [SMILES: C=CCn1c(=O)c2cnc(Nc3ccc4c(ccn4C4CCNCC4)c3)nc2n1-c1ccc(=O)n(C(C)C)n1] | 526 |
| 270 | 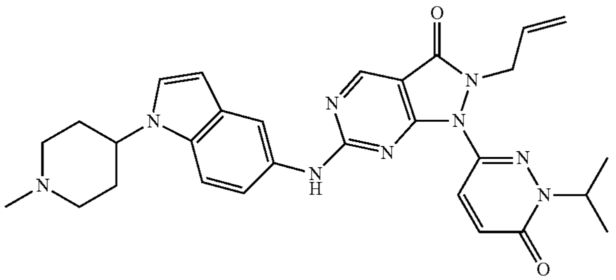 [SMILES: C=CCn1c(=O)c2cnc(Nc3ccc4c(ccn4C4CCN(C)CC4)c3)nc2n1-c1ccc(=O)n(C(C)C)n1] | 540 |
| 271 | 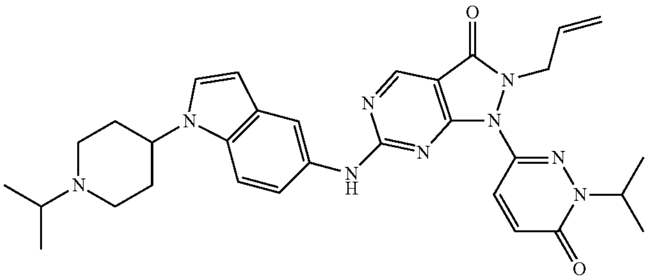 [SMILES: C=CCn1c(=O)c2cnc(Nc3ccc4c(ccn4C4CCN(C(C)C)CC4)c3)nc2n1-c1ccc(=O)n(C(C)C)n1] | 568 |
| 272 | 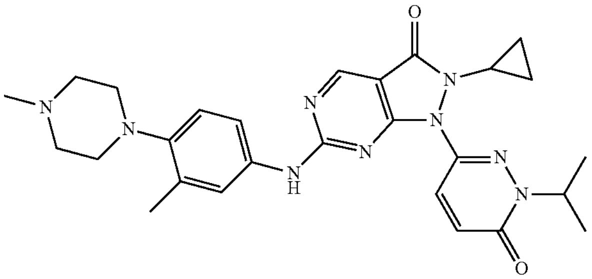 [SMILES: Cc1cc(Nc2ncc3c(=O)n(C4CC4)n(-c4ccc(=O)n(C(C)C)n4)c3n2)ccc1N1CCN(C)CC1] | 516 |
| 273 | 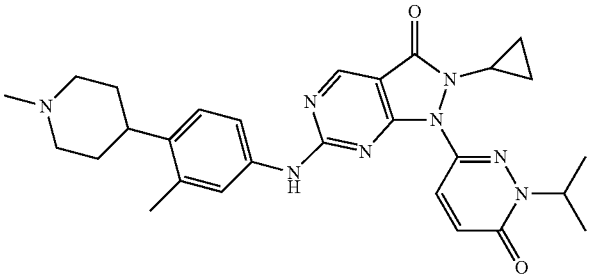 [SMILES: Cc1cc(Nc2ncc3c(=O)n(C4CC4)n(-c4ccc(=O)n(C(C)C)n4)c3n2)ccc1C1CCN(C)CC1] | 515 |

TABLE 3-continued
| Structures of compounds 32-34 | | |
|---|---|---|
| Compound | Compound structure | MS (M + H)$^+$ |
| 274 | 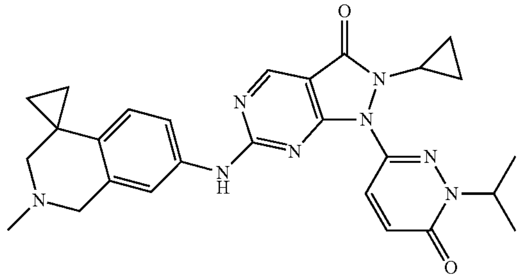 [SMILES: CC(C)n1nc(-n2c3nc(Nc4ccc5c(c4)CN(C)CC54CC4)ncc3c(=O)n2C2CC2)ccc1=O] | 499 |
| 275 | 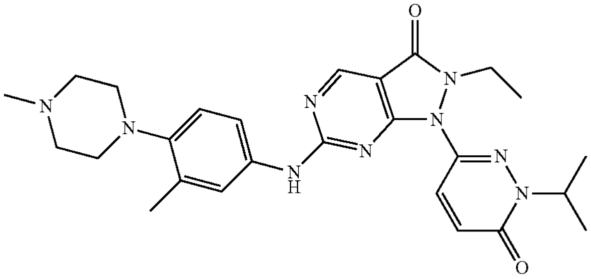 [SMILES: CCn1c(=O)c2cnc(Nc3ccc(N4CCN(C)CC4)c(C)c3)nc2n1-c1ccc(=O)n(C(C)C)n1] | 504 |
| 276 | 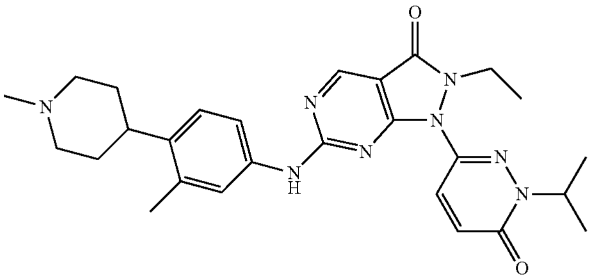 | 503 |
| 277 | 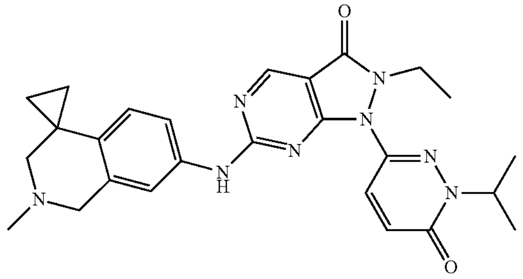 [SMILES: CCn1c(=O)c2cnc(Nc3ccc4c(c3)CN(C)CC43CC3)nc2n1-c1ccc(=O)n(C(C)C)n1] | 487 |
| 278 | 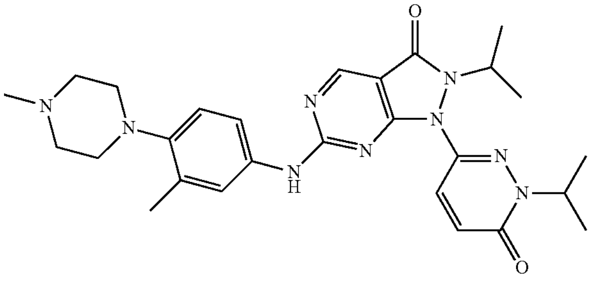 | 518 |

TABLE 3-continued
| Structures of compounds 32-34 | | |
|---|---|---|
| Compound | Compound structure | MS (M + H)$^+$ |
| 279 | 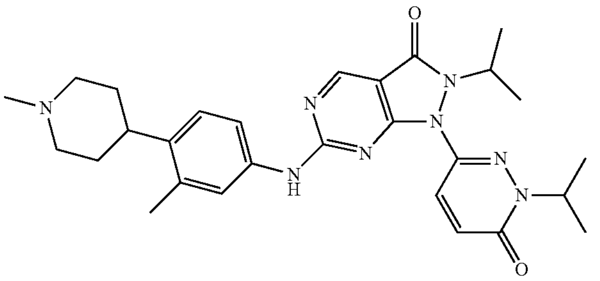 [SMILES: Cc1cc(Nc2ncc3c(=O)n(C(C)C)n(-c4ccc(=O)n(C(C)C)n4)c3n2)ccc1C1CCN(C)CC1] | 517 |
| 280 | 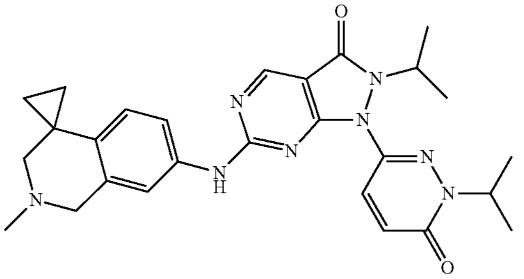 | 501 |
| 281 | 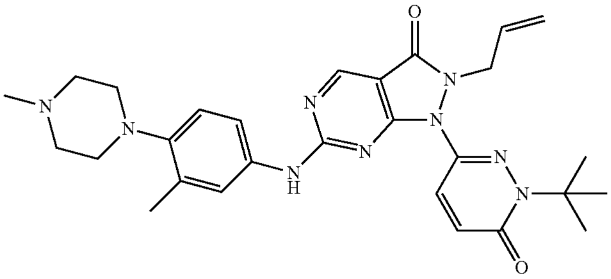 | 530 |
| 282 | 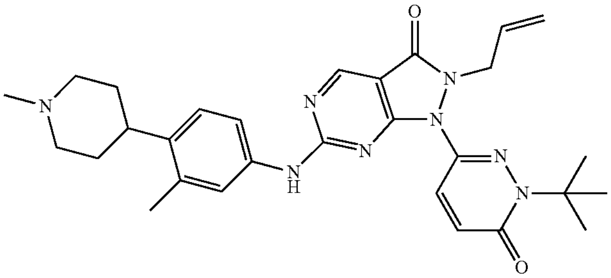 [SMILES: C=CCn1c(=O)c2cnc(Nc3ccc(C4CCN(C)CC4)c(C)c3)nc2n1-c1ccc(=O)n(C(C)(C)C)n1] | 529 |
| 283 | 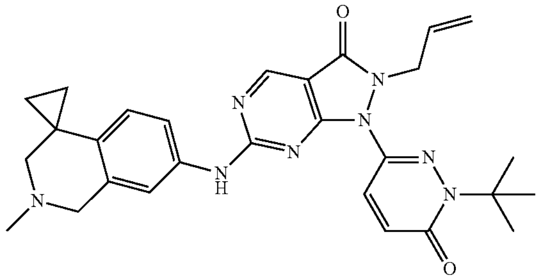 [SMILES: C=CCn1c(=O)c2cnc(Nc3ccc4c(c3)CN(C)CC43CC3)nc2n1-c1ccc(=O)n(C(C)(C)C)n1] | 513 |

TABLE 3-continued
| Structures of compounds 32-34 | | |
|---|---|---|
| Compound | Compound structure | MS (M + H)$^+$ |
| 284 | 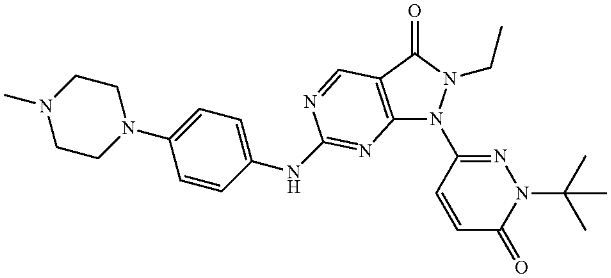 [SMILES: CCn1c(=O)c2cnc(Nc3ccc(N4CCN(C)CC4)cc3)nc2n1-c1ccc(=O)n(C(C)(C)C)n1] | 504 |
| 285 | 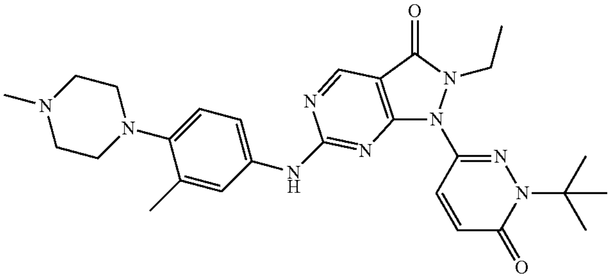 [SMILES: CCn1c(=O)c2cnc(Nc3ccc(N4CCN(C)CC4)c(C)c3)nc2n1-c1ccc(=O)n(C(C)(C)C)n1] | 518 |
| 286 | 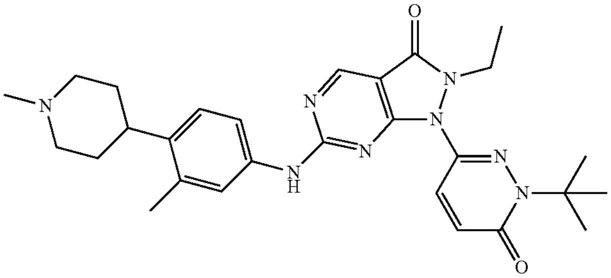 | 517 |
| 287 | 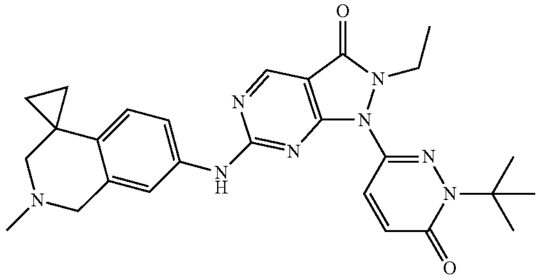 [SMILES: CCn1c(=O)c2cnc(Nc3ccc4c(c3)CN(C)CC43CC3)nc2n1-c1ccc(=O)n(C(C)(C)C)n1] | 501 |
| 288 | 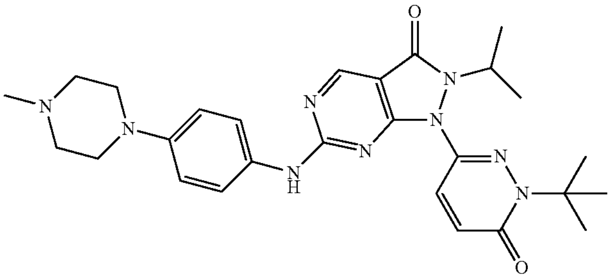 [SMILES: CC(C)n1c(=O)c2cnc(Nc3ccc(N4CCN(C)CC4)cc3)nc2n1-c1ccc(=O)n(C(C)(C)C)n1] | 518 |

TABLE 3-continued
| Structures of compounds 32-34 | | |
|---|---|---|
| Compound | Compound structure | MS (M + H)$^+$ |
| 289 | 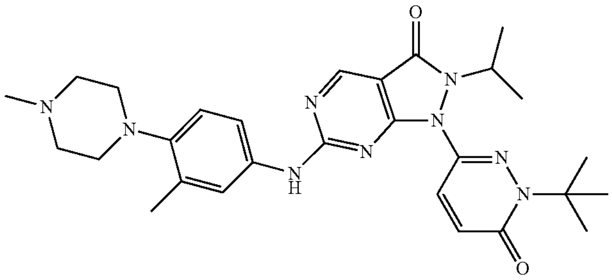 [SMILES: Cc1cc(Nc2ncc3c(=O)n(C(C)C)n(-c4ccc(=O)n(C(C)(C)C)n4)c3n2)ccc1N1CCN(C)CC1] | 532 |
| 290 | 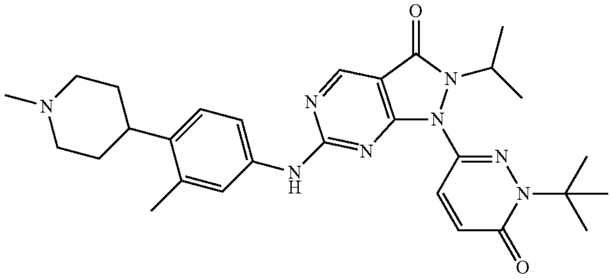 [SMILES: Cc1cc(Nc2ncc3c(=O)n(C(C)C)n(-c4ccc(=O)n(C(C)(C)C)n4)c3n2)ccc1C1CCN(C)CC1] | 531 |
| 291 | 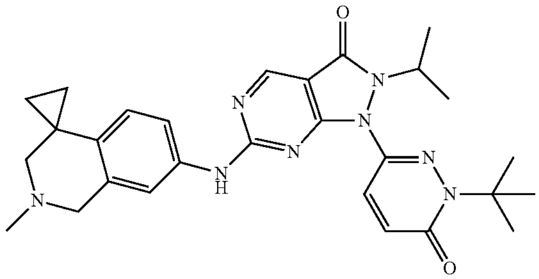 | 515 |
| 292 | 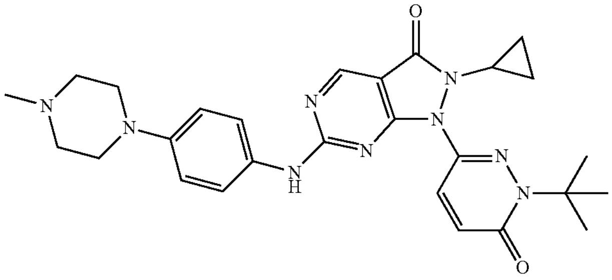 [SMILES: CN1CCN(c2ccc(Nc3ncc4c(=O)n(C5CC5)n(-c5ccc(=O)n(C(C)(C)C)n5)c4n3)cc2)CC1] | 516 |
| 293 | 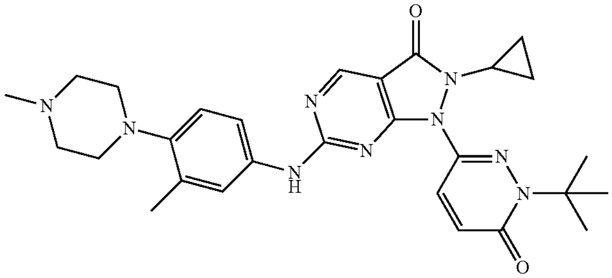 [SMILES: Cc1cc(Nc2ncc3c(=O)n(C4CC4)n(-c4ccc(=O)n(C(C)(C)C)n4)c3n2)ccc1N1CCN(C)CC1] | 530 |

TABLE 3-continued
| Compound | Structures of compounds 32-34<br>Compound structure | MS (M + H)+ |
|---|---|---|
| 294 | 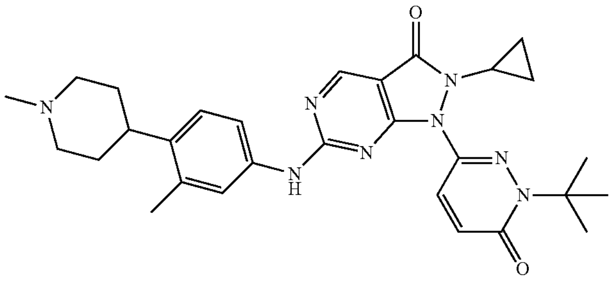 | 529 |
| 295 | 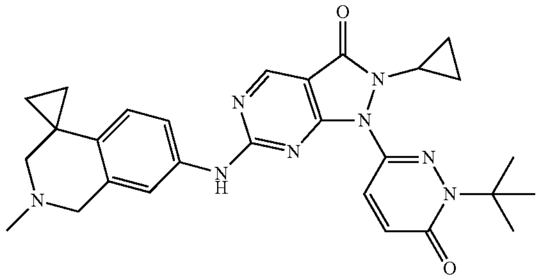 [SMILES: CN1Cc2cc(Nc3ncc4c(=O)n(C5CC5)n(-c5ccc(=O)n(C(C)(C)C)n5)c4n3)ccc2C2(CC2)C1] | 513 |
| 296 | 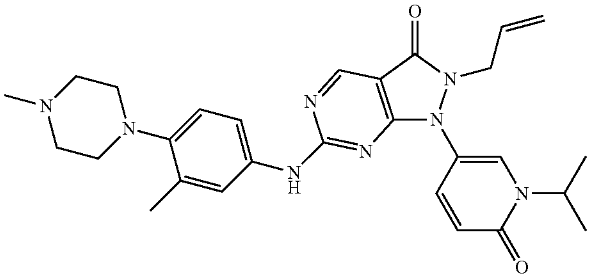 [SMILES: C=CCn1c(=O)c2cnc(Nc3ccc(C4CCN(C)CC4)c(C)c3)nc2n1-c1ccc(=O)n(C(C)C)c1] | 515 |
| 297 | 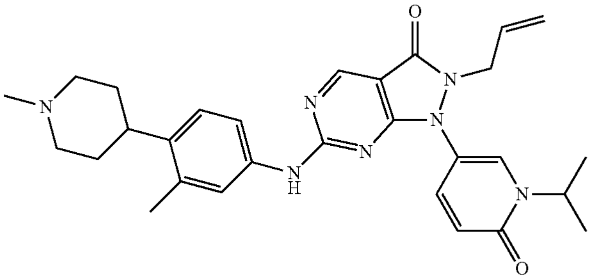 | 514 |
| 298 | 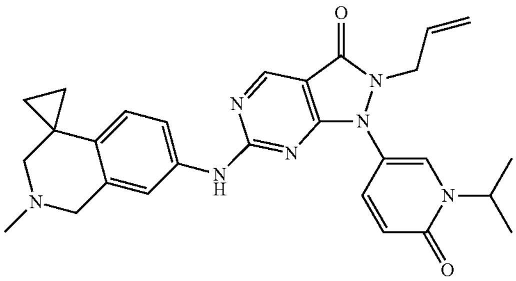 [SMILES: C=CCn1c(=O)c2cnc(Nc3ccc4c(c3)CN(C)CC43CC3)nc2n1-c1ccc(=O)n(C(C)C)c1] | 498 |

TABLE 3-continued
| Structures of compounds 32-34 | | |
|---|---|---|
| Compound | Compound structure | MS (M + H)$^+$ |
| 299 | 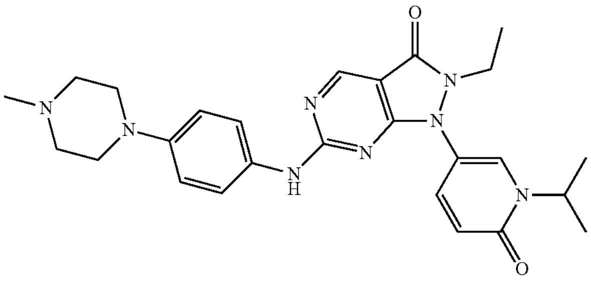 [SMILES: CCn1c(=O)c2cnc(Nc3ccc(N4CCN(C)CC4)cc3)nc2n1-c1ccc(=O)n(C(C)C)c1] | 489 |
| 300 | 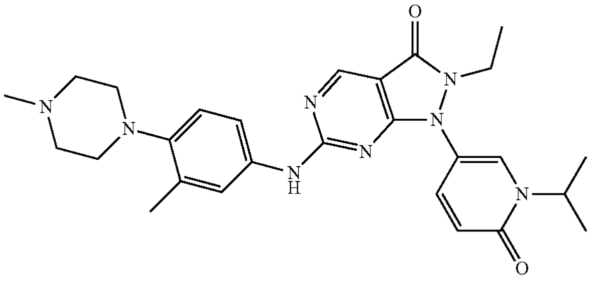 | 503 |
| 301 | 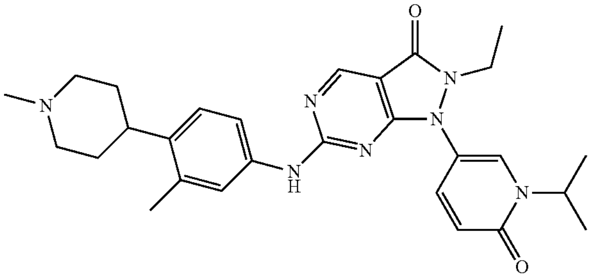 [SMILES: CCn1c(=O)c2cnc(Nc3ccc(N4CCN(C)CC4)c(C)c3)nc2n1-c1ccc(=O)n(C(C)C)c1] | 502 |
| 302 | 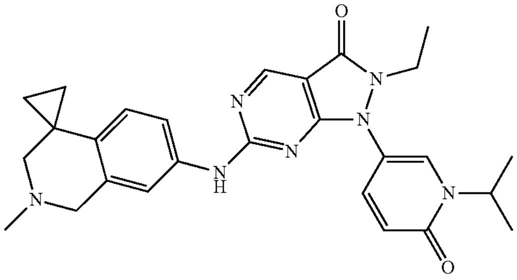 | 486 |
| 303 | 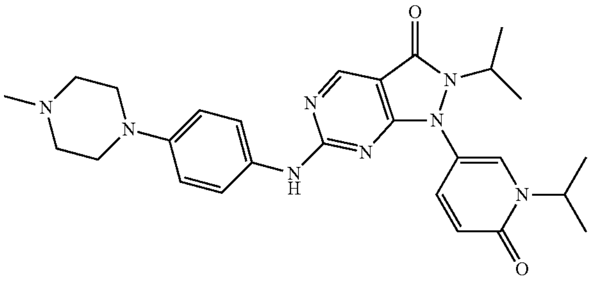 [SMILES: CC(C)n1cc(-n2c3nc(Nc4ccc(N5CCN(C)CC5)cc4)ncc3c(=O)n2C(C)C)ccc1=O] | 503 |

TABLE 3-continued
| Structures of compounds 32-34 | | |
|---|---|---|
| Compound | Compound structure | MS (M + H)+ |
| 304 | 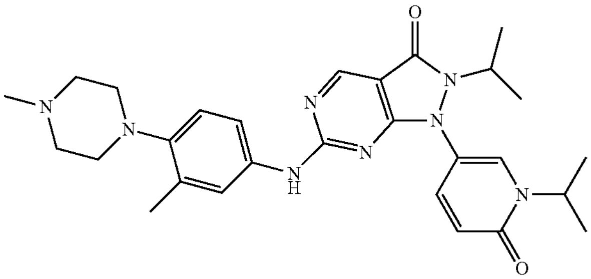 [SMILES: Cc1cc(Nc2ncc3c(=O)n(C(C)C)n(-c4ccc(=O)n(C(C)C)c4)c3n2)ccc1N1CCN(C)CC1] | 517 |
| 305 | 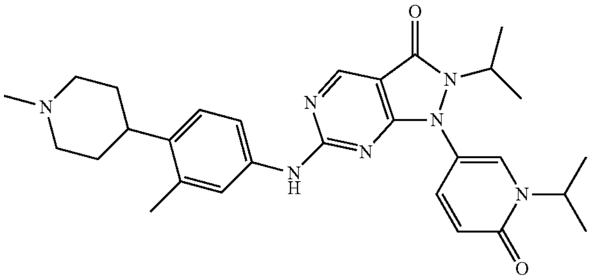 [SMILES: Cc1cc(Nc2ncc3c(=O)n(C(C)C)n(-c4ccc(=O)n(C(C)C)c4)c3n2)ccc1C1CCN(C)CC1] | 516 |
| 306 | 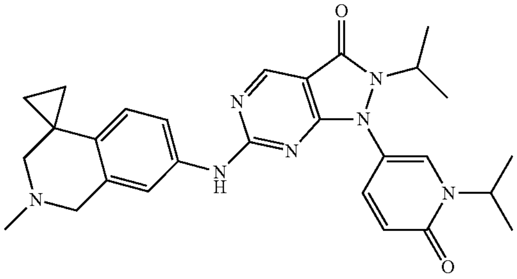 [SMILES: CC(C)n1cc(-n2c3nc(Nc4ccc5c(c4)CN(C)CC54CC4)ncc3c(=O)n2C(C)C)ccc1=O] | 500 |
| 307 | 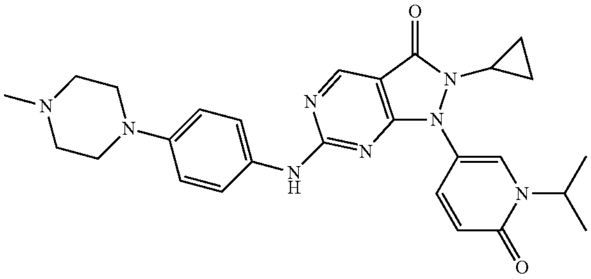 [SMILES: CC(C)n1cc(-n2c3nc(Nc4ccc(N5CCN(C)CC5)cc4)ncc3c(=O)n2C2CC2)ccc1=O] | 501 |
| 308 | 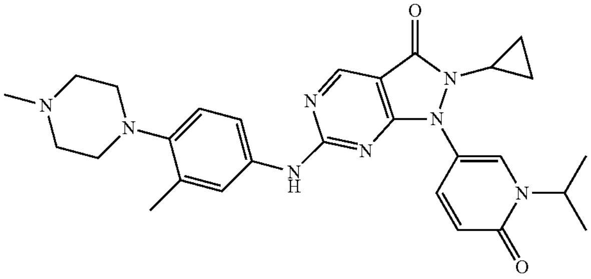 [SMILES: Cc1cc(Nc2ncc3c(=O)n(C4CC4)n(-c4ccc(=O)n(C(C)C)c4)c3n2)ccc1N1CCN(C)CC1] | 515 |

TABLE 3-continued
Structures of compounds 32-34
| Compound | Compound structure | MS $(M + H)^+$ |
|---|---|---|
| 309 | 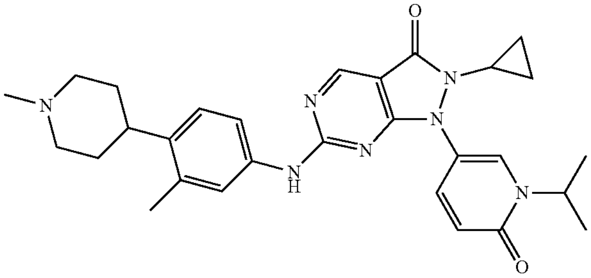 | 514 |
| 310 | 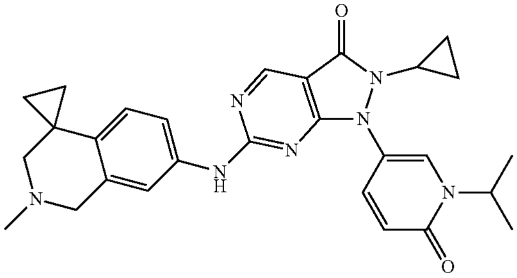 | 498 |
| 311 | 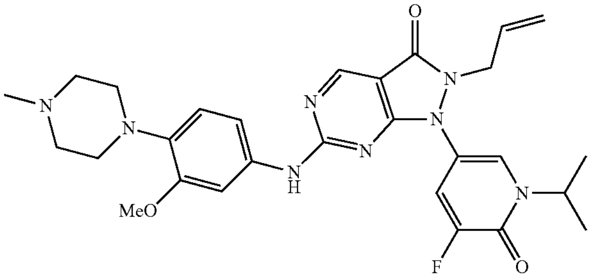 [SMILES: C=CCn1c(=O)c2cnc(Nc3ccc(N4CCN(C)CC4)c(OC)c3)nc2n1-c1cc(F)c(=O)n(C(C)C)c1] | 549 |
| 312 | 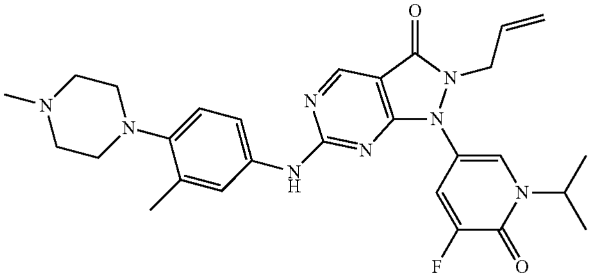 [SMILES: C=CCn1c(=O)c2cnc(Nc3ccc(N4CCN(C)CC4)c(C)c3)nc2n1-c1cc(F)c(=O)n(C(C)C)c1] | 533 |
| 313 | 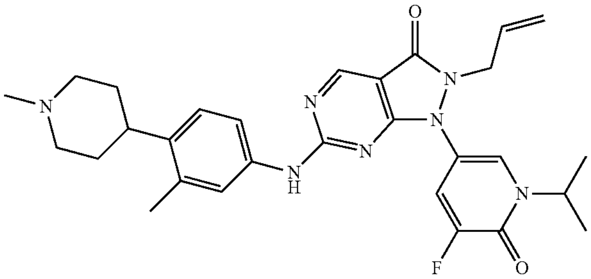 [SMILES: C=CCn1c(=O)c2cnc(Nc3ccc(C4CCN(C)CC4)c(C)c3)nc2n1-c1cc(F)c(=O)n(C(C)C)c1] | 532 |

TABLE 3-continued
Structures of compounds 32-34
| Compound | Compound structure | MS $(M + H)^+$ |
| --- | --- | --- |
| 314 | 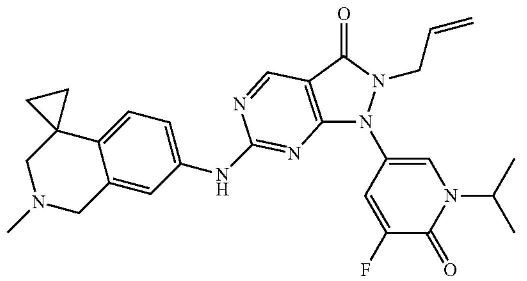 [SMILES: C=CCn1c(=O)c2cnc(Nc3ccc4c(c3)CN(C)CC43CC3)nc2n1-c1cc(F)c(=O)n(C(C)C)c1] | 516 |
| 315 | 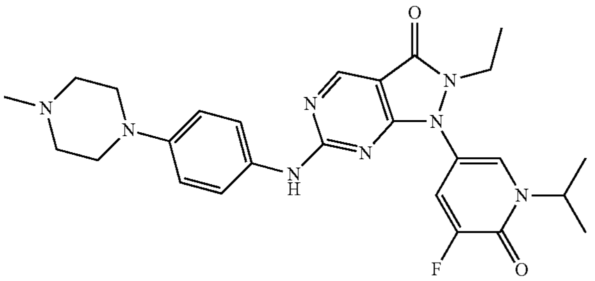 [SMILES: CCn1c(=O)c2cnc(Nc3ccc(N4CCN(C)CC4)cc3)nc2n1-c1cc(F)c(=O)n(C(C)C)c1] | 507 |
| 316 | 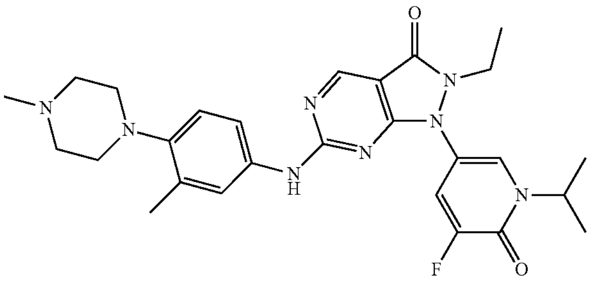 | 521 |
| 317 | 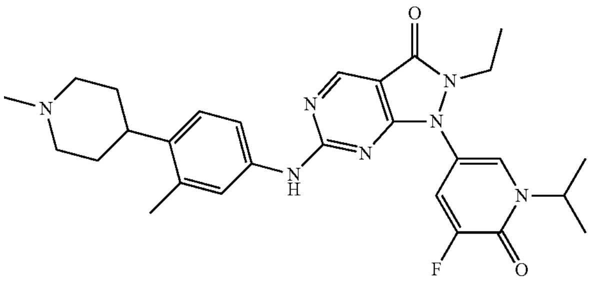 [SMILES: CCn1c(=O)c2cnc(Nc3ccc(N4CCN(C)CC4)c(C)c3)nc2n1-c1cc(F)c(=O)n(C(C)C)c1] | 520 |
| 318 | 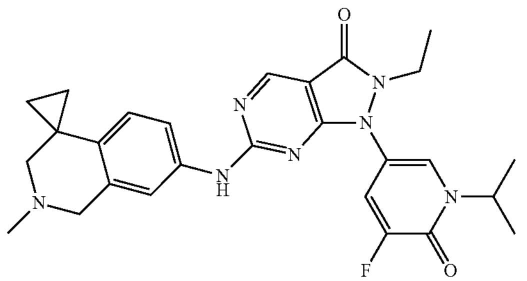 [SMILES: CCn1c(=O)c2cnc(Nc3ccc4c(c3)CN(C)CC43CC3)nc2n1-c1cc(F)c(=O)n(C(C)C)c1] | 504 |

TABLE 3-continued
| Structures of compounds 32-34 | | |
|---|---|---|
| Compound | Compound structure | MS (M + H)+ |
| 319 | 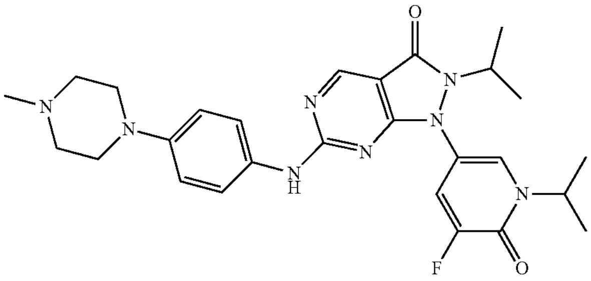 [SMILES: CC(C)n1cc(-n2c3nc(Nc4ccc(N5CCN(C)CC5)cc4)ncc3c(=O)n2C(C)C)cc(F)c1=O] | 521 |
| 320 | 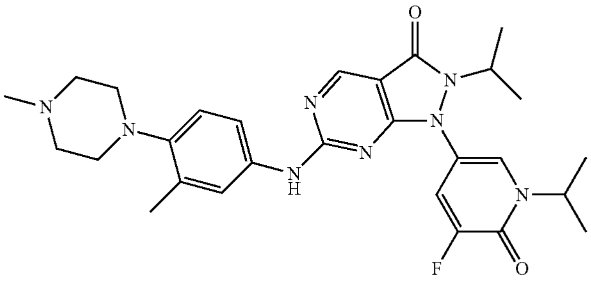 [SMILES: Cc1cc(Nc2ncc3c(=O)n(C(C)C)n(-c4cc(F)c(=O)n(C(C)C)c4)c3n2)ccc1N1CCN(C)CC1] | 535 |
| 321 | 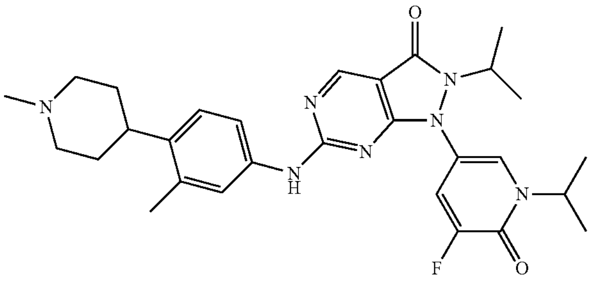 [SMILES: Cc1cc(Nc2ncc3c(=O)n(C(C)C)n(-c4cc(F)c(=O)n(C(C)C)c4)c3n2)ccc1C1CCN(C)CC1] | 534 |
| 322 | 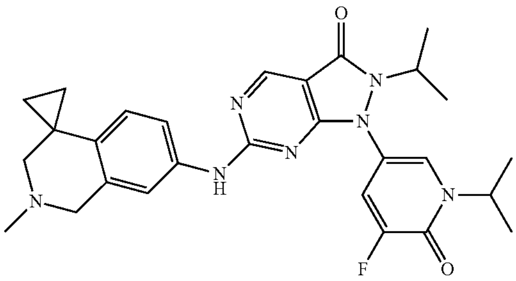 [SMILES: CC(C)n1cc(-n2c3nc(Nc4ccc5c(c4)CN(C)CC54CC4)ncc3c(=O)n2C(C)C)cc(F)c1=O] | 518 |
| 323 | 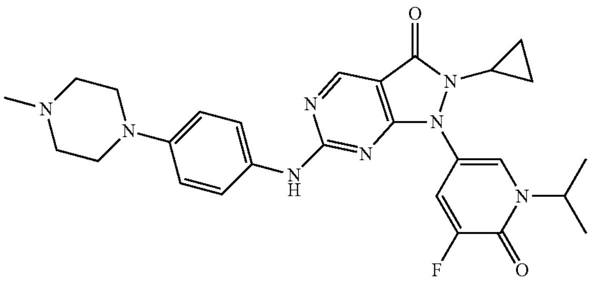 [SMILES: CC(C)n1cc(-n2c3nc(Nc4ccc(N5CCN(C)CC5)cc4)ncc3c(=O)n2C2CC2)cc(F)c1=O] | 519 |

TABLE 3-continued
Structures of compounds 32-34
| Compound | Compound structure | MS (M + H)+ |
| --- | --- | --- |
| 324 | 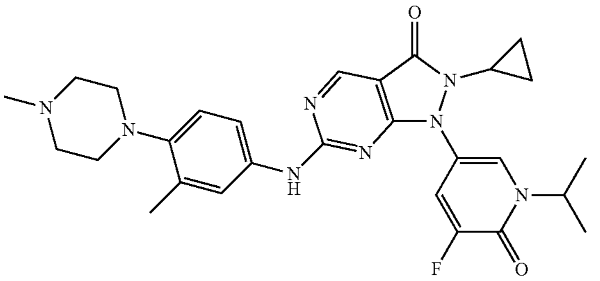 | 533 |
| 325 | 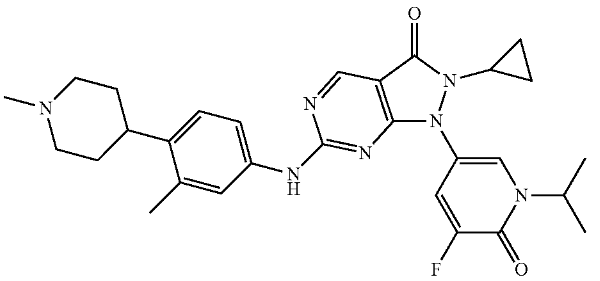 [SMILES: Cc1cc(Nc2ncc3c(=O)n(C4CC4)n(-c4cc(F)c(=O)n(C(C)C)c4)c3n2)ccc1N1CCN(C)CC1] | 532 |
| 326 | 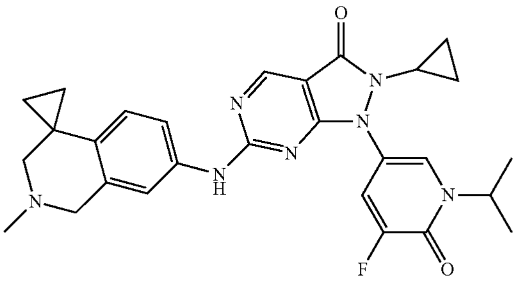 [SMILES: CC(C)n1cc(-n2c3nc(Nc4ccc5c(c4)CN(C)CC54CC4)ncc3c(=O)n2C2CC2)cc(F)c1=O] | 516 |
| 327 | 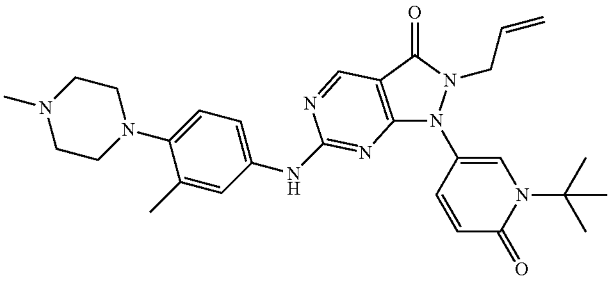 | 529 |
| 328 | 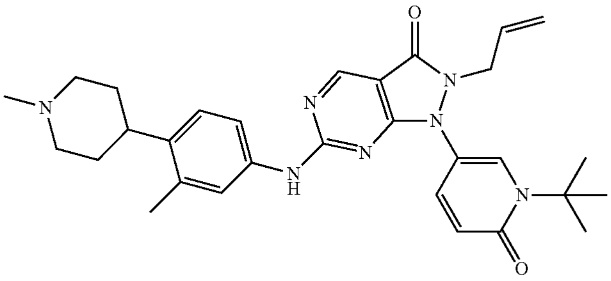 [SMILES: C=CCn1c(=O)c2cnc(Nc3ccc(C4CCN(C)CC4)c(C)c3)nc2n1-c1ccc(=O)n(C(C)(C)C)c1] | 528 |

TABLE 3-continued
| Compound | Compound structure | MS (M + H)+ |
|---|---|---|
| Structures of compounds 32-34 | | |
| 329 | 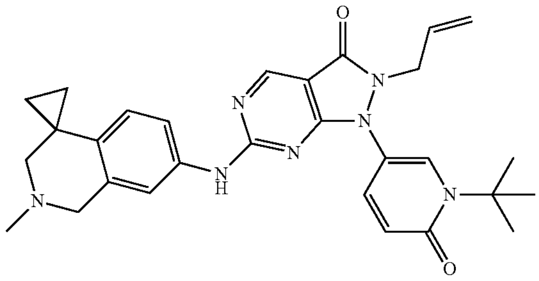 | 512 |
| 330 | 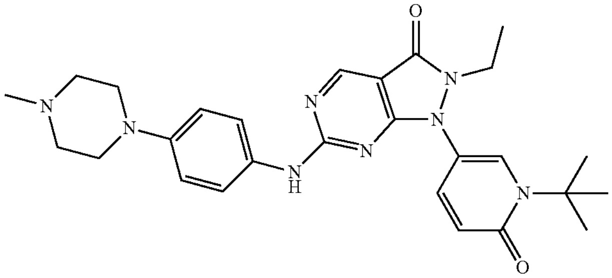 [SMILES: CCn1c(=O)c2cnc(Nc3ccc(N4CCN(C)CC4)cc3)nc2n1-c1ccc(=O)n(C(C)(C)C)c1] | 503 |
| 331 | 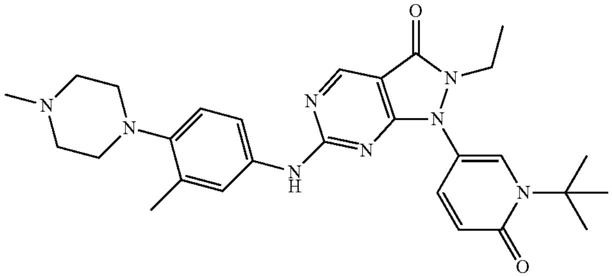 | 517 |
| 332 | 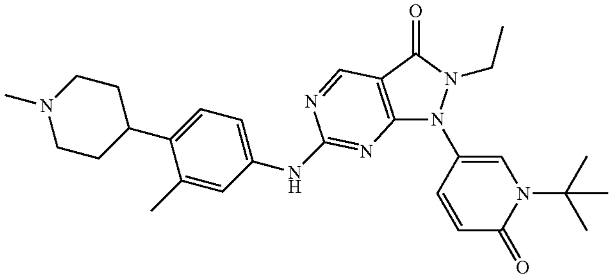 [SMILES: CCn1c(=O)c2cnc(Nc3ccc(N4CCN(C)CC4)c(C)c3)nc2n1-c1ccc(=O)n(C(C)(C)C)c1] | 516 |
| 333 | 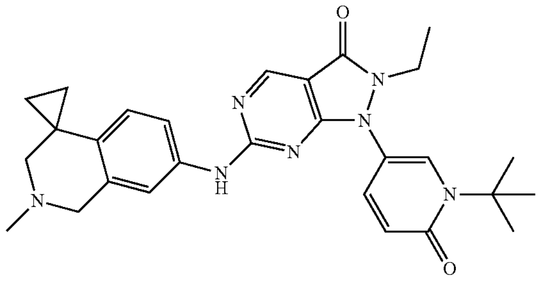 | 500 |

TABLE 3-continued
| Structures of compounds 32-34 | | |
|---|---|---|
| Compound | Compound structure | MS $(M + H)^+$ |
| 334 | 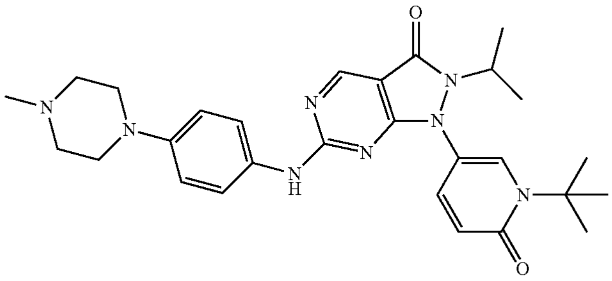 [SMILES: CC(C)n1c(=O)c2cnc(Nc3ccc(N4CCN(C)CC4)cc3)nc2n1-c1ccc(=O)n(C(C)(C)C)c1] | 517 |
| 335 | 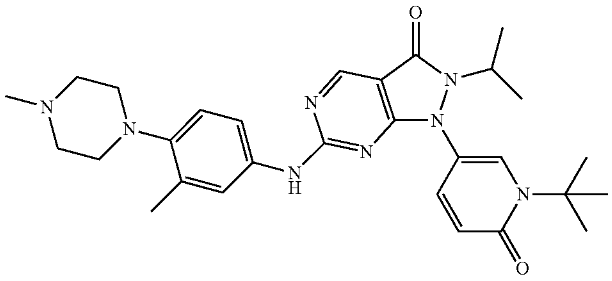 [SMILES: Cc1cc(Nc2ncc3c(=O)n(C(C)C)n(-c4ccc(=O)n(C(C)(C)C)c4)c3n2)ccc1N1CCN(C)CC1] | 531 |
| 336 | 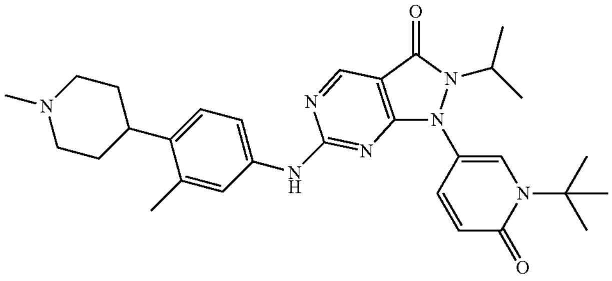 | 530 |
| 337 | 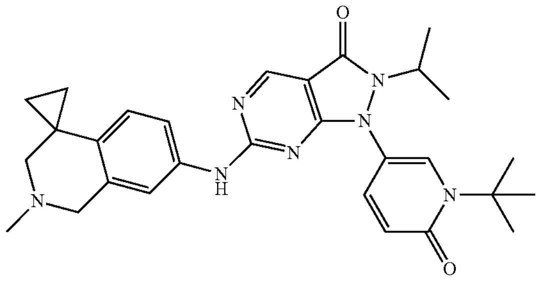 | 514 |
| 338 | 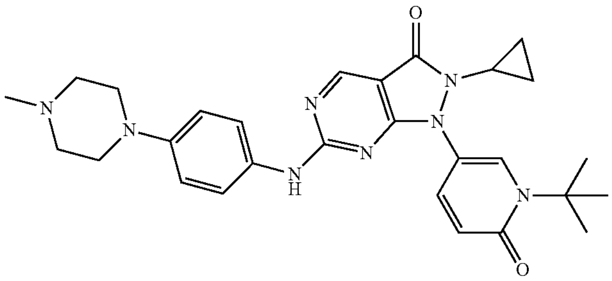 | 515 |

TABLE 3-continued

| Structures of compounds 32-34 | | |
|---|---|---|
| Compound | Compound structure | MS (M + H)+ |
| 339 | 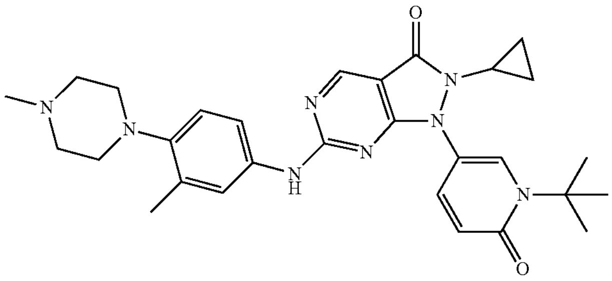 [SMILES: Cc1cc(Nc2ncc3c(=O)n(C4CC4)n(-c4ccc(=O)n(C(C)(C)C)c4)c3n2)ccc1N1CCN(C)CC1] | 529 |
| 340 | 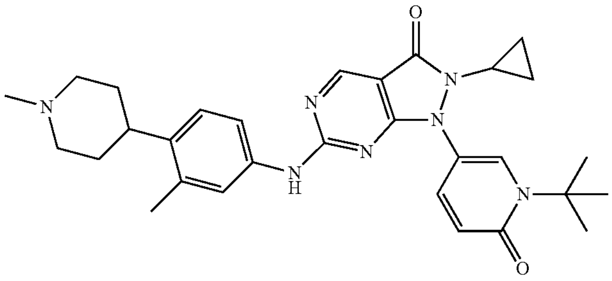 [SMILES: Cc1cc(Nc2ncc3c(=O)n(C4CC4)n(-c4ccc(=O)n(C(C)(C)C)c4)c3n2)ccc1C1CCN(C)CC1] | 528 |
| 341 | 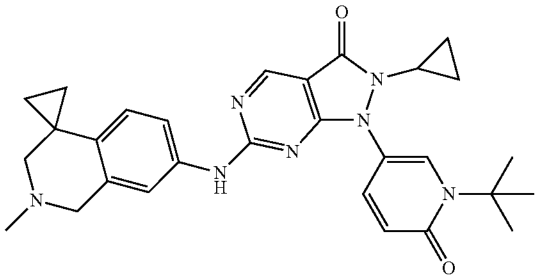 [SMILES: CN1Cc2cc(Nc3ncc4c(=O)n(C5CC5)n(-c5ccc(=O)n(C(C)(C)C)c5)c4n3)ccc2C2(CC2)C1] | 512 |

Example 342. Assay for Inhibitory Activity of Compounds Against Wee-1 Kinase The inhibitory activity of compounds against Wee-1 kinase was determined by using the Lanthra Screen Wee-1 kinase kit (Invitrogen). 5 μL of the compound diluted in a gradient with DMSO, 5 μL. of Wee-1 kinase (at a final concentration of 5 nM), 5 μL of an Eu-Anti-GST antibody (at a final concentration of 2 nM) mixture and 5 μL of kinase Tracer 178 (at a final concentration of 50 nM) were mixed well. The plate was read after incubation at room temperature for one hour. For comparison with the DMSO solvent control group, $IC_{50}$ for the inhibition activity of the compounds against Wee-1 kinase was calculated.

TABLE 4

$IC_{50}$ for the inhibitory activity of the compounds of the present invention against Wee-1 kinase

| Compound | Inhibitory activity against Wee-1 | Compound | Inhibitory activity against Wee-1 | Compound | Inhibitory activity against Wee-1 |
|---|---|---|---|---|---|
| 1 | C | 2 | C | 3 | A |
| 4 | B | 5 | A | 6 | B |

TABLE 4-continued $IC_{50}$ for the inhibitory activity of the compounds of the present invention against Wee-1 kinase

| Compound | Inhibitory activity against Wee-1 | Compound | Inhibitory activity against Wee-1 | Compound | Inhibitory activity against Wee-1 |
|---|---|---|---|---|---|
| 7 | B | 8 | B | 9 | A |
| 10 | A | 11 | A | 12 | A |
| 13 | A | 14 | B | 15 | B |
| 16 | B | 17 | B | 18 | A |
| 19 | A | 20 | A | 21 | A |
| 22 | A | 23 | A | 24 | A |
| 25 | A | 26 | A | 27 | B |
| 28 | B | 29 | A | 30 | B |
| 31 | A | 32 | A | 33 | A |
| 34 | A | 35 | A | 36 | A |
| 37 | A | 38 | A | 39 | A |
| 40 | A | 41 | A | 42 | A |
| 43 | A | 44 | A | 45 | A |
| 46 | A | 47 | A | 48 | A |
| 49 | A | 50 | A | 51 | B |
| 52 | A | 53 | A | 54 | A |
| 55 | A | 56 | A | 57 | A |
| 58 | A | 59 | A | 60 | A |
| 61 | A | 62 | A | 63 | A |
| 64 | A | 65 | A | 66 | A |

TABLE 4-continued

IC$_{50}$ for the inhibitory activity of the compounds of the present invention against Wee-1 kinase

| Compound | Inhibitory activity against Wee-1 | Compound | Inhibitory activity against Wee-1 | Compound | Inhibitory activity against Wee-1 |
|---|---|---|---|---|---|
| 67 | A | 68 | A | 69 | A |
| 70 | A | 71 | A | 72 | A |
| 73 | A | 74 | A | 75 | A |
| 76 | A | 77 | A | 78 | A |
| 79 | A | 80 | A | 81 | A |
| 82 | A | 83 | A | 84 | A |
| 85 | A | 86 | A | 87 | A |
| 88 | A | 89 | A | 90 | A |
| 91 | A | 92 | A | 93 | A |
| 94 | A | 95 | A | 96 | A |
| 97 | A | 98 | A | 99 | A |
| 100 | A | 101 | A | 102 | A |
| 103 | A | 104 | A | 105 | A |
| 106 | A | 107 | A | 108 | A |
| 109 | A | 110 | A | 111 | A |
| 112 | A | 113 | A | 114 | A |
| 115 | A | 116 | A | 117 | A |
| 118 | A | 119 | A | 120 | A |
| 121 | A | 122 | A | 123 | A |
| 124 | A | 125 | A | 126 | A |
| 127 | A | 128 | A | 129 | A |
| 130 | A | 131 | A | 132 | A |
| 133 | A | 134 | A | 135 | B |
| 136 | B | 137 | A | 138 | A |
| 139 | A | 140 | A | 141 | A |
| 142 | A | 143 | A | 144 | A |
| 145 | A | 146 | A | 147 | A |
| 148 | A | 149 | A | 150 | A |
| 151 | A | 152 | A | 153 | A |
| 154 | A | 155 | A | 156 | A |
| 157 | A | 158 | A | 159 | A |
| 160 | A | 161 | A | 162 | A |
| 163 | A | 164 | A | 165 | A |
| 166 | B | 167 | B | 168 | B |
| 169 | A | 170 | A | 171 | A |
| 172 | A | 173 | A | 174 | A |
| 175 | A | 176 | A | 177 | A |
| 178 | A | 179 | A | 180 | A |
| 181 | A | 182 | A | 183 | A |
| 184 | A | 185 | A | 186 | A |
| 187 | A | 188 | A | 189 | B |
| 190 | A | 191 | A | 192 | A |
| 193 | A | 194 | A | 195 | A |
| 196 | A | 197 | A | 198 | A |
| 199 | A | 200 | A | 201 | A |
| 202 | A | 203 | A | 204 | A |
| 205 | A | 206 | A | 207 | A |
| 208 | A | 209 | A | 210 | A |
| 211 | A | 212 | A | 213 | A |
| 214 | A | 215 | A | 216 | A |
| 217 | A | 218 | A | 219 | A |
| 220 | A | 221 | A | 222 | A |
| 223 | A | 224 | A | 225 | A |
| 226 | A | 227 | A | 228 | A |
| 229 | A | 230 | A | 231 | A |
| 232 | A | 233 | A | 234 | A |
| 235 | A | 236 | A | 237 | A |
| 238 | A | 239 | A | 240 | A |
| 241 | A | 242 | A | 243 | A |
| 244 | A | 245 | A | 246 | A |
| 247 | A | 248 | A | 249 | A |
| 250 | B | 251 | B | 252 | A |
| 253 | A | 254 | A | 255 | A |
| 256 | A | 257 | A | 258 | A |
| 259 | A | 260 | A | 261 | A |
| 262 | A | 263 | A | 264 | A |
| 265 | A | 266 | A | 267 | A |
| 268 | A | 269 | A | 270 | A |
| 271 | A | 272 | A | 273 | A |
| 274 | A | 275 | A | 276 | A |
| 277 | A | 278 | A | 279 | A |
| 280 | A | 281 | A | 282 | A |
| 283 | A | 284 | A | 285 | A |
| 286 | A | 287 | A | 288 | A |
| 289 | A | 290 | A | 291 | A |
| 292 | A | 293 | A | 294 | A |
| 295 | A | 296 | A | 297 | A |
| 298 | A | 299 | A | 300 | A |
| 301 | A | 302 | A | 303 | A |
| 304 | A | 305 | A | 306 | A |
| 307 | A | 308 | A | 309 | A |
| 310 | A | 311 | A | 312 | A |
| 313 | A | 314 | A | 315 | A |
| 316 | A | 317 | A | 318 | A |
| 319 | A | 320 | A | 321 | A |
| 322 | A | 323 | A | 324 | A |
| 325 | A | 326 | A | 327 | A |
| 328 | A | 329 | A | 330 | A |
| 331 | A | 332 | A | 333 | A |
| 334 | A | 335 | A | 336 | A |
| 337 | A | 338 | A | 339 | A |
| 340 | A | 341 | A | AZD-1775 | A |

A indicates that the IC$_{50}$ is less than or equal to 30 nM;
B indicates that the IC$_{50}$ is greater than 30 nM but less than or equal to 100 nM;
C indicates that the IC$_{50}$ is greater than 100 nM.

As can be seen from the data in Table 4, the compounds of the present invention have strong inhibitory effect on Wee-1 kinase.

Example 343. Assay for Antiproliferative Activity Against HT29 Cells

3000 HT29 cells were seed in a 384-well plate (Fisher 142762). After the cells adhered to the wall overnight, the compounds diluted in a gradient were added. 72 later, Cell Titer-Lumi (Beyotime C0068XL) was added to determine the content of ATP in the cells. The growth of the cells was evaluated, and the IC$_{50}$ for the inhibition of the compounds against cell growth was calculated.

TABLE 5

IC$_{50}$ for the inhibition of the compounds of the present invention against HT-29 cell growth

| Compound | HT-29 cells Anti-proliferative activity | Compound | HT-29 cells Anti-proliferative activity | Compound | HT-29 cells Anti-proliferative activity |
|---|---|---|---|---|---|
| 1 | C | 2 | C | 3 | A |
| 4 | B | 5 | A | 6 | B |
| 7 | B | 8 | B | 9 | A |
| 10 | A | 11 | A | 12 | A |
| 13 | A | 14 | C | 15 | B |
| 16 | B | 17 | B | 18 | B |
| 19 | B | 20 | A | 21 | A |
| 22 | A | 23 | C | 24 | A |
| 25 | A | 26 | A | 27 | C |
| 28 | C | 29 | A | 30 | C |
| 31 | A | 32 | A | 33 | A |
| 34 | A | 35 | A | 36 | A |
| 37 | A | 38 | A | 39 | A |
| 40 | A | 41 | A | 42 | A |
| 43 | A | 44 | A | 45 | A |
| 46 | A | 47 | A | 48 | A |
| 49 | A | 50 | A | 51 | B |

TABLE 5-continued

| $IC_{50}$ for the inhibition of the compounds of the present invention against HT-29 cell growth | | | | | |
|---|---|---|---|---|---|
| Compound | HT-29 cells Antiproliferative activity | Compound | HT-29 cells Antiproliferative activity | Compound | HT-29 cells Antiproliferative activity |
| 52 | B | 53 | A | 54 | A |
| 55 | A | 56 | A | 57 | A |
| 58 | A | 59 | A | 60 | A |
| 61 | A | 62 | A | 63 | A |
| 64 | A | 65 | A | 66 | A |
| 67 | A | 68 | A | 69 | A |
| 70 | A | 71 | A | 72 | A |
| 73 | A | 74 | A | 75 | A |
| 76 | A | 77 | A | 78 | A |
| 79 | A | 80 | B | 81 | A |
| 82 | A | 83 | A | 84 | A |
| 85 | A | 86 | A | 87 | A |
| 88 | A | 89 | A | 90 | A |
| 91 | A | 92 | A | 93 | A |
| 94 | A | 95 | A | 96 | A |
| 97 | A | 98 | A | 99 | A |
| 100 | A | 101 | B | 102 | A |
| 103 | A | 104 | A | 105 | A |
| 106 | A | 107 | A | 108 | A |
| 109 | A | 110 | A | 111 | A |
| 112 | A | 113 | A | 114 | A |
| 115 | A | 116 | A | 117 | A |
| 118 | A | 119 | A | 120 | A |
| 121 | A | 122 | A | 123 | A |
| 124 | A | 125 | A | 126 | A |
| 127 | A | 128 | A | 129 | A |
| 130 | A | 131 | A | 132 | A |
| 133 | A | 134 | A | 135 | B |
| 136 | B | 137 | B | 138 | B |
| 139 | A | 140 | A | 141 | A |
| 142 | A | 143 | A | 144 | A |
| 145 | A | 146 | A | 147 | A |
| 148 | A | 149 | A | 150 | A |
| 151 | A | 152 | A | 153 | A |
| 154 | B | 155 | A | 156 | B |
| 157 | A | 158 | A | 159 | A |
| 160 | B | 161 | B | 162 | A |
| 163 | A | 164 | A | 165 | A |
| 166 | B | 167 | B | 168 | B |
| 169 | B | 170 | A | 171 | A |
| 172 | A | 173 | A | 174 | A |
| 175 | B | 176 | A | 177 | A |
| 178 | A | 179 | A | 180 | A |
| 181 | B | 182 | A | 183 | A |
| 184 | A | 185 | A | 186 | A |
| 187 | A | 188 | A | 189 | A |
| 190 | A | 191 | A | 192 | A |
| 193 | A | 194 | A | 195 | A |
| 196 | A | 197 | A | 198 | A |
| 199 | A | 200 | A | 201 | A |
| 202 | A | 203 | A | 204 | A |
| 205 | A | 206 | A | 207 | A |
| 208 | A | 209 | A | 210 | A |
| 211 | A | 212 | A | 213 | A |
| 214 | A | 215 | A | 216 | A |
| 217 | A | 218 | A | 219 | A |
| 220 | A | 221 | B | 222 | A |
| 223 | A | 224 | A | 225 | A |
| 226 | A | 227 | A | 228 | A |
| 229 | A | 230 | A | 231 | A |
| 232 | A | 233 | A | 234 | A |
| 235 | A | 236 | A | 237 | A |
| 238 | A | 239 | A | 240 | A |
| 241 | A | 242 | A | 243 | A |
| 244 | A | 245 | A | 246 | A |
| 247 | A | 248 | A | 249 | A |
| 250 | B | 251 | B | 252 | A |
| 253 | A | 254 | A | 255 | A |
| 256 | A | 257 | A | 258 | A |
| 259 | A | 260 | A | 261 | A |
| 262 | A | 263 | A | 264 | A |

TABLE 5-continued

| $IC_{50}$ for the inhibition of the compounds of the present invention against HT-29 cell growth | | | | | |
|---|---|---|---|---|---|
| Compound | HT-29 cells Antiproliferative activity | Compound | HT-29 cells Antiproliferative activity | Compound | HT-29 cells Antiproliferative activity |
| 265 | A | 266 | A | 267 | A |
| 268 | A | 269 | A | 270 | A |
| 271 | A | 272 | A | 273 | A |
| 274 | A | 275 | A | 276 | A |
| 277 | A | 278 | A | 279 | A |
| 280 | A | 281 | A | 282 | A |
| 283 | A | 284 | A | 285 | A |
| 286 | A | 287 | A | 288 | A |
| 289 | A | 290 | A | 291 | A |
| 292 | A | 293 | A | 294 | A |
| 295 | A | 296 | A | 297 | A |
| 298 | A | 299 | A | 300 | A |
| 301 | A | 302 | A | 303 | A |
| 304 | A | 305 | A | 306 | A |
| 307 | A | 308 | A | 309 | A |
| 310 | A | 311 | A | 312 | A |
| 313 | A | 314 | A | 315 | A |
| 316 | A | 317 | A | 318 | A |
| 319 | A | 320 | A | 321 | A |
| 322 | A | 323 | A | 324 | A |
| 325 | A | 326 | A | 327 | A |
| 328 | A | 329 | A | 330 | A |
| 331 | A | 332 | A | 333 | A |
| 334 | A | 335 | A | 336 | A |
| 337 | A | 338 | A | 339 | A |
| 340 | A | 341 | A | AZD1775 | A |

A indicates that the $IC_{50}$ is less than or equal to 1 μM;

B indicates that the $IC_{50}$ is greater than 1 μM but less than or equal to 3 μM;

C indicates that the $IC_{50}$ is greater than 3 μM.

As can be seen from the data in Table 5, the compounds of the present invention have strong antiproliferative activity against HT-29 cells.

Example 344. Pharmacokinetic Evaluation in Mice

The compounds were administered by intravenous injection at a dose of 2 mg/kg and oral gavage at a dose of 10 mg/kg (0.5% CMC-Na suspension). 15 male ICR mice were selected for each group, and each mouse was subjected to blood collection at 3 discrete time points, with 3 mice at each time point. The time points of sampling were as follows: before administration, and 5 min, 15 min, 30 min, 1 h, 3 h, 5 h, 8 h, 12 h and 24 h after administration. 80 μL of blood was collected from the orbits or hearts of the mice at each time point after administration. All whole blood samples were collected in tubes containing EDTA $K_2$ and centrifuged (1500-1600 rmp/min) at 4° C. for 10 min to isolate plasma, which was then stored in a refrigerator at −90° C. to −60° C. for sample analysis. The compound concentration in the plasma was determined by liquid chromatography-tandem mass spectrometry, and the corresponding pharmacokinetic parameters were obtained according to a plasma concentration-time curve.

TABLE 6

| Pharmacokinetic parameters of compound 3 in mice | | | | | | | | | |
|---|---|---|---|---|---|---|---|---|---|
| Compound | Route of administration | Dose (mg/kg) | $t_{1/2}$ (h) | $T_{max}$ (h) | $C_{max}$ (ng/mL) | $AUC_{0-t}$ (ng · h/L) | Vss (L/kg) | Cl (mL/h/kg) | F (%) |
| 3 | iv | 2 | 0.718 | NA | NA | 736 | 1.8 | 45.3 | NA |
| | po | 10 | 1.91 | 0.25 | 533 | 1210 | NA | NA | 32.9 |
| AZD-1775 | iv | 2 | 0.30 | NA | NA | 152 | 3.51 | 220 | NA |
| | po | 10 | 1.45 | 0.5 | 247 | 215 | NA | NA | 28.3 |

NA indicates that the data are not available.

As can be seen from the above table, compound 3 has good oral absorption characteristics, and has half-life ($t_{1/2}$), maximum plasma concentration ($C_{max}$), area under the drug-time curve ($AUC_{0-t}$), oral bioavailability metabolic parameters and the like thereof all superior to those of the control drug AZD-1775. Good oral absorption properties are of great significance in improving the efficacy of drugs, reducing the dose of administration and reducing the costs. Further experiments have proved that other compounds of the present invention also have good oral absorption characteristics, and have half-life ($t_{1/2}$), maximum plasma concentration ($C_{max}$), area under the drug-time curve ($AUC_{0-t}$), oral bioavailability metabolic parameters and the like thereof all superior to those of the control drug AZD-1775.

The invention claimed is:

1. A compound of formula (1):

(1)

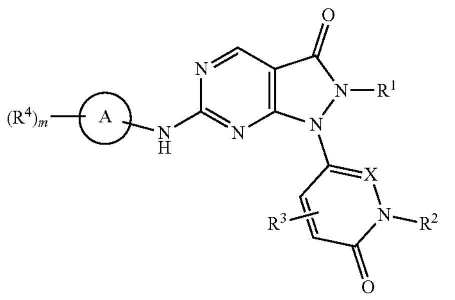

or a pharmaceutically acceptable salt or stereoisomer thereof, wherein:

$R^1$ is $C_1$-$C_6$ alkyl, $C_1$-$C_3$ haloalkyl, $CH_2$—$C_3$-$C_6$ cycloalkyl, $C_3$-$C_5$ alkenyl, or $C_3$-$C_6$ cycloalkyl;

$R^2$ is $C_1$-$C_6$ alkyl, $C_3$-$C_6$ cycloalkyl, or 4- to 6-membered heterocycloalkyl;

wherein the $C_1$-$C_6$ alkyl is optionally substituted with 1, 2, or 3 substituents independently selected from the group consisting of halogen, OH, and $OCH_3$; and wherein the $C_3$-$C_6$ cycloalkyl or 4- to 6-membered heterocycloalkyl is optionally substituted with 1, 2, or 3 substituents independently selected from the group consisting of halogen, $CH_3$, OH, and $OCH_3$;

each $R^3$ is independently H, halogen, CN, $C_1$-$C_3$ alkyl, $C_1$-$C_3$ haloalkyl, or $OC_1$-$C_3$ alkyl;

X is CH or N;

ring A is aryl, aryl(cycloalkyl), aryl(heterocycloalkyl), heteroaryl, or heteroaryl(heterocycloalkyl);

each $R^4$ is independently halogen, $C_1$-$C_3$ alkyl, $C_1$-$C_3$ haloalkyl, $C_1$-$C_3$ alkylene-$N(CH_3)_2$, $C_1$-$C_3$ hydroxyalkyl, $CH_2$-4- to 12-membered heterocycloalkyl, $N(CH_3)_2$, $N(CH_3)CH_2CH_2N(CH_3)_2$, $OC_1$-$C_3$ alkyl, $OC_1$-$C_3$ alkylene-$N(CH_3)_2$, $C_3$-$C_6$ cycloalkyl, or 4- to 12-membered heterocycloalkyl, wherein the 4- to 12-membered heterocycloalkyl is optionally substituted with 1, 2, or 3 independently selected $R^5$ substituents; or two $R^4$, together with any carbon atoms to which they are attached, form a spirocyclopropylene or spirocyclobutylene;

each $R^5$ is independently halogen, CN, $C_1$-$C_3$ alkyl, $C_1$-$C_3$ haloalkyl, $C_1$-$C_3$ cyanoalkyl, $C_1$-$C_3$ alkylene-$NR^6R^7$, $C_1$-$C_3$ hydroxyalkyl, $NR^6R^7$, OH, $C_3$-$C_6$ cycloalkyl, $C_3$-$C_6$ halocycloalkyl, or oxetan-3-yl;

each $R^6$ is independently H or $C_1$-$C_3$ alkyl;

each $R^7$ is independently H or $C_1$-$C_3$ alkyl; or any $R^6$ and $R^7$, together with the nitrogen atom to which they are both attached, independently forms a 4- to 7-membered heterocycloalkyl; and m is 0, 1, 2, or 3;

with the proviso that if $R^4$ is halogen or $R^5$ is halogen, then $R^4$ or $R^5$ is not bonded to a heteroatom.

2. The compound according to claim 1, or a pharmaceutically acceptable salt or stereoisomer thereof, wherein $R^1$ is $CH_3$, $CH_2CH_3$, $CH_2CH_2CH_3$, $CH(CH_3)_2$, $CH_2C(CH_3)_3$, $CH_2CH(CH_3)_2$, $CH_2CF_3$, $CH_2$-cyclopropyl, $CH_2$-cyclobutyl, $CH_2$-cyclopentyl, $CH_2CH{=}CH_2$, cyclopropyl, cyclobutyl, or cyclopentyl.

3. The compound according to claim 1, or a pharmaceutically acceptable salt or stereoisomer thereof, wherein $R^2$ is $CH_3$, $CH_2CH_3$, $CH_2CH_2CH_3$, $CH(CH_3)_2$, $CH_2CH(CH_3)_2$, $CH_2C(CH_3)_2OH$, $CH_2C(CH_3)_2OCH_3$, $C(CH_3)_3$, $C(CH_3)_2CH_2OH$, $C(CH_3)_2CH_2OCH_3$, $C(CH_3CH_2CH_3$, $CH_2C(CH_3)_3$, $CH_2CHF_2$, $CH_2CF_3$, $C(CH_3)_2CF_3$, cyclopropyl, cyclobutyl, 3,3-difluorocyclobutyl, cyclopentyl, or oxetan-3-yl.

4. The compound according to claim 1, or a pharmaceutically acceptable salt or stereoisomer thereof, wherein each $R^3$ is independently H, F, $CH_3$, $CH_2CH_3$, $CHF_2$, $CF_3$, $OCH_3$, or $OCH_2CH_3$.

5. The compound according to claim 1, or a pharmaceutically acceptable salt or stereoisomer thereof, wherein

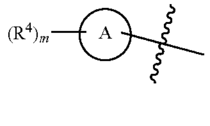

is:

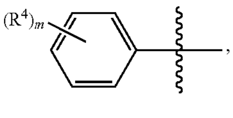

,

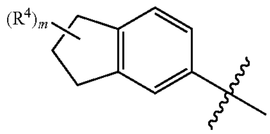

,

-continued

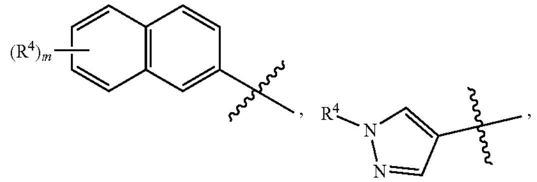

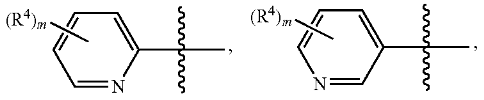

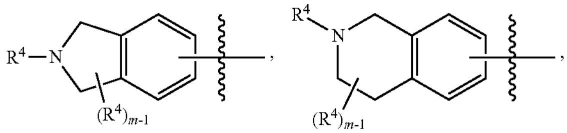

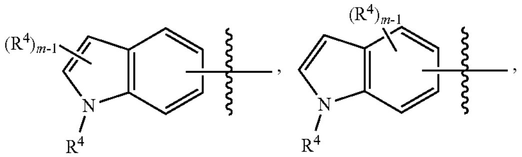

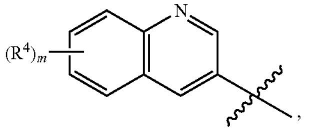

or

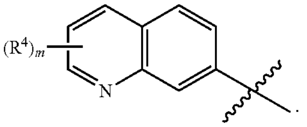

6. The compound according to claim 5, or a pharmaceutically acceptable salt or stereoisomer thereof, wherein:

each $R^4$ is independently: H, F, Cl, $CH_3$, $CH_2CH_3$, $CH_2CH_2CH_3$, $CH(CH_3)_2$, $CF_3$, $CH_2CF_3$, $CH_2N(CH_3)_2$, $CH_2CH_2N(CH_3)_2$, $CH_2CH_2CH_2N(CH_3)_2$, $CH_2OH$, $CH_2CH_2OH$, $N(CH_3)_2$, $N(CH_3)CH_2CH_2N(CH_3)_2$, $OCH_3$, $OCH_2CH_3$, $OCH_2CH_2N(CH_3)$, cyclopropyl, cyclobutyl, cyclopentyl,

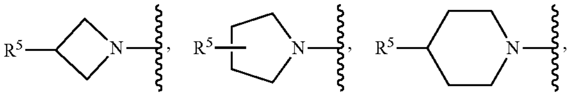

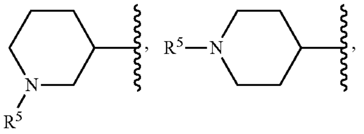

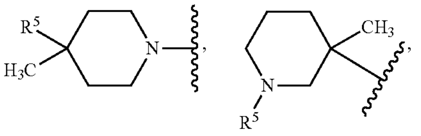

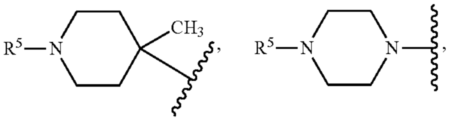

-continued

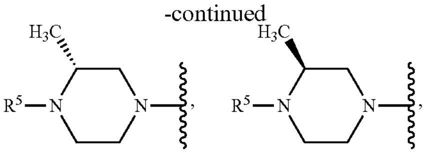

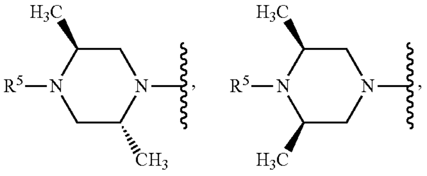

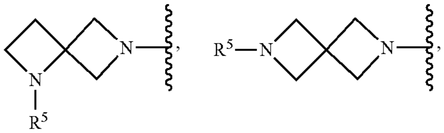

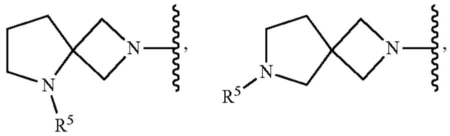

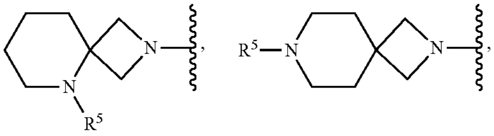

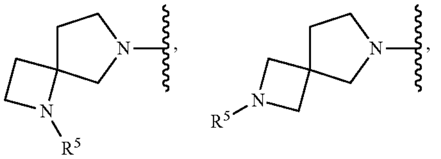

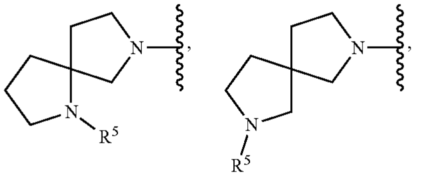

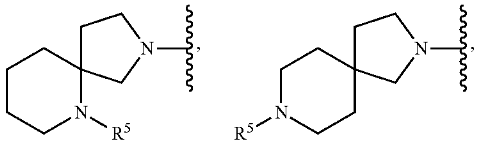

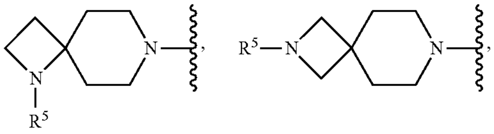

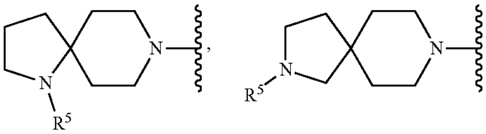

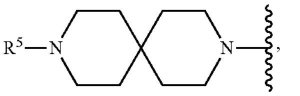

or

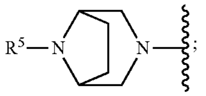

two $R^4$, together with any carbon atoms to which they are attached, form spirocyclopropylene or spirocyclobutylene; and each $R^5$ is independently H, halogen, CN, $C_1$-$C_3$ alkyl, $C_1$-$C_3$ haloalkyl, $C_1$-$C_3$ cyanoalkyl, $C_1$-$C_3$ hydroxyalkyl, $NH_2$, $NHCH_3$, $N(CH_3)_2$, OH, $C_3$-$C_6$ cycloalkyl, $C_3$-$C_6$ halocycloalkyl, azetidin-1-yl, oxetan-3-yl, pyrrolidin-1-yl, piperidin-1-yl, or morpholin-4-yl.
7. The compound according to claim 6, or a pharmaceutically acceptable salt or stereoisomer thereof, wherein
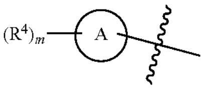
is:
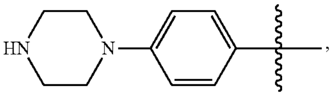
,
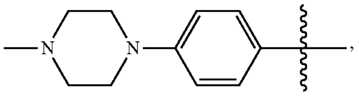
,
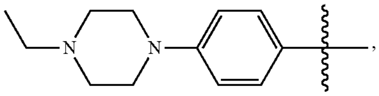
,
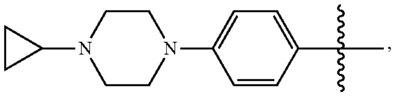
,
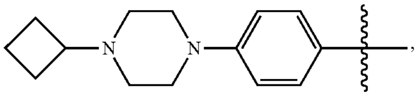
,
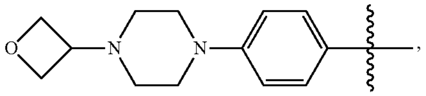
,
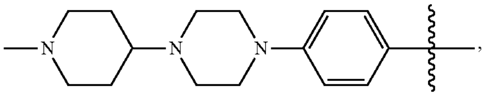
,
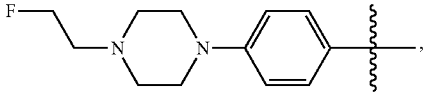
,
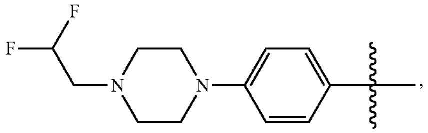
,
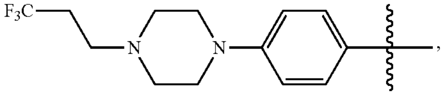
,
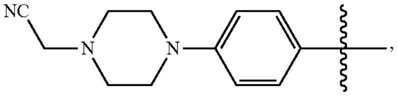
,
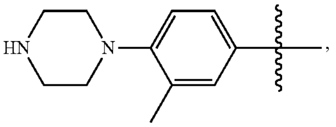
,
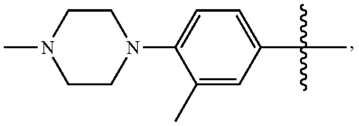
,
-continued
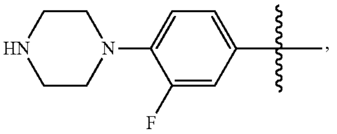
,
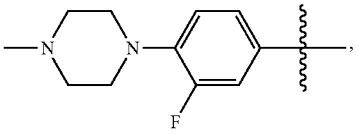
,
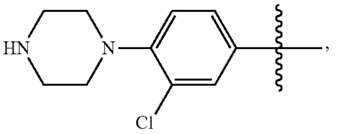
,
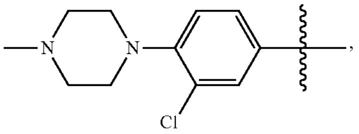
,
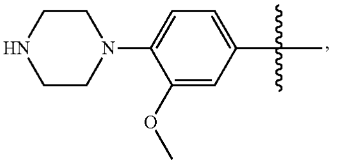
,
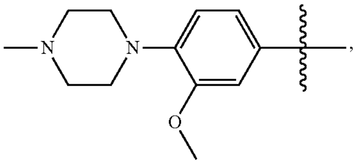
,
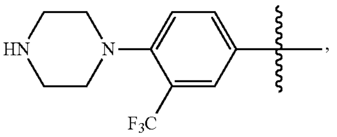
,
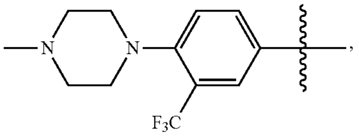
,
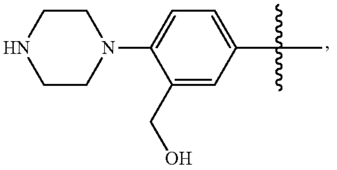
,
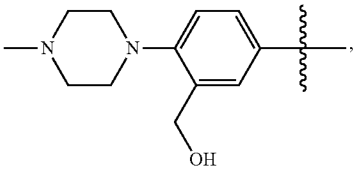
,
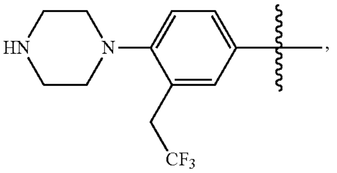
, -continued
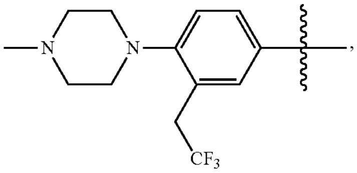,
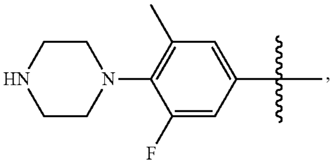,
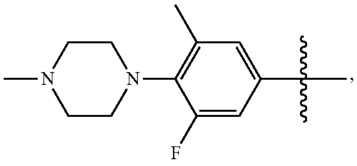,
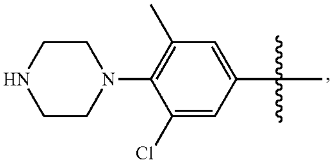,
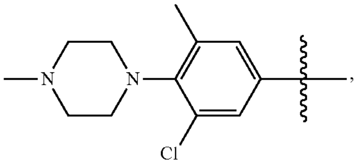,
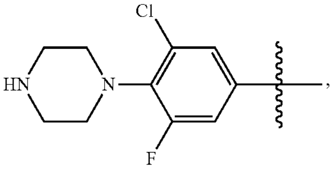,
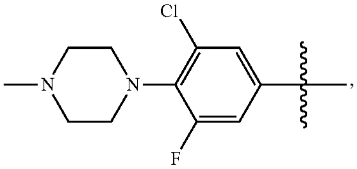,
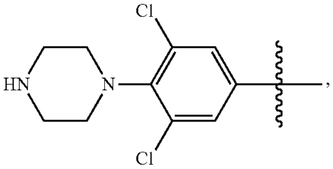,
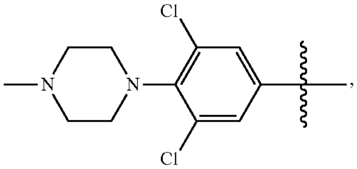,
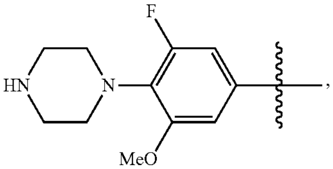,
-continued
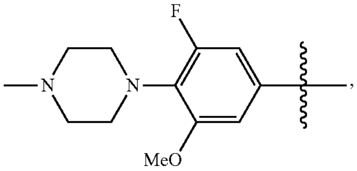,
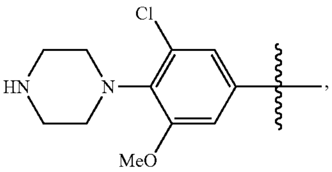,
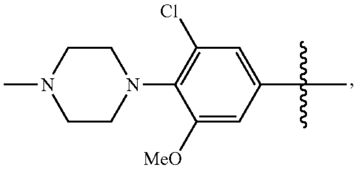,
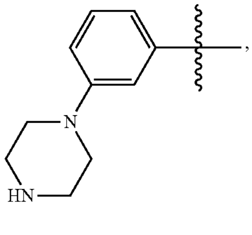, 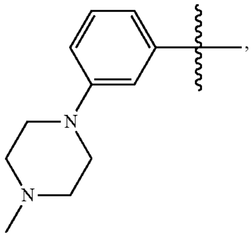,
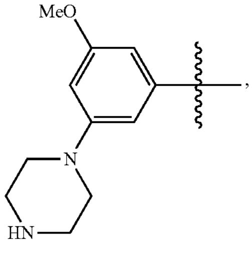, 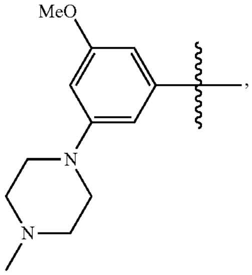,
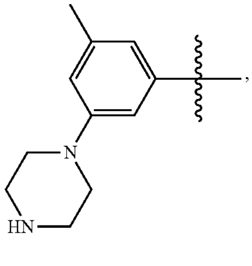, 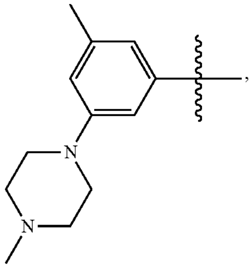,
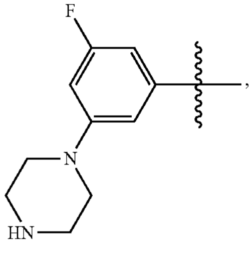, 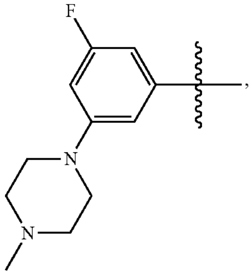, -continued
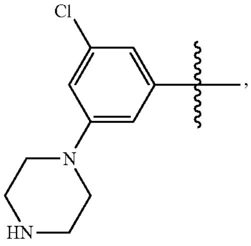,
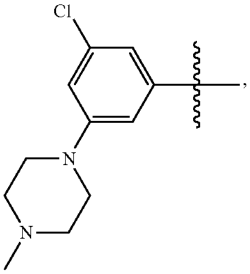,
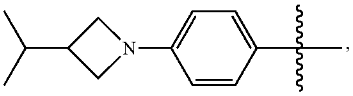,
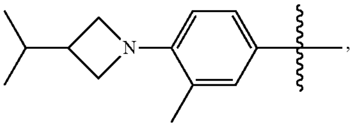,
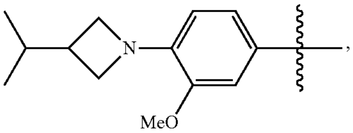,
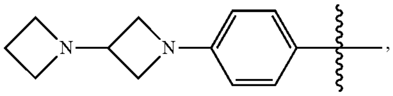,
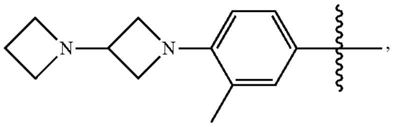,
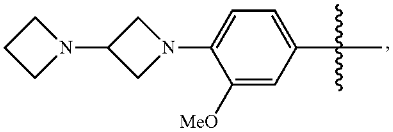,
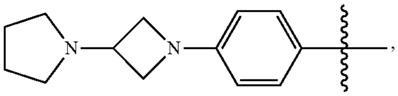,
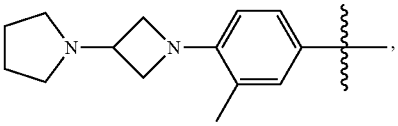,
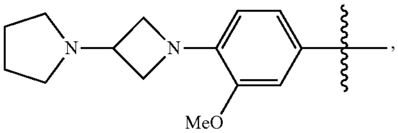,
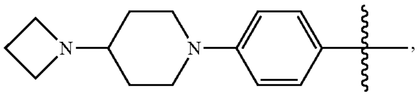,
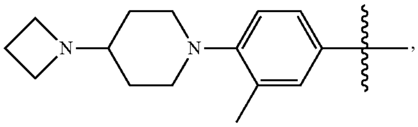,
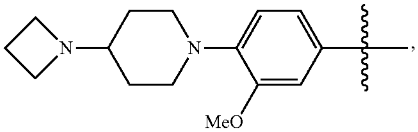,
-continued
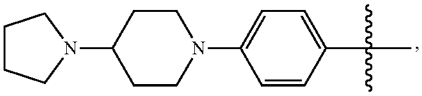,
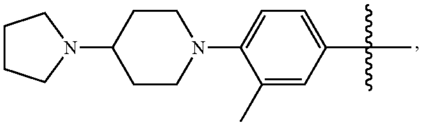,
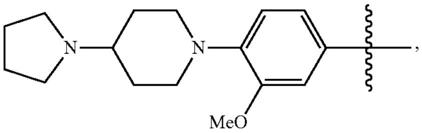,
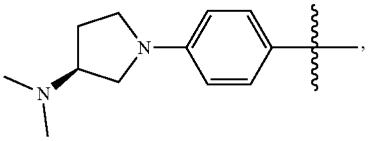,
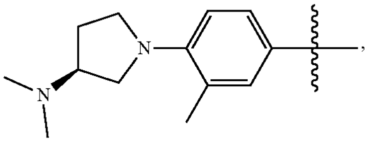,
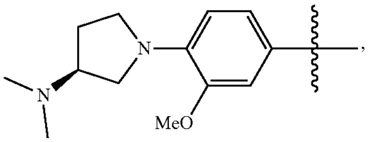,
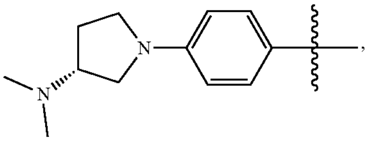,
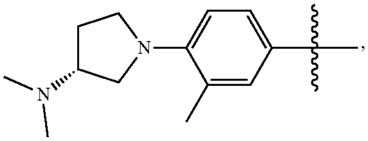,
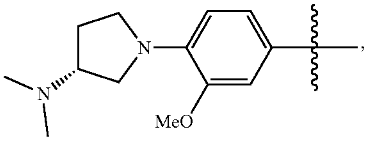,
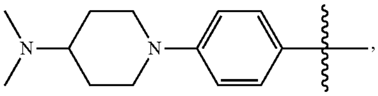,
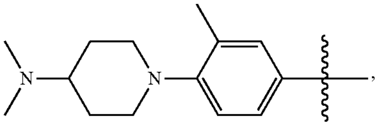,
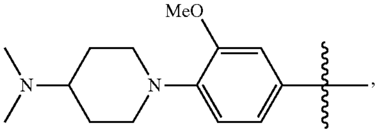,
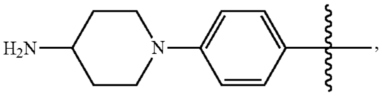, -continued
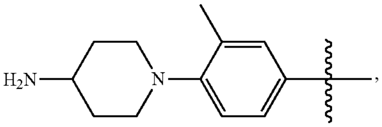,
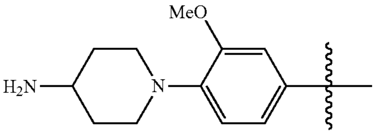
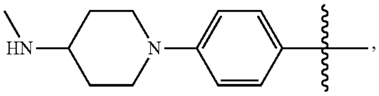,
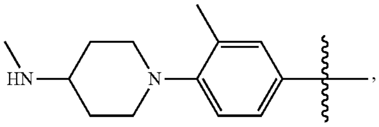,
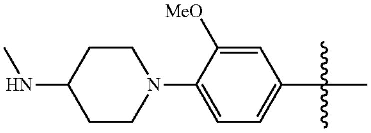
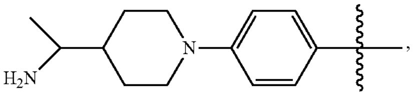,
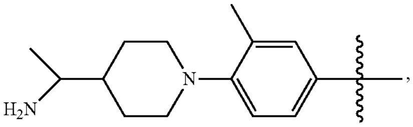,
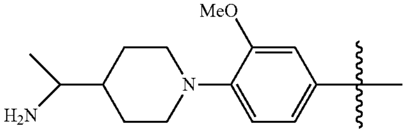
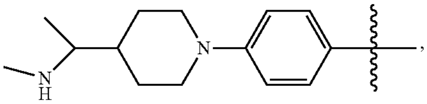,
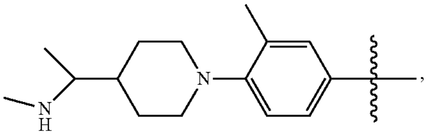,
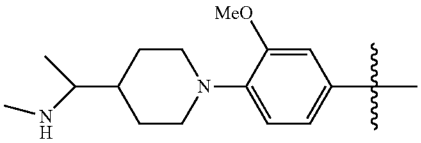
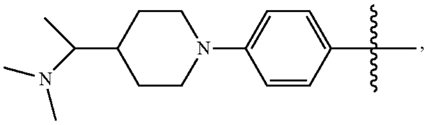,
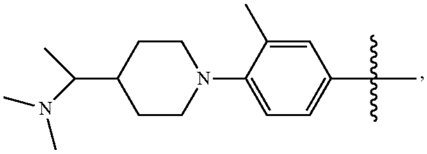,
-continued
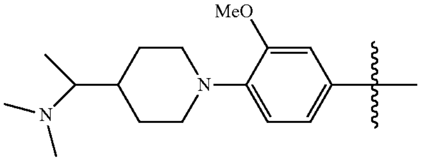
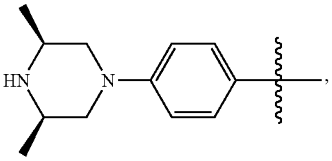,
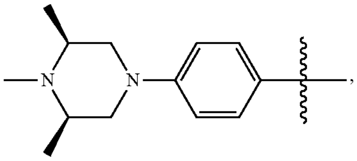,
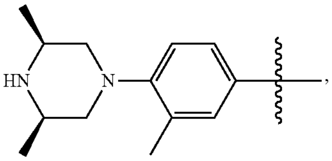,
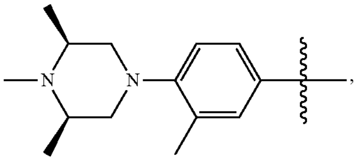,
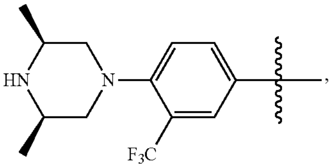,
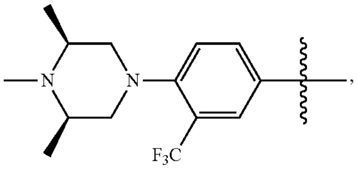,
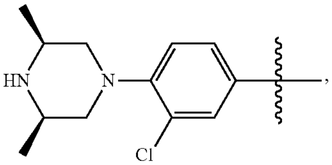,
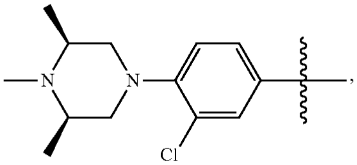,
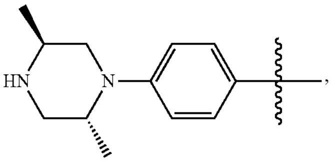, -continued
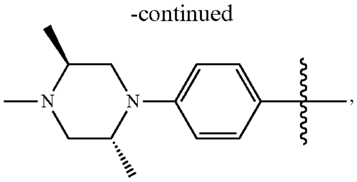,
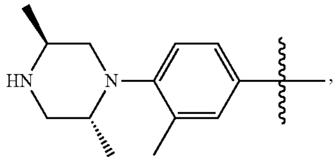,
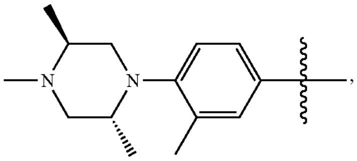,
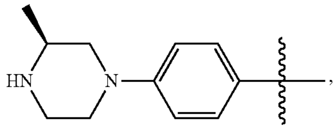,
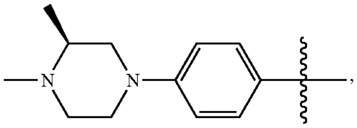,
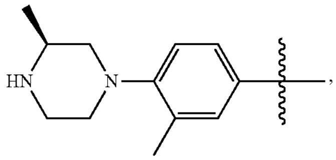,
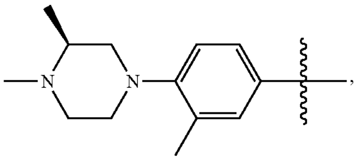,
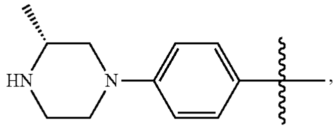,
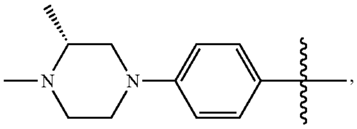,
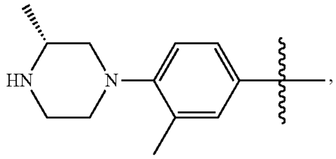,
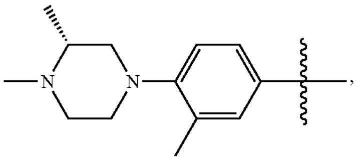,
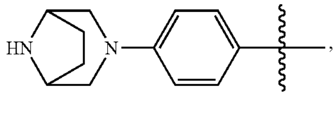,
-continued
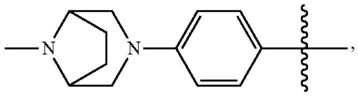,
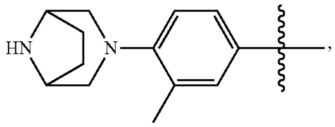,
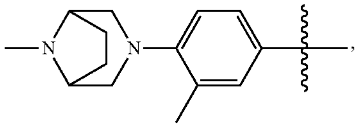,
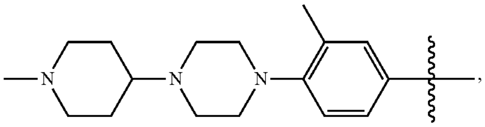,
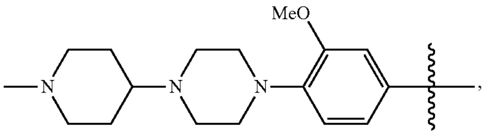,
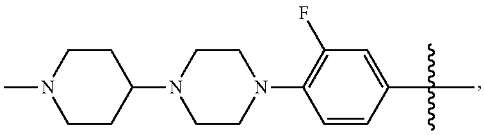,
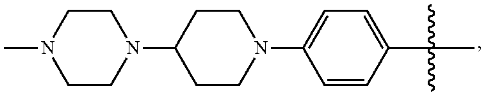,
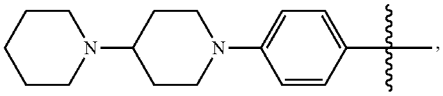,
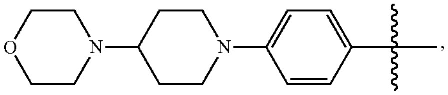,
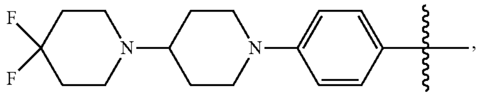,
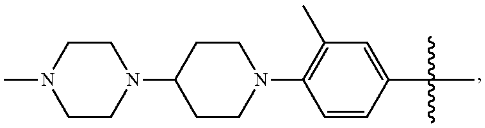,
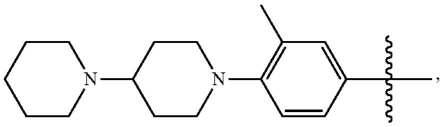,
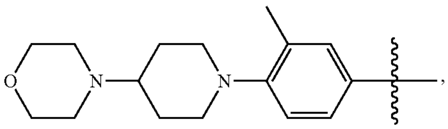,
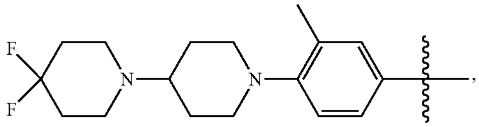, -continued
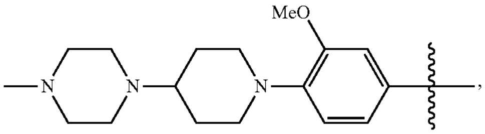,
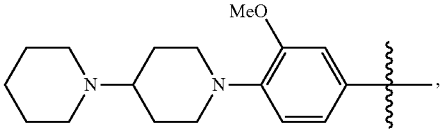,
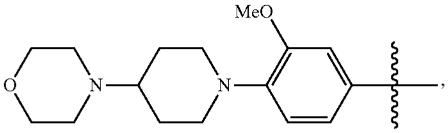,
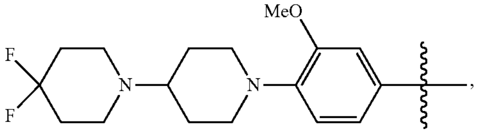,
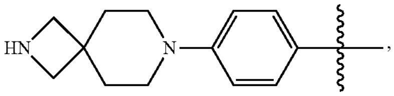,
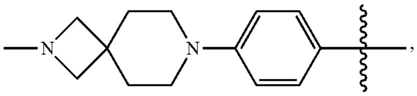,
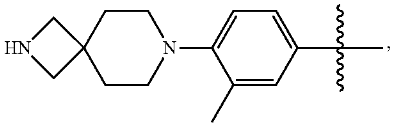,
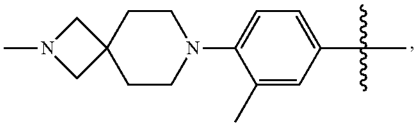,
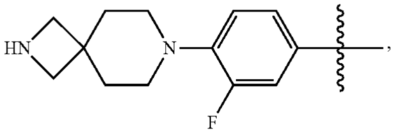,
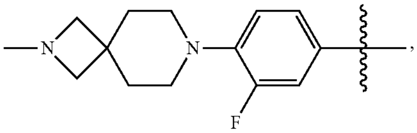,
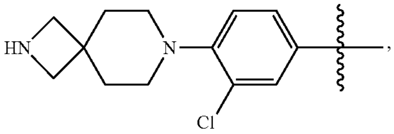,
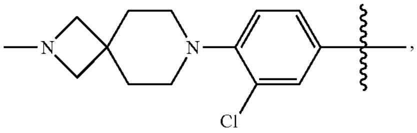,
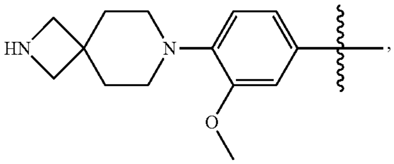,
-continued
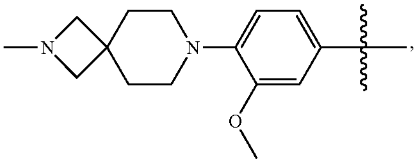,
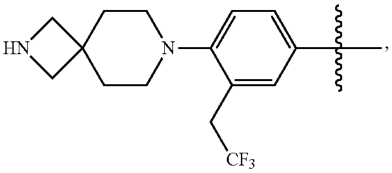,
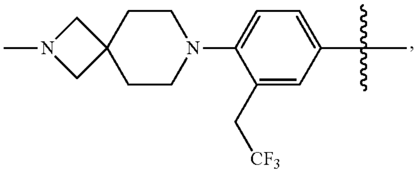,
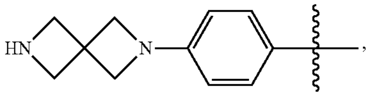,
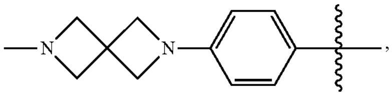,
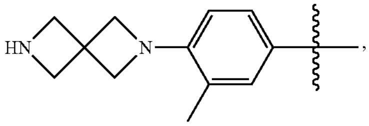,
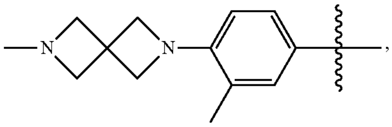,
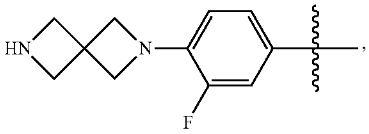,
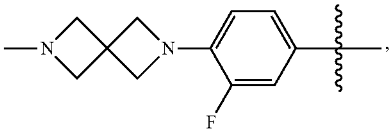,
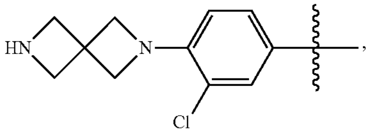,
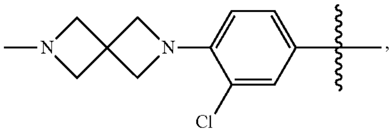,
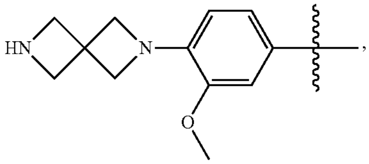, -continued
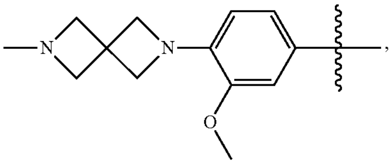,
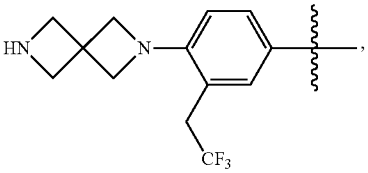,
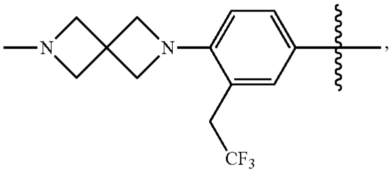,
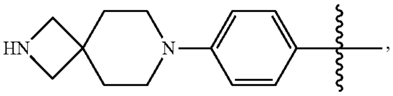,
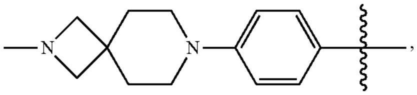,
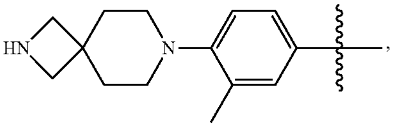,
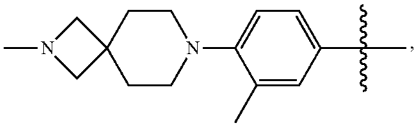,
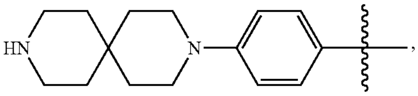,
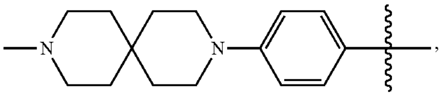,
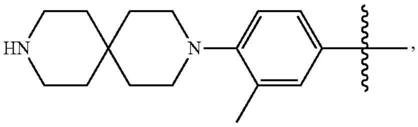,
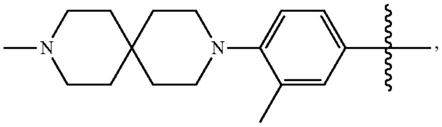,
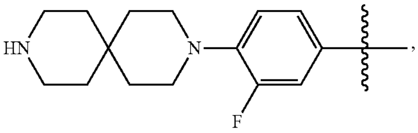,
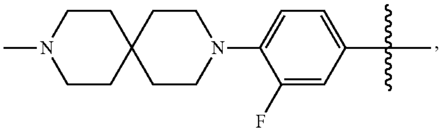,
-continued
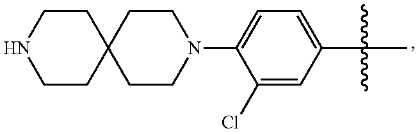,
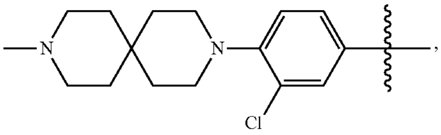,
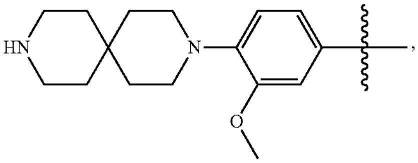,
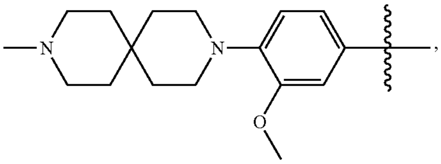,
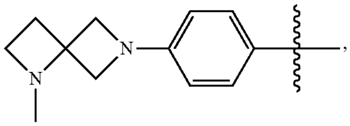,
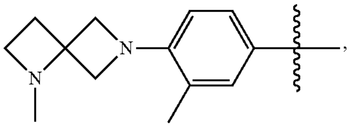,
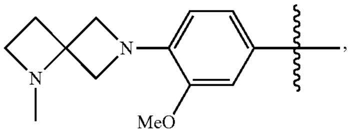,
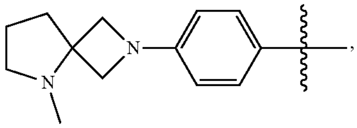,
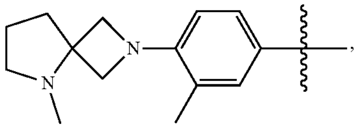,
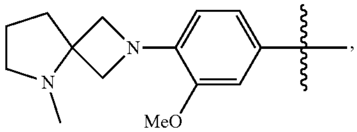,
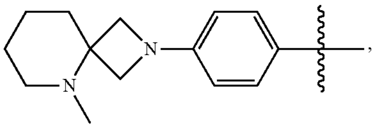,
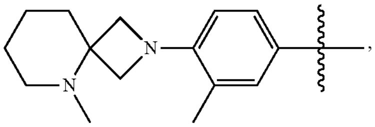, -continued
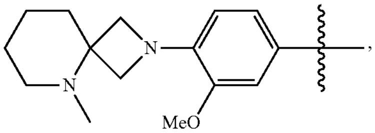,
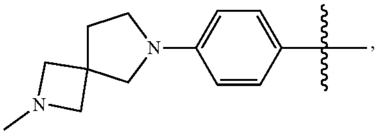,
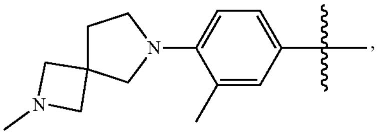,
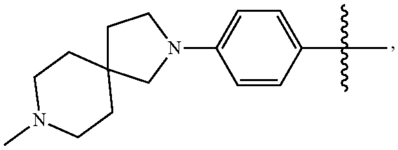,
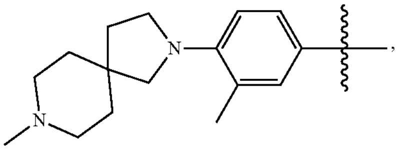,
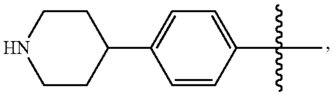,
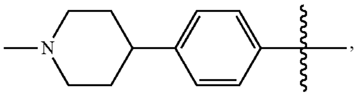,
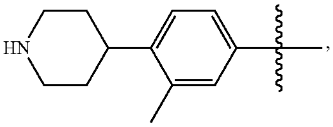,
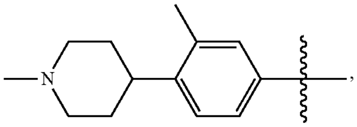,
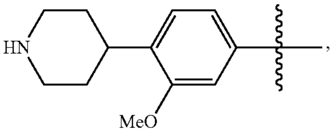,
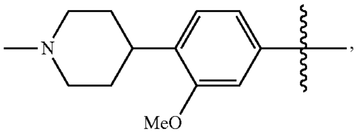,
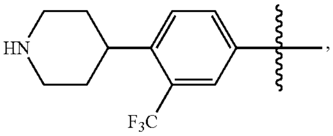,
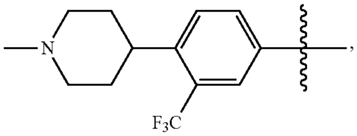,
-continued
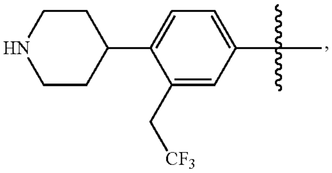,
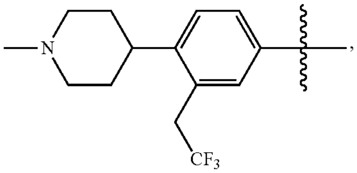,
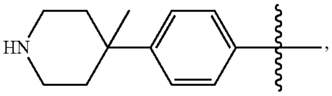,
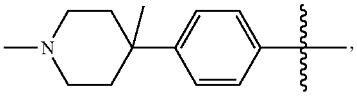,
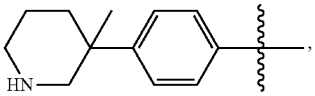,
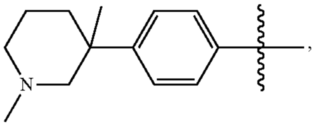,
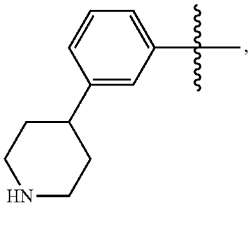, 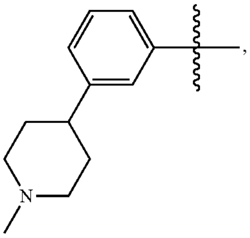,
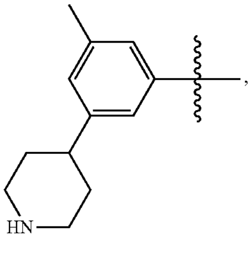, 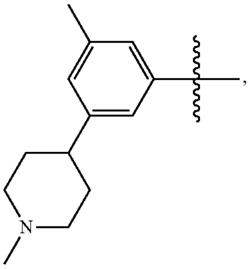,
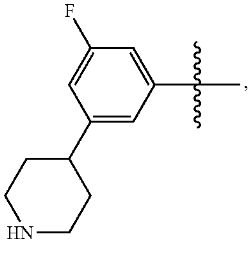, 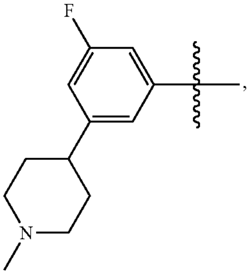, -continued
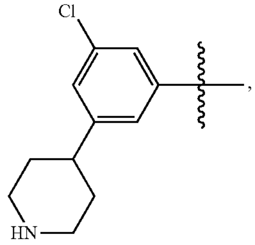,
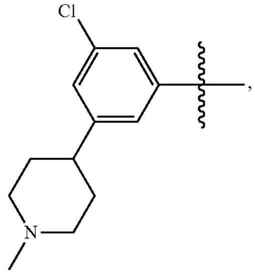,
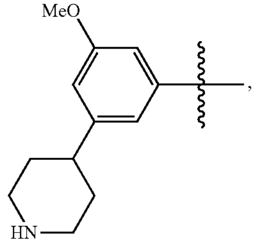,
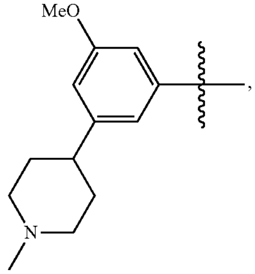,
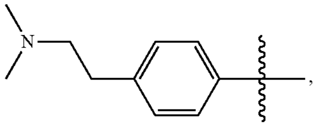,
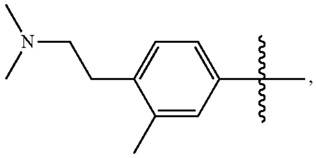,
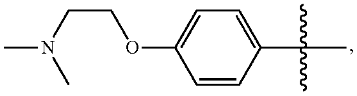,
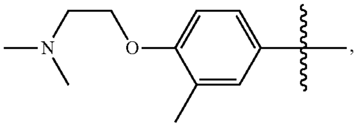,
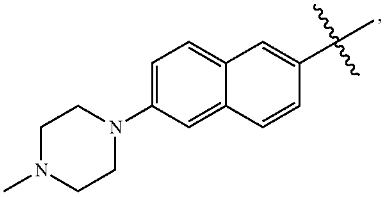,
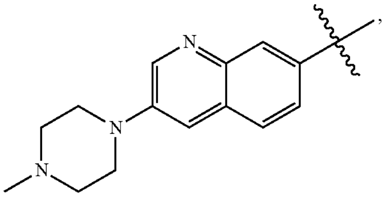,
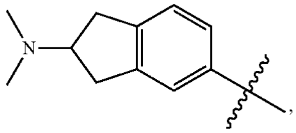,
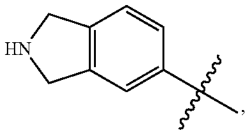,
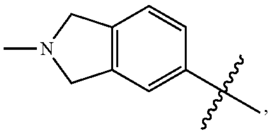,
-continued
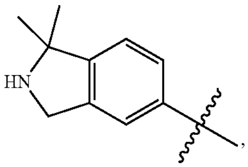,
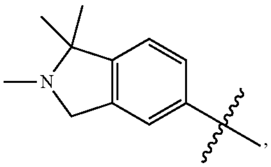,
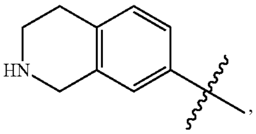,
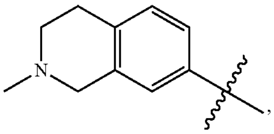,
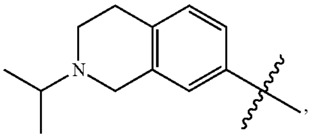,
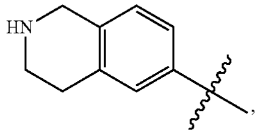,
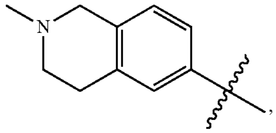,
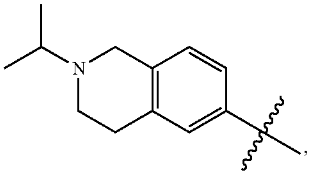,
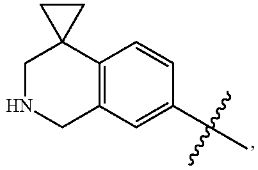,
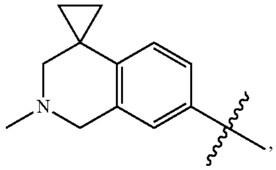,
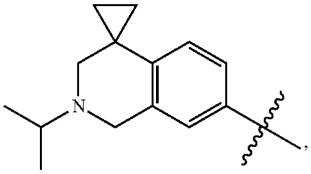,
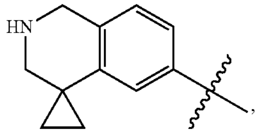,
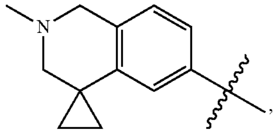,
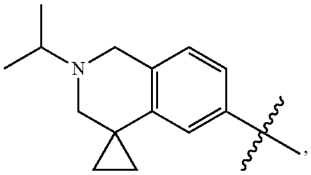,
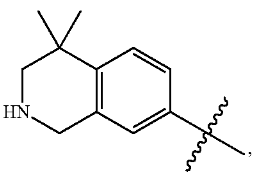,
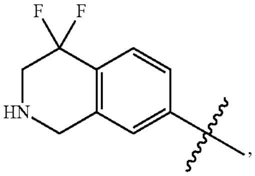, -continued
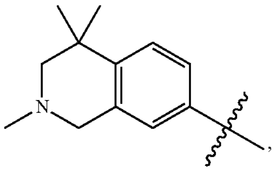,
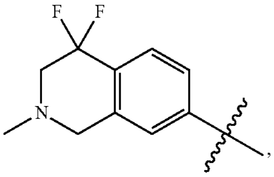,
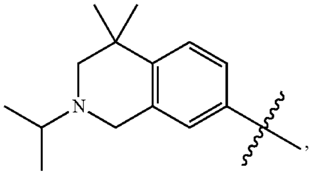,
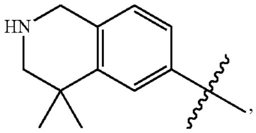,
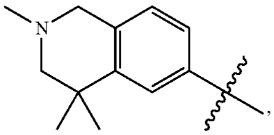,
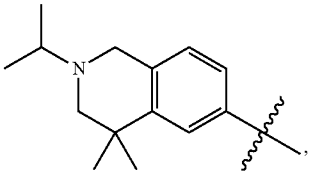,
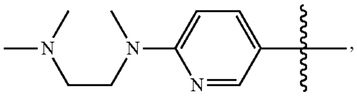,
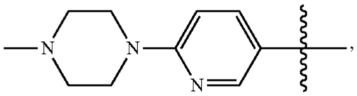,
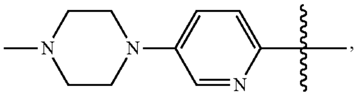,
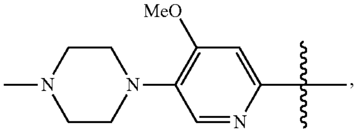,
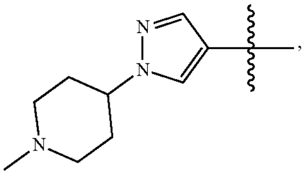,
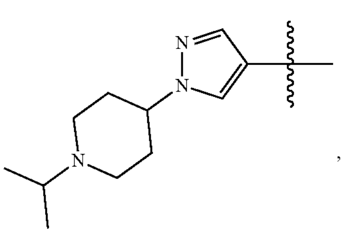,
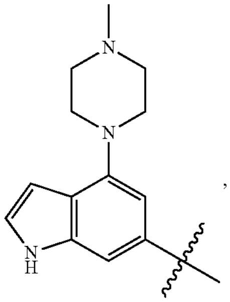,
-continued
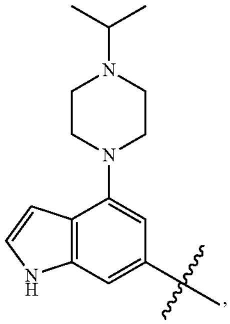,
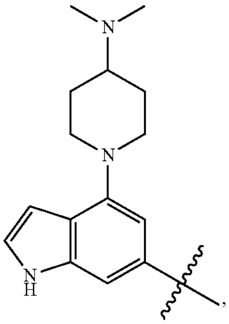,
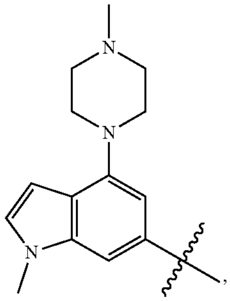,
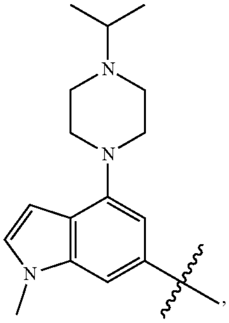,
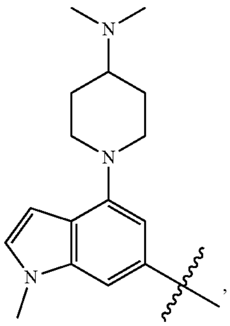,
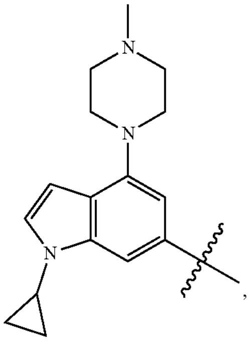,
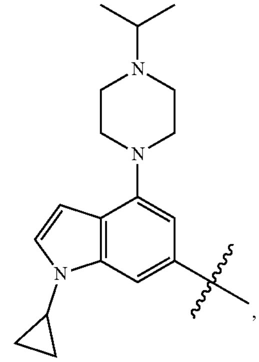,
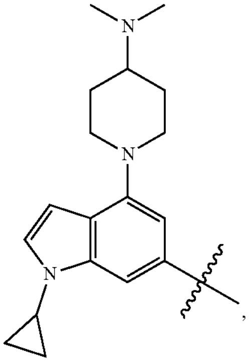,
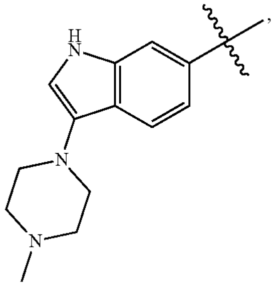,
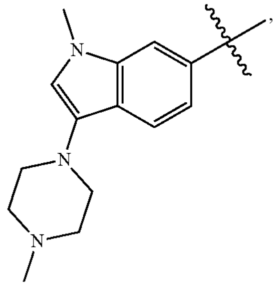, -continued
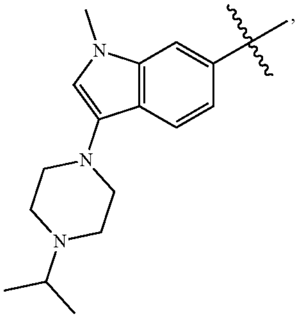,
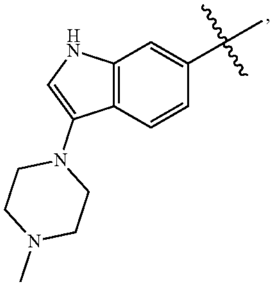,
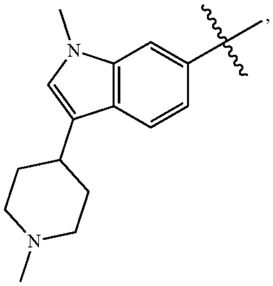,
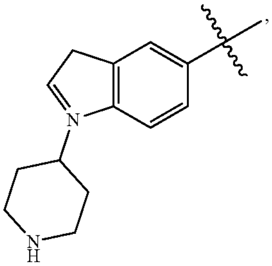,
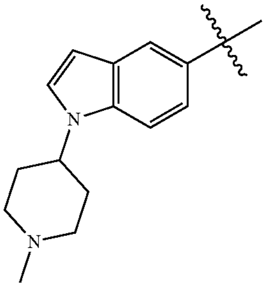 or
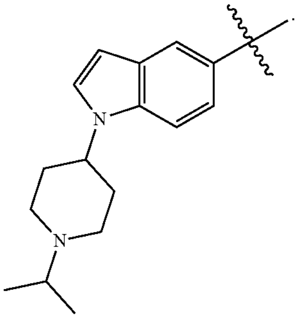.
8. A pharmaceutical composition comprising a pharmaceutically acceptable carrier, diluent, and/or excipient and a therapeutically effective dose of a compound according to claim 1, or a pharmaceutically acceptable salt or stereoisomer thereof.
9. A compound selected from the group consisting of:
1
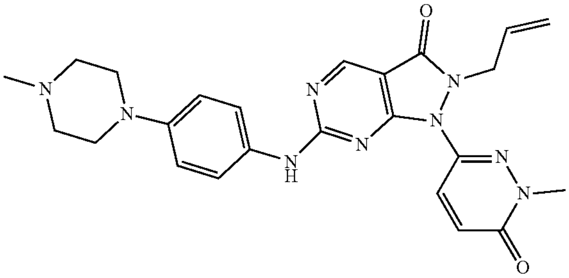
2
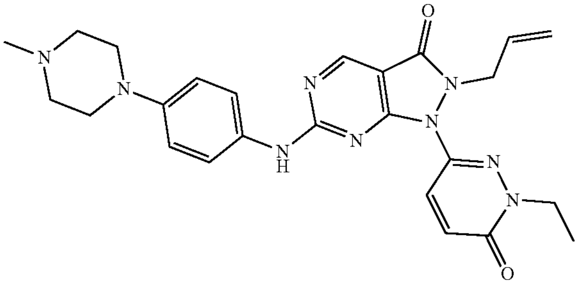
3
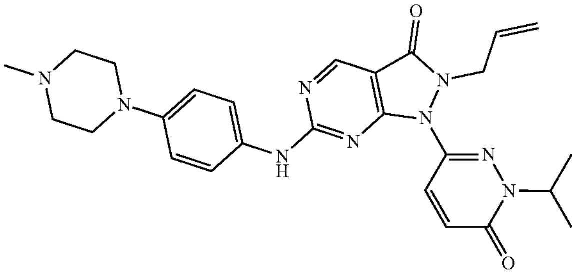
4
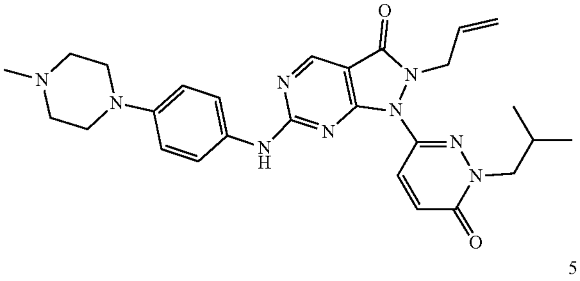
5
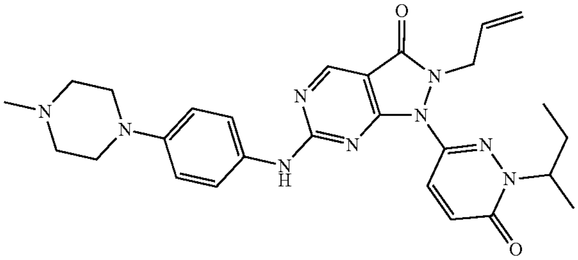

-continued
6
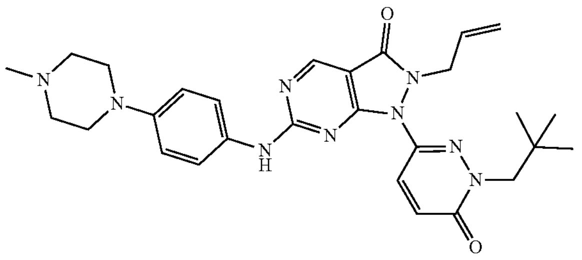
7
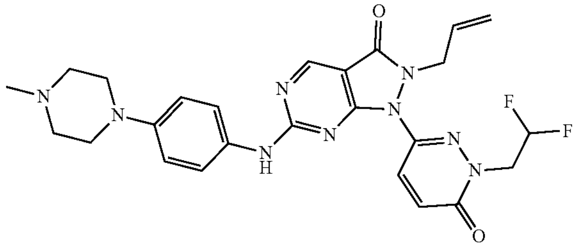
8
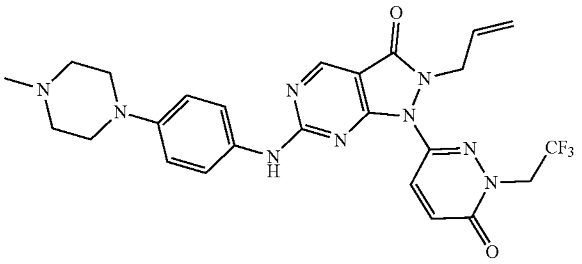
9
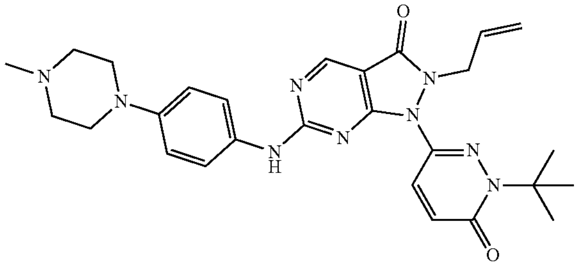
10
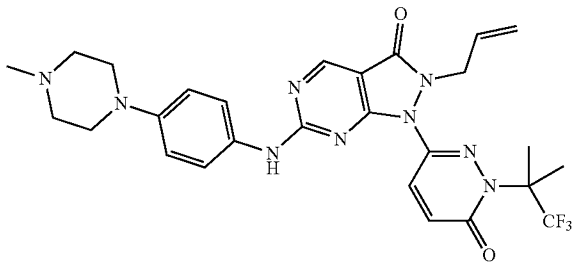
-continued
11
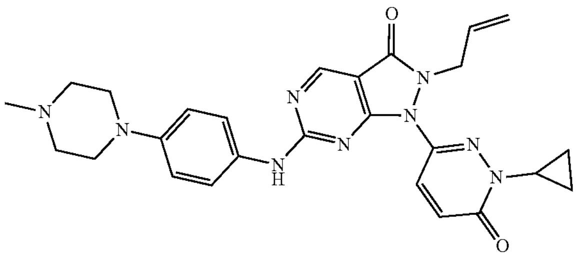
12
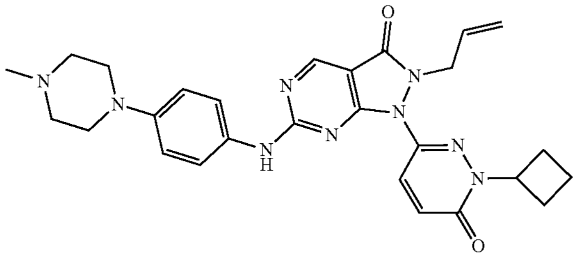
13
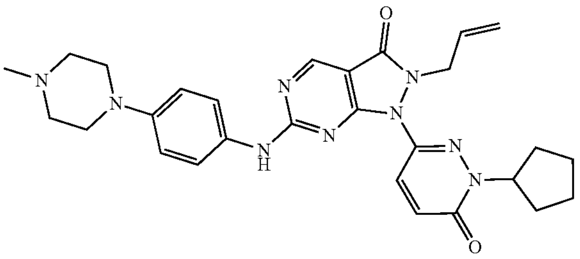
14
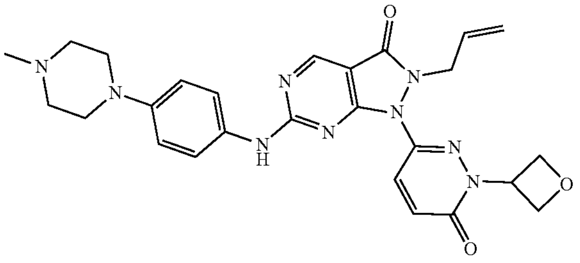
15
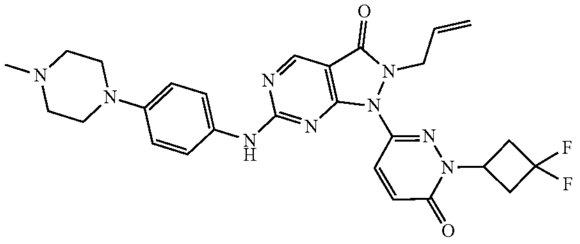

-continued
16
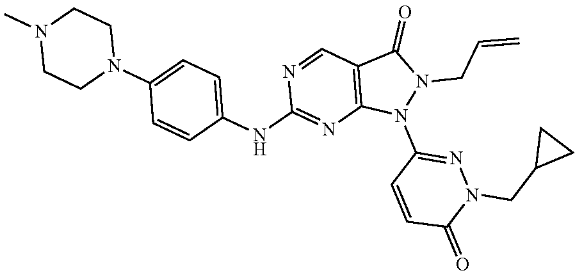
17
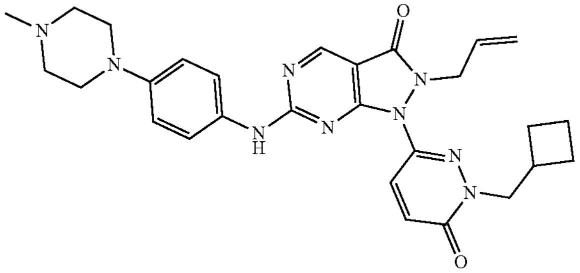
18
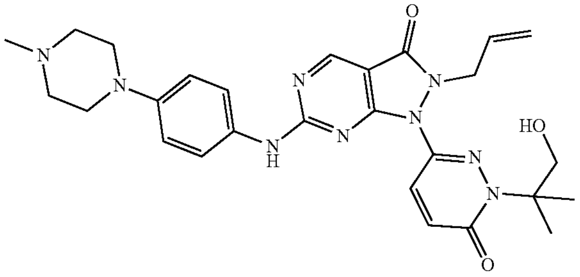
19
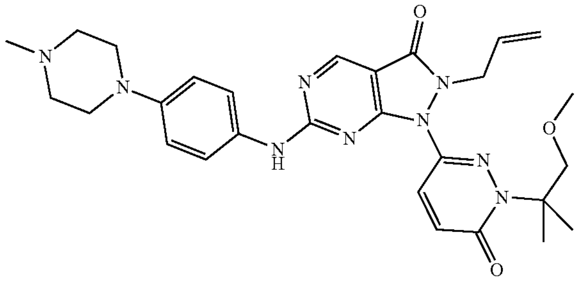
20
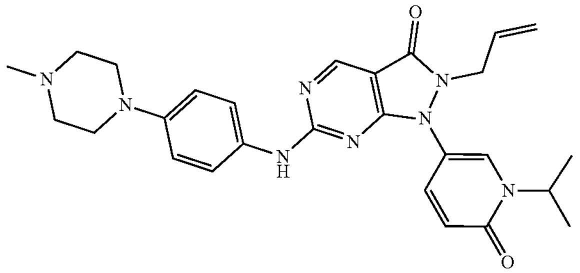
-continued
21
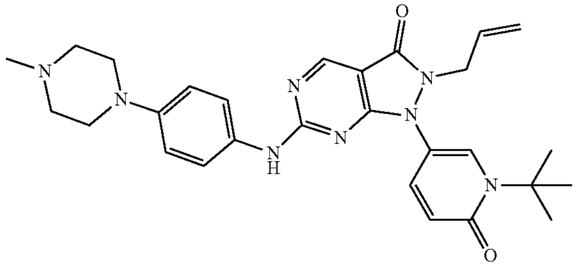
22
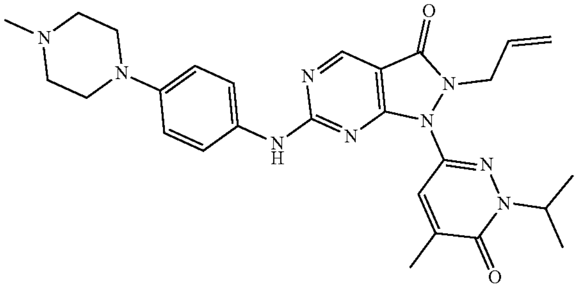
23
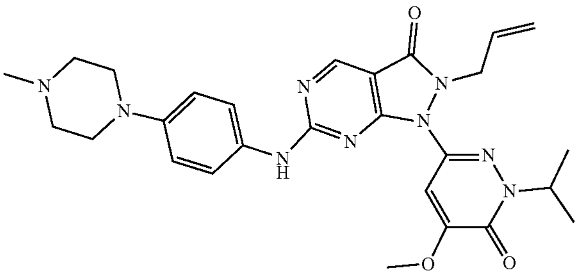
24
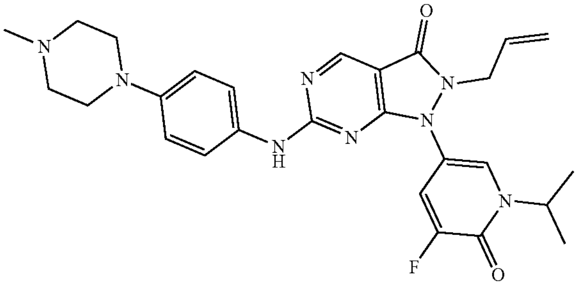
25
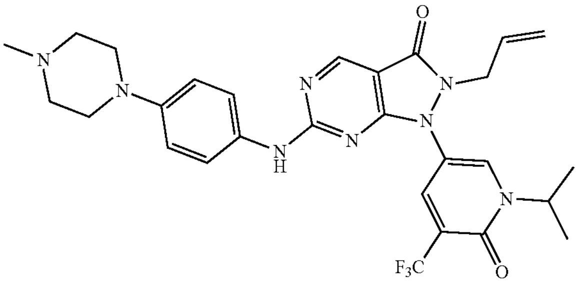

-continued
26
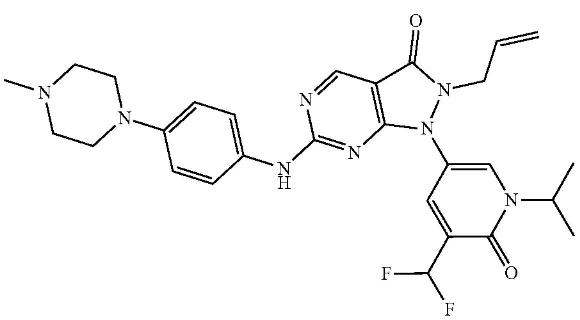
27
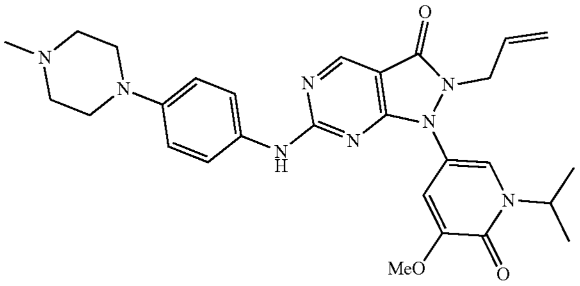
28
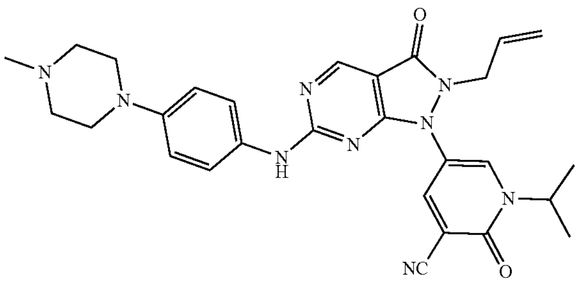
29
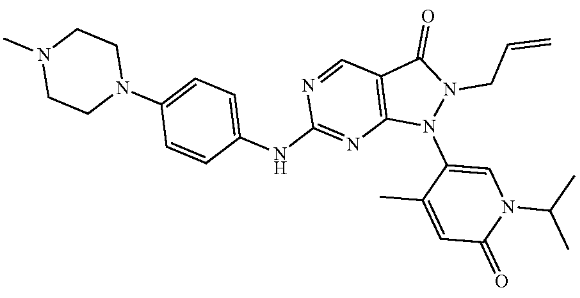
30
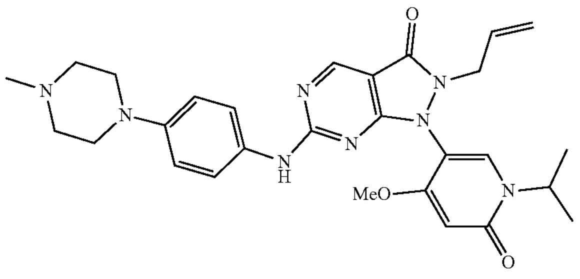
-continued
31
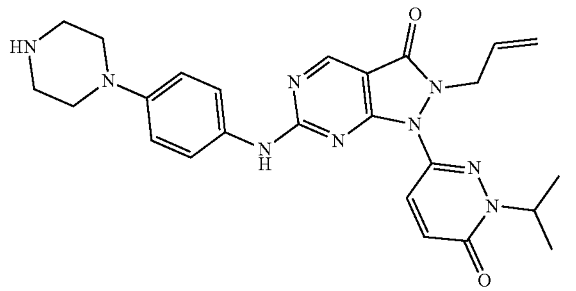
32
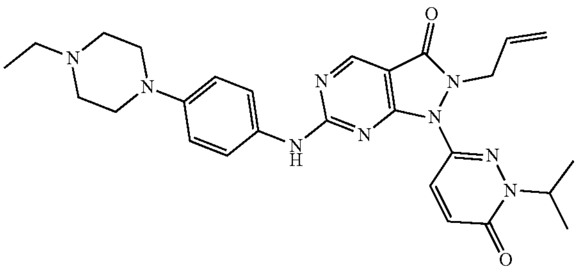
33
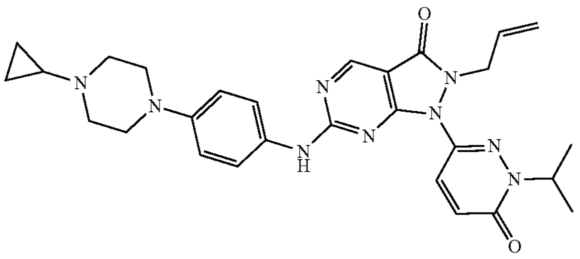
34
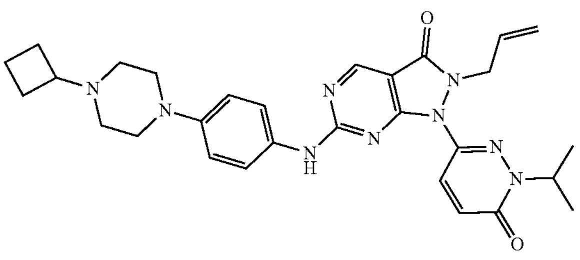
35
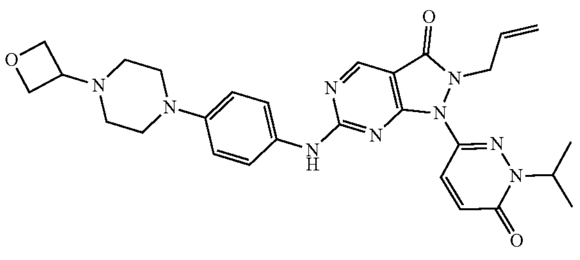

-continued
36
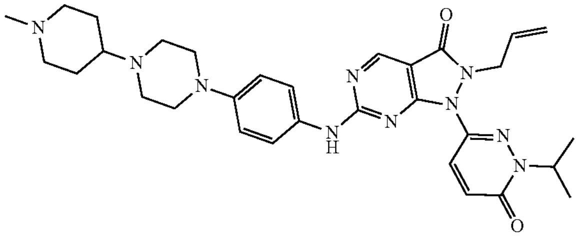
37
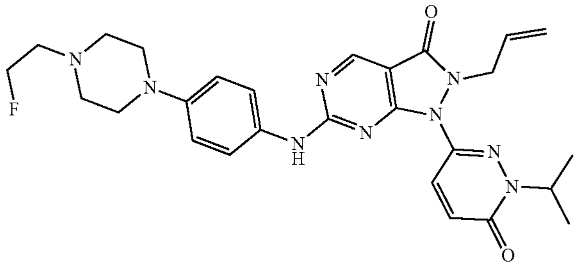
38
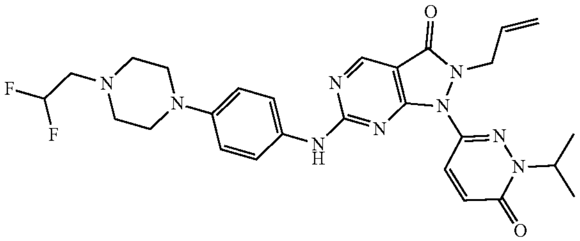
39
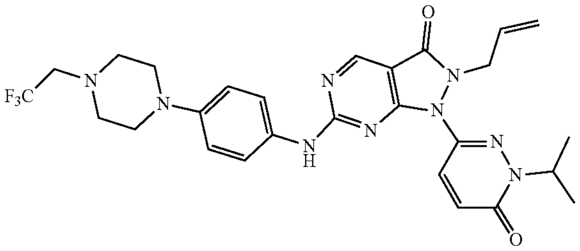
40
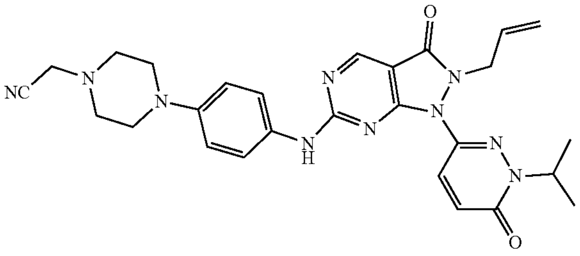
-continued
41
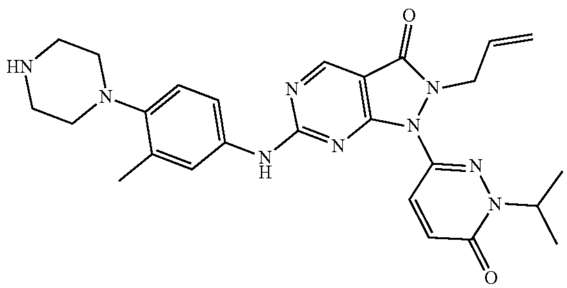
42
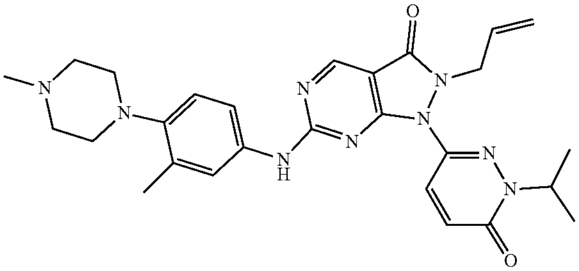
43
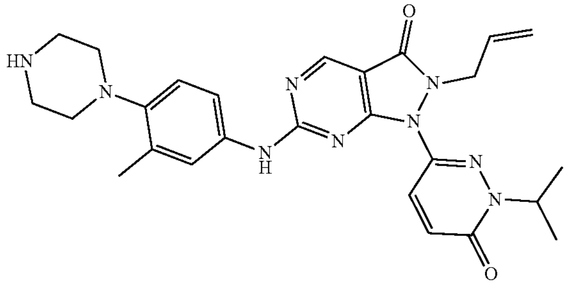
44
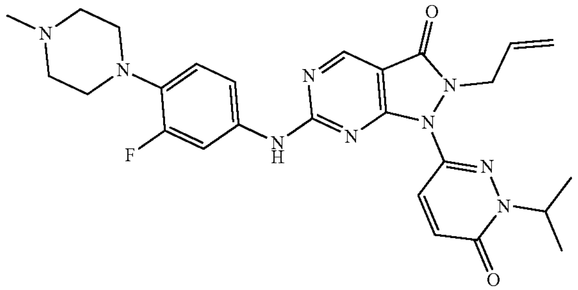
45
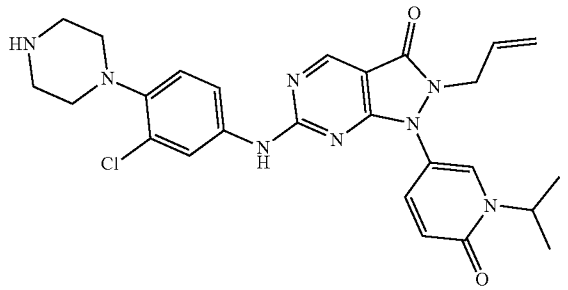

-continued
46
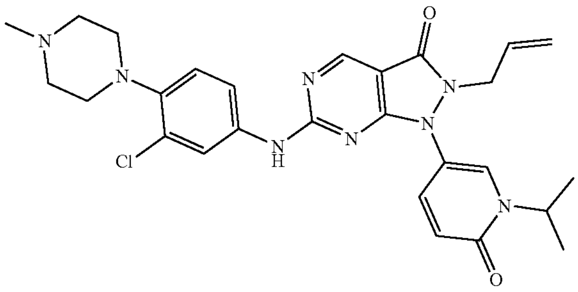
47
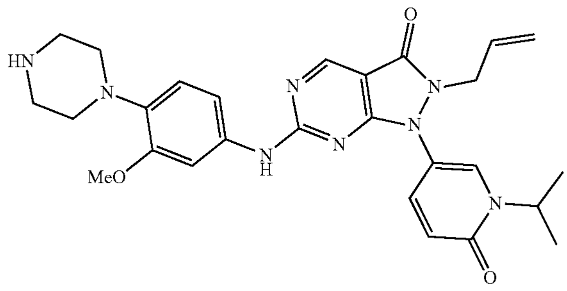
48
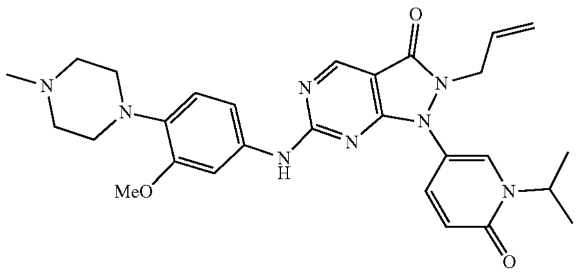
49
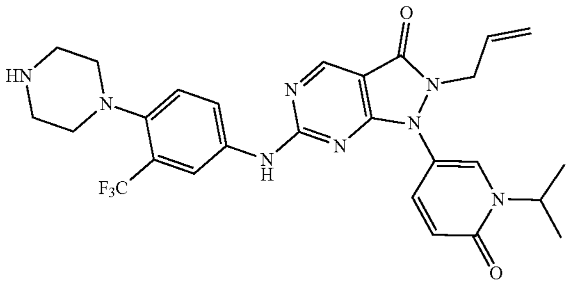
50
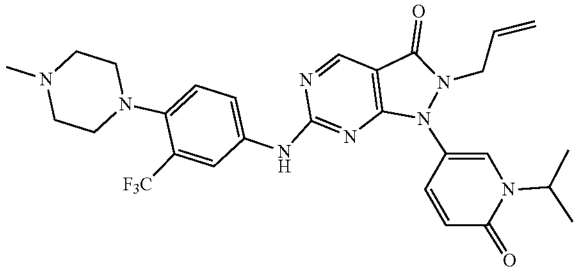
-continued
51
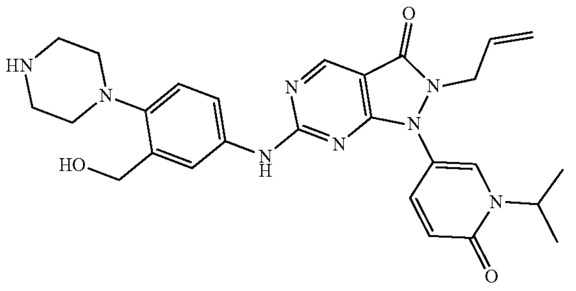
52
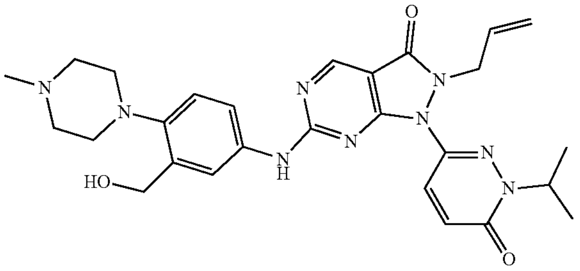
53
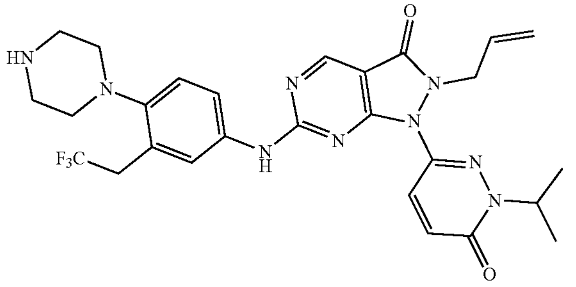
54
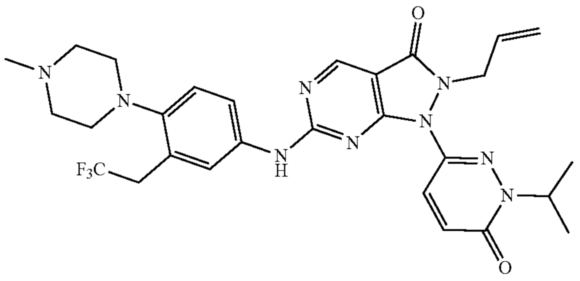
55
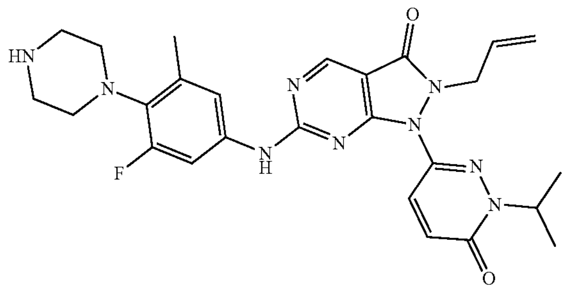

-continued
56
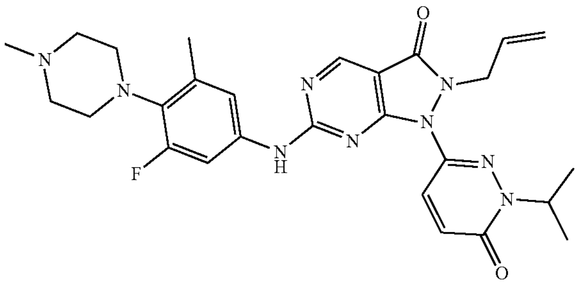
57
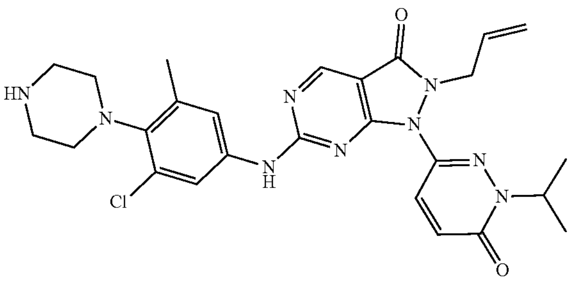
58
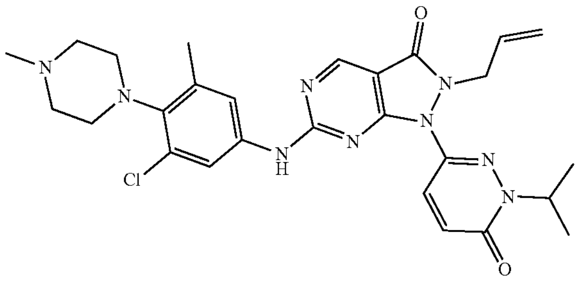
59
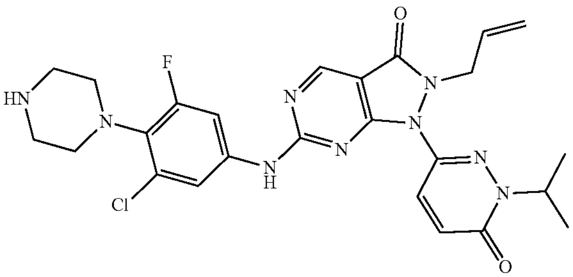
60
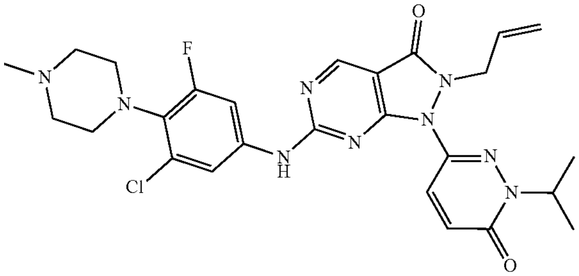
-continued
61
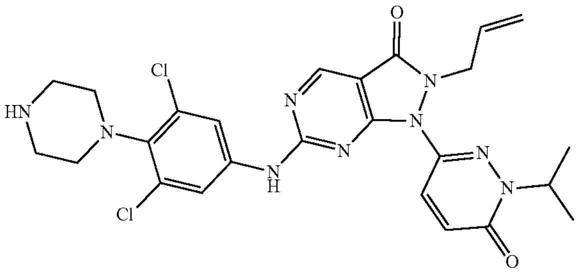
62
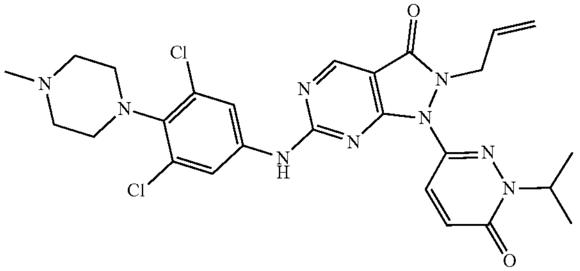
63
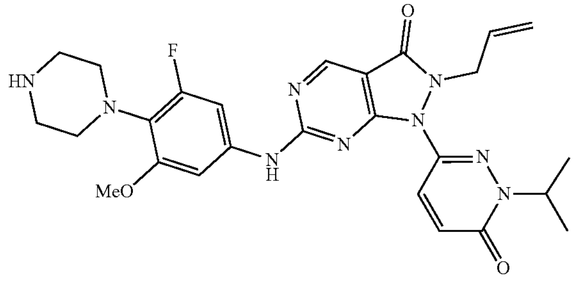
64
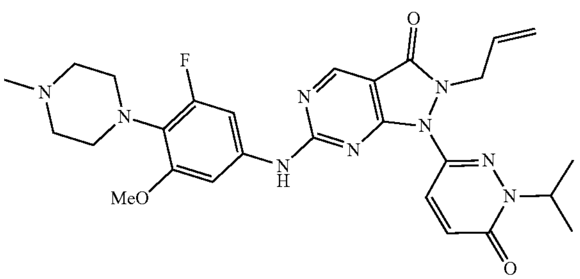
65
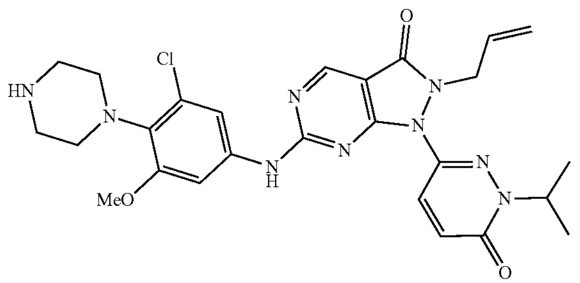

-continued
66
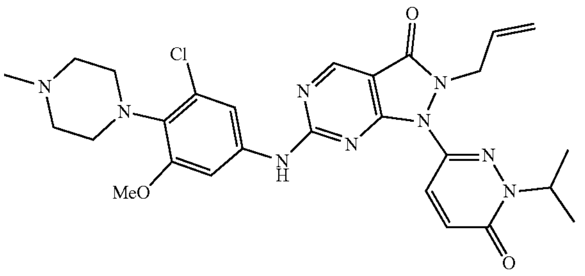
67
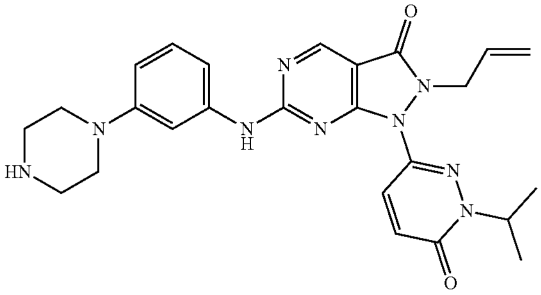
68
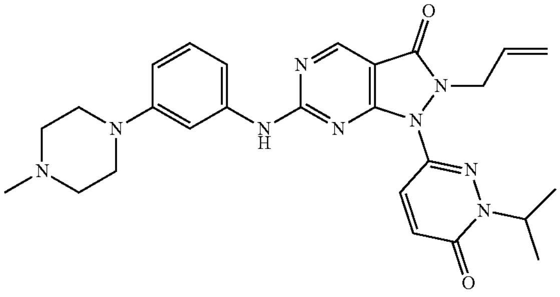
69
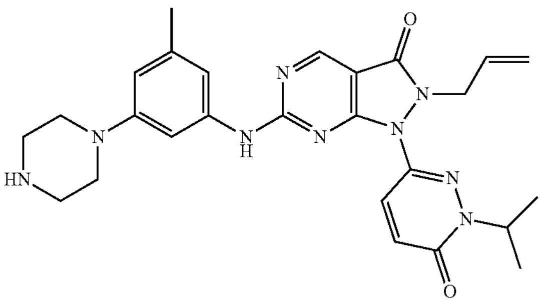
70
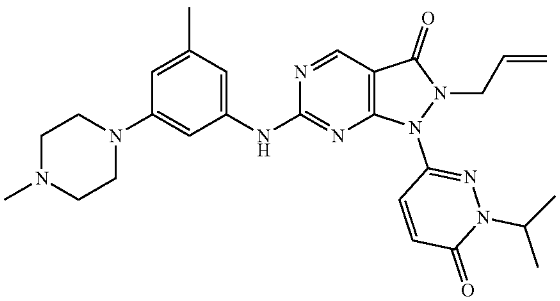
-continued
71
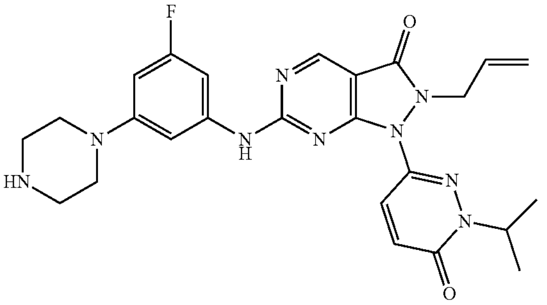
72
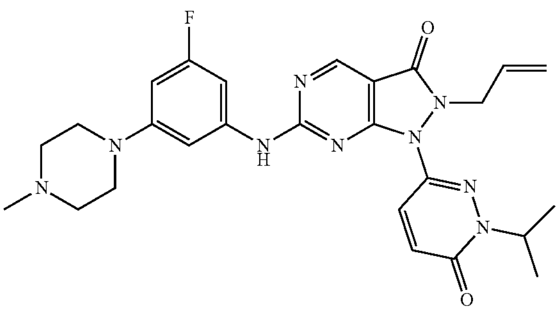
73
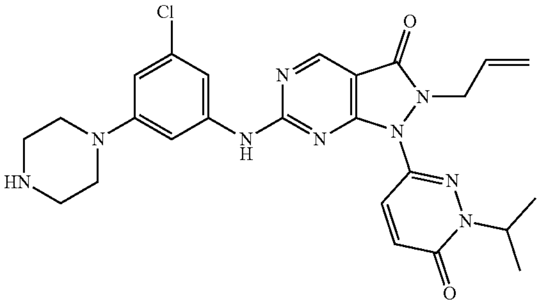
74
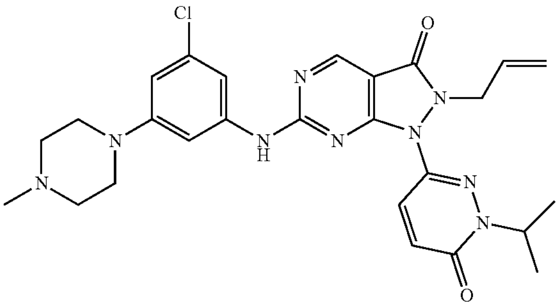
75
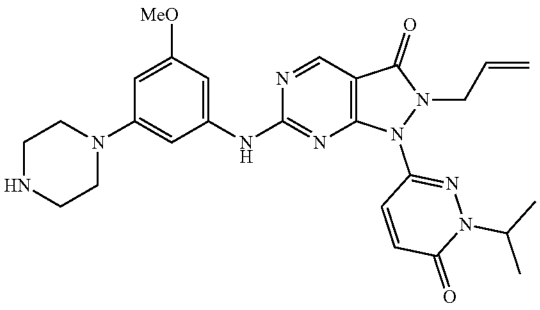

-continued
76
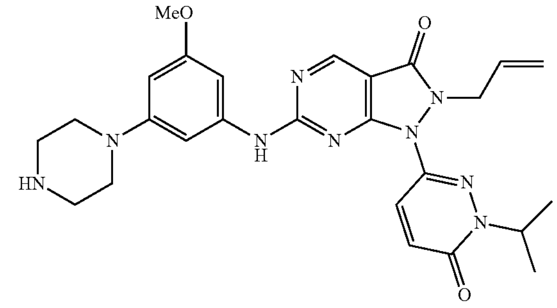
77
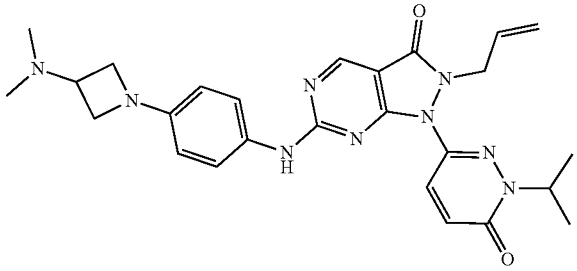
78
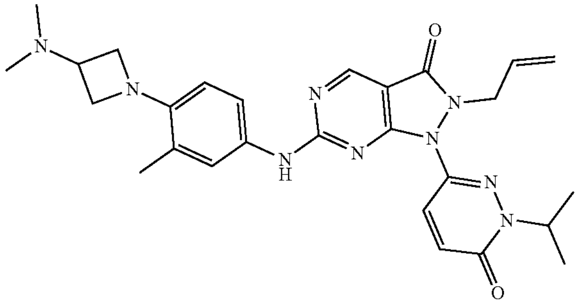
79
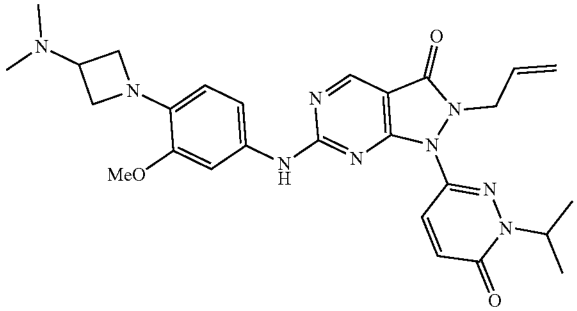
80
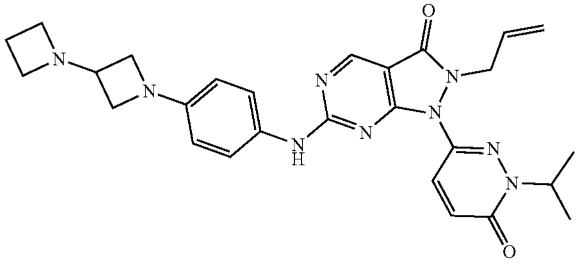
-continued
81
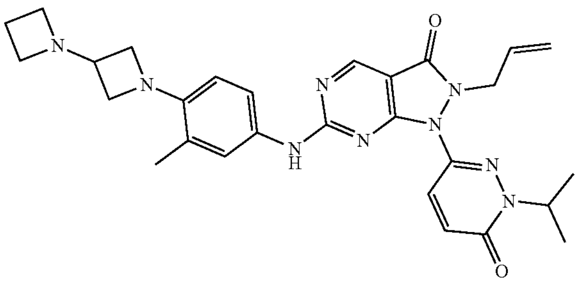
82
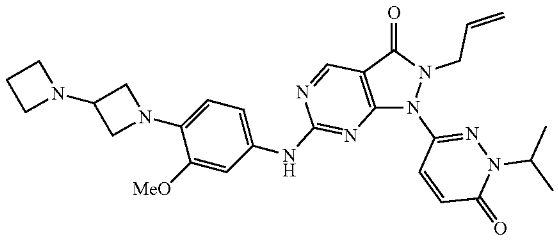
83
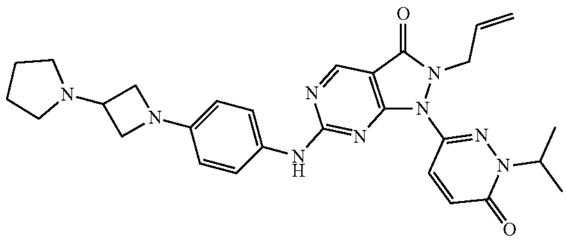
84
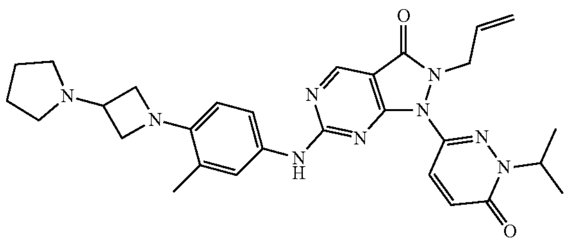
85
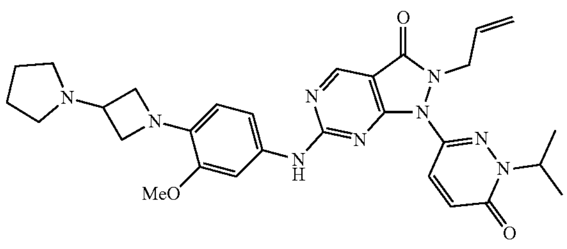

86
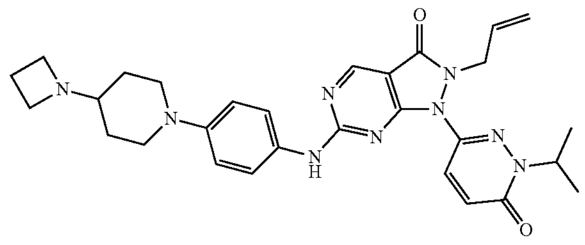
87
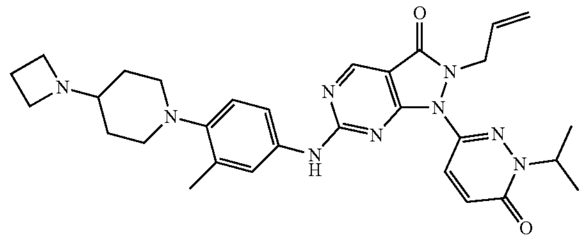
88
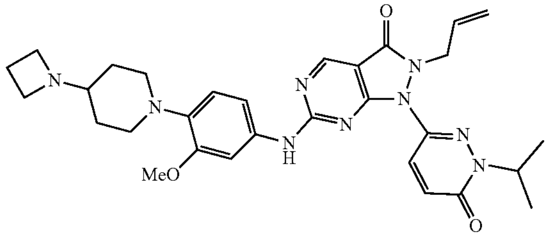
89
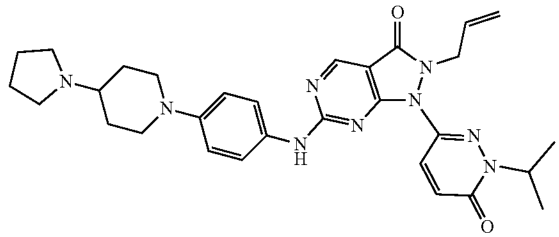
90
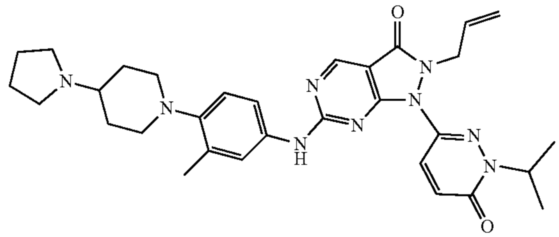
91
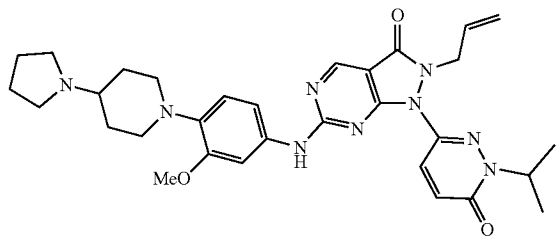
92
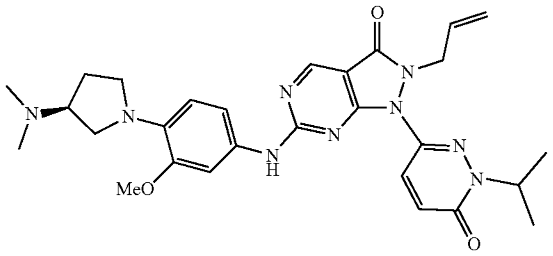
93
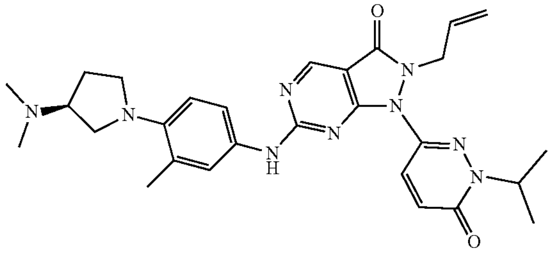
94
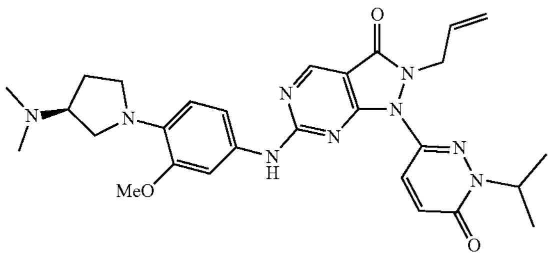
95
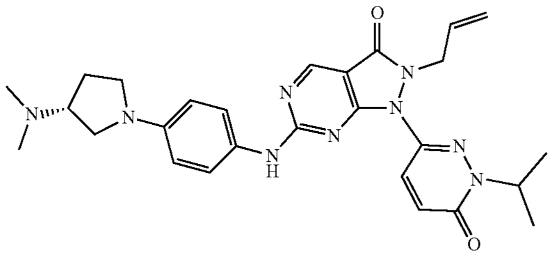
96
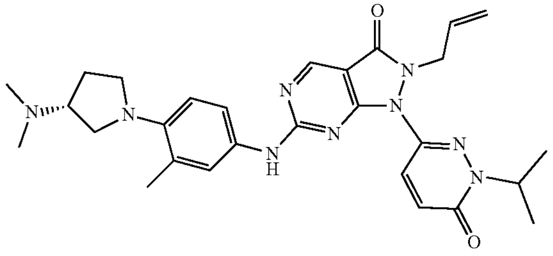

-continued
97
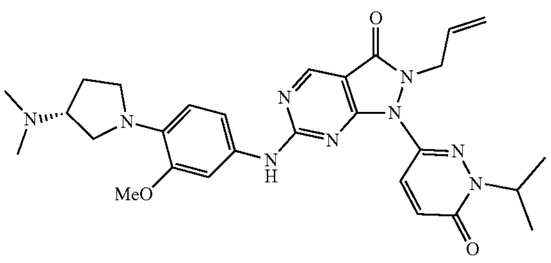
98
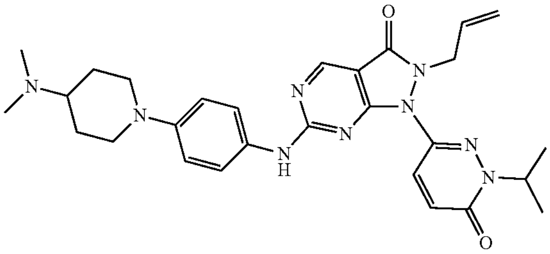
99
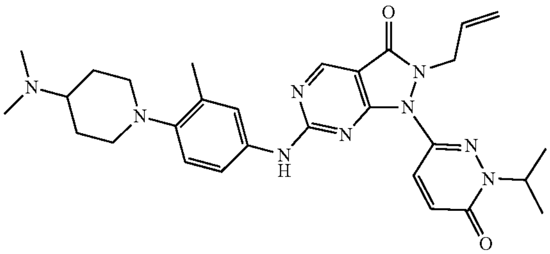
100
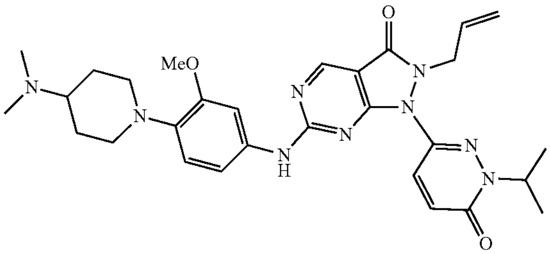
101
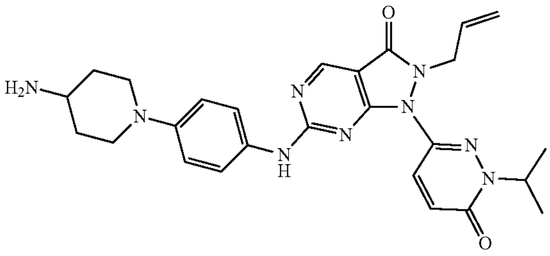
-continued
102
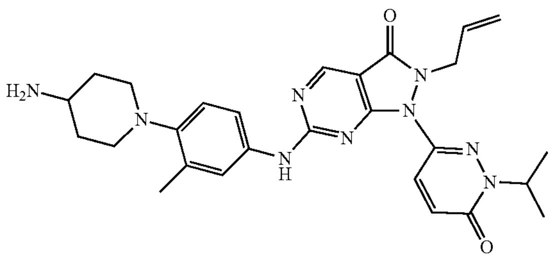
103
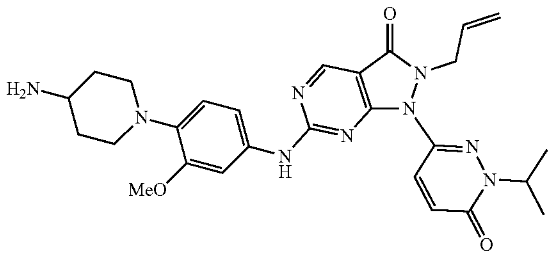
104
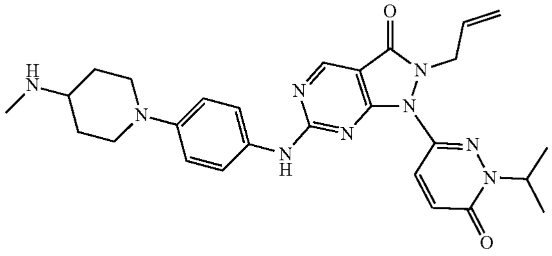
105
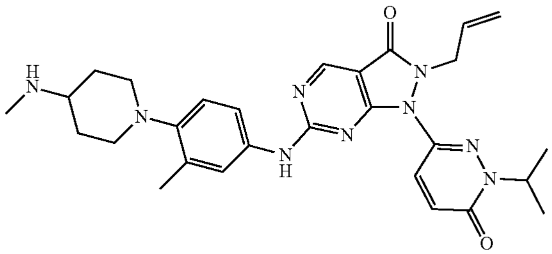
106
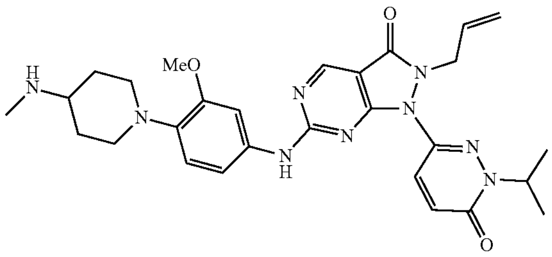

-continued
107
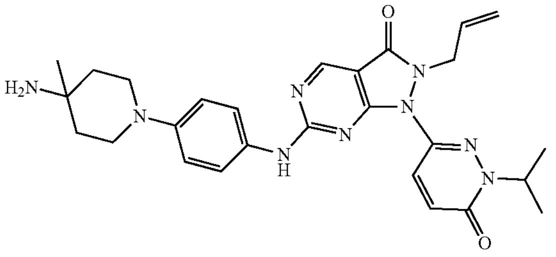
108
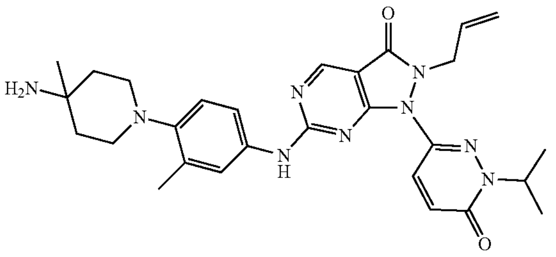
109
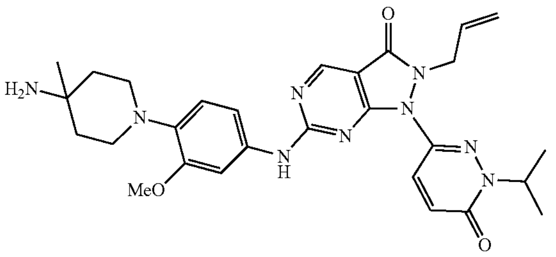
110
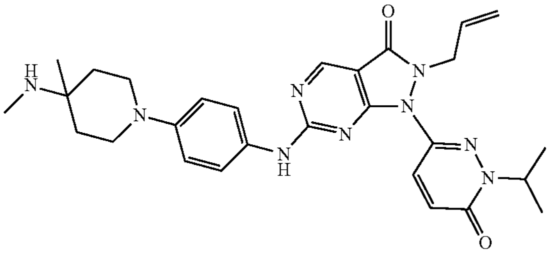
111
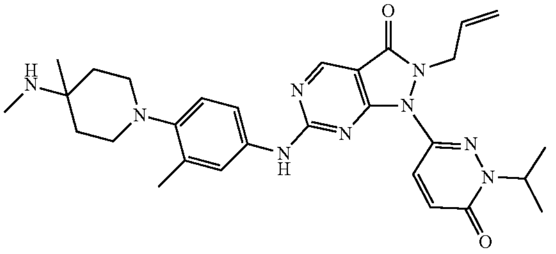
-continued
112
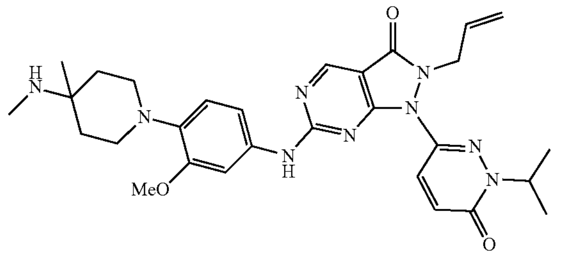
113
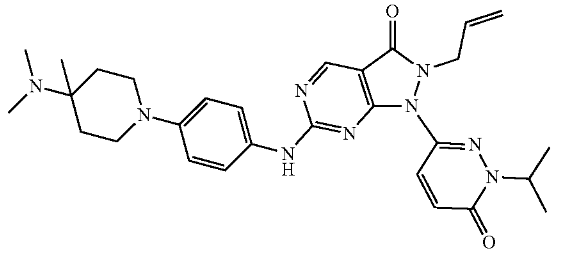
114
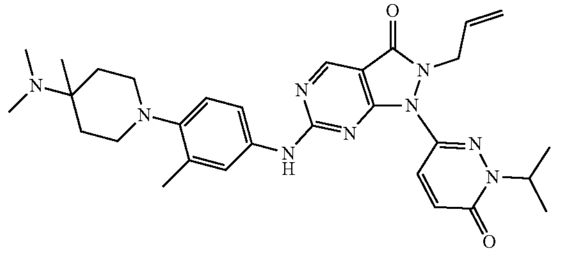
115
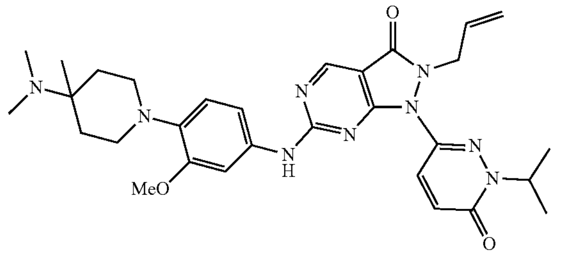
116
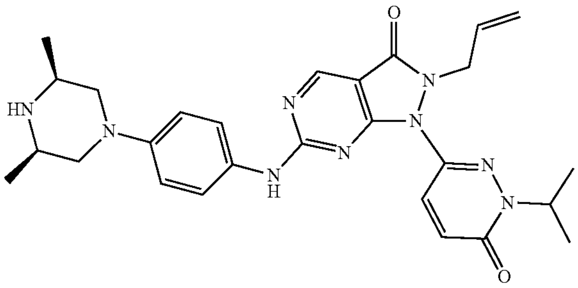

-continued
117
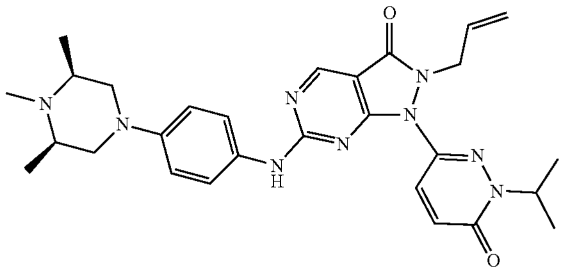
118
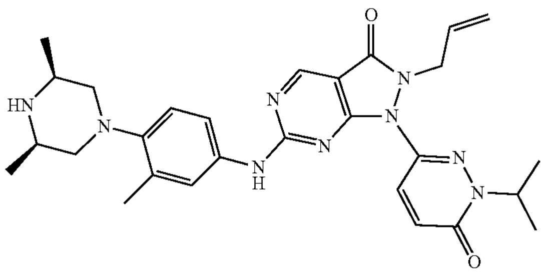
119
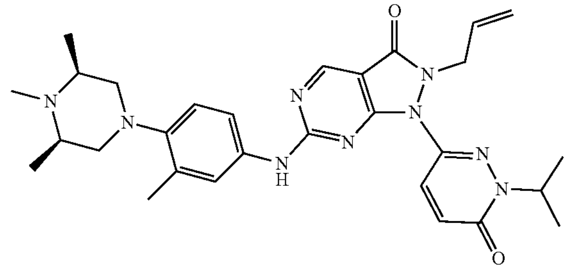
120
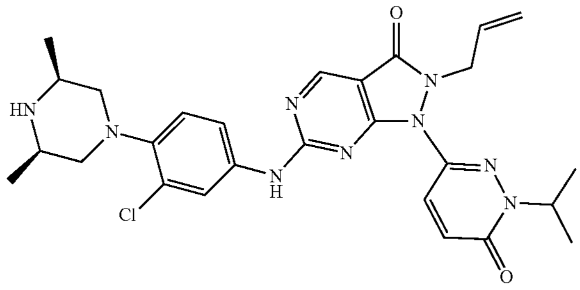
121
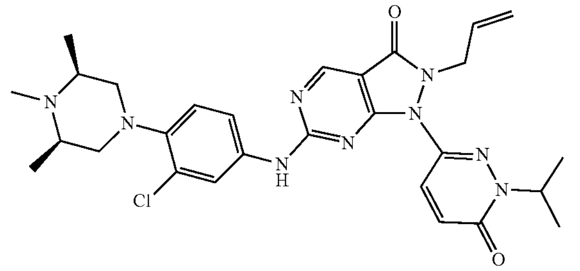
-continued
122
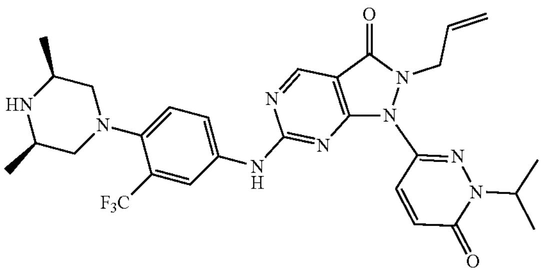
123
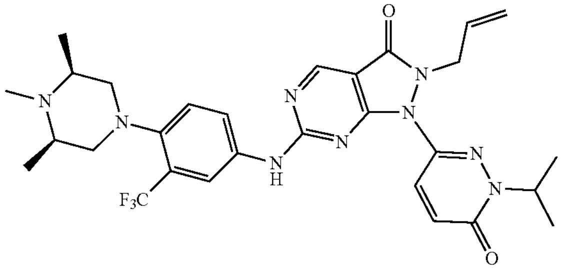
124
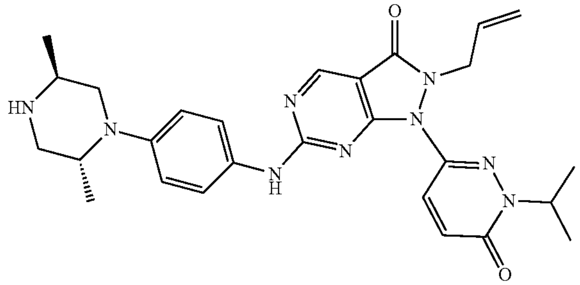
125
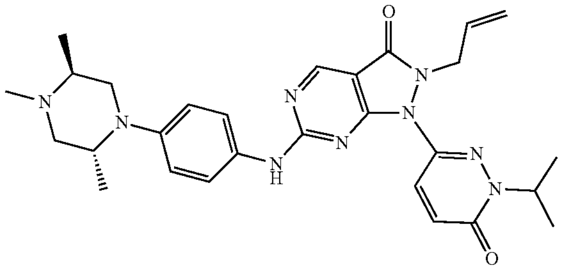
126
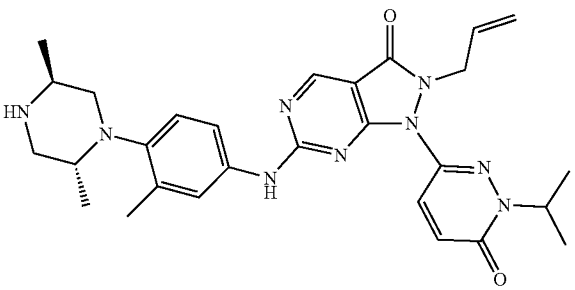

-continued
127
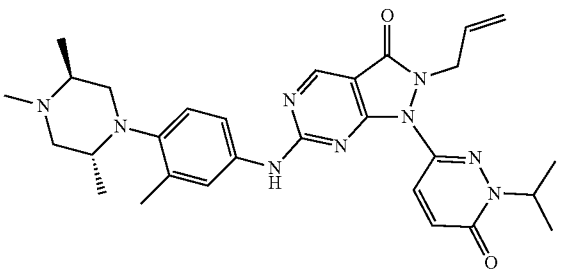
128
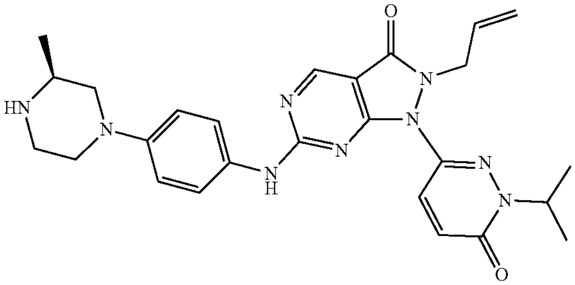
129
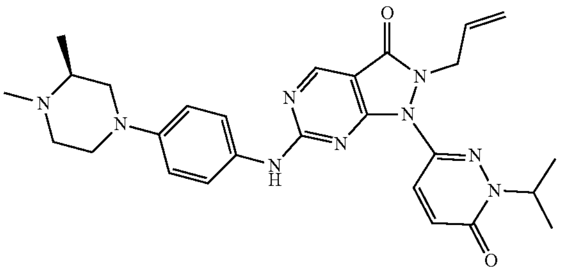
130
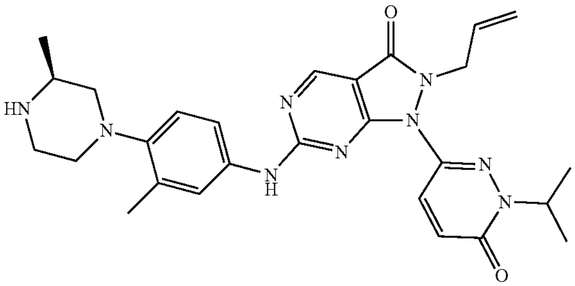
131
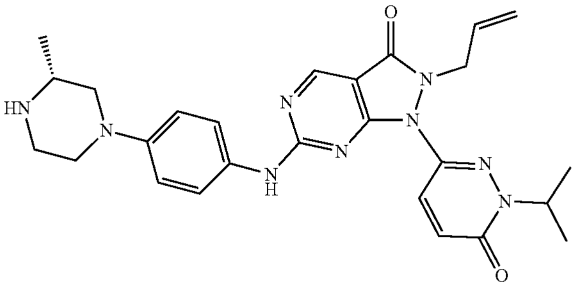
-continued
132
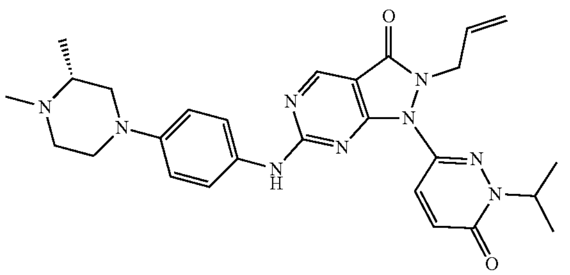
133
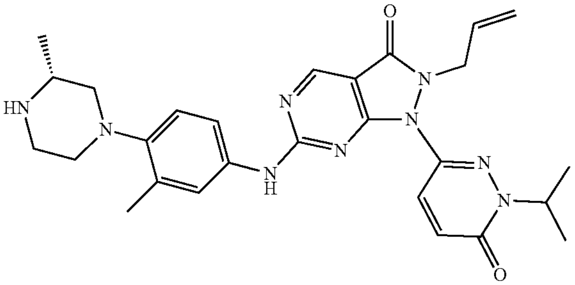
134
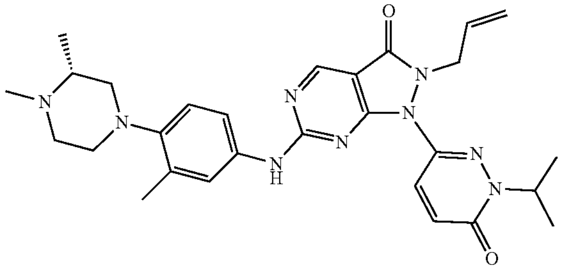
135
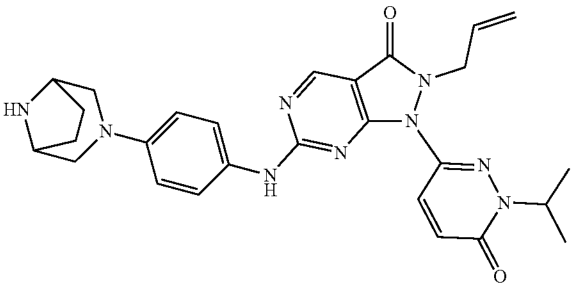
136
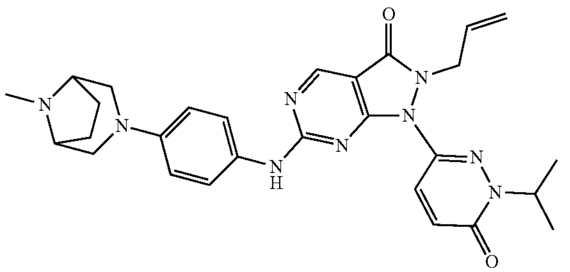

-continued
137
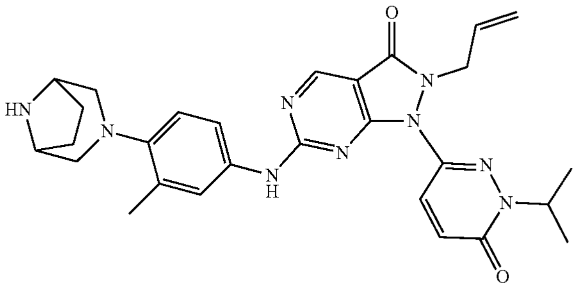
138
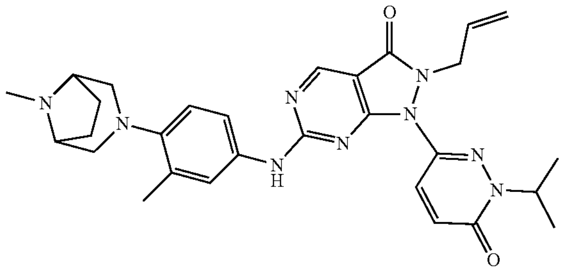
139
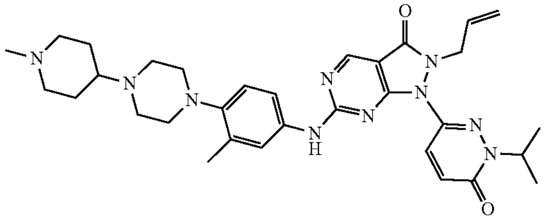
140
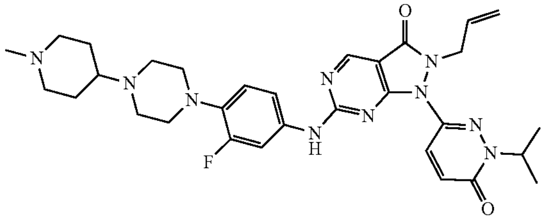
141
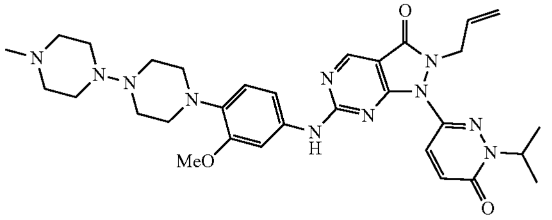
142
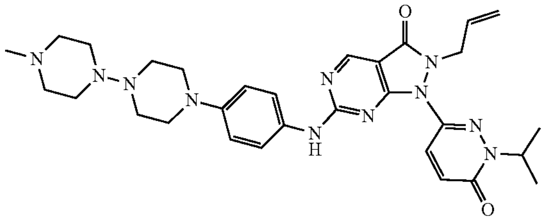
-continued
143
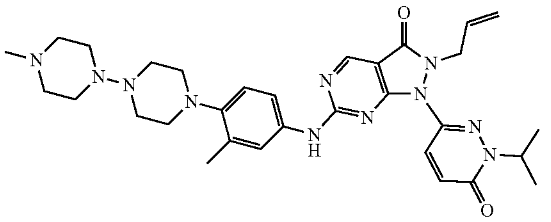
144
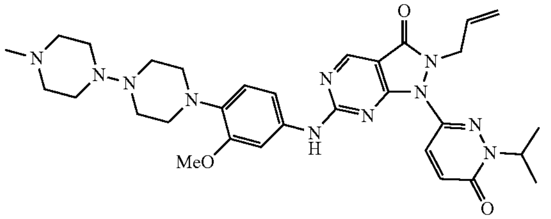
145
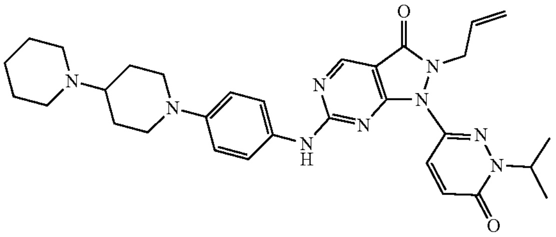
146
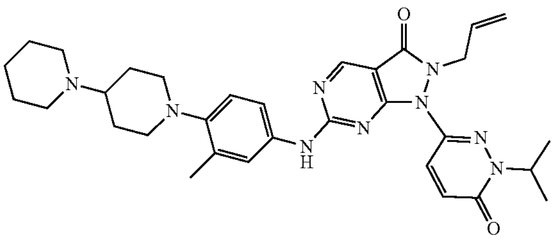
147
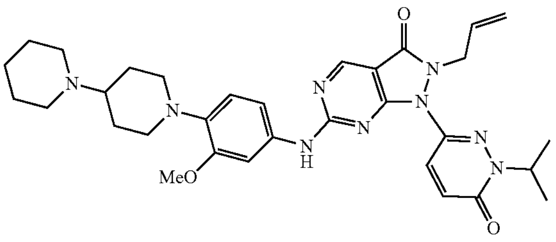
148
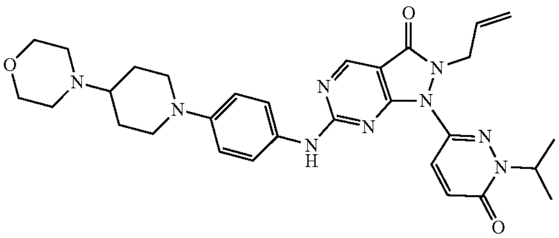

-continued
149
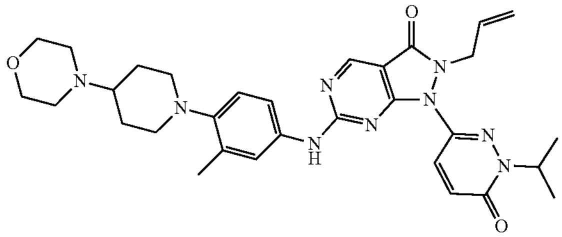
150
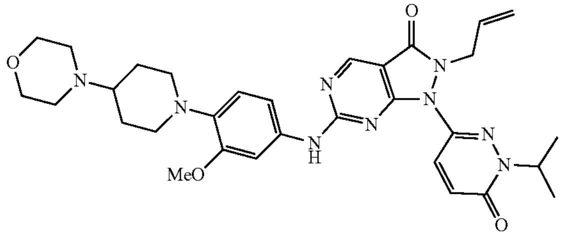
151
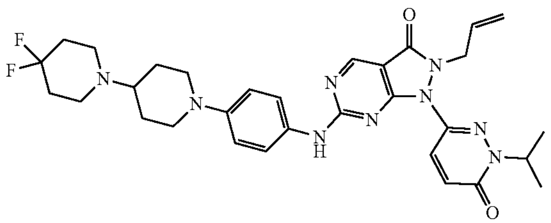
152
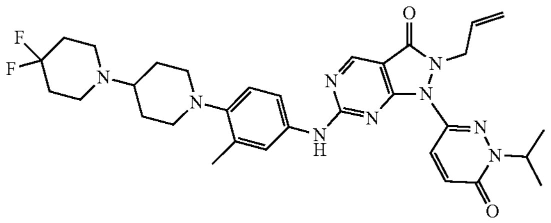
153
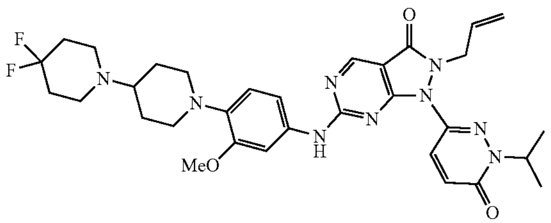
154
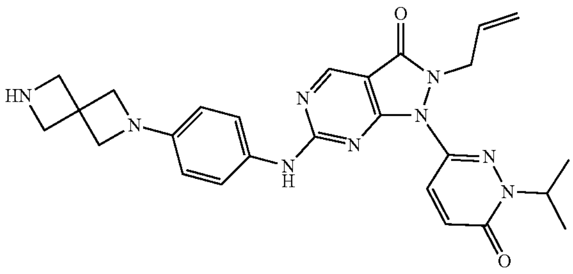
-continued
155
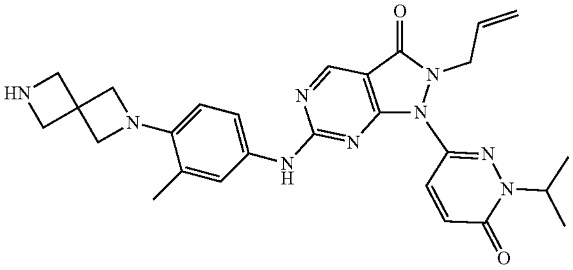
156
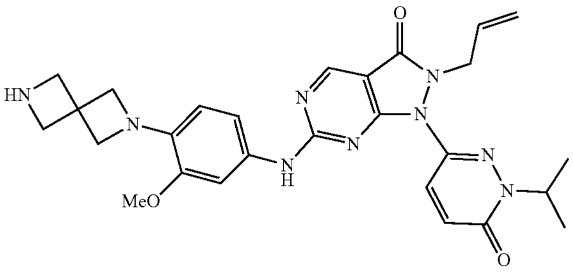
157
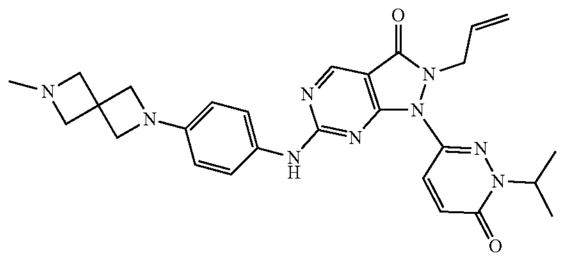
158
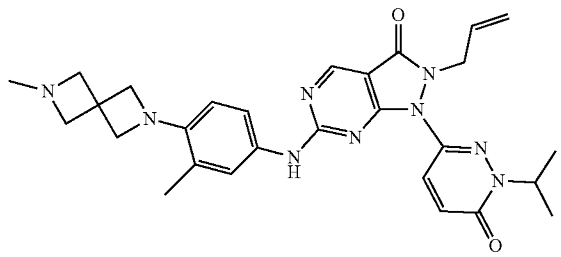
159
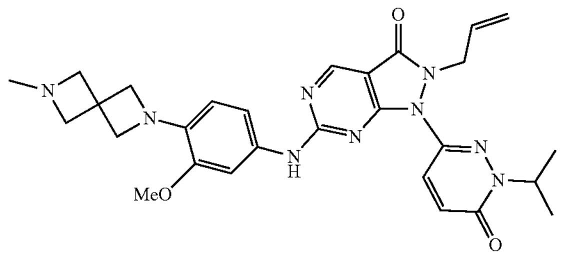

-continued
160
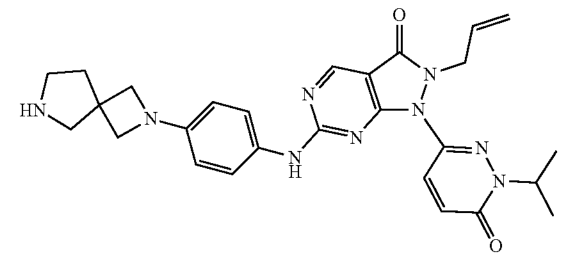
161
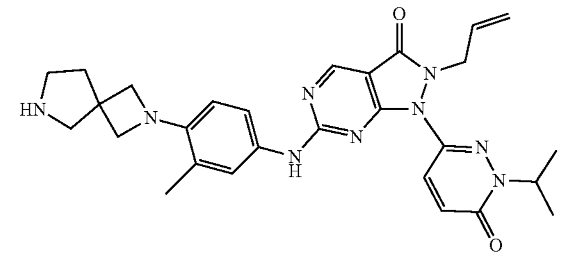
162
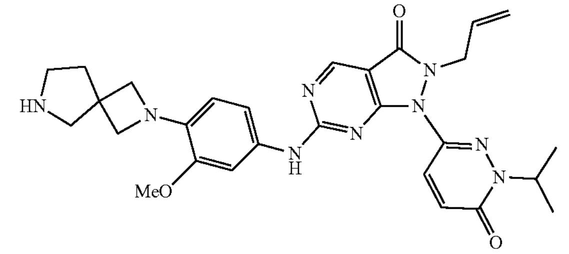
163
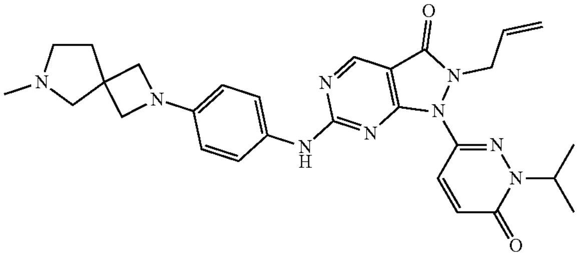
164
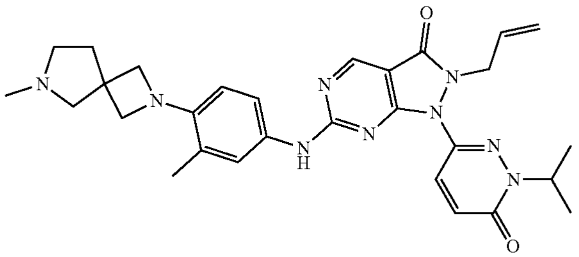
-continued
165
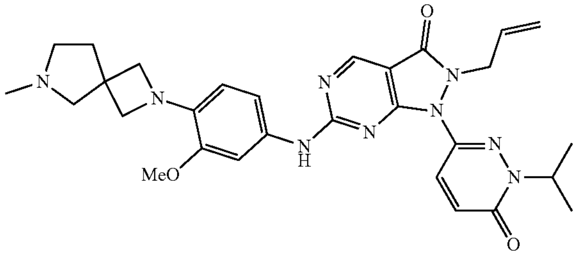
166
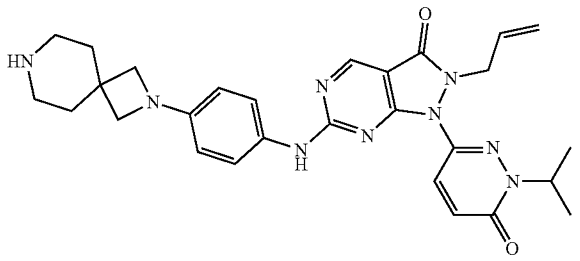
167
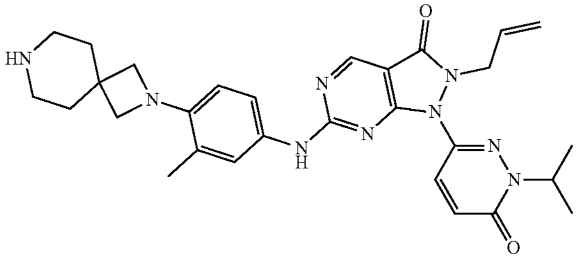
168
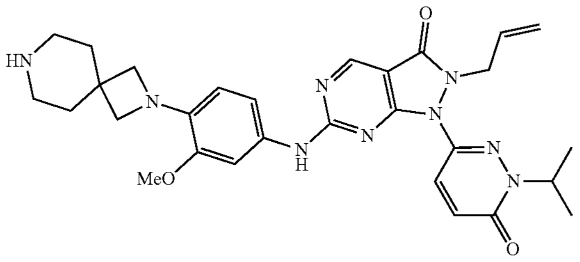
169
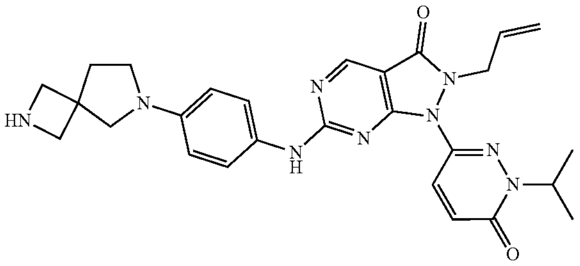

-continued
170
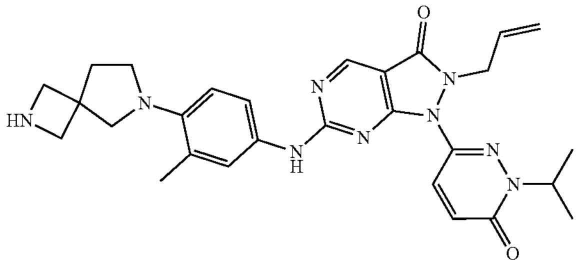
171
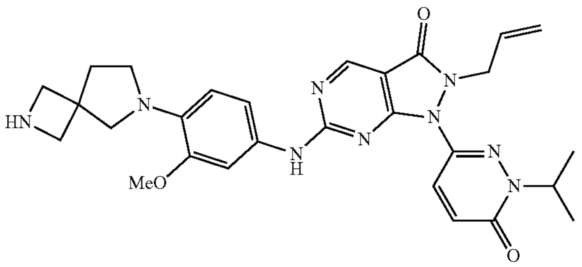
172
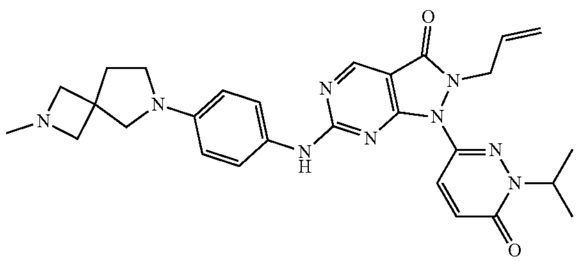
173
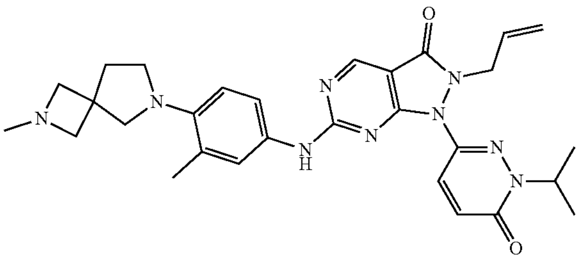
174
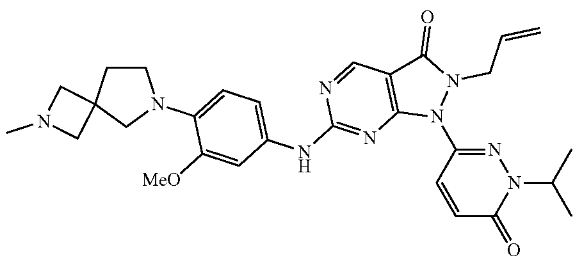
-continued
175
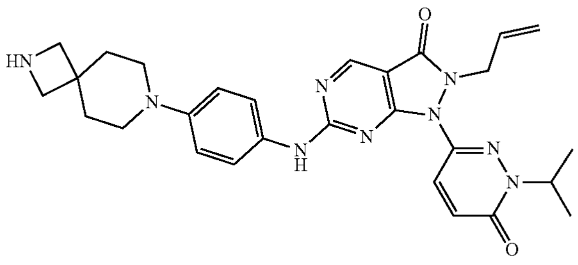
176
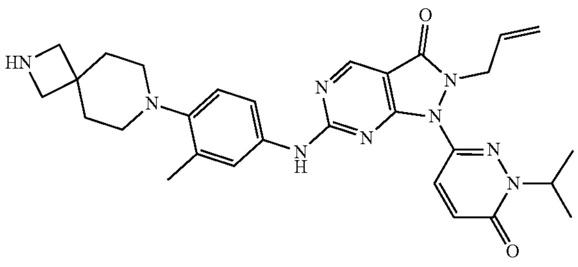
177
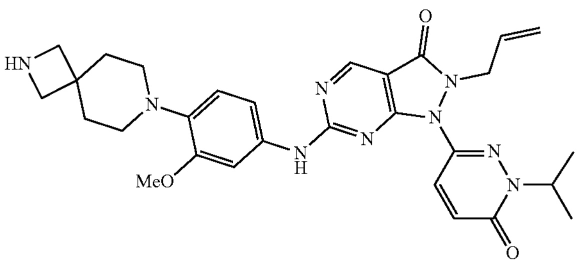
178
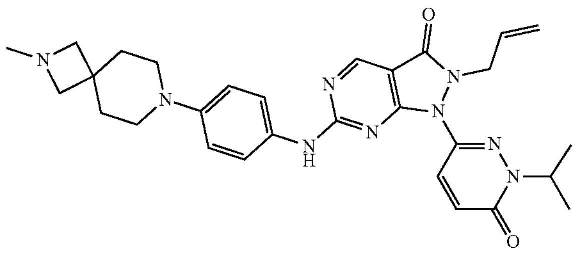
179
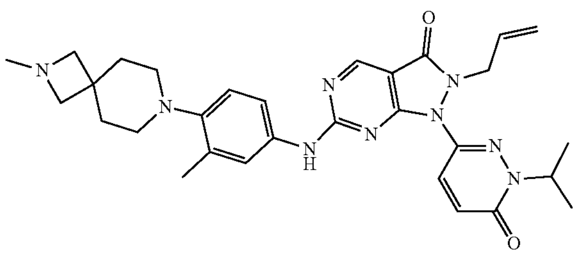

-continued
180
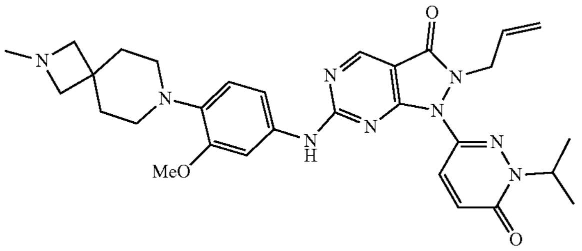
181
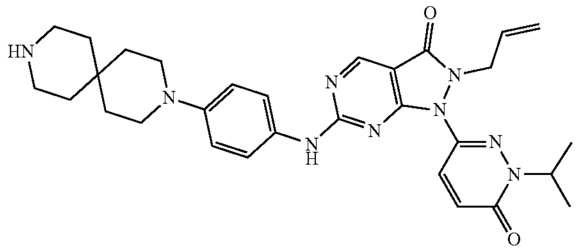
182
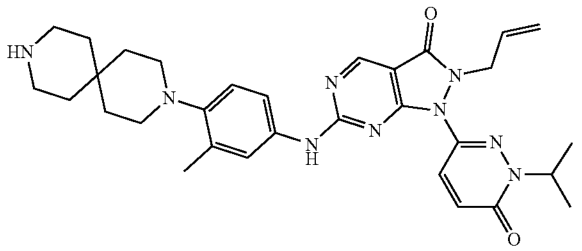
183
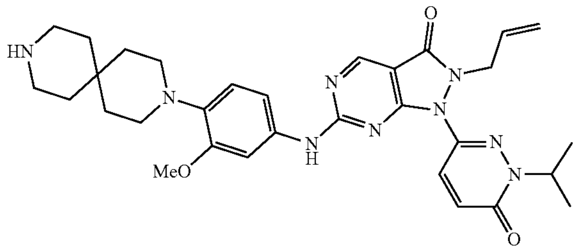
184
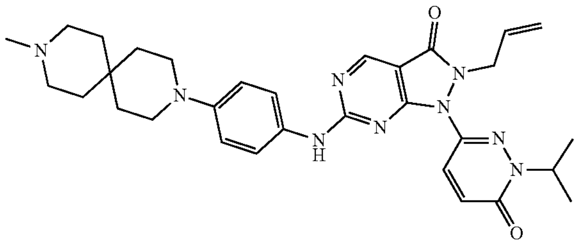
185
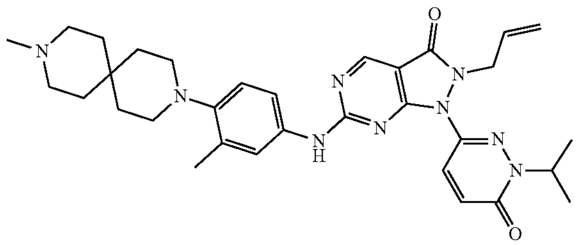
-continued
186
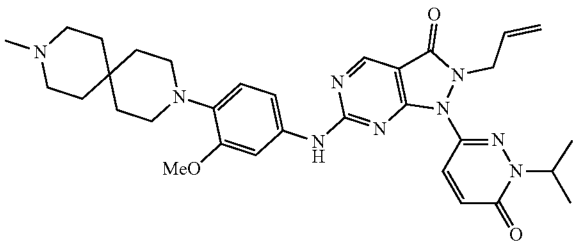
187
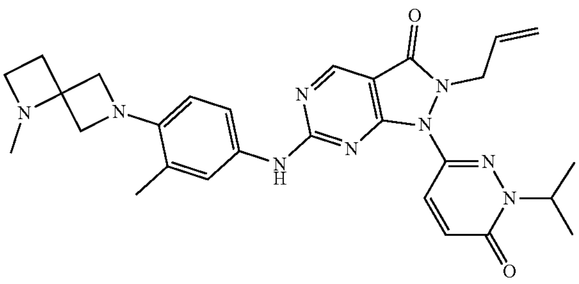
188
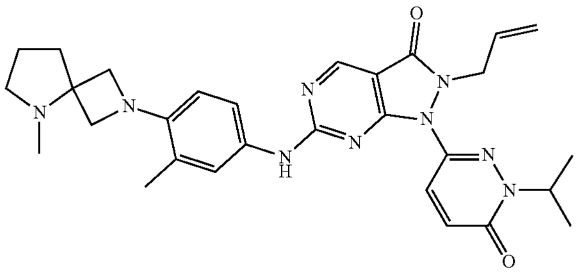
189
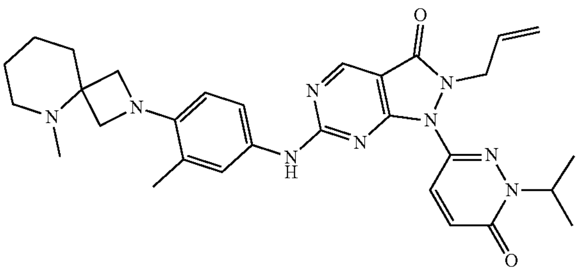
190
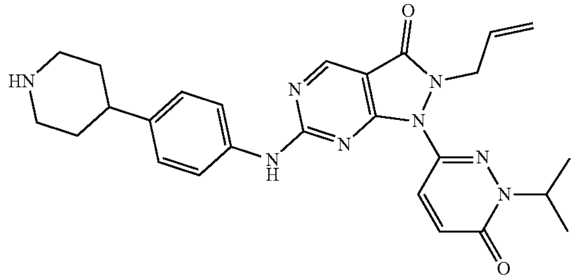

-continued
191
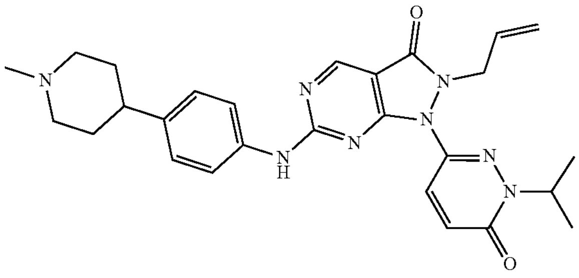
192
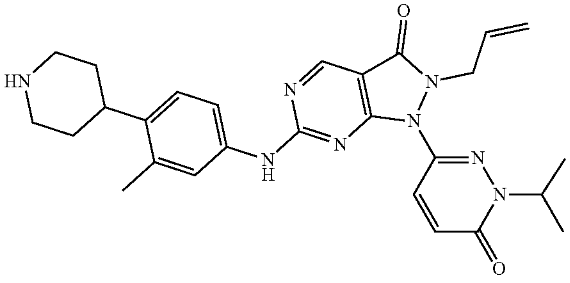
193
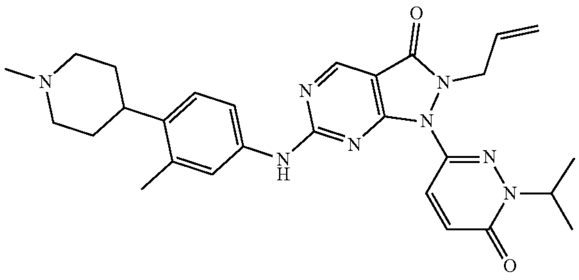
194
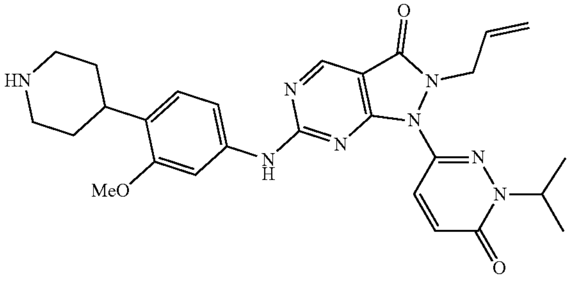
195
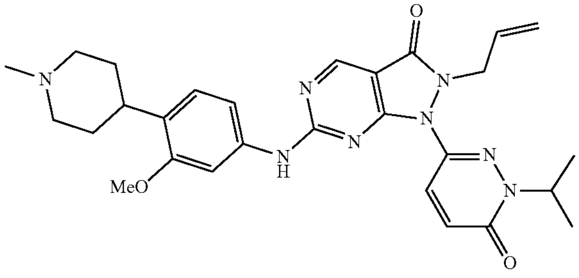
-continued
196
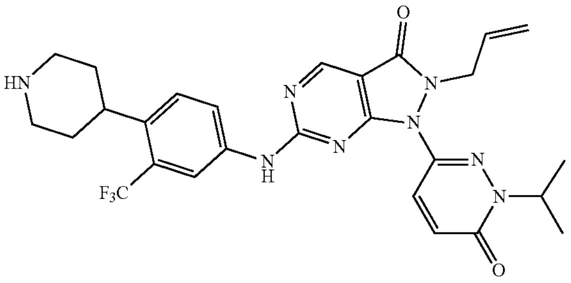
197
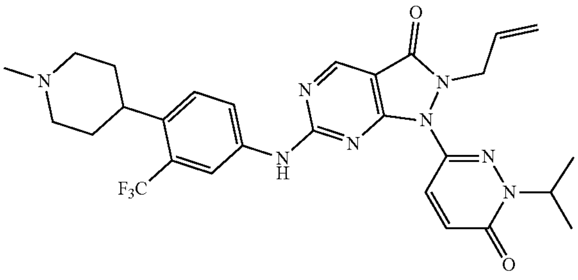
198
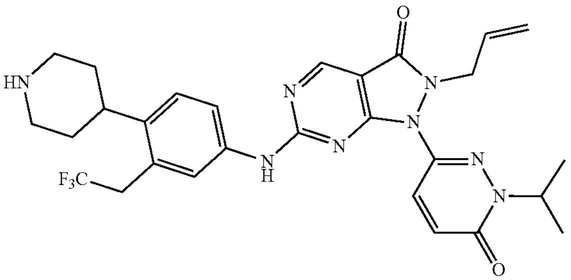
199
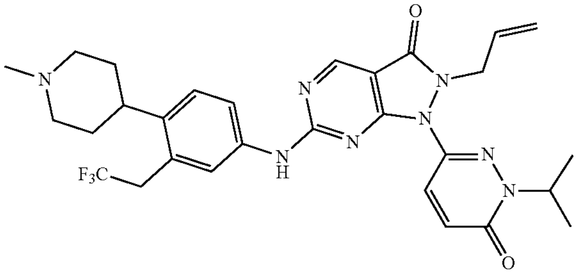
200
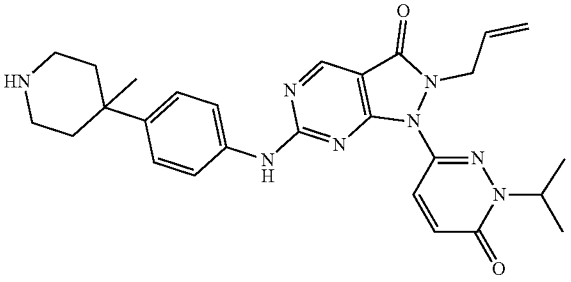

-continued
201
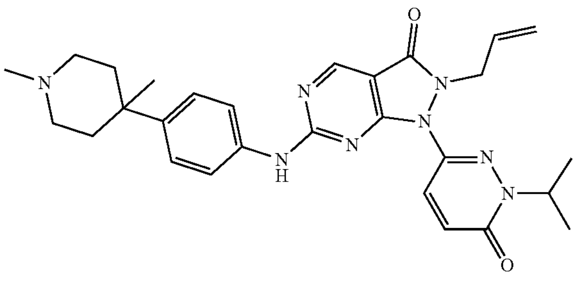
202
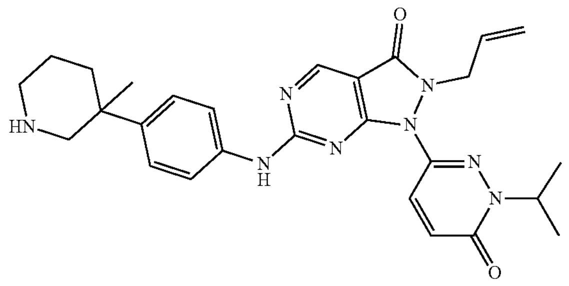
203
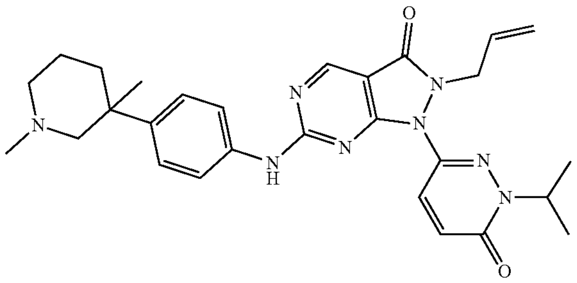
204
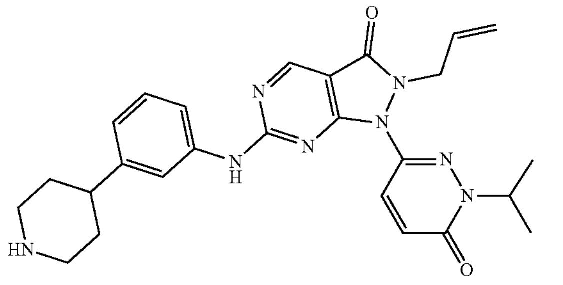
205
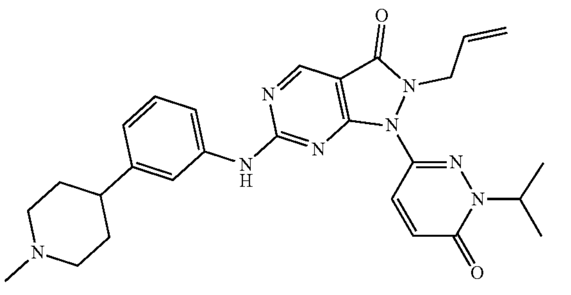
-continued
206
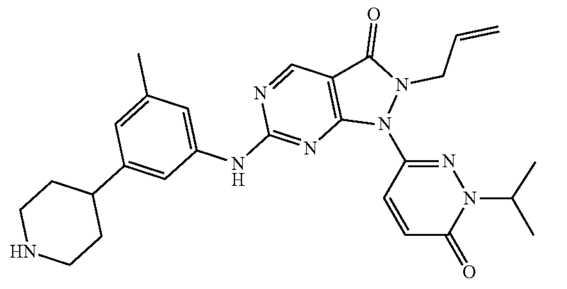
207
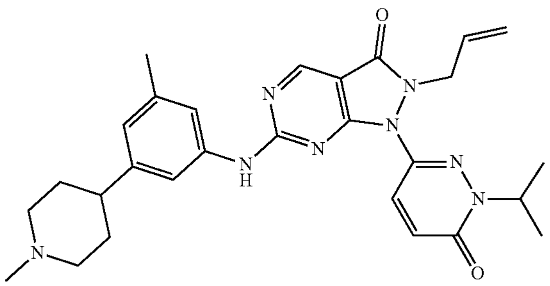
208
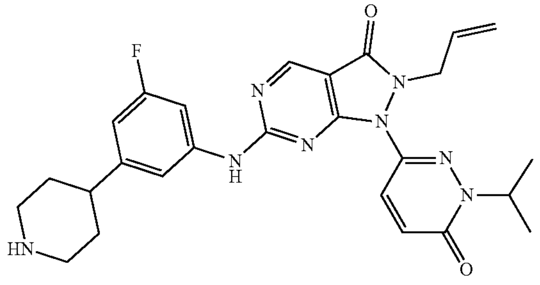
209
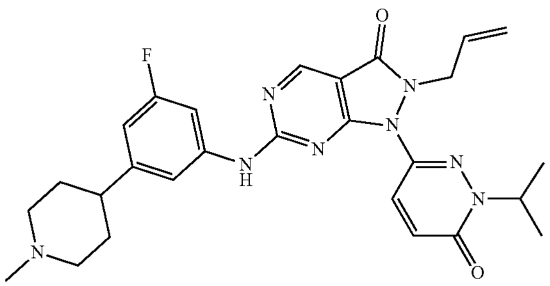
210
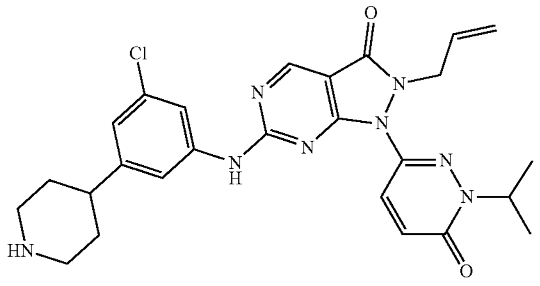

-continued
211
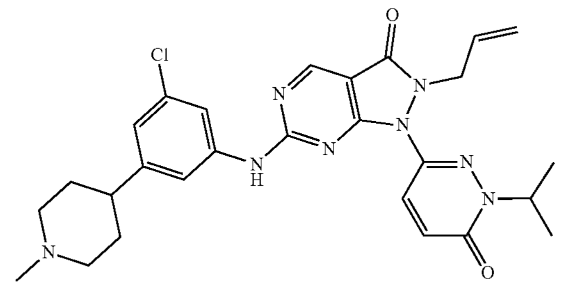
212
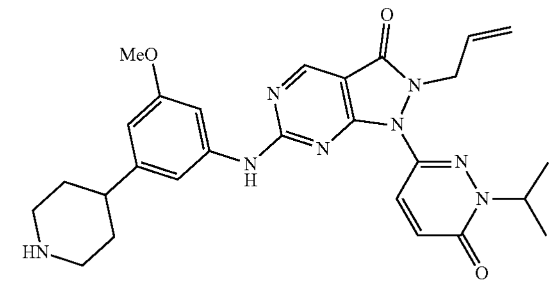
213
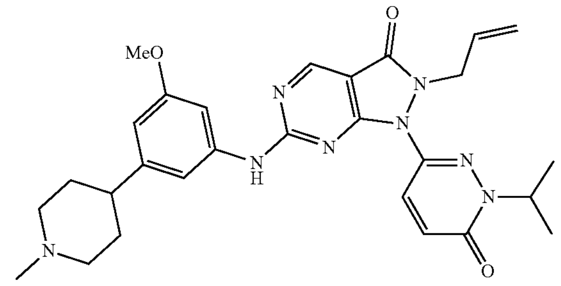
214
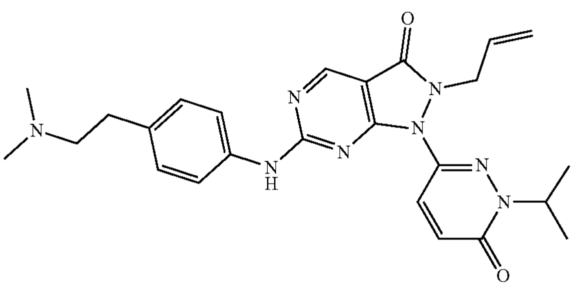
215
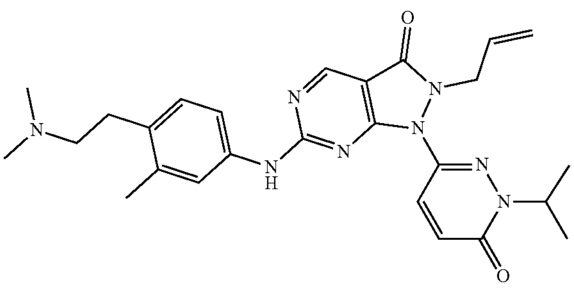
-continued
216
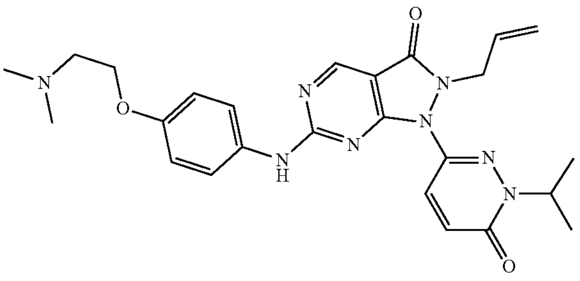
217
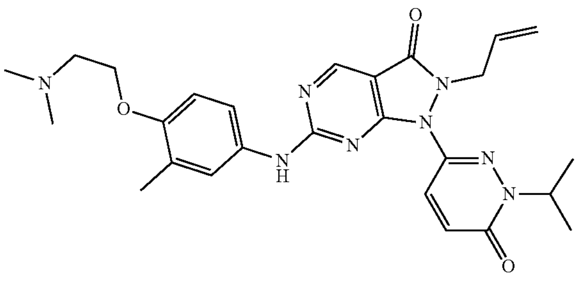
218
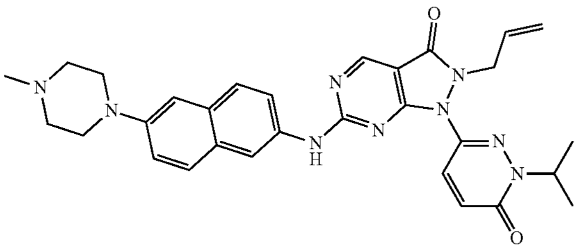
219
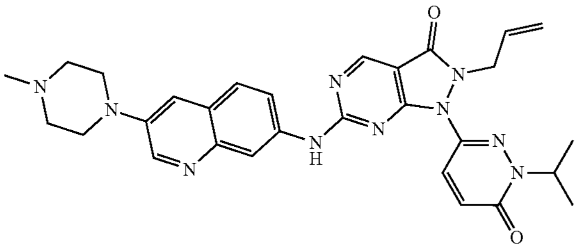
220
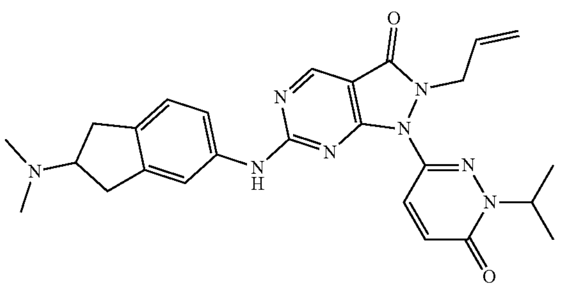

-continued
221
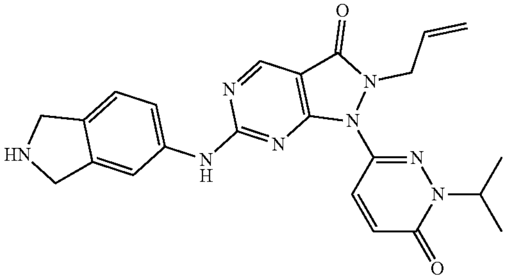
222
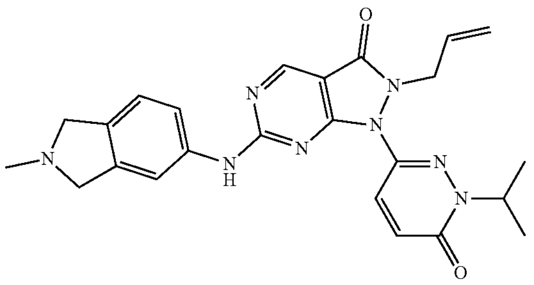
223
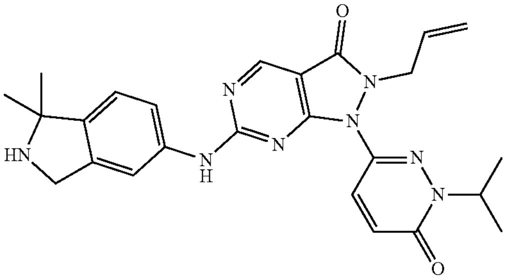
224
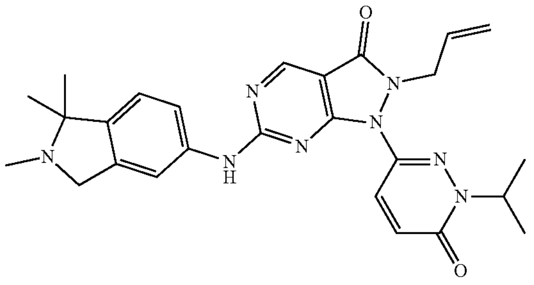
225
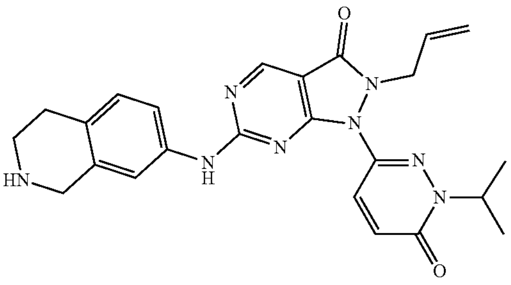
-continued
226
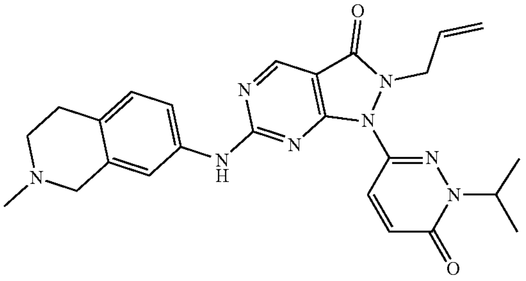
227
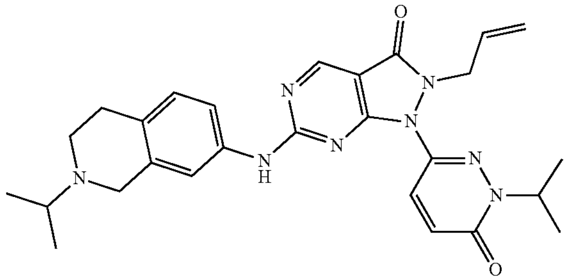
228
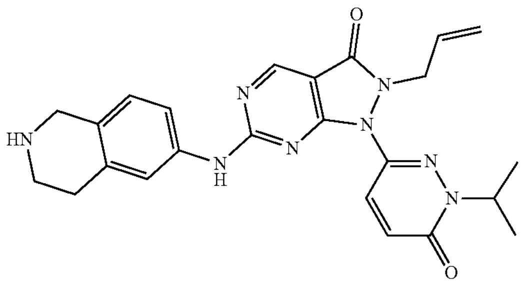
229
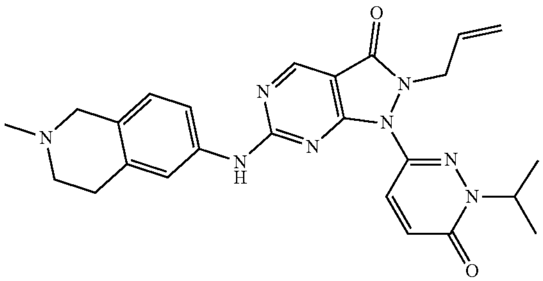
230
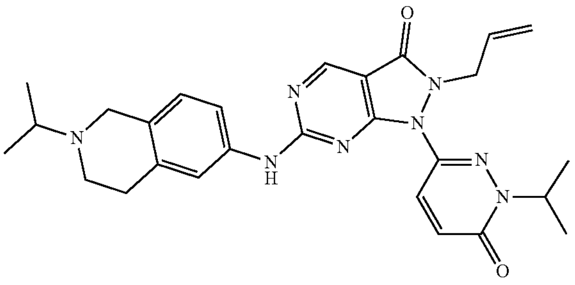

-continued
231
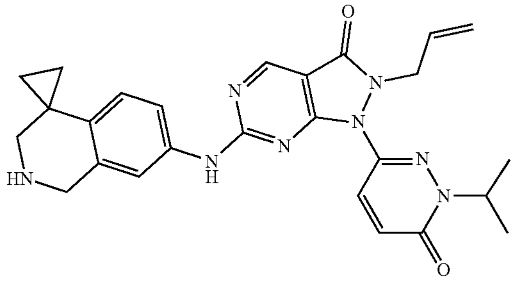
232
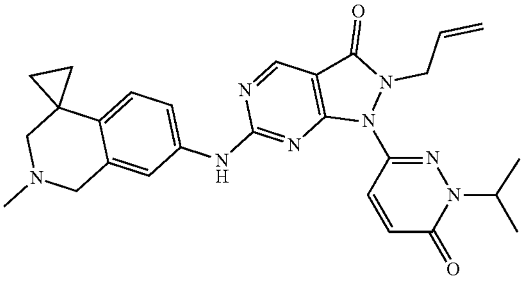
233
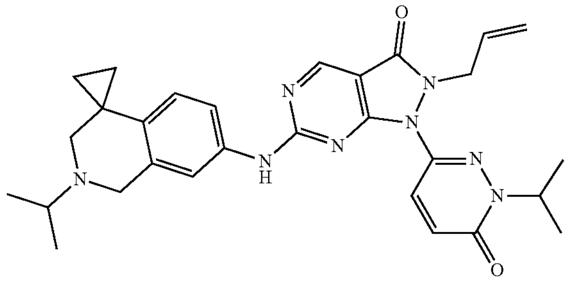
234
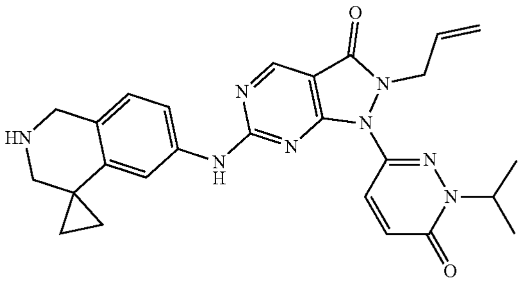
235
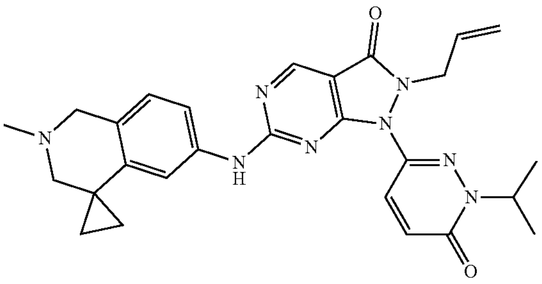
-continued
236
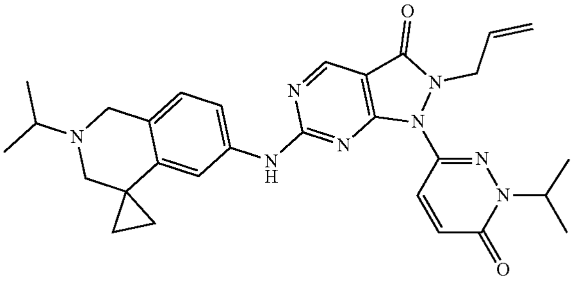
237
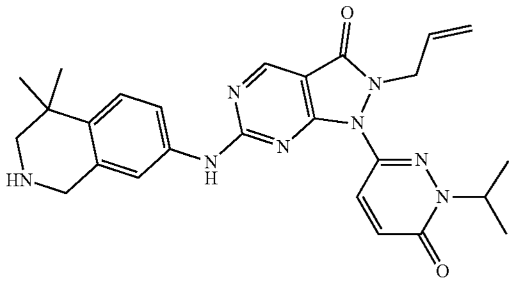
238
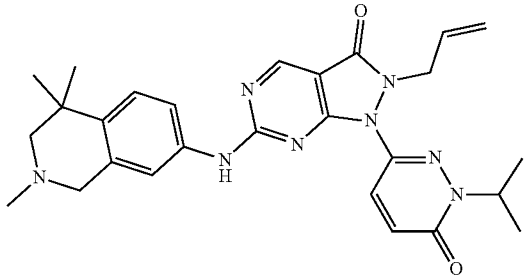
239
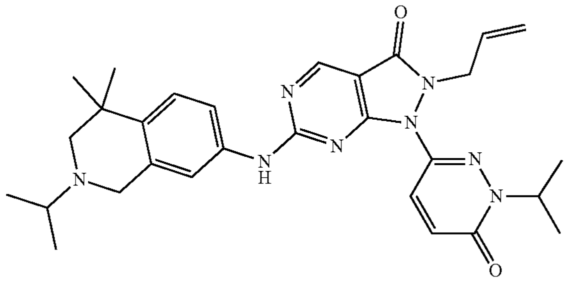
240
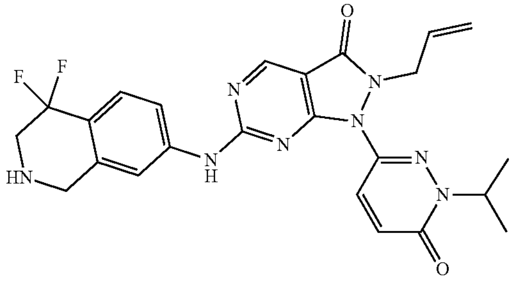

-continued
241
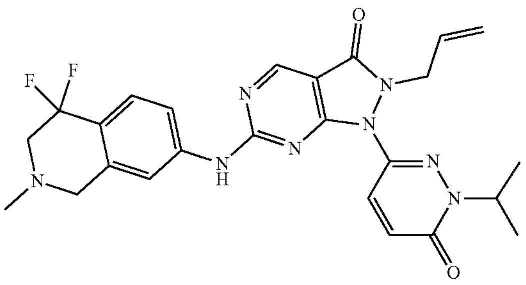
242
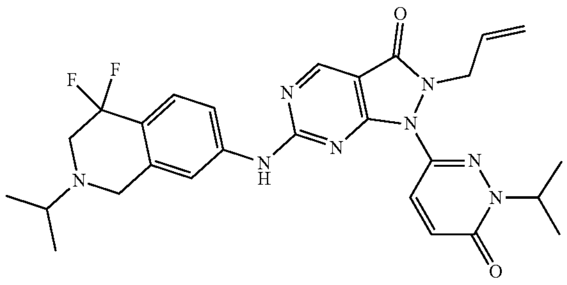
243
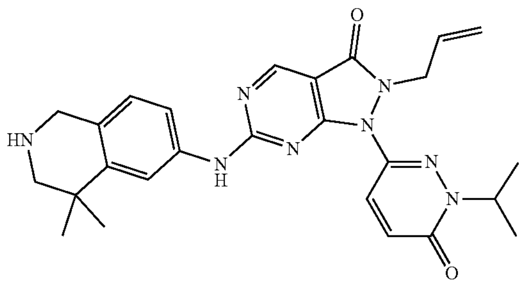
244
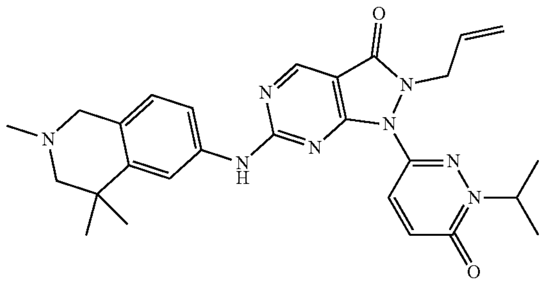
245
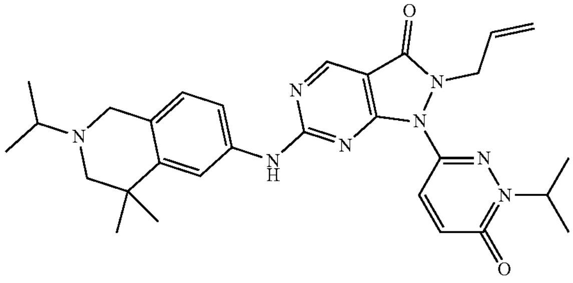
-continued
246
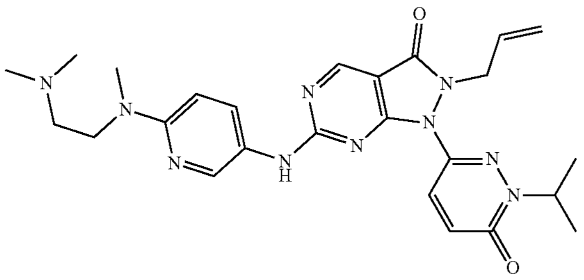
247
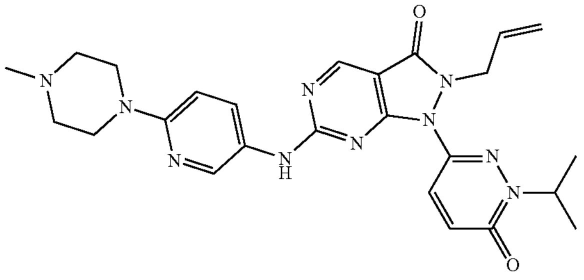
248
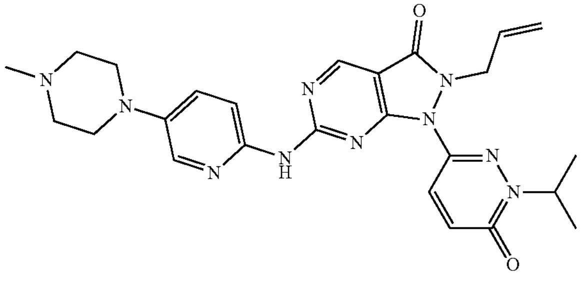
249
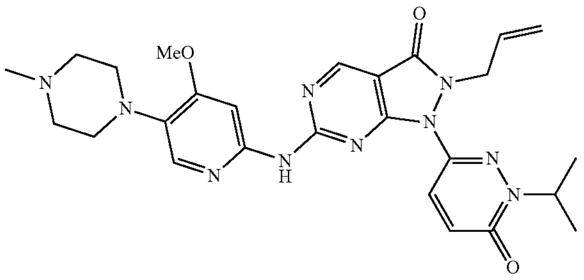
250
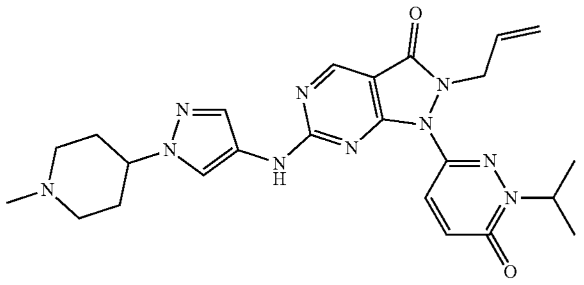

-continued
251
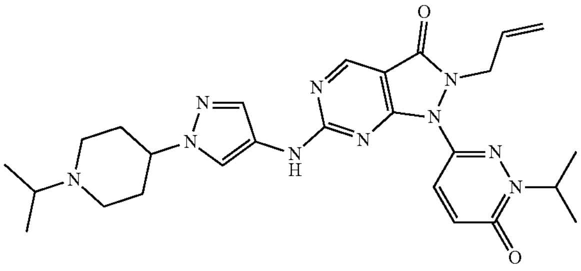
252
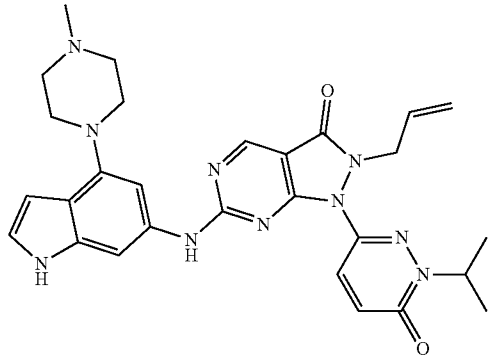
253
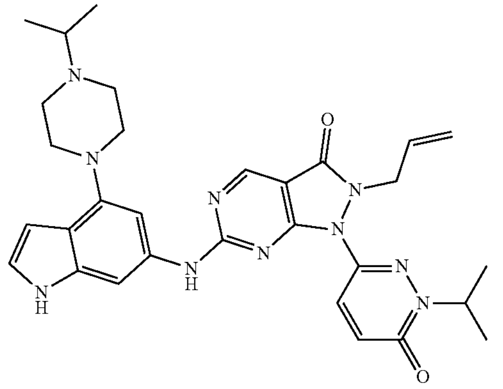
254
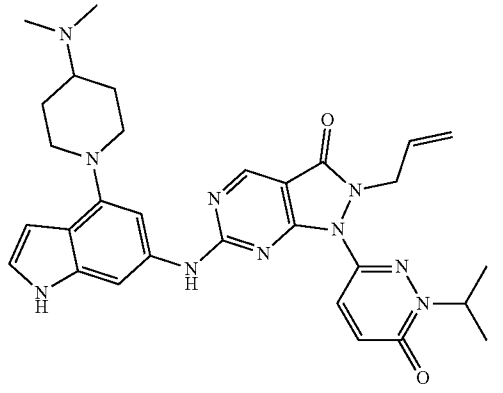
-continued
255
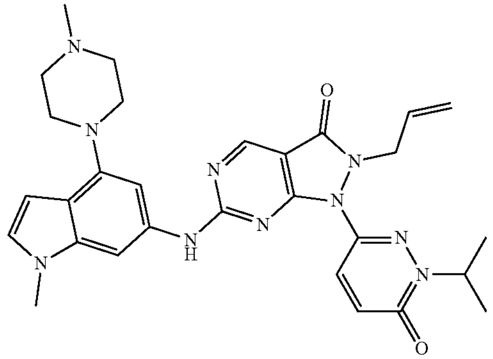
256
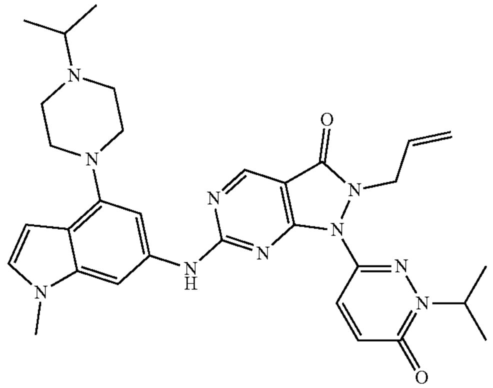
257
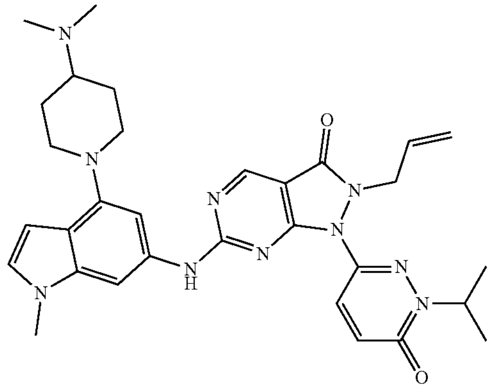
258
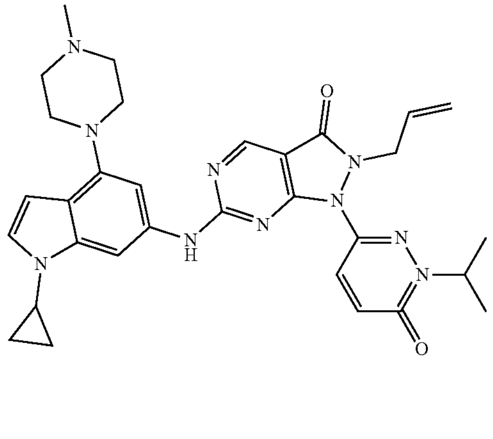

-continued
259
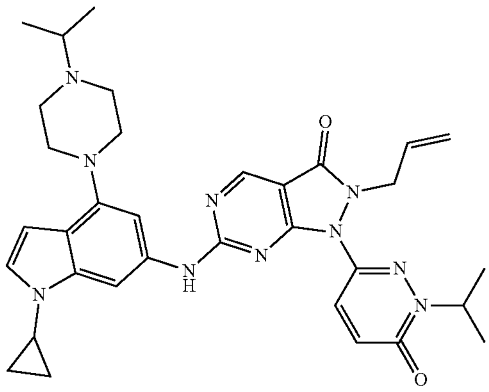
260
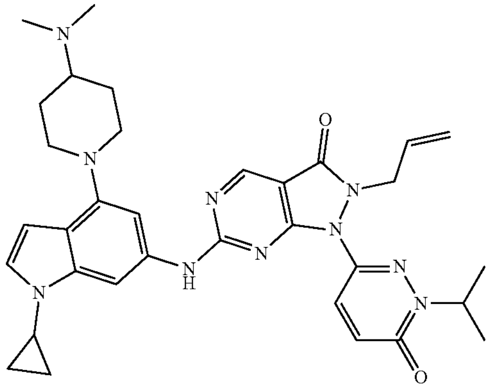
261
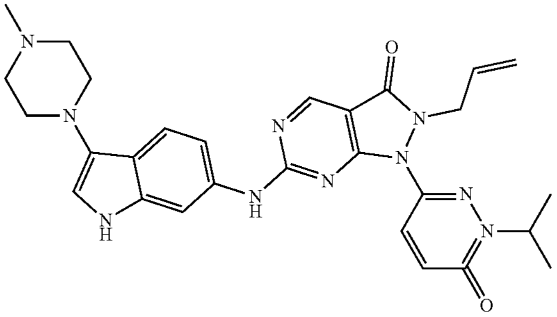
262
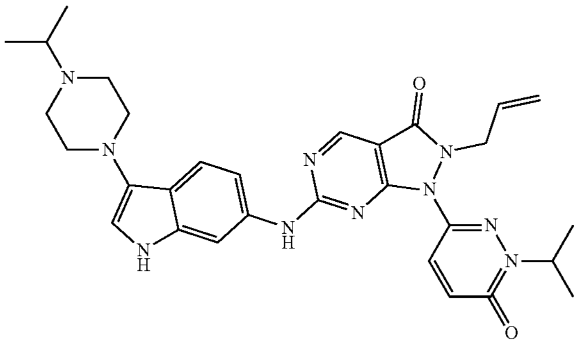
-continued
263
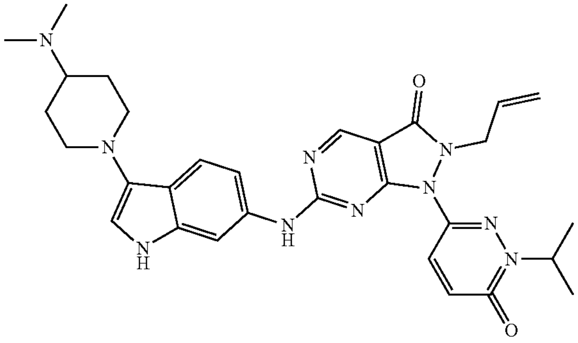
264
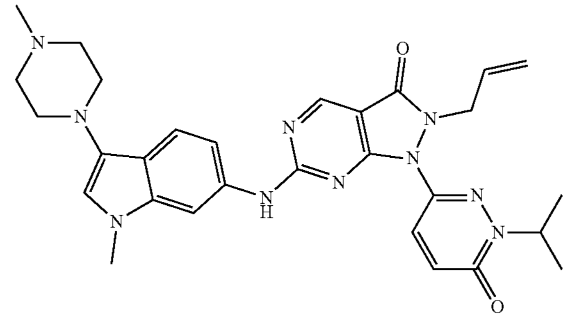
265
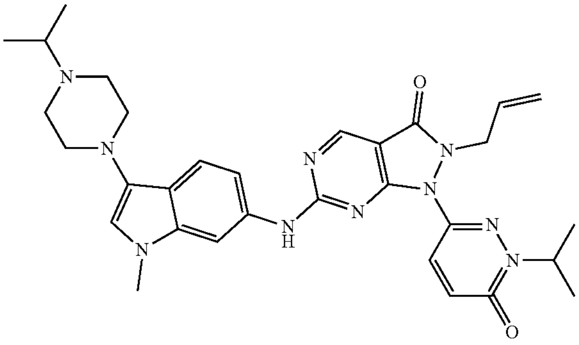
266
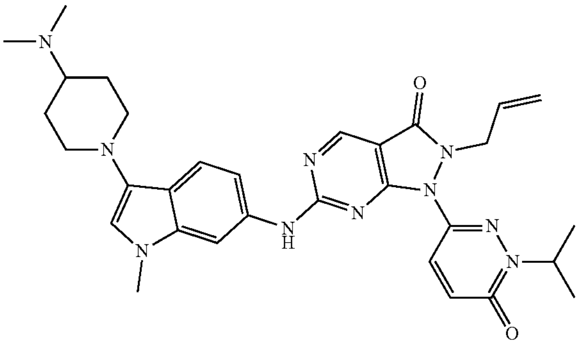

-continued
267
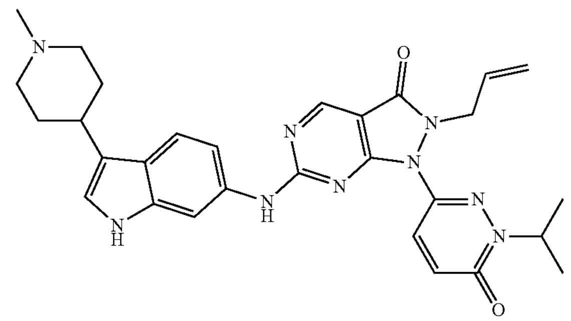
268
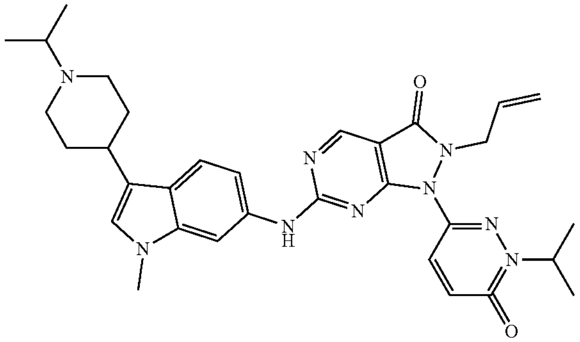
269
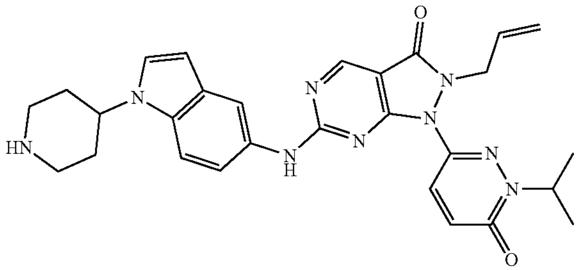
270
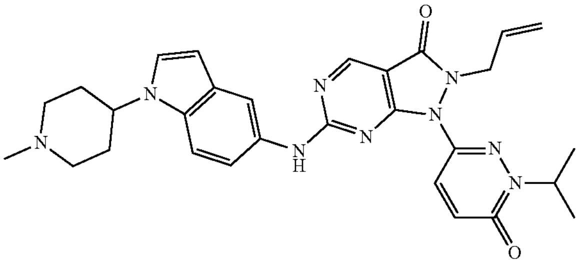
271
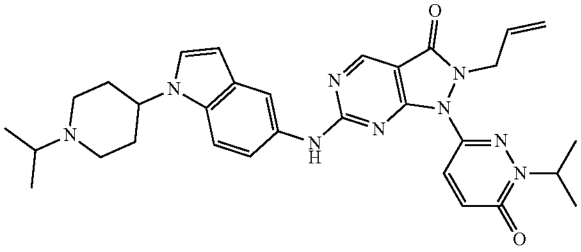
-continued
272
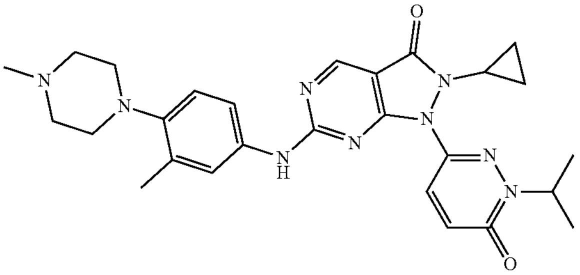
273
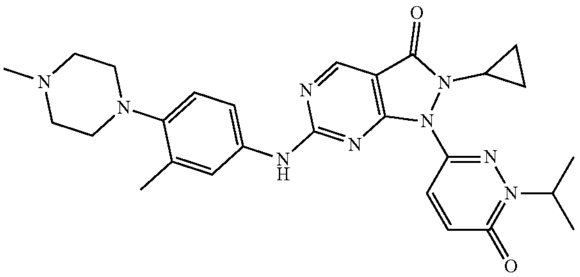
274
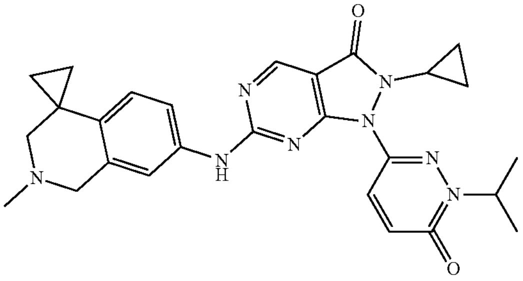
275
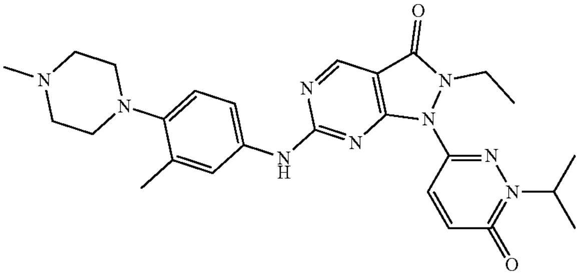
276
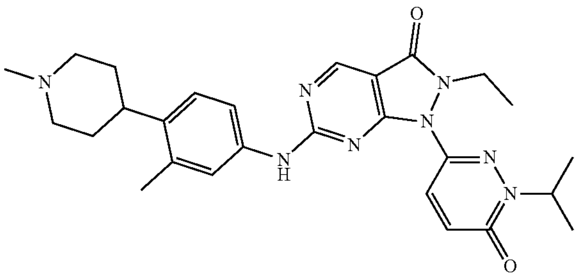

-continued
277
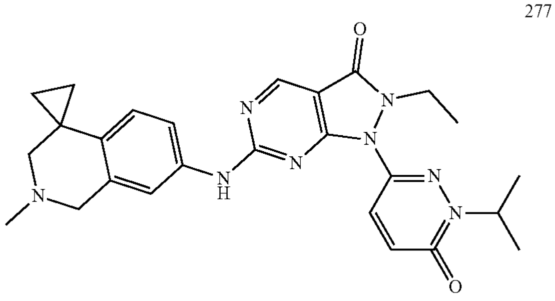
278
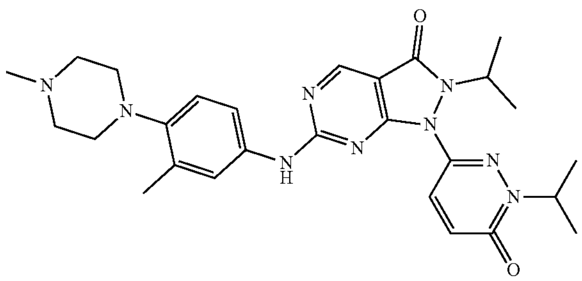
279
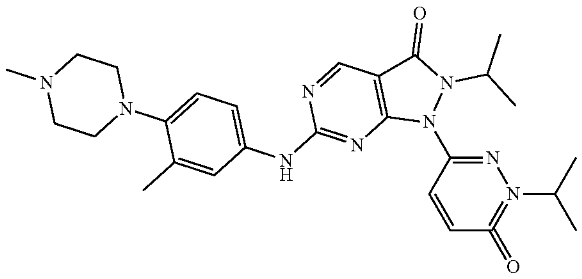
280
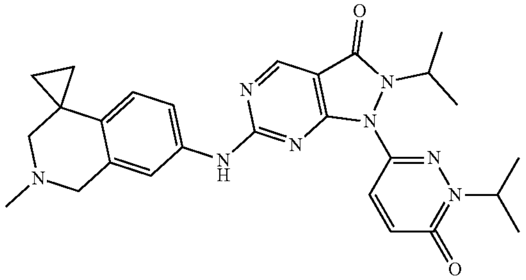
281
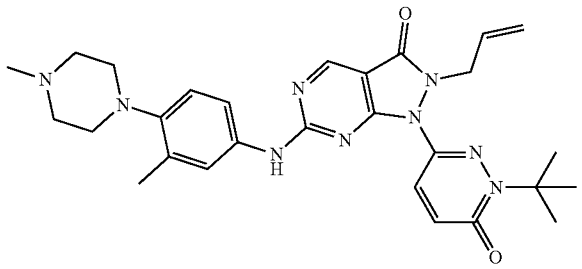
-continued
282
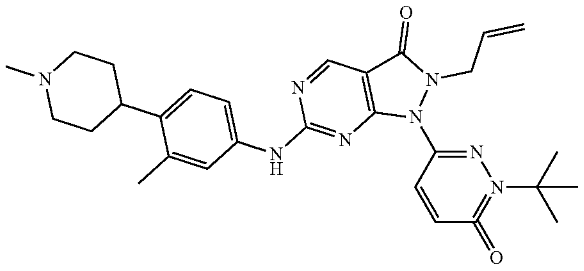
283
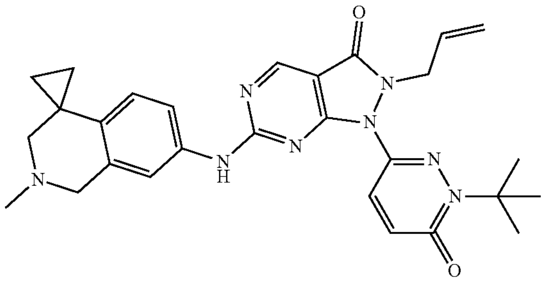
284
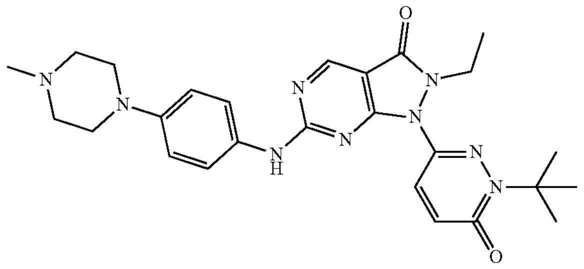
285
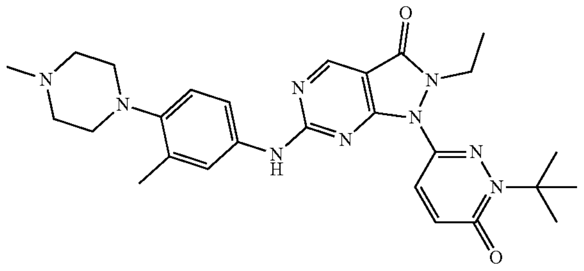
286
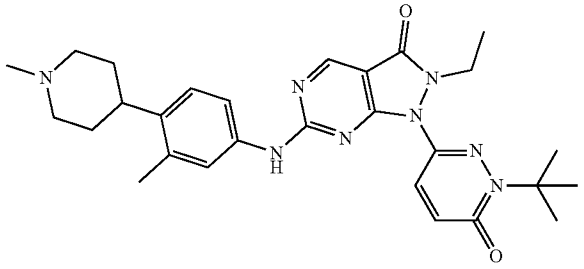

287
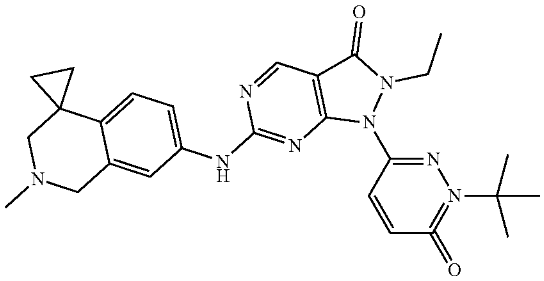
288
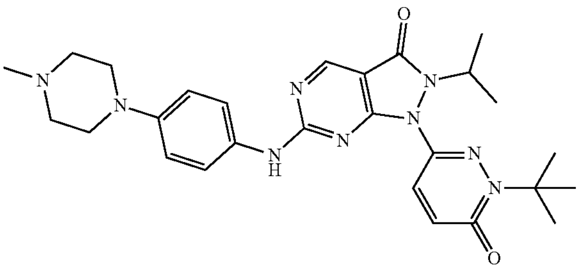
289
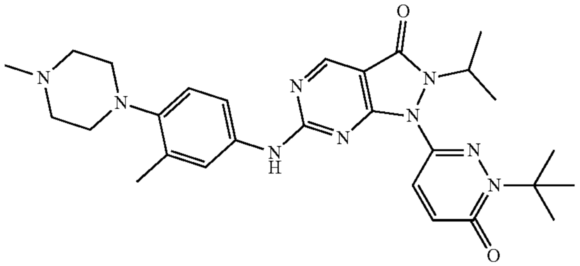
290
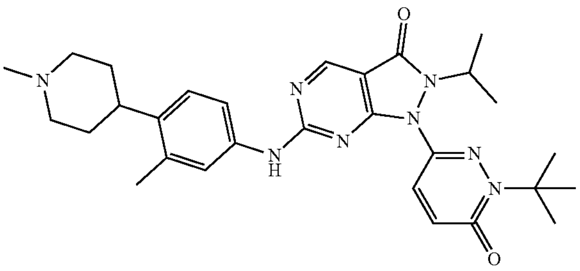
291
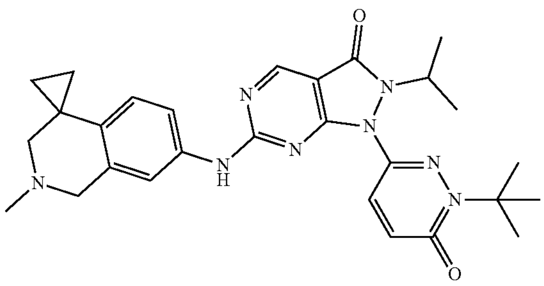
292
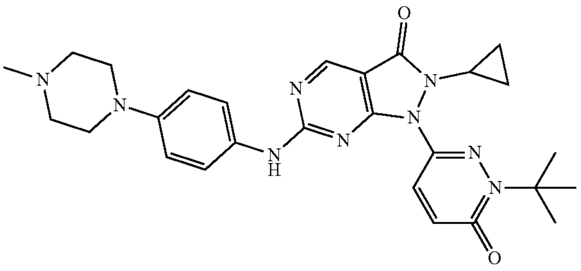
293
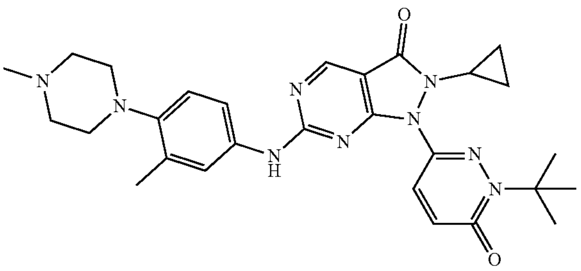
294
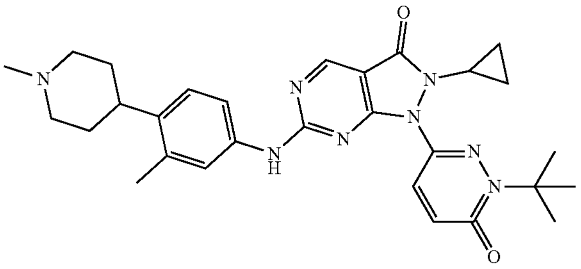
295
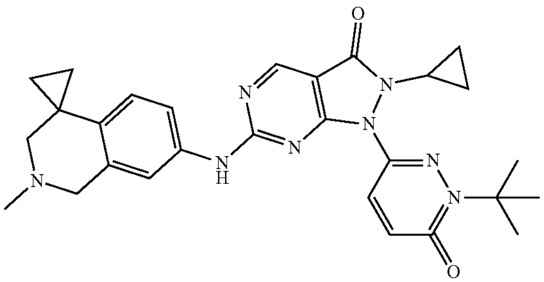
296
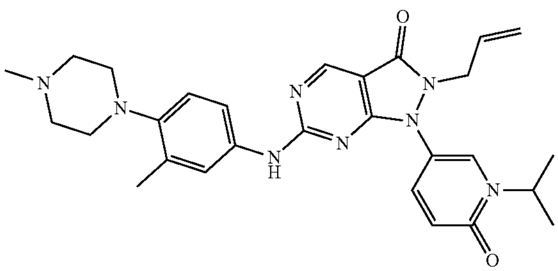

-continued
297
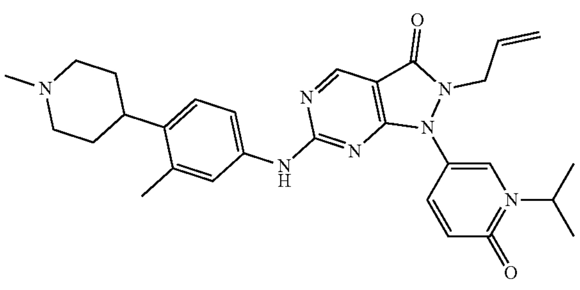
298
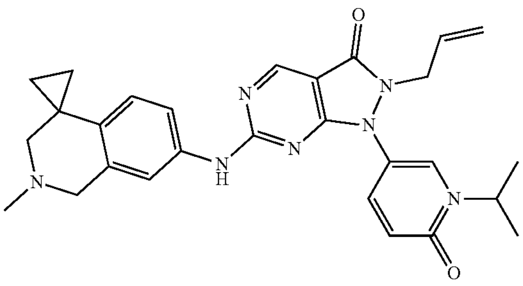
299
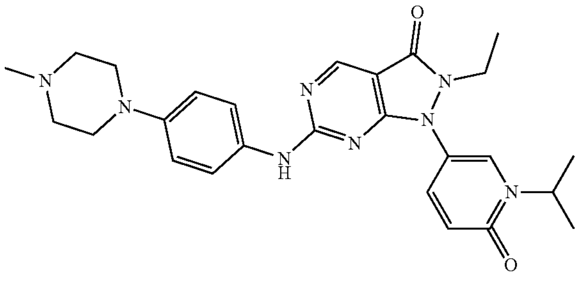
300
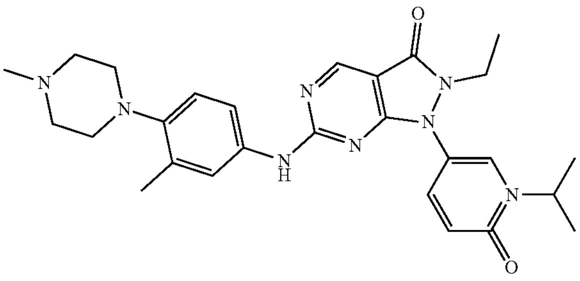
301
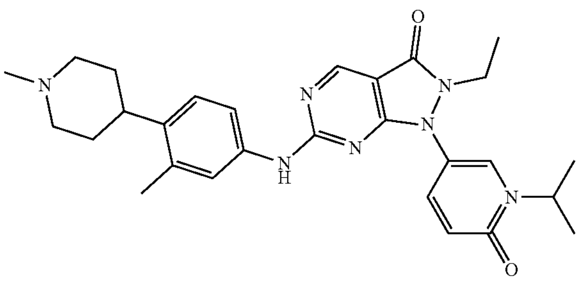
-continued
302
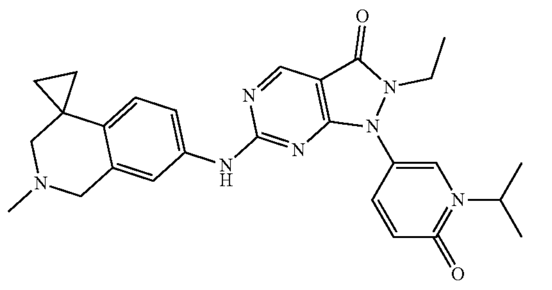
303
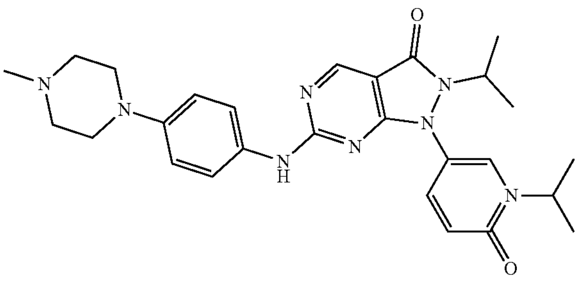
304
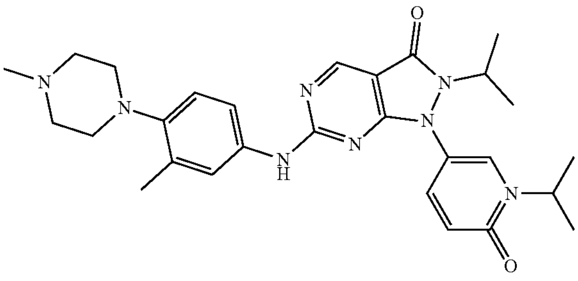
305
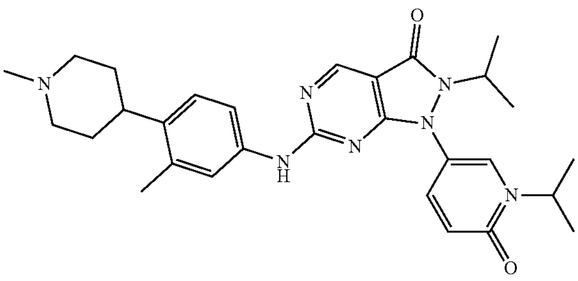
306
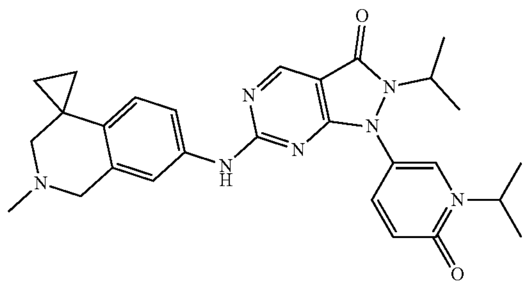

-continued
307
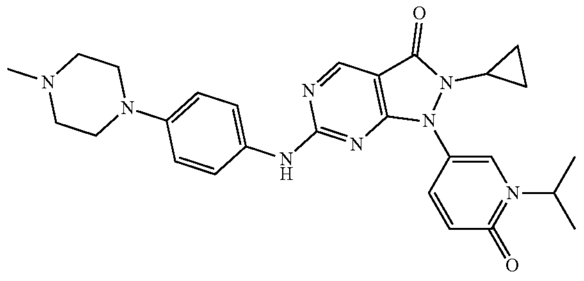
308
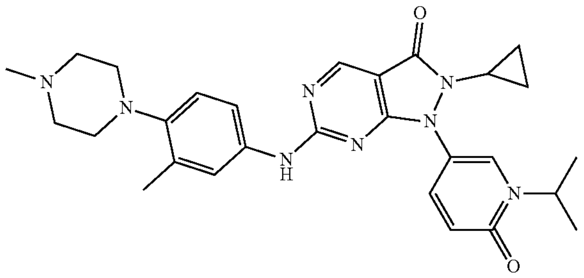
309
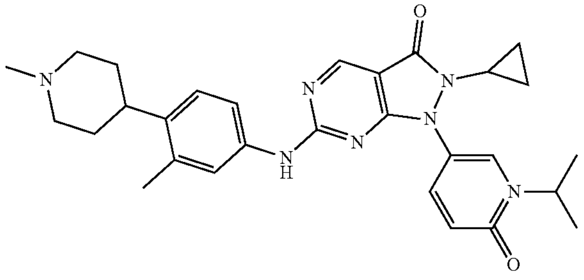
310
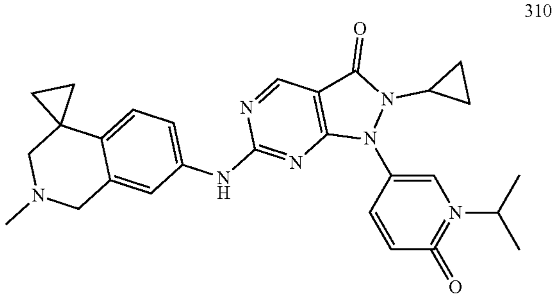
311
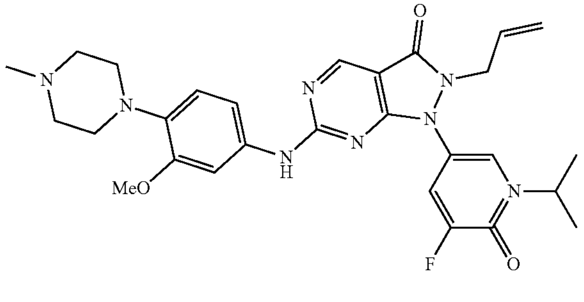
-continued
312
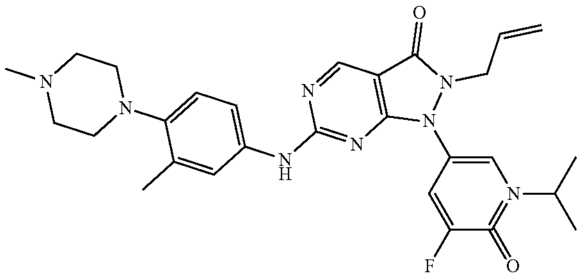
313
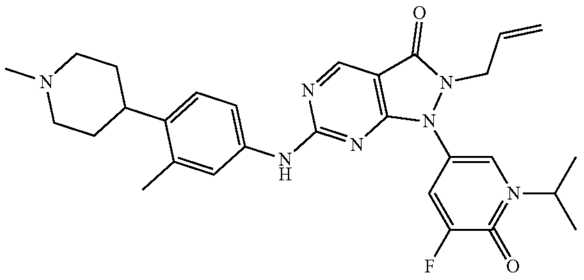
314
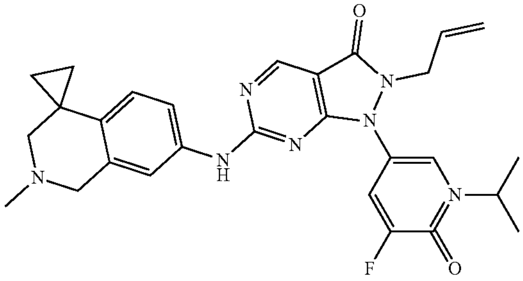
315
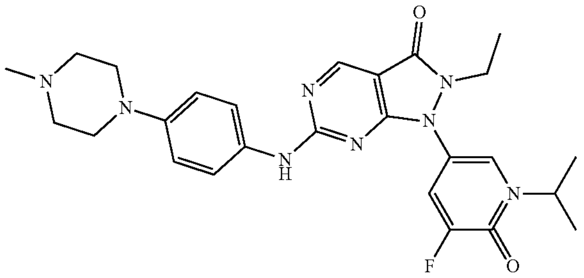
316
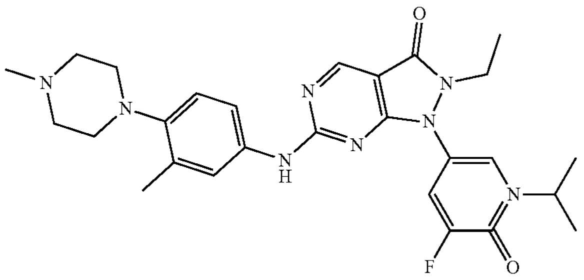

-continued
317
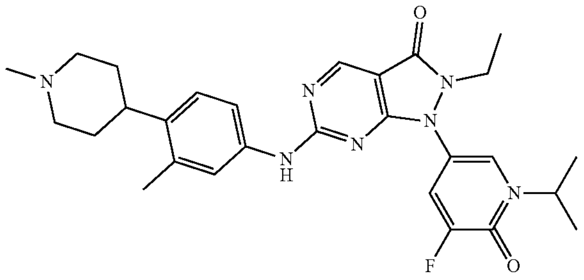
318
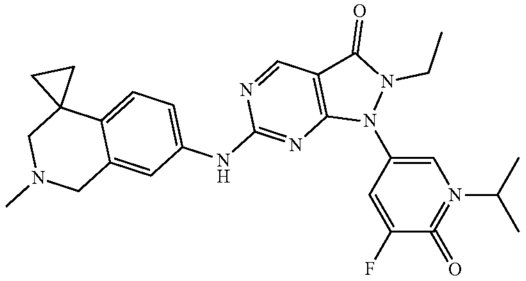
319
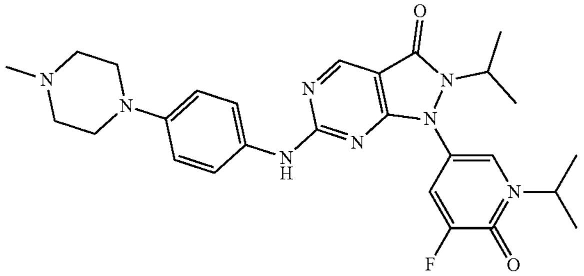
320
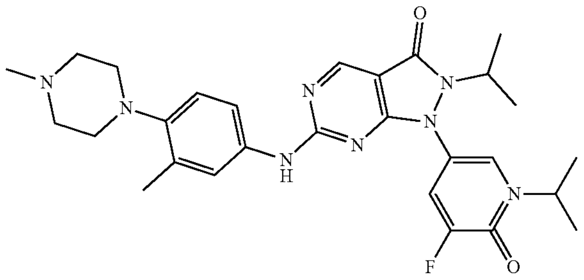
321
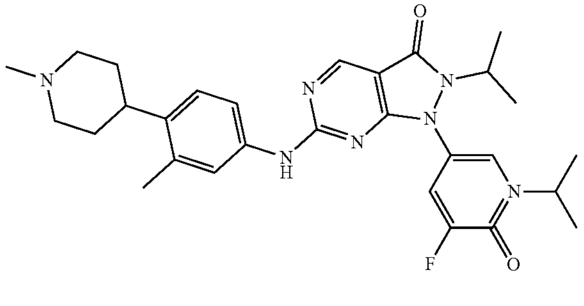
-continued
322
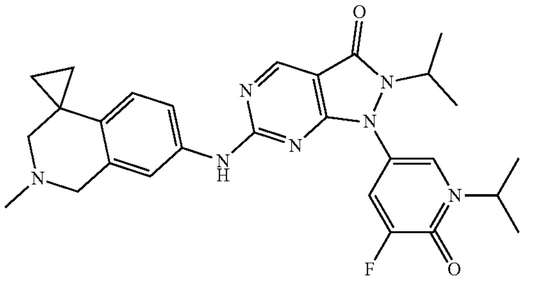
323
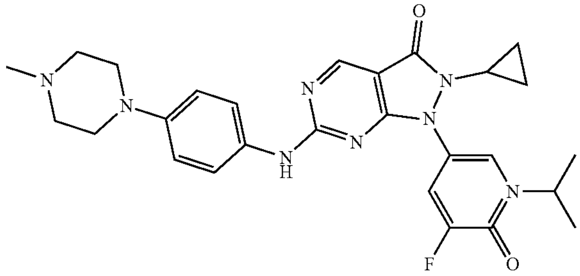
324
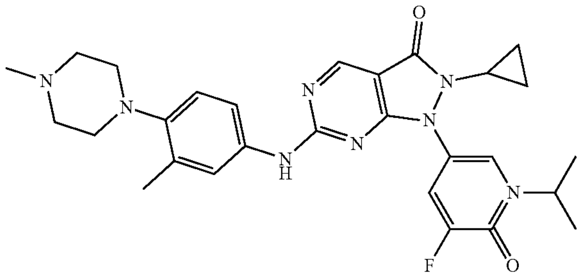
325
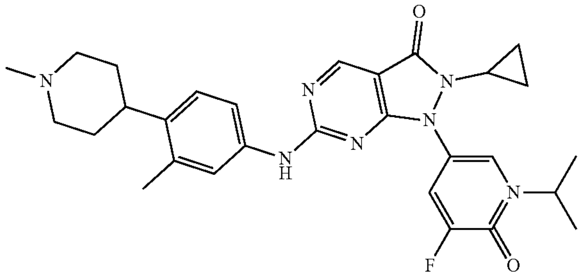
326
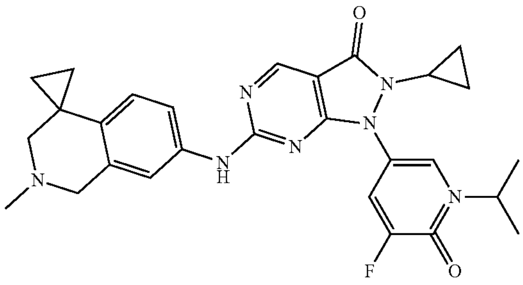

-continued
327
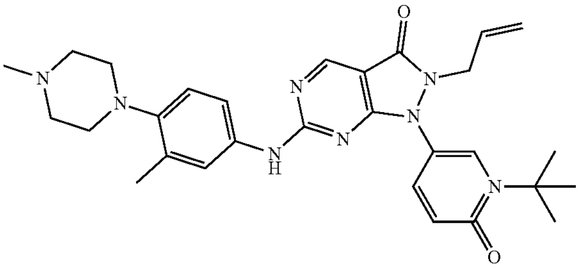
328
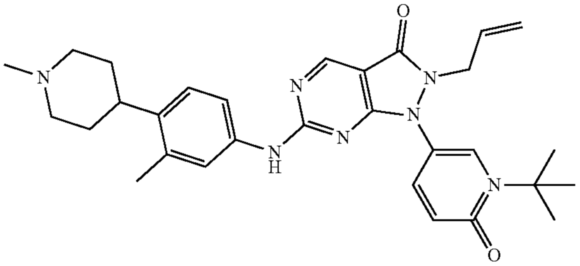
329
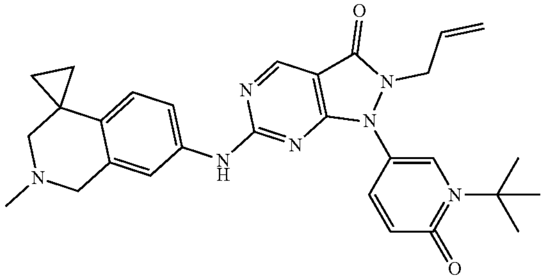
330
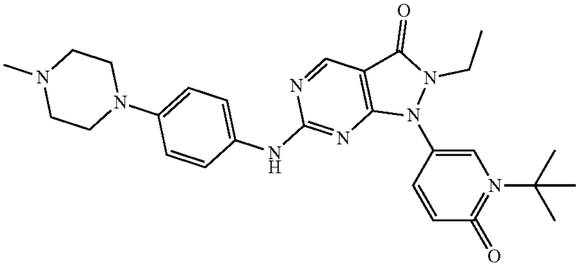
331
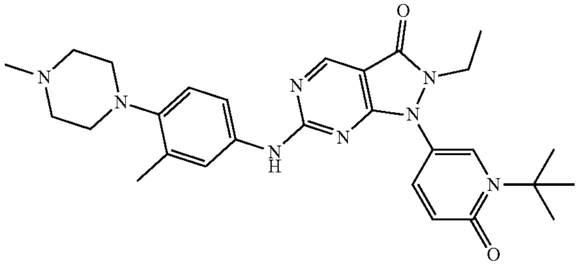
-continued
332
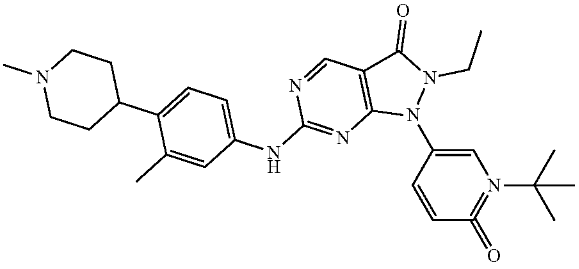
333
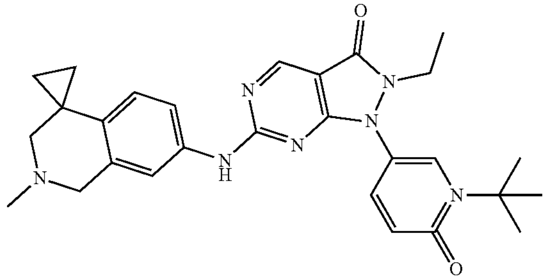
334
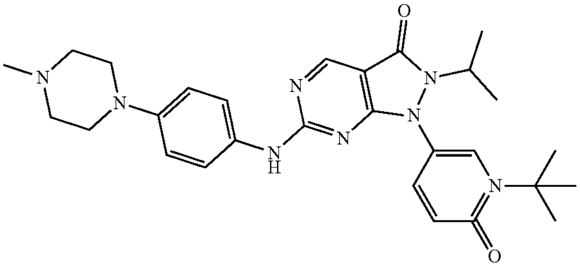
335
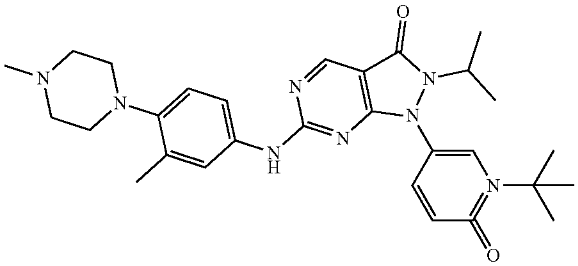
336
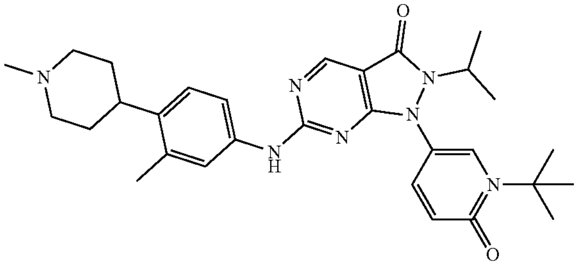

-continued
337
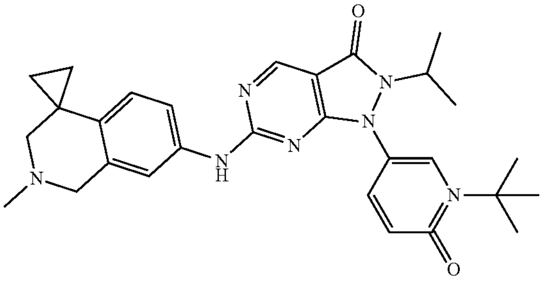
338
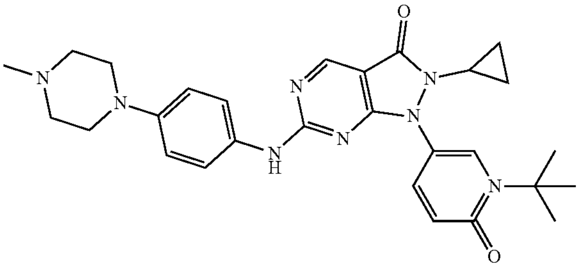
339
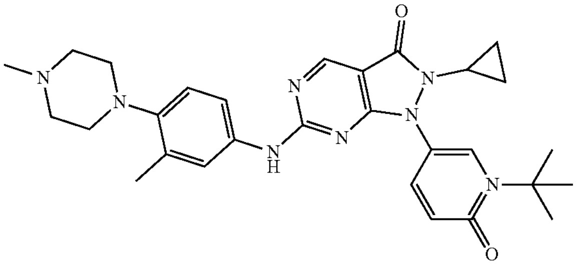
-continued
340
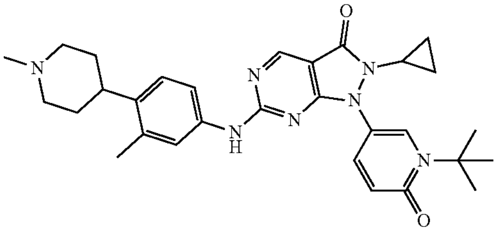
and
341
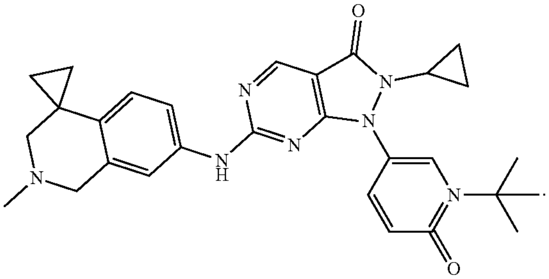
or a pharmaceutically acceptable salt thereof.
* * * * *